United States Patent
Kanes et al.

(10) Patent No.: US 12,083,131 B2
(45) Date of Patent: *Sep. 10, 2024

(54) NEUROACTIVE STEROIDS, COMPOSITIONS, AND USES THEREOF

(71) Applicant: Sage Therapeutics, Inc., Cambridge, MA (US)

(72) Inventors: Stephen Jay Kanes, Brynlawn, PA (US); Helen Colquhoun, Arlington, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/786,160

(22) Filed: Feb. 10, 2020

(65) Prior Publication Data

US 2020/0253985 A1    Aug. 13, 2020

Related U.S. Application Data

(62) Division of application No. 15/509,656, filed as application No. PCT/US2015/048937 on Sep. 8, 2015, now abandoned.

(60) Provisional application No. 62/213,015, filed on Sep. 1, 2015, provisional application No. 62/170,596, filed on Jun. 3, 2015, provisional application No. 62/047,599, filed on Sep. 8, 2014.

(51) Int. Cl.
| | |
|---|---|
| *A61K 31/573* | (2006.01) |
| *A61K 9/00* | (2006.01) |
| *A61K 31/57* | (2006.01) |
| *A61K 47/40* | (2006.01) |

(52) U.S. Cl.
CPC .......... *A61K 31/573* (2013.01); *A61K 9/0019* (2013.01); *A61K 9/0053* (2013.01); *A61K 31/57* (2013.01); *A61K 47/40* (2013.01)

(58) Field of Classification Search
CPC ...... A61K 31/57; A61K 31/573; A61K 47/40; A61K 9/0019; A61K 9/0053; A61K 31/157; A61P 25/14; A61P 25/24; A61P 25/28
USPC ....................................................... 514/171
See application file for complete search history.

(56) References Cited

U.S. PATENT DOCUMENTS

| | | |
|---|---|---|
| 3,117,142 A | 1/1964 | Candido et al. |
| 3,169,134 A | 2/1965 | Klimstra et al. |
| 3,580,937 A | 5/1971 | Campbell et al. |
| 3,865,939 A | 2/1975 | Jandacek |
| 3,943,124 A | 3/1976 | Phillipps et al. |
| 3,983,111 A | 9/1976 | Phillipps et al. |
| 4,071,625 A | 1/1978 | Grunwell et al. |
| 4,192,871 A | 3/1980 | Phillipps et al. |
| 5,719,197 A | 2/1998 | Kanios et al. |
| 5,925,630 A | 7/1999 | Upasani et al. |
| 5,939,545 A | 8/1999 | Upasani et al. |
| 6,143,736 A | 11/2000 | Upasani et al. |
| 6,245,757 B1 | 6/2001 | Chopp et al. |
| 6,277,838 B1 | 8/2001 | Upasani et al. |
| 6,376,531 B1 | 4/2002 | Bell |
| 6,455,516 B1 | 9/2002 | Backstrom et al. |
| 6,603,008 B1 | 8/2003 | Ando et al. |
| 6,780,853 B1 | 8/2004 | Upasani et al. |
| 7,060,255 B2 | 6/2006 | Rabinowitz et al. |
| 7,064,116 B2 | 6/2006 | Calogeropoulou et al. |
| 7,090,830 B2 | 8/2006 | Hale et al. |
| 7,630,757 B2 | 12/2009 | Dorfmeister et al. |
| 7,816,074 B2 | 10/2010 | Smith et al. |
| 7,858,609 B2 | 12/2010 | Shaw et al. |
| 7,998,971 B2 | 8/2011 | Barlow et al. |
| 8,012,958 B2 | 9/2011 | Sabnani et al. |
| 8,618,087 B2 | 12/2013 | Shaw et al. |
| 8,697,678 B2 | 4/2014 | Goodchild et al. |
| 8,969,329 B2 | 3/2015 | Brinton et al. |
| 9,056,116 B2 | 6/2015 | Shaw et al. |
| 9,084,797 B2 | 7/2015 | Caufriez et al. |
| 9,339,508 B2 | 5/2016 | Baulieu et al. |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,676,812 B2 | 6/2017 | Covey et al. |
| 9,725,481 B2 | 8/2017 | Martinez Botella et al. |
| 9,765,110 B2 | 9/2017 | Covey |
| 10,023,606 B2 | 7/2018 | Martinez Botella et al. |
| 10,172,871 B2 | 1/2019 | Martinez Botella et al. |

(Continued)

FOREIGN PATENT DOCUMENTS

| | | |
|---|---|---|
| CA | 2443266 A1 | 8/2002 |
| CA | 2443466 A1 | 12/2002 |

(Continued)

OTHER PUBLICATIONS

Walton N, Maguire J. Allopregnanolone-based treatments for postpartum depression: Why/how do they work?. Neurobiol Stress. 2019;11:100198. Published Oct. 24, 2019. doi:10.1016/j.ynstr.2019.100198.*

(Continued)

*Primary Examiner* — Shobha Kantamneni

(74) *Attorney, Agent, or Firm* — Honigman LLP

(57) ABSTRACT

Described herein are methods of treating tremor, e.g., essential tremor, depression, e.g., postpostum depression; and anxiety disorder, the method comprising administering to a human subject suffering from tremor, e.g., essential tremor; depression, e.g., postpostum depression, an anxiety disorder with a neuroactive steroid or a composition comprising a neuroactive steroid (e.g., pregnanolone, allopregnanolone, alphadalone, ganaxolone, or alphaxolone).

16 Claims, 8 Drawing Sheets

(56) References Cited

U.S. PATENT DOCUMENTS

| | | |
|---|---|---|
| 10,246,482 B2 | 4/2019 | Harrison et al. |
| 10,251,894 B2 | 4/2019 | Rogawski et al. |
| 10,322,139 B2 | 6/2019 | Reddy |
| 10,323,059 B2 | 6/2019 | Martinez Botella et al. |
| 10,329,320 B2 | 6/2019 | Robichaud et al. |
| 10,342,809 B2 | 7/2019 | Covey et al. |
| 10,342,810 B2 | 7/2019 | Martinez Botella et al. |
| 10,377,790 B2 | 8/2019 | Martinez Botella et al. |
| 10,391,106 B2 | 8/2019 | Martinez Botella et al. |
| 10,426,786 B2 | 10/2019 | Rogawski et al. |
| 10,426,837 B2 | 10/2019 | Robichaud et al. |
| 10,435,431 B2 | 10/2019 | Upasani et al. |
| 10,577,390 B2 | 3/2020 | Martinez Botella et al. |
| 10,745,436 B2 | 8/2020 | Harrison et al. |
| 10,774,108 B2 | 9/2020 | Martinez Botella et al. |
| 10,822,370 B2 | 11/2020 | Martinez Botella et al. |
| 10,870,677 B2 | 12/2020 | Martinez Botella et al. |
| 10,940,156 B2 | 3/2021 | Kanes et al. |
| 11,046,728 B2 | 6/2021 | Martinez Botella et al. |
| 11,124,538 B2 | 9/2021 | Robichaud et al. |
| 11,147,877 B2 | 10/2021 | Robichaud et al. |
| 11,149,057 B2 | 10/2021 | Harrison et al. |
| 11,236,121 B2 | 2/2022 | Watson et al. |
| 11,241,446 B2 | 2/2022 | Martinez Botella et al. |
| 11,261,211 B2 | 3/2022 | Martinez Botella et al. |
| 11,344,563 B2 | 5/2022 | Martinez Botella et al. |
| 11,396,525 B2 | 7/2022 | Robichaud et al. |
| 11,426,417 B2 | 8/2022 | Reddy |
| 11,498,940 B2 | 11/2022 | Martinez Botella et al. |
| 11,510,929 B2 | 11/2022 | Rogawski et al. |
| 11,530,237 B2 | 12/2022 | Martinez Botella et al. |
| 11,542,297 B2 | 1/2023 | Martinez Botella et al. |
| 11,554,125 B2 | 1/2023 | Kanes et al. |
| 11,634,453 B2 | 4/2023 | Blanco-Pillado et al. |
| 2002/0032203 A1 | 3/2002 | Swope |
| 2002/0072509 A1 | 6/2002 | Stein et al. |
| 2002/0183293 A1 | 12/2002 | Banerjee et al. |
| 2002/0198174 A1 | 12/2002 | Lyons |
| 2003/0032638 A1 | 2/2003 | Kim et al. |
| 2004/0121010 A1 | 6/2004 | Hirsh et al. |
| 2005/0201888 A1 | 9/2005 | Amar et al. |
| 2006/0063707 A1 | 3/2006 | Baudry et al. |
| 2006/0198896 A1 | 9/2006 | Liversidge et al. |
| 2007/0014719 A1 | 1/2007 | Reading et al. |
| 2007/0020299 A1 | 1/2007 | Pipkin et al. |
| 2007/0081948 A1 | 4/2007 | Morton et al. |
| 2007/0287931 A1 | 12/2007 | Dilorenzo |
| 2008/0195160 A1 | 8/2008 | Wingeier et al. |
| 2008/0269183 A1 | 10/2008 | Mellon et al. |
| 2009/0074677 A1 | 3/2009 | Marx et al. |
| 2009/0130216 A1 | 5/2009 | Cartt et al. |
| 2009/0162441 A1 | 6/2009 | Bartus et al. |
| 2009/0198145 A1 | 8/2009 | Chow |
| 2009/0203658 A1 | 8/2009 | Marx et al. |
| 2009/0209551 A1 | 8/2009 | Sokoloff et al. |
| 2009/0221544 A1 | 9/2009 | Stein et al. |
| 2009/0239942 A1 | 9/2009 | Cloyd |
| 2009/0325920 A1 | 12/2009 | Hoffman et al. |
| 2010/0136105 A1 | 6/2010 | Chen et al. |
| 2010/0234335 A1 | 9/2010 | Gravanis et al. |
| 2010/0297181 A1 | 11/2010 | Hanada et al. |
| 2010/0316678 A1 | 12/2010 | Goodchild |
| 2010/0317638 A1 | 12/2010 | Covey et al. |
| 2010/0331762 A1 | 12/2010 | Wingeier et al. |
| 2011/0054038 A1 | 3/2011 | Glozman |
| 2011/0152840 A1 | 6/2011 | Lee et al. |
| 2011/0288059 A1 | 11/2011 | Marx et al. |
| 2011/0306579 A1 | 12/2011 | Stein |
| 2011/0319386 A1 | 12/2011 | Barlow et al. |
| 2012/0142645 A1 | 6/2012 | Marx |
| 2012/0302535 A1 | 11/2012 | Caufriez et al. |
| 2012/0316146 A1 | 12/2012 | Goodchild et al. |
| 2013/0210783 A1 | 8/2013 | Marx et al. |
| 2013/0309306 A1 | 11/2013 | Rogawski et al. |
| 2014/0050789 A1 | 2/2014 | Rogawski et al. |
| 2014/0057885 A1 | 2/2014 | Reddy et al. |
| 2014/0058079 A1 | 2/2014 | Mensah-Nyagan et al. |
| 2014/0148412 A1 | 5/2014 | Hogenkamp |
| 2014/0235600 A1 | 8/2014 | Covey et al. |
| 2014/0322198 A1 | 10/2014 | Buchwald-Werner et al. |
| 2014/0343027 A1 | 11/2014 | Rogawski |
| 2015/0018327 A1 | 1/2015 | Reddy |
| 2015/0158903 A1 | 6/2015 | Upasani et al. |
| 2015/0175651 A1 | 6/2015 | Salituro et al. |
| 2015/0265632 A1 | 9/2015 | Goodchild et al. |
| 2015/0290181 A1 | 10/2015 | Lee et al. |
| 2015/0291654 A1 | 10/2015 | Upasani et al. |
| 2015/0313915 A1 | 11/2015 | Rogawski et al. |
| 2015/0315230 A1 | 11/2015 | Covey et al. |
| 2016/0068563 A1 | 3/2016 | Martinez Botella et al. |
| 2016/0083417 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2016/0152658 A1 | 6/2016 | Martinez Botella et al. |
| 2016/0229887 A1 | 8/2016 | Martinez Botella et al. |
| 2017/0190732 A1 | 7/2017 | Covey et al. |
| 2017/0232006 A1 | 8/2017 | Covey et al. |
| 2017/0233432 A1 | 8/2017 | Martinez Botella et al. |
| 2017/0233433 A1 | 8/2017 | Martinez Botella et al. |
| 2017/0240589 A1 | 8/2017 | Martinez Botella et al. |
| 2017/0246191 A1 | 8/2017 | Martinez Botella et al. |
| 2017/0247406 A1 | 8/2017 | Harrison et al. |
| 2017/0319695 A1 | 11/2017 | Robichaud et al. |
| 2017/0342102 A1 | 11/2017 | Martinez Botella et al. |
| 2017/0342103 A1 | 11/2017 | Upasani et al. |
| 2017/0348326 A1 | 12/2017 | Reddy |
| 2017/0348327 A1 | 12/2017 | Kanes et al. |
| 2018/0037602 A1 | 2/2018 | Robichaud et al. |
| 2018/0050005 A1 | 2/2018 | DiMauro et al. |
| 2018/0050107 A1 | 2/2018 | DiMauro et al. |
| 2018/0051052 A1 | 2/2018 | Martinez Botella et al. |
| 2018/0064728 A1 | 3/2018 | Chang et al. |
| 2018/0071315 A1 | 3/2018 | Cashman et al. |
| 2018/0133229 A1 | 5/2018 | Rogawski et al. |
| 2018/0141971 A1 | 5/2018 | Martinez Botella et al. |
| 2018/0153906 A1 | 6/2018 | Rogawski et al. |
| 2018/0179247 A1 | 6/2018 | Botella et al. |
| 2018/0193357 A1 | 7/2018 | Rogawski et al. |
| 2018/0215779 A1 | 8/2018 | Martinez Botella et al. |
| 2018/0235916 A1 | 8/2018 | Kaufman et al. |
| 2018/0256726 A1 | 9/2018 | Rogawski |
| 2018/0296487 A1 | 10/2018 | Saporito et al. |
| 2018/0311258 A1 | 11/2018 | Robichaud et al. |
| 2018/0311262 A1 | 11/2018 | Martinez Botella et al. |
| 2018/0369171 A1 | 12/2018 | Pinna et al. |
| 2019/0008873 A1 | 1/2019 | Salituro et al. |
| 2019/0038639 A1 | 2/2019 | Reddy et al. |
| 2019/0112331 A1 | 4/2019 | Botella et al. |
| 2019/0142845 A1 | 5/2019 | Rogawski et al. |
| 2019/0160078 A1 | 5/2019 | Masuoka et al. |
| 2019/0169226 A1 | 6/2019 | Harrison et al. |
| 2019/0177358 A1 | 6/2019 | Martinez Botella et al. |
| 2019/0177359 A1 | 6/2019 | Watson et al. |
| 2019/0233465 A1 | 8/2019 | Robichaud et al. |
| 2019/0247402 A1 | 8/2019 | Reddy |
| 2019/0248831 A1 | 8/2019 | Robichaud et al. |
| 2019/0269699 A1 | 9/2019 | Reddy |
| 2019/0337975 A1 | 11/2019 | Bryson et al. |
| 2019/0350944 A1 | 11/2019 | Salituro et al. |
| 2020/0016178 A1 | 1/2020 | Martinez Botella et al. |
| 2020/0024301 A1 | 1/2020 | Martinez Botella et al. |
| 2020/0024302 A1 | 1/2020 | Martinez Botella et al. |
| 2020/0048300 A1 | 1/2020 | Martinez Botella et al. |
| 2020/0113917 A1 | 2/2020 | Kanes et al. |
| 2020/0017542 A1 | 4/2020 | Martinez Botella et al. |
| 2020/0113916 A1 | 4/2020 | Covey et al. |
| 2020/0147071 A1 | 5/2020 | Jindal |
| 2020/0155522 A1 | 5/2020 | Osten et al. |
| 2020/0155576 A1 | 5/2020 | Martinez Botella et al. |
| 2020/0171049 A1 | 6/2020 | Kanes et al. |
| 2020/0179350 A1 | 6/2020 | During |
| 2020/0179351 A1 | 6/2020 | During |

(56) References Cited

U.S. PATENT DOCUMENTS

| | | |
|---|---|---|
| 2020/0179403 A1 | 6/2020 | Aimetti et al. |
| 2020/0188412 A1 | 6/2020 | Bryson et al. |
| 2020/0215078 A1 | 7/2020 | Rogawski et al. |
| 2020/0223884 A1 | 7/2020 | Upasani et al. |
| 2020/0246459 A1 | 8/2020 | Robichaud et al. |
| 2020/0253985 A1 | 8/2020 | Kanes et al. |
| 2020/0276209 A1 | 9/2020 | Colquhoun et al. |
| 2020/0281943 A1 | 9/2020 | Hoffmann et al. |
| 2020/0306262 A1 | 10/2020 | Doherty |
| 2020/0306265 A1 | 10/2020 | Kanes et al. |
| 2020/0354399 A1 | 11/2020 | Robichaud et al. |
| 2020/0377547 A1 | 12/2020 | Salituro et al. |
| 2020/0392177 A1 | 12/2020 | Martinez Botella et al. |
| 2021/0017218 A1 | 1/2021 | Martinez Botella et al. |
| 2021/0040141 A1 | 2/2021 | Upasani et al. |
| 2021/0061848 A1 | 3/2021 | Martinez Botella et al. |
| 2021/0061850 A1 | 3/2021 | Martinez Botella et al. |
| 2021/0087223 A1 | 3/2021 | Martinez Botella et al. |
| 2021/0094981 A1 | 4/2021 | Harrison et al. |
| 2021/0100817 A1 | 4/2021 | Rogawski et al. |
| 2021/0101928 A1 | 4/2021 | Robichaud et al. |
| 2021/0113590 A1 | 4/2021 | Robichaud et al. |
| 2021/0139531 A1 | 5/2021 | Botella et al. |
| 2021/0308149 A1 | 10/2021 | Covey et al. |
| 2021/0338692 A1 | 11/2021 | Kanes et al. |
| 2021/0340172 A1 | 11/2021 | Blanco-Pillado et al. |
| 2021/0347812 A1 | 11/2021 | Robichaud et al. |
| 2021/0363175 A1 | 11/2021 | Salituro et al. |
| 2021/0369734 A1 | 12/2021 | Doherty |
| 2021/0403502 A1 | 12/2021 | Harrison et al. |
| 2022/0023313 A1 | 1/2022 | Kanes et al. |
| 2022/0098231 A1 | 3/2022 | Salituro et al. |
| 2022/0110949 A1 | 4/2022 | Doherty et al. |
| 2022/0110950 A1 | 4/2022 | Martinez Botella et al. |
| 2022/0152050 A1 | 5/2022 | Reddy et al. |
| 2022/0169674 A1 | 6/2022 | Watson et al. |
| 2022/0213137 A1 | 7/2022 | Martinez Botella et al. |
| 2022/0220150 A1 | 7/2022 | Martinez Botella et al. |
| 2022/0315621 A1 | 10/2022 | Robichaud et al. |
| 2022/0323462 A1 | 10/2022 | Kanes et al. |
| 2022/0372067 A1 | 11/2022 | Blanco-Pillado et al. |
| 2022/0380405 A1 | 12/2022 | Salituro et al. |
| 2023/0018765 A1 | 1/2023 | Kanes et al. |
| 2023/0021308 A9 | 1/2023 | Robichaud et al. |
| 2023/0046825 A1 | 2/2023 | Blanco-Pillado et al. |
| 2023/0057130 A1 | 2/2023 | Watson et al. |
| 2023/0085354 A1 | 3/2023 | Robichaud et al. |
| 2023/0113666 A1 | 4/2023 | Martinez Botella et al. |
| 2023/0116347 A1 | 4/2023 | Robichaud et al. |

FOREIGN PATENT DOCUMENTS

| | | |
|---|---|---|
| CN | 1190404 A | 8/1998 |
| CN | 104136452 A | 11/2014 |
| EP | 0233849 A1 | 8/1987 |
| EP | 0554436 A1 | 8/1993 |
| EP | 0656365 A1 | 6/1995 |
| EP | 0701444 A1 | 3/1996 |
| EP | 0808325 A1 | 11/1997 |
| EP | 1038880 A2 | 9/2000 |
| GB | 1430942 A | 4/1976 |
| GB | 1570394 A | 7/1980 |
| GB | 1581234 A | 12/1980 |
| WO | 1991011172 A1 | 8/1991 |
| WO | 1991016897 A1 | 11/1991 |
| WO | 9303732 A1 | 3/1993 |
| WO | 9305786 A1 | 4/1993 |
| WO | 9318053 A1 | 9/1993 |
| WO | 9427608 A1 | 12/1994 |
| WO | 1995021617 A1 | 8/1995 |
| WO | 9526325 A2 | 10/1995 |
| WO | 1996003421 A1 | 2/1996 |
| WO | 1996016076 A1 | 5/1996 |
| WO | 9640043 A2 | 12/1996 |
| WO | 1997003677 A1 | 2/1997 |
| WO | 9805337 A1 | 2/1998 |
| WO | 1999045931 A1 | 9/1999 |
| WO | 2002030409 A2 | 4/2002 |
| WO | 2004019953 A1 | 3/2004 |
| WO | 2005105822 A2 | 11/2005 |
| WO | 2006102644 A2 | 9/2006 |
| WO | 2007062266 A2 | 5/2007 |
| WO | 2008128049 A2 | 10/2008 |
| WO | 2008157460 A1 | 12/2008 |
| WO | 2009088530 A1 | 7/2009 |
| WO | 2010003391 A2 | 1/2010 |
| WO | 2010042925 A2 | 4/2010 |
| WO | 2010063030 A2 | 6/2010 |
| WO | 2010107815 A1 | 9/2010 |
| WO | 2011088503 A1 | 7/2011 |
| WO | 2012059456 A1 | 5/2012 |
| WO | 2012075286 A2 | 6/2012 |
| WO | 2012110010 A1 | 8/2012 |
| WO | 2012116290 A2 | 8/2012 |
| WO | 2013036835 A1 | 3/2013 |
| WO | 2013043985 A1 | 3/2013 |
| WO | 2013056181 A1 | 4/2013 |
| WO | 2013112605 A2 | 8/2013 |
| WO | 2013188792 A2 | 12/2013 |
| WO | 2014028398 A2 | 2/2014 |
| WO | 2014031792 A2 | 2/2014 |
| WO | 2014085668 A1 | 6/2014 |
| WO | 2014100228 A1 | 6/2014 |
| WO | 2014108808 A2 | 7/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A2 | 1/2015 |
| WO | 2015027227 A1 | 2/2015 |
| WO | 2015180679 A1 | 12/2015 |
| WO | 2015195962 A1 | 12/2015 |
| WO | 2016040322 A1 | 3/2016 |
| WO | 2016061527 A1 | 4/2016 |
| WO | 2016061537 A1 | 4/2016 |
| WO | 2016082789 A1 | 6/2016 |
| WO | 2016123056 A1 | 8/2016 |
| WO | 2016127170 A1 | 8/2016 |
| WO | 2016134301 A1 | 8/2016 |
| WO | 2016164763 A1 | 10/2016 |
| WO | 2016205721 A1 | 12/2016 |
| WO | 2017021325 A1 | 2/2017 |
| WO | 2017066240 A1 | 4/2017 |
| WO | 2017087864 A1 | 5/2017 |
| WO | 2017156103 A1 | 9/2017 |
| WO | 2018013613 A1 | 1/2018 |
| WO | 2018013615 A1 | 1/2018 |
| WO | 2018035095 A1 | 2/2018 |
| WO | 2018039378 A1 | 3/2018 |
| WO | 2018048789 A1 | 3/2018 |
| WO | 2018169798 A1 | 9/2018 |
| WO | 2018195186 A1 | 10/2018 |
| WO | 2018236955 A1 | 12/2018 |
| WO | 2018237282 A1 | 12/2018 |
| WO | 2019051264 A1 | 3/2019 |
| WO | 2019051477 A1 | 3/2019 |
| WO | 2019055764 A1 | 3/2019 |
| WO | 2019094724 A1 | 5/2019 |
| WO | 2019113494 A1 | 6/2019 |
| WO | 2019126741 A1 | 6/2019 |
| WO | 2019126761 A1 | 6/2019 |
| WO | 2019140272 A1 | 7/2019 |
| WO | 2019241442 A1 | 12/2019 |
| WO | 2020077255 A1 | 4/2020 |
| WO | 2020082065 A1 | 4/2020 |
| WO | 2020118060 A1 | 6/2020 |
| WO | 2020132504 A1 | 6/2020 |
| WO | 2020243027 A1 | 12/2020 |
| WO | 2020243488 A1 | 12/2020 |
| WO | 2020264495 A1 | 12/2020 |
| WO | 2020264509 A1 | 12/2020 |
| WO | 2020264512 A1 | 12/2020 |
| WO | 2021113786 A1 | 6/2021 |
| WO | 2021188778 A1 | 9/2021 |

(56) References Cited

FOREIGN PATENT DOCUMENTS

| | | |
|---|---|---|
| WO | 2021195297 A1 | 9/2021 |
| WO | 2021195301 A1 | 9/2021 |
| WO | 2021262836 A1 | 12/2021 |
| WO | 2022020363 A1 | 1/2022 |
| WO | 2022020363 A9 | 3/2022 |
| WO | 2022115381 A1 | 6/2022 |
| WO | 2022165017 A1 | 8/2022 |
| WO | 2022177718 A1 | 8/2022 |
| WO | 2022197901 A1 | 9/2022 |
| WO | 2022221195 A1 | 10/2022 |
| WO | 2022232494 A1 | 11/2022 |
| WO | 2022232504 A1 | 11/2022 |

OTHER PUBLICATIONS

Kask, K. et al. Allopregnanolone impairs episodic memory in healthy women. Psychopharmacology 199, 161 (2008). https://doi.org/10.1007/s00213-008-1150-7.*

Hellgren C et al. (Low Serum Allopregnanolone is Associated with Symptoms of Depression in Late Pregnancy. Neuropsychobiology 2014; 69:147-153. doi: 10.1159/000358838).*

Eser et al., "Neuropsychopharmacological properties of neuroactive steroids in depression and anxiety disorders", Psychopharmacolody, (2006) 186: pp. 373-387.

Evans, et al. "Allopregnanolone regulates neurogensis and depressive/anxiety-like behaviour in social isolation rodent model of chronic stress", Neuropharmacology 63 (2012) 1315-1326.

Extended European Search Report for application PCT/CN2014075593 dated Aug. 26, 2016.

Extended European Search Report for application PCT/CN2014075594 dated Aug. 26, 2016.

Extended European Search Report for European Application No. 13740743.3 dated Jan. 14, 2016.

Extended European Search Report for European Application No. 13830765.7 dated Jan. 12, 2016.

Extended European Search Report for European Application No. 13857993.3 dated May 2, 2016.

Finn et al., "The Estrus Cycle, Sensitivity to Convulsants and the Anticonvulsant Effect of Neuroactive Steroid", The Journal of Pharmacology and Experimental Therapeutics (1994), vol. 271, pp. 164-170.

Fitelson et al., "Treatment of postpartum despression: clinical, psychological and pharmacological options", International Journal of Women's Health, 2011, pp. 1-14.

Foster, "Deuterium isotope effects in studies of drug metablosim". Trends in Pharmacological Sciences, vol. 5, pp. 524-527 (Abstract) (1984).

Frank et al., "Neuroprotective effects of allopregnenolone on hippocampal irreversible neurotoxicity in vitro", Prog. Neuropsychopharmacol. & Biol Psychiat. 2000, vol. 24, pp. 1117-1126.

Freeman et al., "Allopregnanolone levels and sympotom improvement in severe premenstrual syndrome", J. Clin. Psychopharmacol 2002; 22:516-520.

Frye et al. "Hippocampal 3a,5a-THP may alter depressive behavior of pregnant an lactating rats", Pharmacology, Biochemistry and Behavior 78 (2004) 531-540.

Frye et al., "Changes in Progesterone metabolites in the hippocampus can modulate open field and forced swim test behavior of proestrous rats", Hormones and Behavior 41, 306-315 (2002).

Frye et al., "Infusion of 3a,5a-THP to the pontine reticular formation attenuates PTZ-induced seizures", Brain Research (2000), vol. 881, pp. 98-102.

Frye, "The neurosteroid 3-a, 5 a-THP has antiseizure and possible neuroprotective effects in an animal model of epilepsy," Brain Research, (1995), 696:113-120.

Frye, et al., "Effects and mechanism of 3a,5a,-THP on emotion, motivation, and reward functions involving pregnane xenobiotic receptor", Frontiers in Neuroscience (2012), vol. 5, Article 136, pp. 1-18.

Galvin et al., "Midazolam: an effective intravenous agent for seizure control," Archives of emergency medicine, (1987), 4:169-172.

Gasior et al., "Anticonvulsant and behaviorial effects of neuroactive steroids alone and in conjunction with diazepam", The Journal of Pharmacology and Experimental Therapeutics (1997), vol. 282, No. 2, pp. 543-553.

Gasior et al., "Neuroactive steroids: potential therapeutic use in neurological and psychiatric disorders", Trends in Pharmacological Science, (1999), vol. 20, No. 3, pp. 107-112.

Gaynes et al., "Perinatal Depression: Prevalence, Screening Accuracy, and Screening Outcomes", Evidence Report/Technology Assessment, (2005), No. 119, pp. 1-8.

Gilbert et al., "3a-reduced neuroactive steroids and their precursors during pregnancy and the postpartum period", Gynecol Endocrinol., (2005), 21(5): pp. 268-279.

Girdler et al. "Neurosteroids in the context of stress: Implications for depressive disorders", Pharmacology & Therapeutics 116 (2007) 125-139.

Griffin et al., "Current perspectives on the role of neurosteroids in PMS and depression", International Review of Neurobiology, vol. 46, 2001, pp. 479-492.

Guidotti et al., "The socially-isolated mouse: a model to study the putative role of allopregnanolone and 5a-dihydroprogesterone in psychiatric disorders", Brain Research Reviews 37 (2001) 110-115.

Gul et al., "Sterols and the phytosterol content in oilseed rape (*Brassica napus* L.)", Journal of Cell and Molecular Biology (2006), 5: 71-79.

Haas et al., "Ketamine: A Review of Its Pharmacologic Properties and Use in Ambulatory Anesthesia", Anesthesia, Anesthesia Progress, The American Dental Society of Anesthesiology (1992), vol. 39, pp. 61-68.

Hanley et al., "Use of midazolam in the treatment of refractory status epilepticus", Clinical Therapeutics, (1998), 20(6):1093-1105.

Hardoy et al. "The link between neurosteroids and syndromic/syndromal components of the mood spectrum disorders in women during the premenstrual phase", Clinical Practice and Epidemiology in Mental Health 2008, 4:3.

Hardoy, et al., "Increased neuroactive steroids concentrations in women with bipolar disorder or major depressive disorder", J. Clin Psychopharmacol 2006;26:379-384.

Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.

Haut et al., "Seizure clustering during epilepsy monitoring", Epilepsia, (2002), 43(7): 711-715.

Haut, "Seizure clustering", Epilepsy & Behavior, (2006), 8:50-55.

Haut, "Seizure Clusters: characteristics and treatment," Current Opin. Neurol., (2015), 28(2):143-150, Abstract only.

Hawkinson et al., "3a-Hydroxy-3b-trifluoromethyl-5a-pregnan-20-one (Co 2-1970): A Partial Agonist at the Neuroactive Steroid Site of the y-Aminobutyric acidA Receptor" Molecular Pharmacology (1996) vol. 49, pp. 897-906.

Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.

Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.

Hay et al., "Pathways to Violence in the Children of Mothers Who Were Depressed Postpartum", Developmental Psychology, 2003, vol. 39, No. 6, pp. 1083-1094.

He J et al., "Allopregnanolone facilitates spatial learning after traumatic brain injury", Abstracts of the Annual Meeting of the Society for Neuroscience (2000) p. 2296.

Hellgren et al., "Low serum allopregnanolone is associated with symptoms of depression in late pregnancy," Neuropsychobiology, (2014), 69:147-153.

(56) References Cited

OTHER PUBLICATIONS

Hincal, "Recent advances in drug delivery using amphiphilic cyclodextrin nanoparticles", European Journal of Pharmaceutical Sciences (2005), vol. 23S1, pp. S3-S4.
Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.
Hu et al., "Neurosteroid Analogues: Structure-Activity Studies of Benz(e] indene Modulators of GABAA Receptor Function. 1. The Effect of 6-Melhyl Substitution on the Electrophysiological Activity of 7-Substituted Benz[e]indene-3-carbonitriles", Journal of Medicinal Chemistry, (1993), pp. 3956-3967.
Huber, et al. "Effect of an oral contrceptive with chlormadinone Acetate on depressive mood", Clin Drug Invest 2008: 28 (12): 783-791.
Hunter et al., "Status Epilepticus: A Review, With Emphasis on Refractory Cases" Can. J. Neurol. Sci. (2012), vol. 39, pp. 157-169.
International Search Report and Written Opinion (Declaration of non-establishment of International Search Report) for corresponding International Application No. PCT/US2011/062888 dated Jun. 15, 2012.
International Search Report and Written Opinion for corresponding International Application No. PCT/US13/56062 dated Jan. 29, 2014.
International Search Report and Written Opinion for corresponding International Application No. PCT/US2012/056509 dated Dec. 27, 2012.
International Search Report and Written Opinion for corresponding International Application No. PCT/US2013/054562 dated Jan. 13, 2014.
International Search Report and Written Opinion for corresponding International Application No. PCT/US2013/072351 dated Mar. 17, 2014.
Zia et al., "Thermodynamics of Binding of Neutral Molecules to Sulfobutyl Ether b-Cyclodextrins (SBE-b-CDs):The Effect of Total Degree of Substitution", Pharmaceutical Research (2000), vol. 17, No. 8, pp. 936-941.
Zolkowska et al., "Anticonvulsant Activity of Intravenous and Intramuscular Allopregnenalone". 1-25. 26a-30a. 26b-30b. American Epilepsy Society: 2012 Annual Meeting Abstracts.
Zolkowska et al., "Anticonvulsant activity of intravenous and intramuscular allopregnenalone," American Epilepsy Society, (Poster), UC Davis, University of California, (2012), 1 page.
Zonana et al., "The Neurobiology of Postpartum Depression", CNS Spectrums, (2005), pp. 792-799, 805.
Zsuzsa, "Neurological and psychiatric aspects of some endocrine diseases. The role of neurosteroids and neuroactive steroids", Medical Journal (2007), 148(41): pp. 1929-1937, machine translated into English.
Rosenthal et al., "Brexanolone as adjunctive therapy in super-refractory status epilepticus," Annals of Neurology, John Wiley & Sons, (2017), 32pp.
Rossetti et al., "A Randomized Trial for the Treatment of Refractory Status Epilepticus", Neurocritical Care Society (2011), vol. 14, No. 1, pp. 4-10.
Rouge-Pont et al., "The neurosteroid allopregnanolone increases dopamine release and dopaminergic response to morphine in the rat nucleus accumbens", European Journal of Neuroscience, vol. 16, pp. 169-173, 2002.
Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.
Rupprecht et al.. "Neuroactive steroids; mechanisms of action and neuropsychopharmacological perspectives", Trends Neurosci. (1999) 22, 410-416.
Saady et al., "Case Report: Althesin in Status Epilepticus" Aneasth. Intens. Care (1979), vol. 7, No. 3, pp. 267-270.
Saalmann et al., "Neurosteroids involved in regulating inhibition in the inferior colliculus" J. Neurophysiol 96:3064-3073, 2006.
Sahin et al., "Outcome of Severe Refractory Status Epilepticus in Children", Epilepsia (2001), vol. 41, No. 11, pp. 1461-1467.
Sanborn et al., "Identifying and managing adverse environmental health effects: 4. Pesticides," CMAJ, (2002) 166 (11):1431-1436.
Santoru et al., "Decreased allopregnanolone induced by hormonal contraceptives is associated with a reduction in social behavior and sexual motivation in female rats," Psychopharmacology, (2014), 14pp.
Saporito et al., "Intravenously Administered Ganaxolone Blocks Diazepam-Resistant Lithium-Pilocarpine-Induced Status Epilepticus in Rats: Comparison with Allopregnanolone", Journal of Pharmacology Exp. Ther. 2019, 368(3), pp. 326-327.
Schiller et al., "Allopregnanolone as a mediator of affective switching in reproductive mood disorders," Psychopharmacology, (2014), 11pp.
Schiller et al., "The role of reproductive hormones in postpartum depression," CNS Spectrums, (2015), 20(1):48-59.
Schule et al., "Neuroactive steriods in Affective Disorders: target for Novel antidepressant or anxiolytic drugs", Neuroscience 191 (2011) p. 55-77.
Schule et al., "The role of allopregnanolone in depression and anxiety", Progress in Neurobiology 113 (2014) 79-87.
Shah et al., "Peripheral WBC Count and Serum Prolactin Level in Various Seizure Types and Nonepileptic Events", Epilepsia (2011), vol. 42, No. 11, pp. 1472-1475.
Shimizu et al., "Allopregnanolone increases mature excitatory synapses along dendrites via protein kinase A signaling," Neuroscience, (2015), 305:139-145.
Shorvon et al., "The Outcome of Therapies in Refractory and Super-Refractory Convulsive Status Epilepticus and Recommendations for Therapy", Brain (2012), vol. 135, No. 8, pp. 2314-2328.
Shorvon et al., "The Proceedings of the First London Colloquium on Status Epilepticus", University College London, Apr. 12-15, Epilepsia (2007), vol. 48, No. 8, pp. 1-3.
Shorvon et al., "The Treatment of Super-Refractory Status Epilepticus: A Critical Review of Available Therapies and a Clinical Treatment Protocol", Brain (2011,) vol. 134, No. 10, pp. 2802-2818.
Shu et al., "Characteristics of concatemeric GABM receptors containing alpha4/d subunits expressed in Xenopus oocytes" British Journal of Phannacology (2012) 165, 2228-2243.
Smith et al., "The influence of stress at puberty on mood and learning: Role of the a4136 GABAA receptor," Neuroscience, (2013), 249:192-213.
Stevens et al., "Hormonal Therapy for Epilepsy", Curr Neurol. Neurosci Rep. 11: 2011, pp. 435-442.
Supplemental European Search Report, European Patent Application No. 14826212.4, mailed Feb. 16, 2017.
Timby et al., "Pharmacokinetic and behavioral effects of allopregnanolone in healthy women", Psycopharmacology (2006), vol. 186, pp. 414-424.
Timby et al., "Women with premenstrual dysphoric disorder have altered sensitivity to allopregnanolone over the menstrual cycle compared to controls—a pilot study," Psychopharmacology, (2016), 233:2109-2117.
Tolmacheva et al., "The role of ovarian steroid hormones in the regulation of basal and stress induced absence seizures", Journal of Steroid Biochemistry & Molecular Biology (2007), vol. 104, pp. 281-288.
Tongiani et al., "Sulfobutyl Ether-Alkyl Ether Mixed Cyclodextrin Derivatives With Enhanced Inclusion Ability", Journal of Pharmaceutical Sciences (2009), vol. 98, No. 12, pp. 4769-4780.
Turkmen et al., "Tolerance to Allopregnanolone with Focus on the GABA-A Receptor", British Journal of Pharmacology (2011), vol. 162, pp. 311-327.
Ueda et al., "Evaluation of a Sulfobutyl Ether b-Cyclodextrin as a Aolubilizing/Stabilizing Agent for Several Drugs", Drug Development and Industrial Pharmacy (2008), vol. 24, No. 9, pp. 863-867.
Ungard et al., "Modification of behavioral effects of drugs in mice by neuroactive steroids", Psychopharmacology (2000) 148:336-343.

(56) References Cited

OTHER PUBLICATIONS

Upasani et al., "3a-Hydroxy-3ß-(phenylethynyl)-5ß-pregnan-20-ones: Synthesis and Pharmacological Activity of Neuroactive Steroids with High Affinity for GABAA Receptors", J. Med. Chem. (1997) vol. 40, No. 1, pp. 73-84.
Uzunova et al. "Region-specific dysregulation of allopregnanolone brain contante tin the olfactory bulbectomized rat model of depression", Brain Research 976 (2003) 1-8.
Uzunova et al., "Relevance of endogenous 3a-reduced neurosteroids to depression and antidepressant action", Psycopharmacology (2006) 186: 351-361.
Vaitkevicius et al., "First-in-man allopregnanolone use in super-refractory stats epilepticus", Annals of Clinical and Translational Neurology, vol. 4, No. 6, 2017, pp. 411-414.
Vaitkevicius et al., "Successful allopregnanolone treatment of new onset refractory status epilepticus (Norse) syndrome: First in man experience," Epilepsia, (2013), Abstract p. 114.
Van Broekhoven et al., "Neurosteroids in depression: a review", Psychopharmacology (2003) 165:97-110.
Vanlandingham et al., "Progesterone and its metabolite allopregnanolone differentially regulate hemostatic proteins after traumatic brain injury", Journal of Cerebral Blood Flow & Metabolism (2008), vol. 28, pp. 1786-1794.
Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.
Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.
Vanover et al., "Response-Rate Suppression in Operant Paradigm as Predictor of Soporific Potency in Rats and Identification of Three Novel Sedative-Hypnotic Neuroactive Steroids", The Journal of Pharmacology and Experimental Therapeutics, (1999), vol. 291, No. 3, pp. 1317-1323.
Vine et al., "2H-Labelled 3a-Hydroxy-5a-Pregnane-11, 20-Dione and 3a, 21-Dihydroxy-5a-Pregnane-11, 20-Dione 21-Acetate", Journal of Labelled Compounds and Radiopharmaceuticals, vol. IX, No. 4, 1982, pp. 597-604.
Weisberg et al., "Seizure disorders," Essentials of Clinical Neurology, Chapter 11, (1983), pp. 167-175.
Wirth, "Beyond the HPA axis; progesterone-derived neuroactive steroids in human stress and emotion," Frontiers in Endocrinology (2011) vol. 2, Article 19.
Wolkowitz, et al. "Of Sound Mind and Body; depression, disease, and accelerated aging", Dialogues in Clinical Neuroscience, vol. 13, No. 1, 2011, p. 25-39.
Yunes et al., "Postnatal administration of allopregnanolone modifies glutamate release but not BDNF content in striatum samples of rats prenatally exposed to ethanol", Biomed Research International, vol. 2015, 2015, pp. 1-6.
Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.
Zhu et al., "Evaluation and comparison of the pharmacokinetic and pharmacodynamic properties of allopregnanolone and pregnanolone at induction of anaesthesia in the male rat", British Journal of Anaesthesia (2001,) vol. 86, No. 3, pp. 403-412.
Zia et al., "Effect of Alkyl Chain and Degree of Substitution on the Complexation of Sulfoalkyl Ether b-Cyclodextrins with Steroids", Journal of Pharmaceutical Sciences (1996), vol. 86, No. 2, pp. 220-224.

Zia et al., "Effect of Cyclodextrin Charge on Complexation of Neutral and Charged Substrates: Comparison of (SBE) 7M-b-CD to HP-b-CD", Pharmaceutical Research (2001) vol. 18, No. 5, pp. 667-673.
"Allopregnanolone for the Treatment of Traumatic Brain Injury" ClinicalTrials.gov, Updated May 22, 2013, pp. 1-4.
"Sage Therapeutics Announces Brexalone Achieves Primary Endpoints in Both Phase 3 Clinical Trials in Postpartum Depression", Press Release, Nov. 9, 2017.
"Sage Therapeutics Welcome to R&D day 2016", Jan. 1, 2016, pp. 1-143.
"Sage Therapeutics Wins Big in Depression Trial", Press Release, 247Chrislange, Nov. 9, 2017.
Abend et al., "Treatment of refratory status epilepticus: Literature review and a proposed protocol", Pediatric Neurology, vol. 38, No. 6, 2008, pp. 377-390.
Akhondzadeh et al., "Induction of a novel form of hippocampal long-term depression by muscimol: involvement of GABAA but not glutamate receptors", British Journal of Pharmacology (1995) 115, 527-533.
Aladdin et al., "Refractory Status Epilepticus During Pregnancy Secondary to Cavernous Angiona", Epilepsia, vol. 49, No. 9, (2008), pp. 1627-1629.
Allen et al., "Menstrual phase, depressive symptoms, and allopregnanolone during short-term smoking cessation," Experimental and Clinical Psychopharmacology, (2013) 21(6):427-433.
Amin et al., "The interaction of neuroactive steroids and GABA in the development of neuropsychiatric disorders in women", Pharmacology, Biochemistry and Behavior 84 (2006) 635-643.
Anderson et al., "Oxidative/nitrosative stress and immuno-inflammatory pathways in depression: Treatment implications," Current Pharmaceutical Design, (2014) 20(25):4126-4161.
Anovadiya et al., "Epilepsy: Novel Therapeutic Targets", Journal of Pharmacology and Pharmacotherapeutics, 2012, pp. 112-117.
Backstrom et al. "Pathogensis in Menstrual cycle-linked CNS disorders", Ann. N.Y. Acad. Sci. 1007: 42-53 (2003).
Baker et al., "Efficacy of progesterone vaginal suppositories in Alleviation of Nervous Symptoms in Patients with Premenstrual Syndrome", Journal of Assisted Reproduction and Genetics, vol. 12, No. 3 1995, pp. 205-209.
Bali, et al. Multifunctional aspects of allopregnanolone in stress and related disorders, Progress in Neuro-Psychopharmacology & Biological Psychiatry 48 (2014) 64-78.
Bancaud et al., (From the Commission on Classification and Terminology of the International League Against Epilepsy) (Aug. 1981) "Proposal for Revised Clinical and Electroencephalographic Classification of Epileptic Seizures," Epilepsia, 22:489-501.
Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs," Bioorganic & Medicinal Chemistry Letters 20:6680-6684 (2010).
Beckley et al., "Progesterone receptor antagonist CDB-4124 increases depression-like behavior in mice without affecting locomotor ability," Psychoneuroendocrinology, (2011) 36:824-833.
Bernardi, et al., "Disadaptive disorders in women: allopregnanolone, a sensitive steroid", Gynecol Endocrinol 2004; 19:344-353.
Biagini et al., "Endogenous neurosteroids modulate epileptogenesis in a model of temporal lobe epilepsy", Experimental Neurology, (2006), vol. 201, pp. 519-524.
Bicikova et al., "Serum concentrations of some neuroactive steroids in women suffering from mixed anxiety-depressive disorder", Neurochemical Research, vol. 25, No. 12, 2000, pp. 1623-1627.
Birzniece et al., "Neuroactive steroid effects of cognitive functions with a focus on the serotonin and GABA systems" Brain Research Reviews 51 (2006) 212-239.
Bleck et al., "Refractory Status Epileptics", Current Opinion in Critical Care, (2005), vol. 11, pp. 117-120.
Bobb et al., "Allopregnanolone to treat refractory status epilepticus," presented at American Clinical Neurophysiology, Society (ACNS) Annual Meeting & Courses, The Westin Peachtree Plaza, Atlanta, Georgia, (Feb. 4-9, 2014) Abstract S26.

(56) References Cited

OTHER PUBLICATIONS

Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, pp. 3500-3511.

Botella et al., "Neuroactive Steroids. 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp. A-J.

Broomall et al., "Pediatric super-refractory status epilipticus treated with allopregnanolone," Ann. Neurol, (2014), 76:911-915.

Brown et al., "A randomized, double-blind, placebo-controlled trial of pregnenolone for bipolar depression," Neuropsychopharmacology, (2014) 39:2867-2873.

Brunn et al., "Combined treatment with diazepam and allopregnanolone reverses tetramethylenedisulfotetramine (TETS)-induced calcium dysregulation in cultured neurons and protects TETS-intoxicated mice against lethal seizures," Neuropharmacology, (2015), 95:332-342.

Burdock, "Encyclopedia of food additives and coloring," Taylor & Francis, 3 Volume Set, (1997), pp. 2410-2413.

Cao et al., "Tetramethylenedisulfotetramine alters Ca2+ dynamics in cultured hippocampal neurons: Mitigation by NMDA receptor blockade and GABAA receptor-positive modulation," Toxicological Sciences, (2012), 130(2):362-372.

Carta, et al. "GABAergic neuroactive steroids: a new frontier in bipolar disorders", Behavioral and Brain Functions 2012, 8:61.

Chen et al., "Ibogaine block of the NMDA receptor: In vitro and in vivo studies," Neuropharmacology, (1996) 35(4):423-431.

Chiasari et al., "The Influence of Neuroactive Steroid Lipophilicity on GABA Receptor Modulation: Evidence for a Low-Affinity Interaction", Journal of Neurophysiology (2009), vol. 102, pp. 1254-1264.

Claassen et al., "Treatment of Refractory Status Epilepticus with Pentobarbital, Propofol, or Midazolam: A Systematic Review", Epilepsia (2002), vol. 43, No. 2, pp. 146-153.

D'Aquila, et al. ."Dopamine is involved in the anti-depressant-like effect of allopregnanolone in the forced swimming test in female rats", Behavioural Pharmacology 2010, 21:21-28.

Database CAPLUS in STN, Acc. No. 1995:986323, Upasani et al., WO 9521617 A1 (Aug. 17, 1995) (abstract). [Upasani, Ravindra B. "Androstanes and pregnanes for allosteric modulation of GABA receptor, and preparation and therapeutic uses of compounds".].

Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].

De Crescenzo et al., "Selective serotonin reuptake inhibitors (SSRIs) for post-partum depression (PPD): A systematic review of randomized clinical trials", Journal of Affective Disorders, 152-154 (2014) 39-44.

Deligianndis et al., "Peripartum neuroactive steroid and y-aminobutyric acid profiles in women at-risk for postpartum depression," Psychoneuroendocrinology, Accepted Manuscript, (2016), 33p.

Deligiannidis, et al. "GABAergic neuroactive steroids and resting-state functional connectivity in postpartum depression; A preliminary study", Journal of Psychiatric Research 47 (2013) 816-828.

Delorenzo et al., "Epidemiology of Status Epilepticus" Journal of Clinical Neurophysiology (1995), vol. 12, No. 4, pp. 316-325.

Deutsch et al., "Evaluation of In Vivo Interactions in Mice Between Flurazepam and Two Neuroactive Steroids", Pharmacology Biochemistry & Behavior (1996), vol. 55, No. 3, pp. 323-326.

Dhir et al., "Role of neurosteroids in the anticonvulsant activity of midazolam," British Journal of Pharmacology, (2012), 165(8): 2684-2691.

Dhir et al., "Seizure protection by intrapulmonary delivery of midazolam in mice, " Neuropharmacology, (2013), 73:425-431.

Dhir et al., "Seizure protection by intrapulmonary delivery of propofol hemisuccinate," The Journal of Pharmacology and Experimental Therapeutics, (2011), 336(1):215-222.

Dorwald, "Side Reactions in Organic Synthesis", 2005, Wiley-VCH, Preface, p. IX.

Drugan et al. "Resilience in shock and swim stress models of depression", Frontiers in Behavorial Neuroscience, Feb. 2013, vol. 7, Article 14.

Dyck et al., "Effects of Deuterium Substitution on the Catabolism of beta-Phenylethylamine: An In Vivo Study". J. Neurochem., vol. 46(2), pp. 399-404 (1986).

Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.

Eser et al., "Neuroactive Steroids in Depression and Anxiety Disorders: Clinical Studies", Neuroendocrinology, (2006) 84: pp. 244-254.

Martini et al., "Nasal and pulmonary drug delivery systems", Exp. Opin. Ther. Patents, (2000), 10(3):315-323.

Marx et al., "Neuroactive steroids are altered in schizophrenia and bipolar disorder: relevance to pathophysiology and therapeutics", Neuropsychopharmacology (2006) 31, 1249-1263.

Matsumoto et al., "GAGAâ receptor neutrotransmission dysfunction in a mouse model of social isolation-induced stress: Possible insights into a non-serotonergic mechanism of action of SSRIs in mood and anxiety disorders", Stress, Mar. 2007; 10(1): 3-12.

Mayer et al., "Refractory Status Epilepticus Frequency, Risk Factors, and Impact on Outcome", Archives of Neurology (2002), vol. 59, pp. 205-210.

Meierkord et al., "EFNS Guideline on the Management of Status Epilepticus in Adults", European Journal of Neurology (2010), vol. 17, pp. 348-355.

Meltzer-Brody et al., "Phase 2 and 3 Studies Evaluating Brexanolone iv, a GABAA Receptor Positive Allosteric Modulator, in Postpartum Depression", Presented at the 56th Annual Meeting of the American College of Neuropsychopharmacology; Dec. 3, 2017, 14 pages.

Melville, "New drug shows rapid, robust effect in postpartum", Medscape, (2017), 2 pages.

Merzlikine et al., "Development of machine learning models of b-cyclodextrin and sulfobutylether-b-cyclodextrin complexation free energies", International Journal of Pharmaceutics (2011), vol. 418, pp. 207-216.

Miller, "Postpartum Depression", Clinician's Corner, vol. 287, No. 6, (2002), pp. 762-765.

Monagle et al., "A Phase 1c Trial Comparing the Efficacy and Safety of a New Aqueous Formulation of Alphaxalone with Propofol", Anesthesia & Analgesia (2015), vol. 121, No. 4, pp. 914-924.

Morgan, et al. "Neuroactive steroids after estrogen exposure in depressed postmenopausal women treated with sertraline and asymptomatic postmenopausal woman", Arch Womens Ment, Health (2010) 13:91-98.

Moses Kolko et al., "Antepartum and Postpartum Depression: Healthy Mom, Healthy Baby", Journal of the American Medical Women's Association, 2004; 59: pp. 181-191.

Munari et al., "The Use of Althesin in Drug-Resistant Status Epilepticus", Epilepsia (1979), vol. 20, pp. 475-484.

Murayama et al., "Effects of neurosteroid 3a-hydroxy-5a-pregnan-20-one on ethanol-mediated paired-pulse depression of population spikes in the CA1 region of rat hippocampal slices", Neuroscience Letters 394 (2006) 28-32.

Murray et al., "Maternal Postnatal Depression and the Development of Depression in Offspring Up to 16 Years of Age", Journal of the American Academy of Child & Adolescent Psychiatry, 2011; 50 (5), pp. 460-470.

Murray et al., "Prediction, detection, and treatment of post natal depression", Archives of Disease in Childhood, The Journal of the Royal College of Paediatrics and Child Health, 1997, 77: 97-101.

Másson et al., "Cyclodextrins and the liquid-liquid phase distribution of progesterone, estrone and prednicarbate", J Incl Phenom Macrocycl Chem (2007), vol. 57, pp. 481-487.

(56) References Cited

OTHER PUBLICATIONS

Naert, et al. "Neuroactive steroids modulate HPA axis actiity and cerebral brain-derived neurotrophic factor (BDNF) protein levels in adult male rats", Psychoneuroendocrinology (2007) 32, 1062-1078.
Nanjwade et al., Pulmonary Drug Delivery: Novel Pharmaceutical Technologies Breathe New Life into the Lungs, PDA JPharm Sci and Tech, (2015), 65: 513-534.
Nappi et al., "Serum Allopregnanolone in women with postpartum blues", Obstetrics & Gynecology, vol. 97, No. 1, 2001: 77-80.
Nin et al. "Neurosteroids reduce social insolation-induced behavioral deficits; a proposed link with neurosteroid-mediated upregulation of BDNF expression", Frontiers in Endocrinology (2011) vol. 2, Article 73.
Nin et al., "The effect of intra-nucleus accumbens administration of allopregnanolone on 6 and y2 GABAA receptor subunit mRNA expression in the hippocampus and on depressive-like and grooming behaviors in rats," Pharmacology, Biochemistry and Behavior, (2012), 103:359-366.
Northdurfter et al., "Recent Developments in Potential Anxiolytic Agents Targeting GABAA/BzR Complex or the Translocator Protein (18kDa) (TSPO)", Current Topics in Medicinal Chemistry, 2012, 12; 360-370.
Notification of Transmittal of the International Search Report and the Written Opinion of the International Searching authority, or the Declaration, International Application No. PCT/US13/45933, Dec. 3, 2013, 5 Pages.
Novy et al., "Refractory Status Epilepticus: A Prospective Observational Study", Epilepsia (2010), vol. 51, No. 2, pp. 251-256.
Oka et al., "A reliable method for intratracheal instillation of materials to the entire lung in rats," J Toxicol Pathol, (2006), 19:107-109.
Osborne et al., "Replication of epigenetic postpartum depression biomarkers and variation with hormone levels," Neuropsychopharmacology, Accepted Manuscript (2015), pp. 1-32.
Park et al., "Multiple effects of allopregnanolone on GABAergic responses in single hippocampal CA3 pyramidal neurons", European Journal of Pharmacology (2011), vol. 652, pp. 46-54.
Pearlstein, et al. "Premenstrual dysphoric disorder: burden of illness and treatment update", J Psychiatry Neurosci 2008:33(4):291-301.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Pieribone et al., "Clinical Evaluation of Ganaxolone in Pediatric and Adolescent Patients with Refractory Epilepsy", Epilepsia (2007), vol. 48, No. 10, pp. 1870-1874.
Pinna, et al., "Up-Regulation of Neutrosteriod Biosynthesis as a Pharmacological Strategy to improve behavioural Deficits in a Putative mouse model of Post-traumatic stress disorder", Journal of Neuroendocrinology 24 (2011), p. 102-116.
Pires et al., "Intranasal Drug Delivery: How, Why and What for?" Journal of Pharm, Pharmaceut Sci, (2009), 12(3):288-311.
Poromaa et al., "GABA receptor, progresteron and premenstrual dysphoric disorder", Arch Womens Ment Health (2003) 6:23-41.
Pubchem, CID 92786.
Puia, et al. "Novel modulatory effects of neurosteriods and benzodiazepines on excitatory and inhibitory neurons excitability: a multi-electrode array recording study", Frontiers in Neutral Circuits, (2012) vol. 6, Article 94.
Ramsay, "Treatment of status epilepticus", Epilepsia, 2013, 34 Suppl.:S71-S81.
Rasheed et al., "Cyclodextrins as Drug Carrier Molecule: A Review", Scientia Pharmaceutica, Review, (2008), pp. 567-598.
Rasmusson, et al. "Decreased Cerebrospinal Fluid Allopregnanolone levels in women with posttraumatic stress disorder", Biol. Psychiatry 2006;60:704-713.
Reddy "Role of anticonvulsant and antiepileptogenic neurosteroids in the pathophysiology and treatment of epilepsy," Frontiers in Endocrinology, 2:38, (2011).
Reddy "The clinical potentials of endogenous neurosteroids" Drugs of Today 2002, 38 (7): 465-485.
Reddy et al., "Neurosteroids—Endogenous Regulators of Seizure Susceptibility and Role in Treatment of Epilepsy", Jasper's Basic Mechanisms of the Epilepsies Fourth Edition (2012), pp. 1-23.
Reddy, "Neurosteroids: Endogenous role in the human brain and therapeutic potentials", Progress in Brain Research, (2010) vol. 186, pp. 113-137.
Reddy, "Pharmacology of Endogenous Neuroactive Steroids", Critical Reviews in Neurobiology, 15 (3&4) 197-234 (2003).
Reddy, "SGE-102: a novel therapy for refractory status epilepticus", Epilepsia, Abstract 34 Suppl 6: 81-82.
Rogawski et al., "Neuroactive Steroids for the Treatment of Status Epilepticus", Epilepsia (2013), vol. 54, No. 6, pp. 93-98.
Romeo, et al. "Effect of antidepressant treatment on neuroactive steroids in major deprssion" Am. J. Psychiatry 1998; 155:910-913.
International Search Report and Written Opinion for corresponding International Application No. PCT/US2013/22772 dated Mar. 27, 2013.
International Search Report and Written Opinion for corresponding International Application No. PCT/US2013/56062 dated Jan. 29, 2014.
International Search Report and Written Opinion for corresponding International Application No. PCT/US2015/48937 dated Feb. 5, 2016.
International Search Report and Written Opinion for Corresponding International Application No. PCT/US2016/018748 dated Aug. 29, 2016.
International Search Report and Written Opinion for corresponding International Application No. PCT/US2016/026705 dated Aug. 19, 2016.
International Search Report and Written Opinion for corresponding International Application No. PCT/US2016/038195 dated Oct. 20, 2016.
International Search Report and Written Opinion for corresponding International Application No. PCT/US2017/021325 dated May 22, 2017.
International Search Report and Written Opinion for corresponding International Application No. PCT/US2018/050444 dated Dec. 3, 2018.
International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 4, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, mailed Jan. 22, 2015.
International Search Report for International Application No. PCT/US2012/060136 dated Mar. 27, 2013.
Irwin et al., "Allopregnanolone preclinical acute pharmacokinetic and pharmacodynamic studies to predict tolerability and efficacy for alzheimer's disease", Plos One, vol. 10, No. 6, 2015, pp. 1-31.
Jain et al., "Hygroscopicity, phase solubility and dissolution of various substituted sulfobutylether b-cyclodextrins (SBE) and danazol-SBE inclusion complexes", International Journal of Pharmaceutics (2001), vol. 212, pp. 177-186.

(56) References Cited

OTHER PUBLICATIONS

Jin et al., "A sensitive and selective LC-differential mobility-mass spectrometric analysis of allopregnanolone and pregnanolone in human plasma", Analytical and Bioanalytical Chemistry, vol. 405, No. 29, 2013, pp. 1-23.
Johnson et al., "Deuterium Labelled Steroid Hormones: Syntheses and Applications in Quantitation and Endocrinology", Journal of Steroid Biochemistry, vol. 14, 1981, pp. 793-800.
Jones, "Post-partum depression—a glimpse of light in the darkness?", Published online Jun. 12, 2017, 2 pages.
Kaminski et al., "Allopregnanolone analogs that positively modulate GABAA receptors protect against partial seizures induced by 6-Hz electrical stimulation in mice," Epilepsia, (2004), 45(7):864-867.
Kanes et al., "Brexanolone (SAGE-547 injection) in post partum depression: a randomised controlled trial", The Lancet, 2017; vol. 390, Issue 10093, pp. 480-489.
Kanes et al., "Open-label, proof-of-concept study of brexanolone in the treatment of severe postpartum depression", Hum Psychopharmacol Clin Exp. (2017).
Kanto, "Midazolam: The first water-soluble benzodiazepine pharmacology, pharmacokinetics and efficacy in insomnia and anesthesia", Pharmacotherapy, (1985), 5(3): 138-155.
Kask et al., "Allopregnanolone has no effect on startle response and prepulse inhibition of startle response in patients with premenstrual dysphoric disorder or healthy controls", Pharmacology, Biochemistry and Behavior (2009), vol. 92, pp. 608-613.
Kask et al., "Allopregnanolone impairs episodic memory in healthy women", Psycophamacology (2008), vol. 199, pp. 161-168.
Kaura et al., "The Progesterone metabolite allopregnanolone potentiates GABAA rceptor-mediated inhibition of 5-HT neuronal activity", European Neuropsychopharmacology, (2007), 17, pp. 108-115.
Khanna et al., "Nanotoxicity: An interplay of oxidative stress, inflammation and cell death," nanomaterials, (2015), 5:1163-1180.
Khisti et al., "Serotonergic agents modulate anti-depressant-like effect of the neurosteroid 3a-hydroxy-5a-pregnan-20-one in mice" Brain Research 865 (2000) 291-300.
Kim et al., "Modulation of presynaptic GABAA receptors by endogenous neurosteroids", British Journal of Pharmacology (2011), vol. 164, pp. 1698-1710.
Kimmel et al., "Oxytocin receptor DNA methylation inpostpartum depression," Psychoneuroendocrinology, (2016), 69:150-160.
Klatzkin et al. "Associations of histories of depression and PMDD diagnosis with allopregnanolone concentrations following the oral administration of micronized progesterone", Psychoneuroendocrinology (2006) 31, 1208-1219.
Klatzkin et al., "Histories of depression, allopregnanolone responses to stress, and premenstrual symptoms in women:", Biological Psychology 71 (2006) 2-11.
Kokate et al., "Anticonvulsant Activity of Neurosteroids: Correlation with g-Aminobutyric Acid-Evoked Chloride Current Potentiation", The Journal of Pharmacology and Experimental Therapeutics (1994), vol. 270, No. 3, pp. 1223-1229.
Kokate et al., "Convulsant actions of the neurosteroid pregnenolone sulfate in mice", Brain Research (1999), vol. 831, pp. 119-124.
Kokate et al., "Neuroactive Steroids Protect Against Pilocarpine- and Kainic Acid-induced Limbic Seizures and Status Epilepticus in Mice", Neuropharmacology (1996) vol. 35, No. 8, pp. 1049-1056.
Kramer, "Early Ketamine to Treat Refractory Status Epilepticus" Neurocrit. Care (2012), vol. 16, pp. 299-305.
Kushner et al., "Pharmacological uses and perspectives of heavy water and deuterated compounds". Candian Journal Physiology and Pharmacology, vol. 77, pp. 79-88 (1999).
Lahiani-Skiba et al., "Solubility and Dissolution Rate of Progesterone-Cyclodextrin-Polymer Systems", Drug Development and Industrial Pharmacy (2006), vol. 32, pp. 1043-1058.
Larsen et al., "Phase Solubility and Structure of the Inclusion Complexes of Prednisolone and 6a-Methyl Prednisolone with Various Cyclodextrins", Journal of Pharmaceutical Sciences (2005), vol. 94, No. 3, pp. 507-515.
Leroy et al., "Pharmacological plasticity of GABAA receptors at dentate gyrus synapses in a rat model of temporal lobe epilepsy", J. Physol. (2004), vol. 557, No. 2, pp. 473-487.
Li et al., "Nanoparticle-induced pulmonary toxicity," Experimental Biology and Medicine, (2010), 235:1025-1033.
Lonsdale et al., "The Anticonvulsant effects of allopregnanolone against amygdala-kindled seizures in female rats", Neuroscience Letters (2007), vol. 411, pp. 147-151.
Lossin et al., "Allopregnanolone treatment in a rat pediatric status epilepticus model: Comparison with diazepam", American Epilepsy Society (2012), (Abst. 3.220).
MacKenzie et al., "Neurosteriods and GABAergic signaling in health and disease", BioMol Concepts 2013; 4(1): 29-42.
Madl et al., "Nanoparticles, lung injury, and the role of oxidant stress," Annu Rev Physiol., (2014), 76:447-465.
Maguire et al., "GABAAR plasticity during pregnancy relevance to postpartum Depression," Neuron, (2008), 59:207-213.
Bäckström, T., et al, "Isoallopregnanolone; an antagonist to the anaesthetic effect of allopregnanolone in male rats", European Journal of Pharmacology, 2015, vol. 512, No. 1, p. 15-21.
Bengtsson SK, et al., "Isoallopregnanolone antagonize allopregnanolone-induced effects on saccadic eye velocity and self-reported sedation in humans.", Psychoneuroendocrinology, 2015, vol. 52, pp. 22-31.
Meltzer-Brody S, et al., "Brexanolone injection in post-partum depression: two multicentre, double-blind, randomised, placebo-controlled, phase 3 trials.", Lancet, Sep. 22, 2018, 392, pp. 1058-1070.
Meltzer-Brody et al., "Phase 2 and 3 Sudies Evaluating Brexanolone iv, a GABAA Receptor Positive Allosteric Modulator, in Postpartum Depression", Presented at the 56th Annual Meeting of the American College of Neuropsychopharmacology; Dec. 3-7, 2017; 14 pages.
Parizek et al., "Steroid hormones in the development of postpartum depression", Physiological Research, 2014, vol. 63, No. Suppl. 2, pp. S277-S282.
Pearlstein et al. "Premenstrual dysphoric disorder: burden of illness and treatment update", J Psychiatry Neurosci 2008:33(4): pp. 291-301.
Rapkin et al., "Progesterone metabolite allopregnanolone in women with premenstrual syndrome", Obstet. Gynecol 1997; 90-709-714.
Reddy (Sep. 2013) "SGE-102: a novel therapy for refractory status epilepticus," Epilepsia, Abstratc, 54 Suppl 6:81-83, 2 pages [retrieved on Sep. 7, 2015 at http://www.ncbi.nlm.nih.gov/pubmed/24001082].
Sage Therapeutics: "Sage Therapeutics Announces Brexalone Achieves Primary Endpoints in Both Phase 3 Clinical Trials in Postpartum Depression", Press Release, Nov. 9, 2017.
Sage therapeutics: "A study to Evaluate SAGE-547 in Participants With Severe Postpartum Depression", ClinicalTrials.gov [online], NCT02614547, history of changes Jan. 2016, <URL: https://clinicaltrials.gov/ct2/history/NCT02614547>, [retrieved online Nov. 26, 2021].
Wang, M.D, et al., "The inhibitory effects of allopregnanolone and pregnanolone on the population spike, evoked in the rat hippocampal CA1 stratum pyramidale in vitro, can be blocked selectively by epiallopregnanolone", Acta Physiol Scand 2000; 169(4), pp. 333-341.
Ahokas et al. "Estrogen deficiency in severe postpartum depression: successful treatment with sublingual physiologic 17beta-estradiol: a preliminary study", Journal Clinical Psychiatry 2001; 62:332-336.
Gregoire et al. "Transdermal oestrogen for treatment of severe postnatal depression" LANCET, Jun. 4, 1996 (Apr. 6, 1996).
Shirayama et al. "Infusions of allopregnanolone into the hippocampus and amygdala, but not into the nucleus accumbent and medial prefrontal cortex, produce antidepressant effects on the learned helplessness rats" Hippocampus, vol. 21, issue 10, Oct. 2011, pp. 1105-1113.

* cited by examiner

| Screening Period | Active Treatment Period in PPIU | | | | Follow-up Period | |
|---|---|---|---|---|---|---|
| Days -3 to -1 | Day 1 | Day 2 | Day 3 | Day 4 | Day 11±1 | Day 34±1 |
| | 12 hr Dose Titration (% of full dose): 25 → 50 → 75 | 36-hour Maintenance Infusion (full dose infusion) | 12 hr Taper (% of full dose): 75 → 50 → 25 | Post infusion | AEs | SAEs |

FIG. 4

NEUROACTIVE STEROIDS, COMPOSITIONS, AND USES THEREOF

CLAIMS OF PRIORITY

This application is a continuation of U.S. Ser. No. 15/509,656 filed Mar. 8, 2017, which is a national stage application under 35 U.S.C. § 371 of International Application No. PCT/US2015/048937 filed Sep. 8, 2015, which claims priority to U.S. Ser. No. 62/047,599, filed Sep. 8, 2014; U.S. Ser. No. 62/170,596, filed Jun. 3, 2015; and U.S. Ser. No. 62/213,015, filed Sep. 1, 2015, the entire contents of which are incorporated herein by reference.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization, e.g., a change of potential from −70 mV to −50 mV. This effect is mediated by postsynaptic nicotinic receptors which are stimulated by acetylcholine to increase membrane permeability to Nations. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D, et al., *Science* 232:1004-1007 (1986): Harrison, N. L, et al., *J Pharmacol. Exp. Ther.* 241:346-353 (1987)).

The ovarian hormone progesterone and its metabolites have been demonstrated to have profound effects on brain excitability (Backstrom, T, et al., *Acta Obstet. Gynecol. Scand.* Suppl. 130:19-24 (1985); Pfaff, D. W and McEwen, B. S., *Science* 219:808-814 (1983); Gyermek et al., *J Med Chem.* 11: 117 (1968): Lambert, J, et al., *Trends Pharmacol. Sci.* 8:224-227 (1987)). The levels of progesterone and its metabolites vary with the phases of the menstrual cycle. It has been well documented that the levels of progesterone and its metabolites decrease prior to the onset of menses. The monthly recurrence of certain physical symptoms prior to the onset of menses has also been well documented. These symptoms, which have become associated with premenstrual syndrome (PMS), include stress, anxiety, and migraine headaches (Dalton, K., *Premenstrual Syndrome and Progesterone Therapy*, 2nd edition, Chicago Yearbook, Chicago (1984)). Subjects with PMS have a monthly recurrence of symptoms that are present in premenses and absent in postmenses.

A syndrome also related to low progesterone levels is postnatal depression (PND) or postpartum depression (PPD). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants, and women experiencing PND show an increased incidence of PMS (Dalton, K., *Premenstrual Syndrome and Progesterone Therapy*, 2nd edition, Chicago Yearbook, Chicago (1984)).

Additionally, several lines of evidence suggest that cerebellar dysfunction through the cerebello-thalamocortical pathway play a key role in essential tremor (ET) (McAuley 2000; Pinto 2003: Elble 2009; Schnitzler 2009; Deuschl 2009). Thalamotomy and deep brain stimulation of the ventral intermediate nucleus and of the subthalamic nucleus improve ET (Rajput 2014: Deuschl 2011: Zappia 2013). Microscopic cerebellar pathology has been identified, including gliosis, Purkinje cell loss, and increased torpedoes (swellings) in the Purkinje cell axons (Louis 2007, 2009; Axelrad 2008: Shill 2008). Activation studies with positron emission tomography (PET) indicate abnormally increased regional cerebral blood flow in the cerebellum both at rest and when tremor is provoked by unilateral arm extension (Boechker 1994, Wills 1996). Post-mortem analysis revealed a 35% reduction of $GABA_A$ receptors and a 22-31% reduction of $GABA_B$ receptors in the dentate nucleus of cerebella from ET patients (Paris-Robidas 2012).

There is increasing evidence to support the role of neuroactive steroids in affective dysregulation. Evidence supports the use of neuroactive steroids, e.g., progesterone and its metabolites; allopregnanolone, alphadalone, ganoxalone, alphaxolone, in the treatment and prevention of tremor (e.g., essential tremor), depression (e.g., postpartum depression), and anxiety disorder.

SUMMARY OF THE INVENTION

The disclosure features, inter alia, a method, the method comprising administering a neuroactive steroid, e.g., pregnanolone, allopregnanolone, alphadalone, ganaxolone, or alphaxolone to a subject, for example to treat a CNS-related disorder such as tremor, depression, anxiety disorder. In some embodiments, the neuroactive steroid is formulated for parenteral delivery (e.g., intravenous delivery (IV)). The disclosure features methods of treating a subject having a CNS disorder, e.g., tremor, e.g., essential tremor: depression, e.g., postpartum depression; and anxiety disorder, the methods comprising administering to the subject a composition described herein, e.g., a neuroactive steroid, e.g., pregnanolone, allopregnanolone, alphadalone, ganaxolone, or alphaxolone, and optionally a cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®. The disclosure also features, inter alia, compositions comprising a neuroactive steroid, e.g., pregnanolone, allopregnanolone, alphadalone, ganaxolone, or alphaxolone; and optionally a cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®.

In an aspect, the disclosure features a method of treating a human subject suffering from a movement disorder as described herein (e.g., tremor), the method comprising administering a therapeutically effective amount of a neuroactive steroid. In an aspect, the disclosure features a method of treating a human subject suffering from tremor, the method comprising administering a therapeutically effective amount of a neuroactive steroid. In some embodiments, the method does not result in sedation. In some embodiments, the method results in sedation. In some embodiments, the method provides therapeutic effect in the absence of sedative effect.

In some embodiments, the neuroactive steroid is pregnanolone, allopregnanolone, alphadalone, ganaxolone, or alphaxolone. In some embodiments, the neuroactive steroid is pregnanolone, allopregnanolone, alphadalone, ganaxolone, or alphaxolone. In some embodiments, the neuroactive steroid is allopregnanolone. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 and 8,759,330.

In some embodiments, the methods described herein can be used to treat tremor, for example cerebellar tremor or intention tremor, dystonic tremor, essential tremor, orthostatic tremor, parkinsonian tremor, physiological tremor, psychogenic tremor, or rubral tremor. In some embodiments, the tremor is essential tremor.

In some embodiments, the administering is performed parenterally. In some embodiments, the administering is performed intravenously. In some embodiments, the administering is an intravenous bolus infusion. In some embodiments, the administering is an intravenous continuous infusion. In some embodiments, the administered is performed orally.

In some embodiments, the administering comprises administering one or more cycles of treatment, wherein a cycle of treatment comprises; administering a first dose of the neuroactive steroid, administering a second dose of the neuroactive steroid, and administering a third dose of the neuroactive steroid, said neuroactive steroid doses being sufficient to treat said subject.

In some embodiments, the administering (or course of administration) comprises administering more than one cycle of treatment (e.g., two cycles of treatment, three cycles of treatment). In some embodiments, a rest period follows (e.g., immediately follows, is less than 60, 30, 20, 10, 5, 2, or 1 minute after) the first cycle of treatment. In some embodiments, a rest period precedes the second cycle of treatment. In some embodiments, a rest period follows the first cycle of treatment and precedes the second cycle of treatment. In some embodiments, the rest period is 6 to 8 days (e.g., 7 days) in duration.

In some embodiments, a cycle of treatment comprises a first (titration) dose, a second (maintenance) dose, and a third (taper) dose.

In some embodiments, the first (titration) dose comprises administering a plurality of step doses (e.g., a first, second, and third step dose), wherein each subsequent step dose delivers a larger amount of neuroactive steroid/unit time than the step dose that precedes it. In some embodiments, the amount of neuroactive steroid delivered/unit time varies during the first (titration) dose. In some embodiments, the first step dose delivers a smaller amount of neuroactive steroid/unit time than the second step dose. In some embodiments, the second step dose begins no longer than 90, 60, 30, 10, or 5 minutes after the beginning or end of the administration of the first step dose. In some embodiments, the second step dose begins 0 to 90, 0 to 60, 0 to 30, 0 to 10, or 0 to 5 minutes after the beginning or end of the administration of the first step dose. In some embodiments, the second step dose begins no more than 60, 30, 20, 10, 5, 4, 3, 2, 1 minute(s) after the end of administration of the first step dose. In some embodiments, the second step dose begins at the end of administration of the first step dose. In some embodiments, the first step dose and the initiation of the second step dose are performed with the same delivery device, e.g., with the same cannula or reservoir.

In some embodiments, the first (titration) dose comprises administering a plurality of step doses (e.g., a first, second, and third step dose). For example, a first (titration) dose can be administered to a subject by increasing the amount of neuroactive steroid (e.g., alloprgenanolone) administered to the subject over a period of time. In an embodiment, the period of time can be from about 15 minutes to about 6 hours (e.g., from about 60 minutes to about 4 hours). In an embodiment the period is a time sufficient for the subject to adjust to the effect of the neuroactive steroid. In an embodiment, the first (titration) dose is from about 20 to 100 μg/kg/hr, e.g., from about 20 to about 40 μg/kg/hr, from about 45 to about 65 μg/kg/hr, from about 80 to about 100 μg/kg/hr.

In some embodiments, the first (titration) dose comprises administering a plurality of step doses (e.g., a first, second, and third step dose). In some embodiments, the first step dose is 20 to 40 μg/kg/hr (e.g., about 30 μg/kg/hr, 29 μg/kg/hr). In some embodiments, the second step dose is 45 to 65 μg/kg/hr (e.g., about 60 μg/kg/hr, 58 μg/kg/hr). In some embodiments, the third step dose is 80 to 100 μg/kg/hr (e.g., about 90 μg/kg/hr. 86 μg/kg/hr). In some embodiments, each of the first, second, and third step doses are 2 to 6 hours (e.g., 4 hours) in duration. In some embodiments, each of the first, second, and third step doses are 1, 2, 3, 4, 5, or 6 hours in duration. In some embodiments, each of the first, second, and third step doses are administered for equal periods of duration.

In an embodiment, the first (titration) dose is followed by a second (maintenance) dose. In an embodiment, the second (maintenance) dose is administered within 2 hours after the first (titration) dose, e.g., within 1 hour, 30 minutes, 15 minutes, or less. In an embodiment, the second (maintenance) dose is from about 70 to 175 μg/kg/hr, e.g., from about 90 to about 150 μg/kg/hr. In some embodiments, the second (maintenance) dose comprises administering a single (constant) dose of neuroactive steroid/unit time.

In some embodiments, the third (taper) dose comprises administering a plurality of step doses (e.g., a first, second, and third step dose), wherein each subsequent step dose delivers a smaller amount of neuroactive steroid/unit time than the step dose that precedes it. In some embodiments, the amount of neuroactive steroid delivered/unit time varies during the first step dose. In some embodiments, the first step dose delivers a larger amount of neuroactive steroid/unit time than the second step dose.

In some embodiments, the third (taper) dose comprises administering a plurality of step doses (e.g., a first, second, and third step dose). In some embodiments, the second step dose begins no longer than 90, 60, 30, 10, or 5 minutes after the beginning or end of the administration of the first step dose. In some embodiments, the second step dose begins 0 to 90, 0 to 60, 0 to 30, 0 to 10, or 0 to 5 minutes after the beginning or end of the administration of the first step dose. In some embodiments, the second step dose begins no more than 60, 30, 20, 10, 5, 4, 3, 2, 1 minute(s) after the end of administration of the first step dose. In some embodiments, the second step dose begins at the end of administration of the first step dose. In some embodiments, the first step dose and the initiation of the second step dose are performed with the same delivery device, e.g., with the same cannula or reservoir.

In some embodiments, the third (taper) dose comprises administering a plurality of step doses (e.g., a first, second, and third step dose). For example, a third (taper) dose can be administered to a subject by decreasing the amount of neuroactive steroid (e.g., alloprgenanolone) administered to the subject over a period of time. In an embodiment, the period of time can be from about 15 minutes to about 6 hours (e.g., from about 60 minutes to about 4 hours). In an embodiment, the third (taper) dose is from about 20 to 100 μg/kg/hr, e.g., from about 20 to about 40 μg/kg/hr, from about 45 to about 65 μg/kg/hr, from about 80 to about 100 μg/kg/hr.

In some embodiments, the third (taper) dose comprises administering a plurality of step doses (e.g., a first, second, and third step dose). In some embodiments, the first step dose is 80 to 100 μg/kg/hr (e.g., about 90 μg/kg/hr, 86 μg/kg/hr). In some embodiments, the second step dose is 45 to 65 μg/kg/hr (e.g., about 60 μg/kg/hr, 58 μg/kg/hr). In some embodiments, the third step dose is 20 to 40 μg/kg/hr (e.g., about 30 μg/kg/hr, 29 μg/kg/hr). In some embodiments, each of the first, second, and third step doses are 2 to 6 hours (e.g., 4 hours) in duration. In some embodiments, each of the first, second, and third step doses are 1, 2, 3, 4, 5, or 6 hours in duration. In some embodiments, each of the first, second, and third step doses are administered for equal periods of duration.

In some embodiments, a cycle of treatment comprises a first (titration) dose and a second (maintenance) dose.

In some embodiments, the first (titration) dose comprises administering a plurality of step doses (e.g., a first, second, and third step dose), wherein each subsequent step dose delivers a larger amount of neuroactive steroid/unit time than the step dose that precedes it. In some embodiments, the amount of neuroactive steroid delivered/unit time varies during the first (titration) dose. In some embodiments, the first step dose delivers a smaller amount of neuroactive steroid/unit time than the second step dose. In some embodiments, the second step dose begins no longer than 90, 60, 30, 10, or 5 minutes after the beginning or end of the administration of the first step dose. In some embodiments, the second step dose begins 0 to 90, 0 to 60, 0 to 30, 0 to 10, or 0 to 5 minutes after the beginning or end of the administration of the first step dose. In some embodiments, the second step dose begins no more than 60, 30, 20, 10, 5, 4, 3, 2, 1 minute(s) after the end of administration of the first step dose. In some embodiments, the second step dose begins at the end of administration of the first step dose. In some embodiments, the first step dose and the initiation of the second step dose are performed with the same delivery device, e.g., with the same cannula or reservoir.

In some embodiments, the first (titration) dose comprises administering a plurality of step doses (e.g., a first, second, and third step dose). For example, a first (titration) dose can be administered to a subject by increasing the amount of neuroactive steroid (e.g., alloprgenanolone) administered to the subject over a period of time. In an embodiment, the period of time can be from about 15 minutes to about 6 hours (e.g., from about 60 minutes to about 4 hours). In an embodiment the period is a time sufficient for the subject to adjust to the effect of the neuroactive steroid. In an embodiment, the first (titration) dose is from about 20 to 100 μg/kg/hr, e.g., from about 20 to about 40 μg/kg/hr, from about 45 to about 65 μg/kg/hr, from about 80 to about 100 μg/kg/hr.

In some embodiments, the first (titration) dose comprises administering a plurality of step doses (e.g., a first, second, and third step dose). In some embodiments, the first step dose is 20 to 40 μg/kg/hr (e.g., about 30 μg/kg/hr, 29 μg/kg/hr). In some embodiments, the second step dose is 45 to 65 μg/kg/hr (e.g., about 60 μg/kg/hr, 58 μg/kg/hr). In some embodiments, the third step dose is 80 to 100 μg/kg/hr (e.g., about 90 μg/kg/hr, 86 μg/kg/hr). In some embodiments, each of the first, second, and third step doses are 2 to 6 hours (e.g., 4 hours) in duration. In some embodiments, each of the first, second, and third step doses are 1, 2, 3, 4, 5, or 6 hours in duration. In some embodiments, each of the first, second, and third step doses are administered for equal periods of duration.

In an embodiment, the first (titration) dose is followed by a second (maintenance) dose. In an embodiment, the second (maintenance) dose is administered within 2 hours after the first (titration) dose, e.g., within 1 hour, 30 minutes, 15 minutes, or less. In an embodiment, the second (maintenance) dose is from about 70 to 175 μg/kg/hr, e.g., from about 90 to about 150 μg/kg/hr. In some embodiments, the second (maintenance) dose comprises administering a single (constant) dose of neuroactive steroid/unit time.

In some embodiments, the cycle of treatment does not include a third (taper) dose.

In some embodiments, a cycle of treatment comprises a maintenance dose and a taper dose (e.g., a maintenance dose administered before a taper dose).

In an embodiment, the maintenance dose is from about 70 to 175 μg/kg/hr, e.g., from about 90 to about 150 μg/kg/hr. In some embodiments, the maintenance dose comprises administering a single (constant) dose of neuroactive steroid/unit time.

In some embodiments, the third (taper) dose comprises administering a plurality of step doses (e.g., a first, second, and third step dose), wherein each subsequent step dose delivers a smaller amount of neuroactive steroid/unit time than the step dose that precedes it. In some embodiments, the amount of neuroactive steroid delivered/unit time varies during the first step dose. In some embodiments, the first step dose delivers a larger amount of neuroactive steroid/unit time than the second step dose.

In some embodiments, the third (taper) dose comprises administering a plurality of step doses (e.g., a first, second, and third step dose). In some embodiments, the second step dose begins no longer than 90, 60, 30, 10, or 5 minutes after the beginning or end of the administration of the first step dose. In some embodiments, the second step dose begins 0 to 90, 0 to 60, 0 to 30, 0 to 10, or 0 to 5 minutes after the beginning or end of the administration of the first step dose. In some embodiments, the second step dose begins no more than 60, 30, 20, 10, 5, 4, 3, 2, 1 minute(s) after the end of administration of the first step dose. In some embodiments, the second step dose begins at the end of administration of the first step dose. In some embodiments, the first step dose and the initiation of the second step dose are performed with the same delivery device, e.g., with the same cannula or reservoir.

In some embodiments, the third (taper) dose comprises administering a plurality of step doses (e.g., a first, second, and third step dose). For example, a third (taper) dose can be administered to a subject by decreasing the amount of neuroactive steroid (e.g., alloprgenanolone) administered to the subject over a period of time. In an embodiment, the period of time can be from about 15 minutes to about 6 hours (e.g., from about 60 minutes to about 4 hours). In an embodiment, the third (taper) dose is from about 20 to 100 µg/kg/hr, e.g., from about 20 to about 40 µg/kg/hr, from about 45 to about 65 µg/kg/hr, from about 80 to about 100 µg/kg/hr.

In some embodiments, the third (taper) dose comprises administering a plurality of step doses (e.g., a first, second, and third step dose). In some embodiments, the first step dose is 80 to 100 µg/kg/hr (e.g., about 90 µg/kg/hr, 86 µg/kg/hr). In some embodiments, the second step dose is 45 to 65 µg/kg/hr (e.g., about 60 µg/kg/hr, 58 µg/kg/hr). In some embodiments, the third step dose is 20 to 40 µg/kg/hr (e.g., about 30 µg/kg/hr, 29 µg/kg/hr). In some embodiments, each of the first, second, and third step doses are 2 to 6 hours (e.g., 4 hours) in duration. In some embodiments, each of the first, second, and third step doses are 1, 2, 3, 4, 5, or 6 hours in duration. In some embodiments, each of the first, second, and third step doses are administered for equal periods of duration.

In some embodiments, a cycle of treatment comprises a maintenance dose (e.g., a single infusion). In an embodiment, the second (maintenance) dose is from about 70 to 175 µg/kg/hr, e.g., from about 90 to about 150 µg/kg/hr. In some embodiments, the second (maintenance) dose comprises administering a single (constant) dose of neuroactive steroid/unit time.

In some embodiments, the amount of neuroactive steroid delivered/unit time in the second (maintenance) dose, e.g., as measured in µg/kg/hour, is 1 to 2 times higher than that of the first (titration) dose. In some embodiments, the amount of neuroactive steroid delivered/unit time in the third (taper) dose, e.g., as measured in µg/kg/hour, is 2 to 4 times higher than that of the first (titration) dose.

In some embodiments, said first (titration) dose results in a plasma concentration of 10 to 100 nM, 25 to 75 nM, 40 to 60, or 50 nM. In some embodiments, said second (maintenance) dose results in a plasma concentration of 20 to 200 nM, 50 to 150 nM, 80 to 120, or 100 nM. In some embodiments, said third (taper) dose results in a plasma concentration of 30 to 300 nM, 100 to 200 nM, 120 to 180, or 150 nM. In some embodiments, said first (titration) dose results in a plasma concentration of 50+/−10 nM, 50+/−5 nM, 50+/−2 nM, or 50 nM. In some embodiments, said second (maintenance) dose results in a plasma concentration of 100+/−20 nM. 100+/−10 nM. 100+/−5 nM, or 100 nM. In some embodiments. said third (taper) dose results in a plasma concentration of 150+/−30 nM, 150+/−20 nM, 150+/−10 nM, or 150 nM.

In some embodiments, said first (titration) dose is administered over a period of time that is not longer than 6, 5, 4, or 3 hours. In some embodiments, said first (titration) dose is administered over a period of time that is at least 2, 3, or 4 hours in duration. In some embodiments, the administration of the second (maintenance) dose occurs immediately after administration of the first (titration) dose. In some embodiments, the administration of the third (taper) dose occurs immediately after administration of the second (maintenance) dose.

In some embodiments, the duration of administration is at least 12, 24, 48, 72, 96 hours in duration. In some embodiments, the duration of administration is about 40, 50, 60, or 70 hours.

In some embodiments, the administration is performed continuously.

In some embodiments, the administering (or a course of treatment) comprises administering one or more cycles of treatment, wherein a course of treatment comprises one or more cycles of treatment as described herein. For example, a course of treatment may comprise a cycle of treatment comprising a maintenance dose (e.g., a single infusion). In some embodiments, a course of treatment comprises a cycle of treatment comprising a maintenance dose and a taper dose (e.g., a maintenance dose administered before a taper dose). In some embodiments, a course of treatment comprises a cycle of treatment comprising a first (titration) dose and a second (maintenance) dose. In some embodiments, a course of treatment comprises a cycle of treatment comprising a first (titration) dose, a second (maintenance) dose, and a third (taper) dose.

In some embodiments, the course of treatment comprises a cycle of treatment comprising administration of a first neuroactive steroid. In some embodiments, the course of treatment comprises a cycle of treatment comprising administration of a second neuroactive steroid. In some embodiments, the course of treatment comprises a cycle of treatment comprising administration of a first neuroactive steroid, and a cycle of treatment comprising administration of a second neuroactive steroid.

In some embodiments, the dose comprises an intravenous infusion. For example, in some embodiments, a cycle of treatment comprises: providing a single infusion of the neuroactive steroid. In some embodiments, the administering (or a course of treatment) comprises administering one or more cycles of treatment, a cycle of treatment comprising: administering a first infusion of the neuroactive steroid; and administering a second infusion of the neuroactive steroid: said neuroactive steroid infusions being sufficient to treat said subject. In some embodiments, administration of the second infusion occurs immediately after administration of the first infusion. In some embodiments, the amount of neuroactive steroid delivered/unit time in the second infusion, e.g., as measured in µg/kg/hour, is higher than that of the first infusion. In some embodiments, the amount of neuroactive steroid delivered/unit time in the second infusion, e.g., as measured in µg/kg/hour, is at least 1 to 2 times higher than that of the first infusion. In some embodiments, the amount of neuroactive steroid delivered/unit time in the second infusion, e.g., as measured in µg/kg/hour, is lower than that of the first infusion. In some embodiments, the amount of neuroactive steroid delivered/unit time in the second infusion, e.g., as measured in µg/kg/hour, is at least 1 to 2 times lower than that of the first infusion.

In some embodiments, the method comprises administering a plurality of infusions. In some embodiments, the method comprises administering a first and second infusion. In some embodiments, the administration of the second infusion begins no longer than 90, 60, 30, 10, or 5 minutes after the beginning or end of the administration of the first infusion. In some embodiments, the second infusion begins 0 to 90, 0 to 60, 0 to 30, 0 to 10, or 0 to 5 minutes after the beginning or end of the administration of the first infusion. In some embodiments, the second infusion begins no more than 60, 30, 20, 10, 5, 4, 3, 2, 1 minute(s) after the end of administration of the first infusion. In some embodiments, the second infusion begins at the end of administration of the first infusion. In some embodiments, the first infusion and the initiation of the second infusion are performed with the same delivery device, e.g., with the same cannula or reservoir. In some embodiments, the amount of neuroactive steroid delivered/unit time varies during the first infusion. In some embodiments, the first infusion delivers a smaller amount of neuroactive steroid/unit time than the second infusion. In some embodiments, the first infusion comprises administering a plurality of step doses, wherein each subsequent step dose delivers a larger amount of neuroactive steroid/unit time than the step dose that precedes it. In some embodiments, the amount of neuroactive steroid delivered/unit time varies during the second infusion. In some embodiments, the second infusion delivers a smaller amount of neuroactive steroid/unit time than the first infusion. In some embodiments, the second infusion comprises administering a plurality of step doses, wherein each subsequent step dose delivers a smaller amount of neuroactive steroid/unit time than the step dose that precedes it.

In some embodiments, the subject is 35 to 75 years of age. In some embodiments, the subject has a TETRAS Performance Subscale score of 2 or greater for at least one maneuver selected from forward horizontal reach posture, lateral "wing beating" posture, or finger-nose-finger testing in the 'upper limb tremor' test. In some embodiments, the subject has been diagnosed with essential tremor. In some embodiments, the subject has suffered from tremor for at least 2 years.

In some embodiments, the method provides acute treatment of the tremor (e.g., provides relief from a symptom in less than 1 week (e.g., within 6 days, 5 days, 4 days, 3 days, 2 days, 1 day, or 12 hours).

In some embodiments, the method reduces tremor amplitude by at least 5%, 10%, 20%, 30%, 40%, 50%, 60% (as measured by TETRAS or accelerometry), e.g., as compared to tremor amplitude before the method is provided.

In some embodiments, the method provides rapid onset of efficacy (e.g., rapid reduction in a symptom of tremor: rapidly affective to reduce a symptom of tremor, e.g., a subject experiences relief from a symptom of a tremor within 1 week (e.g., within 6 days, 5 days, 4 days, 3 days, 2 days, 1 day, or 12 hours)).

In some embodiments, the therapeutic effect is sustained (e.g., effectively treats a symptom of tremor and the efficacy is maintained for at least 1 day (e.g., at least 2 days, 3 days, 4 days, 5 days, 6 days, 1 week, 2 weeks, 3 weeks, 1 month, 2 months, 3 months, 4 months, 5 months, or 6 months).

In some embodiments, the efficacy is maintained after a single course of treatment (e.g., single dose, multiple doses, or cycle of treatment) of a compound described herein (e.g., allopregnanolone).

In some embodiments, the therapeutic effect does not cause an adverse event (e.g., does not cause a severe or moderate adverse event, e.g., during treatment or 3 days, 7 days, 10 days, 20 days, 30 days, 60 days, 90 days, 3 months, 4 months, 5 months, 6 months, 7 months, 8 months, 9 months, 10 months, 11 months, 12 months, or more after treatment).

In some embodiments, the method includes a course of treatment with multiple dosages or cycles of treatment (e.g., a first dose or cycle of treatment is a parenteral dose such as an intravenous (i.v.) dose, and a second dose or cycle of treatment is an oral dose). In some embodiments, the first and second dose or cycle of treatment include administering the same compound. In some embodiments, the first dose or cycle of treatment includes administering a first compound (e.g., a first compound described herein such as allopregnanolone) and the second dose or cycle of treatment includes administering a second compound that is different from the first compound.

In some embodiments, the method comprises the steps of evaluating (e.g., diagnosing, prognosing, and determining a course of treatment in) a subject suffering from tremor (e.g., as described herein), comprising the steps of; a) receiving information related to the therapeutic effect of a neuroactive steroid (e.g., allopregnanolone) in reducing tremor (e.g., the symptoms of tremor) in a subject treated with the neuroactive steroid (e.g., allopregnanolone); and b) determining if the tremor (e.g., the symptoms of tremor) is reduced in the subject as compared to the subject before receiving the neuroactive steroid (e.g., allopregnanolone), thereby evaluating the subject.

In an aspect, the disclosure features a method of treating a subject suffering from tremor (e.g., essential tremor), comprising: administering a first dose, wherein administration of said first dose results in a plasma level of neuroactive steroid of 50 to 300 nM neuroactive steroid; a rest period comprising at least 1, 2, 3, 4, 5, 6, 7, 8, 9, or 10 days; and administering a second dose, wherein administration of said second dose results in a plasma level of neuroactive steroid of 50 to 300 nM neuroactive steroid: wherein, collectively, the administrations are provided in sufficient amount to treat said subject. In some embodiments, the method does not result in sedation. In some embodiments, the method results in sedation. In some embodiments, the method provides therapeutic effect in the absence of sedative effect.

In an aspect, the disclosure features a method of treating a subject suffering from tremor (e.g., essential tremor), comprising: administering a first dose, wherein administration of said first dose lasts for at least 1 day and results in a plasma level of neuroactive steroid of 100 to 200 nM neuroactive steroid; a rest period comprising at least 5, 6, or 7 days; and administering a second dose, wherein administration of said second dose lasts for at least 1 day and results in a plasma level of neuroactive steroid of 100 to 200 nM neuroactive steroid: wherein, collectively, the administrations are provided in sufficient amount to treat said subject. In some embodiments, the method does not result in sedation. In some embodiments, the method results in sedation. In some embodiments, the method provides therapeutic effect in the absence of sedative effect.

In an aspect, the disclosure features a method of treating a subject suffering from tremor (e.g., essential tremor), comprising: administering a first dose, wherein administration of said first dose lasts for 1 day and results in a plasma level of neuroactive steroid of 150 nM neuroactive steroid; a rest period comprising 7 days; and administering a second dose, wherein administration of said second dose lasts for 1 day and results in a plasma level of neuroactive steroid of 150 nM neuroactive steroid: wherein, collectively, the administrations are provided in sufficient amount to treat said subject. In some embodiments, the method does not result in sedation. In some embodiments, the method results in sedation. In some embodiments, the method provides therapeutic effect in the absence of sedative effect.

In some embodiments, the administration of the second dose begins no longer than 1, 2, 3, 4, 5, 6, 7, 8, 9, 10, 11, or 12 days after the beginning or end of the administration of the first dose. In some embodiments, the second dose begins 1 to 14, 3 to 12, 5 to 10, or 7 days after the beginning or end of the administration of the first dose. In some embodiments, the second dose begins no more than 14, 12, 10, 9, 8, 7, 6, 5, 3, 2, or 1 day after the end of administration of the first dose. In some embodiments, the first dose and the initiation of the second dose are performed with the same delivery device, e.g., with the same cannula or reservoir. In some embodiments, the plasma concentration of said third dose is measured at a preselected time, e.g., at 10, 15, 20, 30, 45, 60 minutes, 2, 3, 4, 5, 6, 8, 10, 12, 24 hours, 2, 3, 4 days after the initiation of said third dose. In some embodiments, said third dose results in a plasma concentration of 150 nM, e.g., as measured at a preselected time, e.g., at 10, 15, 20, 30, 45, 60 minutes, 2, 3, 4, 5, 6, 8, 10, 12, 24 hours, 2, 3, 4 days after the initiation of said third dose.

In an aspect, provided herein is a method of prophylactically treating a disease or disorder described herein (e.g., tremor (e.g., essential tremor) in a human subject (e.g., as described herein, e.g., a subject identified as a subject at risk of suffering from a disease or disorder as described herein), the method comprising administering a therapeutically effective amount of a neuroactive steroid. In some embodiments, the method does not result in sedation. In some embodiments, the method results in sedation. In some embodiments, the method provides therapeutic effect in the absence of sedative effect.

In some embodiments, the method provides rapid onset of efficacy (e.g., rapid reduction in a symptom of tremor: rapidly affective to reduce a symptom of tremor, e.g., a subject experiences relief from a symptom of a tremor within 1 week (e.g., within 6 days, 5 days, 4 days, 3 days, 2 days, 1 day, or 12 hours)).

In some embodiments, the therapeutic effect is sustained (e.g., effectively treats a symptom of tremor and the efficacy is maintained for at least 1 day (e.g., at least 2 days, 3 days, 4 days, 5 days, 6 days, 1 week, 2 weeks, 3 weeks, 1 month, 2 months, 3 months, 4 months, 5 months, or 6 months).

In some embodiments, the efficacy is maintained after a single course of treatment (e.g., single dose, multiple doses, or cycle of treatment) of a compound described herein (e.g., allopregnanolone).

In an aspect, provided herein is a method of treating a subject suffering from tremor (e.g., essential tremor), comprising the steps of; a) receiving information related to the therapeutic effect of a neuroactive steroid (e.g., allopregnanolone) in reducing the tremor (e.g., symptoms of tremor) in a subject treated with the neuroactive steroid (e.g., allopregnanolone); and b) administering to the subject a therapeutic compound (e.g., neuroactive steroid) if the information indicates that the tremor (e.g., symptoms of the tremor) is reduced in the subject as compared to the subject before having received the neuroactive steroid (e.g., allopregnanolone), thereby treating the subject.

In some embodiments, the therapeutic compound administered according to step a) is allopregnanolone. In some embodiments, the neuroactive steroid of step a) is administered by parenteral administration. In some embodiments, the therapeutic compound administered according to step b) is a different neuroactive steroid as the neuroactive steroid described in part a). In some embodiments, the therapeutic compound administered according to step b) is the same neuroactive steroid as the neuroactive steroid described in part a). In some embodiments, the therapeutic compound of step b) is allopregnanolone. In some embodiments, the neuroactive steroid of step b) is administered by parenteral administration. In some embodiments, the neuroactive steroid of step b) is administered by oral administration.

In some embodiments, the therapeutic compound administered according to step b) is selected from pregnanolone, ganaxolone, alphadalone, alphaxalone, and allopregnanolone. In some embodiments, the neuroactive steroid is allopregnanolone. In some embodiments, the neuroactive steroid is deuterated allopregnanolone. In some embodiments, the neuroactive steroid is an estrol. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/10022, 8, U.S. Pat. Nos. 5,232,917, 8,575,375 and 8,759,330.

In an aspect, provided herein is a method of selecting a therapeutic compound (e.g., a neuroactive steroid) for treating tremor (e.g., essential tremor) in a human subject treated with a neuroactive steroid (e.g., allopregnanolone) comprising the steps of; a) receiving information related to the therapeutic effect of a neuroactive steroid (e.g., allopregnanolone) in reducing the tremor (e.g., symptoms of the tremor) in a subject; and b) selecting the therapeutic compound (e.g., neuroactive steroid) if the information indicates that the tremor (e.g., symptoms of the tremor) is reduced in the subject as compared to the subject before having received the neuroactive steroid (e.g., allopregnanolone).

In some embodiments, the therapeutic compound administered according to step a) is allopregnanolone. In some embodiments, the neuroactive steroid of step a) is administered by parenteral administration. In some embodiments, the therapeutic compound administered according to step b) is a different neuroactive steroid as the neuroactive steroid described in part a). In some embodiments, the therapeutic compound administered according to step b) is the same neuroactive steroid as the neuroactive steroid described in part a). In some embodiments, the therapeutic compound of step b) is allopregnanolone. In some embodiments, the neuroactive steroid of step b) is administered by parenteral administration. In some embodiments, the neuroactive steroid of step b) is administered by oral administration.

In some embodiments, the therapeutic compound administered according to step b) is selected from pregnanolone, ganaxolone, alphadalone, alphaxalone, and allopregnanolone. In some embodiments, the neuroactive steroid is allopregnanolone. In some embodiments, the neuroactive steroid is deuterated allopregnanolone. In some embodiments, the neuroactive steroid is an estrol. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 and 8,759,330.

In an aspect, provided herein is a method of evaluating (e.g., diagnosing, prognosing, and determining a course of treatment in) a subject suffering from tremor (e.g., essential tremor), comprising the steps of; a) receiving information related to the therapeutic effect of a neuroactive steroid (e.g., allopregnanolone) in reducing tremor (e.g., symptoms of the tremor) in a subject treated with the neuroactive steroid (e.g., allopregnanolone); and b) determining if the tremor (e.g., symptoms of the tremor) is reduced in the subject as compared to the subject before receiving the neuroactive steroid (e.g., allopregnanolone), thereby evaluating the subject. In some embodiments, the information is received, e.g., about 1, 2, 3, 4, 5, or 6 days; about 1, 2, or 3 weeks; about 1, 2, or 3 months after administration of the neuroactive steroid (e.g., allopregnanolone).

In some embodiments, the subject has been administered the neuroactive steroid less than about 3 months (e.g., less than about 2 or 1 month: 3, 2, or 1 weeks: 6, 5, 4, 3, 2, or 1 days) prior to receiving the information. In some embodiments, the subject has been administered the neuroactive steroid (e.g., allopregnanolone) by intravenous infusion.

In some embodiments, the therapeutic compound is administered by oral administration. In some embodiments, the therapeutic compound is administered as a solid composition (e.g., a solid dosage form).

In an embodiment, where the evaluation shows that the treatment was effective (e.g., using a method described above), the method comprises administering to the subject a second neuoractive steroid (e.g., wherein the second neuroactive steroid is different than the first neuroactive steroid). In an embodiment, the first neuroactive steroid is allopregnanolone. In an embodiment, the first neuroactive steroid is administered parenterally. In an embodiment, the first neuroactive steroid is administered orally. In some embodiments, the second neuroactive steroid is a different neuroactive steroid than the first neuroactive steroid (e.g., is a neuroactive steroid other than allopregnanolone). In some embodiments, the second neuroactive steroid is the same neuroactive steroid as the first neuroactive steroid (e.g., allopregnanolone). In some embodiments, the second neuroactive steroid is administered as an oral administration. In some embodiments, the second neuroactive steroid is administered parenterally. In some embodiments, the second neuroactive steroid is a compound disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 or 8,759, 330.

In an aspect, provided herein is a method of evaluating (e.g., diagnosing, prognosing, or determining a course of treatment in) a subject suffering from tremor (e.g., essential tremor), comprising the steps of; a) administering to the subject a therapeutic compound (e.g., neuroactive steroid); and b) receiving information related to the therapeutic effect of a neuroactive steroid (e.g., allopregnanolone) in reducing the tremor (e.g., symptoms of the tremor) in a subject treated with the neuroactive steroid (e.g., allopregnanolone), thereby evaluating the subject.

In some embodiments, the information is acquired by imaging the subject or a sample from the subject. In some embodiments, the information is acquired by fMRI. In some embodiments, the information is acquired by SPECT.

In an embodiment, where the evaluation shows that the treatment was effective (e.g., using a method described above), the method comprises administering to the subject a second neuoractive steroid (e.g., wherein the second neuroactive steroid is different than the first neuroactive steroid). In an embodiment, the first neuroactive steroid is allopregnanolone. In an embodiment, the first neuroactive steroid is administered parenterally. In an embodiment, the first neuroactive steroid is administered orally. In some embodiments, the second neuroactive steroid is a different neuroactive steroid than the first neuroactive steroid (e.g., is a neuroactive steroid other than allopregnanolone). In some embodiments, the second neuroactive steroid is the same neuroactive steroid as the first neuroactive steroid (e.g., allopregnanolone). In some embodiments, the second neuroactive steroid is administered as an oral administration. In some embodiments, the second neuroactive steroid is administered parenterally. In some embodiments, the second neuroactive steroid is a compound disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 or 8,759, 330.

In an aspect, the disclosure features a method for treating a human subject suffering from depression (e.g., postpartum depression) or an anxiety disorder, the method comprising administering a therapeutically effective amount of a neuroactive steroid. In some embodiments, the subject is suffering from an anxiety disorder. In some embodiments, the subject is suffering from depression. In some embodiments, the subject is suffering from postpartum depression.

In some embodiments, the method provides rapid onset of efficacy (e.g., rapid reduction in a symptom of depression or anxiety disorder: rapidly affective to reduce a symptom of depression or anxiety disorder, e.g., a subject experiences relief from a symptom of depression or anxiety disorder described herein within 1 week (e.g., within 6 days, 5 days, 4 days, 3 days, 2 days, 1 day, or 12 hours)).

In some embodiments, the therapeutic effect is sustained (e.g., effectively treats a symptom of depression or anxiety disorder and the efficacy is maintained for at least 1 day (e.g., at least 2 days, 3 days, 4 days, 5 days, 6 days, 1 week, 2 weeks, 3 weeks, 1 month, 2 months, 3 months, 4 months, 5 months, or 6 months).

In some embodiments, the efficacy is maintained after a single course of treatment (e.g., single dose, multiple doses, or cycle of treatment) of a compound described herein (e.g., allopregnanolone).

In some embodiments, the neuroactive steroid is pregnanolone, allopregnanolone, alphadalone, ganaxolone, or alphaxolone. In some embodiments, the neuroactive steroid is allopregnanolone. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232, 917, 8,575,375 and 8,759,330.

In some embodiments, the depression is clinical depression (also known as major depression, major depressive disorder, severe depression, unipolar depression, unipolar disorder, or recurrent depression), postnatal or postpartum depression, atypical depression, melancholic depression, Psychotic Major Depression (PMD), catatonic depression, Seasonal Affective Disorder (SAD), dysthymia, double depression, Depressive Personality Disorder (DPD), Recurrent Brief Depression (RBD), minor depressive disorder, bipolar disorder or manic depressive disorder, post-traumatic stress disorders, depression caused by chronic medical conditions, treatment-resistant depression, refractory depression, suicidality, suicidal ideation, or suicidal behavior. In some embodiments, the depression is severe depression. In some embodiments, the depression is postpartum depression. In some embodiments the depression is perinatal depression.

In some embodiments, the administering is performed parenterally. In some embodiments, the administering is performed intravenously. In some embodiments, the administered is performed orally.

In some embodiments, the subject is a female. In some embodiments, the subject is an adult. In some embodiments, the subject is from 18 to 45 years of age. In some embodiments, the subject is suffering from (e.g., has been diagnosed with) postpartum depression (e.g., severe postpartum depression). In some embodiments, the subject has experienced a Major Depressive Episode in the postpartum period. In some embodiments, the period begins within the first 4 weeks following delivery of a baby. In some embodiments, the subject has been identified as being at risk of depression (e.g., postpartum depression), for example by a method of evaluation as described herein. In some embodiments, the subject is in her third trimester of pregnancy. In some embodiments, the subject is suffering from perinatal depression. In some embodiments, the subject has reducded levels of allopregnanolone relative to a reference standard (e.g., relative to the level of allopregnanolone in a subject does not later suffer from depression (e.g., postpartum depression, perinatal depression).

In an embodiment, the method comprises administering a second neuroactive steroid. In an embodiment, the first neuroactive steroid is allopregnanolone. In an embodiment, the first neuroactive steroid is administered parenterally. In some embodiments, the second neuroactive steroid a different neuroactive steroid than the first neuroactive steroid (e.g., is a neuroactive steroid other than allopregnanolone). In some embodiments, the second neuroactive steroid is administered as an oral administration.

In an aspect, the disclosure features a method for treating a human subject suffering from depression (e.g., postpartum depression) or an anxiety disorder, the method comprising administering to the subject a therapeutically effective amount of a neuroactive steroid (e.g., allopregnanolone). In some embodiments, the administration is intravenous administration. In some embodiments, the administration is oral administration. In some embodiments, the subject is suffering from an anxiety disorder. In some embodiments, the subject is suffering from depression. In some embodiments, the subject is suffering from postpartum depression.

In some embodiments, the method provides maintenance treatment or preventative treatment.

In some embodiments, the method provides acute treatment of the depression (e.g., within 72 hours, 48 hours, 24 hours, 12 hours, or less). In some embodiments, the method provides acute treatment of the depression (e.g., provides relief from a symptom in less than 1 week (e.g., within 6 days, 5 days, 4 days, 3 days, 2 days, 1 day, or 12 hours).

In some embodiments, the method provides rapid onset of efficacy (e.g., rapid reduction in a symptom of depression or anxiety disorder: rapidly affective to reduce a symptom of depression or anxiety disorder, e.g., a subject experiences relief from a symptom of depression or anxiety disorder described herein within 1 week (e.g., within 6 days, 5 days, 4 days, 3 days, 2 days, 1 day, or 12 hours)).

In some embodiments, the therapeutic effect is sustained (e.g., effectively treats a symptom of depression or anxiety disorder and the efficacy is maintained for at least 1 day (e.g., at least 2 days, 3 days, 4 days, 5 days, 6 days, 1 week, 2 weeks, 3 weeks, 1 month, 2 months, 3 months, 4 months, 5 months, or 6 months).

In some embodiments, the efficacy is maintained after a single course of treatment (e.g., single dose, multiple doses, or cycle of treatment) of a compound described herein (e.g., allopregnanolone).

In some embodiments, the therapeutic effect is does not cause an adverse event (e.g., does not cause a severe or moderate adverse event, e.g., during treatment or 3 days, 7 days, 10 days, 20 days, 30 days, 60 days, 90 days, 3 months, 4 months, 5 months, 6 months, 7 months, 8 months, 9 months, 10 months, 11 months, 12 months, or more after treatment).

In some embodiments, the method includes a course of treatment with multiple dosages or cycles of treatment (e.g., a first dose or cycle of treatment is a parenteral dose such as an intravenous (i.v.) dose, and a second dose or cycle of treatment is an oral dose). In some embodiments, the first and second dose or cycle of treatment include the same compound. In some embodiments, the first dose or cycle of treatment includes a first compound (e.g., a first compound described herein such as allopregnanolone) and the second dose or cycle of treatment includes a second compound that is different from the first compound.

In some embodiments, the method provides therapeutic effect (e.g., as measured by reduction in Hamilton Depression Score (HAM-D)) within 4, 3, 2, 1 days: 96, 84, 48, 24, 20, 16, 12, 10, 8 hours or less. In some embodiments, the therapeutic effect is a decrease from baseline in HAM-D score at the end of a treatment period (e.g., 12, 24, 48 hours after administration: 24, 48, 72, 96 hours or more). In some embodiments, the decrease from baseline in HAM-D score is from severe (e.g., HAM-D score of 24 or greater) to symptom-free (e.g., HAM-D score of 7 or lower). In some embodiments, the baseline score is about 10 to 52 (e.g., more than 10, 15, or 20: 10 to 52, 12 to 52, 15 to 52, 17 to 52, 20 to 52, 22 to 52). In some embodiments, the baseline score is at least 10, 15, or 20. In some embodiments, the HAM-D score at the end of the treatment period is about 0 to 10 (e.g., less than 10: 0 to 10, 0 to 6, 0 to 4, 0 to 3, 0 to 2, 1.8). In some embodiments, the HAM-D score at the end of the treatment period is less than 10, 7, 5, or 3. In some embodiments, the decrease in HAM-D score is from a baseline score of about 20 to 30 (e.g., 22 to 28, 23 to 27, 24 to 27, 25 to 27, 26 to 27) to a HAM-D score at the end of the treatment period is about 0 to 10 (e.g., less than 10: 0 to 10, 0 to 6, 0 to 4, 0 to 3, 0 to 2, 1.8). In some embodiments, the decrease in the baseline HAM-D score to HAM-D score at the end of the treatment period is at least 1, 2, 3, 4, 5, 7, 10, 25, 40, 50, or 100 fold). In some embodiments, the percentage decrease in the baseline HAM-D score to HAM-D score at the end of the treatment period is at least 50% (e.g., 60%, 70%, 80%, 90%). In some embodiments, assessment (e.g., evaluation) of therapeutic effect is measured by reduction in HAM-D.

In some embodiments, the method provides therapeutic effect (e.g., as measured by reduction in Edinburgh Postnatal Depression Scale (EPDS)) within 4, 3, 2, 1 days: 24, 20, 16, 12, 10, 8 hours or less. In some embodiments, the therapeutic effect is an improvement measured by the EPDS. In some embodiments, assessment (e.g., evaluation) of therapeutic effect is measured by reduction in EPDS.

In some embodiments, the method provides therapeutic effect (e.g., as measured by reduction in Clinical Global Impression-Improvement Scale (CGI)) within 4, 3, 2, 1 days: 24, 20, 16, 12, 10, 8 hours or less. In some embodiments, the therapeutic effect is a CGI score of 2 or less. In some embodiments, assessment (e.g., evaluation) of therapeutic effect is measured by reduction in CGI.

In some embodiments, the method provides therapeutic effect (e.g., as measured by reduction in Generalized Anxiety Disorder 7-Item Scale (GAD-7)) within 4, 3, 2, 1 days: 24, 20, 16, 12, 10, 8 hours or less. In some embodiments, assessment (e.g., evaluation) of therapeutic effect is measured by reduction in GAD-7.

In some embodiments, the subject is substantially relieved of at least one symptom within 3, 2, 1 days: 24, 20, 16, 12, 10, 8 hours or less of said administration. In some embodiments, the subject is substantially relieved of at least one symptom for 1, 2, 3, 4, 5, 6, 7 days: 1, 2, 3, 4 weeks: 1, 2, 3, 4, 5, 6, 7, 8, 9, 10, 11, 12 months or more. In some embodiments, the symptom is sadness, fatigue, changes in sleeping and eating habits, reduced sexual desire, crying episodes, anxiety, or irritability. In some embodiments, the symptom is suicidity. In some embodiments, the symptom is impaired cognitive function.

In some embodiments, the neuroactive steroid is selected from pregnanolone, ganaxolone, alphadalone, alphaxalone, and allopregnanolone. In some embodiments, the neuroactive steroid is allopregnanolone. In some embodiments, the neuroactive steroid is deuterated allopregnanolone. In some embodiments, the neuroactive steroid is an estrol. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 and 8,759,330.

In some embodiments, the subject is a female. In some embodiments, the female is not breast feeding. In some embodiments, the subject is an adult. In some embodiments, the subject is from 18 to 45 years of age. In some embodiments, the subject is suffering from (e.g., has been diagnosed with) postpartum depression (e.g., severe postpartum depression). In some embodiments, the subject has experienced a Major Depressive Episode in the postpartum period. In some embodiments, the period begins within the first 4 weeks following delivery of a baby. In some embodiments, the subject has been identified as being at risk of depression (e.g., severe depression, postpartum depression), for example by a method of evaluation as described herein. In some embodiments, the subject is in her third trimester of pregnancy. In some embodiments, the subject is suffering from perinatal depression.

In some embodiments, the infusion occurs over at least 1, 2, 3, 4, 5, 6, or 7 days.

In some embodiments, the infusion occurs over the course of 1, 2, 3, 4, 5, 6, or 7 days.

In some embodiments, the infusion is bolus infusion (e.g., single dose, single infusion). In some embodiments, the infusion is a plurality of bolus infusions (e.g., multiple bolus infusions, e.g., more than one bolus infusions, e.g., 2, 3, 4, 5 or more bolus infusions. In some embodiments, the plurality of bolus infusions is administered in 1 day, 2 days, 3 days, 4 days, 5 days, 6 days, 1 week, 2 weeks, 3 weeks, 1 month, 2 months, 3 months, 4 months, 5 months, 6 months or more.

In some embodiments, the infusion is an intermittent infusion (e.g., an infusion that occurs at irregular intervals).

In some embodiments, the administering occurs by continuous intravenous infusion. In some embodiments, the infusion occurs over at least 1, 2, 3, 4, 5, 6, or 7 days. In some embodiments, the infusion occurs over the course of 1, 2, 3, 4, 5, 6, or 7 days.

In some embodiments, the administering comprises administering a plurality of infusions. In some embodiments, the administering comprises administering a first, second, and third infusion. In some embodiments, the administration of the second infusion begins no longer than 90, 60, 30, 10, or 5 minutes after the beginning or end of the administration of the first infusion. In some embodiments, the second infusion begins 0 to 90, 0 to 60, 0 to 30, 0 to 10, or 0 to 5 minutes after the beginning or end of the administration of the first infusion. In some embodiments, the second infusion begins no more than 60, 30, 20, 10, 5, 4, 3, 2, 1 minute after the end of administration of the first infusion. In some embodiments, the second infusion begins at the end of administration of the first infusion. In some embodiments, the first infusion and the initiation of the second infusion are performed with the same delivery device, e.g., with the same cannula or reservoir.

In some embodiments, the amount of neuroactive steroid delivered/unit time varies during the first infusion. In some embodiments, the first (step-up) infusion delivers a smaller amount of neuroactive steroid/unit time than the second (maintenance) infusion. In some embodiments, the first (step-up) infusion comprises administering a plurality of step doses, wherein each subsequent step dose delivers a larger amount of neuroactive steroid/unit time than the step dose that precedes it. In some embodiments, the third infusion is administered for a period of time that is between 5 and 20 hours, 8 and 16 hours, 10 and 15 hours, or 10 and 13 hours. In some embodiments, the first infusion is administered for 12+/−2 hours. In some embodiments, the first infusion is administered for 12 hours. In some embodiments, the amount of neuroactive steroid delivered/unit time varies during the first infusion. In some embodiments, administering said step-up dose comprises administering a continuously increasing amount of neuroactive steroid. In some embodiments, administering said step-up dose comprises administering a continuously increasing amount of neuroactive steroid/unit time.

In some aspects of these embodiments, the administration comprises a first, second, and third step dose. In some embodiments, said first step dose is administered at an amount of neuroactive steroid/unit time of 5-50 µg/kg/hour (e.g., 21.5 µg/kg/hour). In some embodiments, said first step dose is administered at an amount of neuroactive steroid/unit time of 5-50 µg/kg/hour, 10-40 µg/kg/hour, 20-30 µg/kg/hour, 20 µg/kg/hour, 21 µg/kg/hour, 22 µg/kg/hour, or 21.5 µg/kg/hour. In some embodiments, said second step dose is administered at an amount of neuroactive steroid/unit time of 10-100 µg/kg/hour (e.g., 43 µg/kg/hour). In some embodiments, said second step dose is administered at an amount of neuroactive steroid/unit time of 10-100 µg/kg/hour, 20-70 µg/kg/hour, 30-50 µg/kg/hour, 42 µg/kg/hour, 43 µg/kg/hour, or 44 µg/kg/hour. In some embodiments, said third step dose is administered at an amount of neuroactive steroid/unit time of 25-150 µg/kg/hour. In some embodiments, said third step dose is administered at an amount of neuroactive steroid/unit time of 25-150 µg/kg/hour, 40-100 µg/kg/hour, 60-70 µg/kg/hour, 63 µg/kg/hour, 64 µg/kg/hour, 65 µg/kg/hour, or 64.5 µg/kg/hour. In some embodiments, said first step dose is 10 to 40% (e.g., 25%) of the second/maintenance infusion: said second step dose is 30 to 70% (e.g., 50%) of the second/maintenance infusion; and said third step dose is 60 to 90% (e.g., 75%) of the second/maintenance infusion. In some embodiments, the amount of neuroactive steroid delivered/unit time in said first step dose is 10 to 40% (e.g., 25%) of the amount of neuroactive steroid delivered/unit time in said second/maintenance infusion: the amount of neuroactive steroid delivered/unit time in said second step dose is 30 to 70% (e.g., 50%) of the amount of neuroactive steroid delivered/unit time in said second/maintenance infusion; and the amount of neuroactive steroid delivered/unit time in said third step dose is 60 to 90% (e.g., 75%) of the amount of neuroactive steroid delivered/unit time in said second/maintenance infusion.

In some embodiments, the third (step-down/downward taper) infusion delivers a smaller amount of neuroactive steroid/unit time than the second (maintenance) infusion. In some embodiments, the third (step-down/downward taper) infusion comprises administering a plurality of step doses, wherein each subsequent step dose delivers a lower amount of neuroactive steroid/unit time than the step dose that precedes it. In some embodiments, said third infusion is administered for a period of time that is between 5 and 20 hours, 8 and 16 hours, 10 and 15 hours, or 10 and 13 hours. In some embodiments, said third infusion is administered for 12+/−2 hours. In some embodiments, said third infusion is administered for 12 hours. In some embodiments, administering said downward taper dose comprises administering a continuously decreasing amount of neuroactive steroid. In some embodiments, administering said downward taper dose comprises administering a continuously decreasing amount of neuroactive steroid/unit time.

In some aspects of these embodiments, the administration comprises a first, second, and third step dose. In some embodiments, said first step dose is administered at an amount of neuroactive steroid/unit time of 15-150 μg/kg/hour. In some embodiments, said first step dose is administered at an amount of neuroactive steroid/unit time of 15-150 μg/kg/hour, 40-100 μg/kg/hour, 60-70 μg/kg/hour, 63 μg/kg/hour, 64 μg/kg/hour, 65 μg/kg/hour, or 64.5 μg/kg/hour. In some embodiments, said second step dose is administered at an amount of neuroactive steroid/unit time of 10-100 μg/kg/hour(e.g., 43 μg/kg/hour). In some embodiments, said second step dose is administered at an amount of neuroactive steroid/unit time of 10-100 μg/kg/hour, 20-70 μg/kg/hour, 30-50 μg/kg/hour, 42 μg/kg/hour, 43 μg/kg/hour, or 44 μg/kg/hour. In some embodiments, said third step dose is administered at an amount of neuroactive steroid/unit time of 5-50 μg/kg/hour (e.g., 21.5 μg/kg/hour). In some embodiments, said third step dose is administered at an amount of neuroactive steroid/unit time of 5-50 μg/kg/hour, 10-40 μg/kg/hour, 20-30 μg/kg/hour, 20 μg/kg/hour, 21 μg/kg/hour, 22 μg/kg/hour, or 21.5 μg/kg/hour.

In some embodiments, said first step dose is 60 to 90% (e.g., 75%) of the second/maintenance infusion: said second step dose is 30 to 70% (e.g., 50%) of the second/maintenance infusion; and said third step dose is 10 to 40% (e.g., 25%) of the second/maintenance infusion.

In some embodiments, the amount of neuroactive steroid delivered/unit time in said first step dose is 60 to 90% (e.g., 75%) of the amount of neuroactive steroid delivered/unit time in said second/maintenance infusion: the amount of neuroactive steroid delivered/unit time in said second step dose is 30 to 70% (e.g., 50%) of the amount of neuroactive steroid delivered/unit time in said second/maintenance infusion; and the amount of neuroactive steroid delivered/unit time in said third step dose is 10 to 40% (e.g., 25%) of the amount of neuroactive steroid delivered/unit time in said second/maintenance infusion.

In some embodiments, the method comprises administering a second/maintenance infusion of 50-150 μg/kg/hour (e.g., 86 μg/kg/hour) of the neuroactive steroid. In some embodiments, the second/maintenance infusion is 50-150 μg/kg/hour, 60-100 μg/kg/hour, 70-90 μg/kg/hour, 85 μg/kg/hour, 86 μg/kg/hour, or 87 μg/kg/hour. In some embodiments, said second/maintenance infusion is administered for a period of time that is between 5 and 80 hours, 10 and 70 hours, 20 and 50 hours, or 30 and 40 hours. In some embodiments, said second/maintenance infusion is administered for 36+/−5 hours. In some embodiments, said second/maintenance infusion is administered for 36 hours.

In some embodiments, the plasma concentration of said second/maintenance infusion is measured at a preselected time, e.g., at 10, 15, 20, 30, 45, 60 minutes, 2, 3, 4, 5, 6, 8, 10, 12, 24 hours, 2, 3, 4 days after the initiation of said second/maintenance infusion. In some embodiments, said second/maintenance infusion results in a plasma concentration of 150 nM, e.g., as measured at a preselected time, e.g., at 10, 15, 20, 30, 45, 60 minutes, 2, 3, 4, 5, 6, 8, 10, 12, 24 hours, 2, 3, 4 days after the initiation of said second/maintenance infusion. In some embodiments, said second/maintenance infusion is administered at the same amount of neuroactive steroid/unit time over the entire second/maintenance infusion.

In an embodiment, the method comprises administering a second neuroactive steroid. In an embodiment, the first neuroactive steroid is allopregnanolone. In an embodiment, the first neuroactive steroid is administered parenterally (e.g., as described in the embodiments above). In some embodiments, the second neuroactive steroid a different neuroactive steroid than the first neuroactive steroid (e.g., is a neuroactive steroid other than allopregnanolone). In some embodiments, the second neuroactive steroid is administered as an oral administration (orally).

In an aspect, the disclosure features a method for treating a human subject suffering from depression (e.g., postpartum depression) or an anxiety disorder, the method comprising: administering a first infusion of a neuroactive steroid, wherein said first/step-up infusion is administered for 8-16 hours (e.g., 12 hours); administering a second/maintenance infusion of a neuroactive steroid, wherein said second/maintenance infusion is administered for 24-48 hours (e.g., 36 hours); and administering a third infusion of a neuroactive steroid, wherein said third/downward taper infusion is administered for 8-16 hours (e.g., 12 hours): said neuroactive steroid doses being sufficient to treat said subject.

In some embodiments, the subject is suffering from an anxiety disorder. In some embodiments, the subject is suffering from depression. In some embodiments, the subject is suffering from postpartum depression.

In some embodiments, the method provides rapid onset of efficacy (e.g., rapid reduction in a symptom of depression or anxiety disorder: rapidly affective to reduce a symptom of depression or anxiety disorder, e.g., a subject experiences relief from a symptom of depression or anxiety disorder described herein within 1 week (e.g., within 6 days, 5 days, 4 days, 3 days, 2 days, 1 day, or 12 hours)).

In some embodiments, the therapeutic effect is sustained (e.g., effectively treats a symptom of depression or anxiety disorder and the efficacy is maintained for at least 1 day (e.g., at least 2 days, 3 days, 4 days, 5 days, 6 days, 1 week, 2 weeks, 3 weeks, 1 month, 2 months, 3 months, 4 months, 5 months, or 6 months).

In some embodiments, the efficacy is maintained after a single course of treatment (e.g., single dose, multiple doses, or cycle of treatment) of a compound described herein (e.g., allopregnanolone).

In an aspect, the disclosure features a method for treating a human subject suffering from depression (e.g., postpartum depression) or an anxiety disorder, the method comprising: administering a first infusion of a neuroactive steroid, said first/step-up infusion comprising administering a continuously increasing amount of neuroactive steroid at an amount of neuroactive steroid/unit time of 5-100 μg/kg/hour, 10-80 μg/kg/hour, or 15-70 μg/kg/hour; administering a second/maintenance infusion of a neuroactive steroid, said second/maintenance infusion comprising administering an amount of neuroactive steroid/unit time of 50-100 μg/kg/hour, 70-100 μg/kg/hour, or 86 μg/kg/hour; and administering a third infusion of a neuroactive steroid, said third/downward taper infusion comprising administering a continuously decreasing amount of neuroactive steroid at an amount of neuroactive steroid/unit time of 5-100 μg/kg/hour, 10-80 μg/kg/hour, or 15-70 μg/kg/hour: said neuroactive steroid doses being sufficient to treat said subject.

In some embodiments, the subject is suffering from an anxiety disorder. In some embodiments, the subject is suffering from depression. In some embodiments, the subject is suffering from postpartum depression.

In some embodiments, the method provides rapid onset of efficacy (e.g., rapid reduction in a symptom of depression or anxiety disorder: rapidly affective to reduce a symptom of depression or anxiety disorder, e.g., a subject experiences relief from a symptom of depression or anxiety disorder described herein within 1 week (e.g., within 6 days, 5 days, 4 days, 3 days, 2 days, 1 day, or 12 hours)).

In some embodiments, the therapeutic effect is sustained (e.g., effectively treats a symptom of depression or anxiety disorder and the efficacy is maintained for at least 1 day (e.g., at least 2 days, 3 days, 4 days, 5 days, 6 days, 1 week, 2 weeks, 3 weeks, 1 month, 2 months, 3 months, 4 months, 5 months, or 6 months).

In some embodiments, the efficacy is maintained after a single course of treatment (e.g., single dose, multiple doses, or cycle of treatment) of a compound described herein (e.g., allopregnanolone).

In some embodiments, the method provides therapeutic effect (e.g., as measured by reduction in Hamilton Depression Score (HAM-D)) within 4, 3, 2, 1 days: 24, 20, 16, 12, 10, 8 hours or less. In some embodiments, the therapeutic effect is a decrease from baseline in HAM-D score at the end of a treatment period (e.g., 12, 24, 48 hours after administration: 24, 48, 72, 96 hours or more). In some embodiments, assessment (e.g., evaluation) of therapeutic effect is measured by reduction in HAM-D.

In some embodiments, the method provides therapeutic effect (e.g., as measured by reduction in Edinburgh Postnatal Depression Scale (EPDS)) within 4, 3, 2, 1 days: 24, 20, 16, 12, 10, 8 hours or less. In some embodiments, the therapeutic effect is an improvement measured by the EPDS. In some embodiments, assessment (e.g., evaluation) of therapeutic effect is measured by reduction in EPDS.

In some embodiments, the method provides therapeutic effect (e.g., as measured by reduction in Clinical Global Impression-Improvement Scale (CGI)) within 4, 3, 2, 1 days: 24, 20, 16, 12, 10, 8 hours or less. In some embodiments, the therapeutic effect is a CGI score of 2 or less. In some embodiments, assessment (e.g., evaluation) of therapeutic effect is measured by reduction in CGI.

In some embodiments, the neuroactive steroid is pregnanolone, allopregnanolone, alphadalone, ganaxolone, or alphaxolone. In some embodiments, the neuroactive steroid is allopregnanolone. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 and 8,759,330.

In some embodiments, the depression is clinical depression (also known as major depression, major depressive disorder, severe depression, unipolar depression, unipolar disorder, or recurrent depression), postnatal or postpartum depression, atypical depression, melancholic depression, Psychotic Major Depression (PMD), catatonic depression, Seasonal Affective Disorder (SAD), dysthymia, double depression, Depressive Personality Disorder (DPD), Recurrent Brief Depression (RBD), minor depressive disorder, bipolar disorder or manic depressive disorder, post-traumatic stress disorders, depression caused by chronic medical conditions, treatment-resistant depression, refractory depression, suicidality, suicidal ideation, or suicidal behavior. In some embodiments, the depression is severe depression. In some embodiments, the depression is postpartum depression. In some embodiments the depression is perinatal depression.

In an embodiment, the method comprises administering a second neuroactive steroid. In an embodiment, the first neuroactive steroid is allopregnanolone. In an embodiment, the first neuroactive steroid is administered parenterally. In some embodiments, the second neuroactive steroid a different neuroactive steroid than the first neuroactive steroid (e.g., is a neuroactive steroid other than allopregnanolone). In some embodiments, the second neuroactive steroid is administered as an oral administration. In some embodiments, the second neuroactive steroid is a compound disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 or 8,759,330.

In an aspect, provided herein is a method of treating a subject suffering from depression or an anxiety disorder, comprising the steps of; a) receiving information related to the therapeutic effect of a neuroactive steroid (e.g., allopregnanolone) in reducing the depression or anxiety disorder (e.g., symptoms of the depression or anxiety disorder) in a subject treated with the neuroactive steroid (e.g., allopregnanolone); and b) administering to the subject a therapeutic compound (e.g., neuroactive steroid) if the information indicates that the depression or anxiety disorder (e.g., symptoms of the depression or anxiety disorder) is reduced in the subject as compared to the subject before having received the neuroactive steroid (e.g., allopregnanolone), thereby treating the subject.

In some embodiments, the subject is suffering from an anxiety disorder. In some embodiments, the subject is suffering from depression. In some embodiments, the subject is suffering from postpartum depression.

In some embodiments, the therapeutic compound administered according to step a) is allopregnanolone. In some embodiments, the neuroactive steroid of step b) is administered by parenteral administration. In some embodiments, the administering step (e.g., the administering step of step b) is oral administration. In some embodiments, the therapeutic compound administered according to step b) is a different neuroactive steroid as the neuroactive steroid described in part a).

In some embodiments, the therapeutic compound administered according to step b) is selected from pregnanolone, ganaxolone, alphadalone, alphaxalone, and allopregnanolone. In some embodiments, the neuroactive steroid is allopregnanolone. In some embodiments, the neuroactive steroid is deuterated allopregnanolone. In some embodiments, the neuroactive steroid is an estrol. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 and 8,759,330.

In some embodiments, the information related to therapeutic effect of a neuroactive steroid (e.g., allopregnanolone) is measured by reduction in HAM-D, EPDS, CGI, or GAD-7.

In an aspect, provided herein is a method of selecting a therapeutic compound (e.g., a neuroactive steroid) for treating depression or an anxiety disorder in a human subject treated with a neuroactive steroid (e.g., allopregnanolone)

comprising the steps of; a) receiving information related to the therapeutic effect of a neuroactive steroid (e.g., allopregnanolone) in reducing the depression or anxiety disorder (e.g., symptoms of the depression or anxiety disorder) in a subject; and b) selecting the therapeutic compound (e.g., a neuroactive steroid) if the information indicates that the depression or anxiety disorder (e.g., symptoms of the depression or anxiety disorder) is reduced in the subject as compared to the subject before having received the neuroactive steroid (e.g., allopregnanolone).

In some embodiments, the subject is suffering from an anxiety disorder. In some embodiments, the subject is suffering from depression. In some embodiments, the subject is suffering from postpartum depression.

In some embodiments, the therapeutic compound administered according to step a) is allopregnanolone. In some embodiments, the neuroactive steroid of step b) is administered by parenteral administration. In some embodiments, the administering step (e.g., the administering step of step b) is oral administration. In some embodiments, the therapeutic compound administered according to step b) is a different neuroactive steroid as the neuroactive steroid described in part a).

In some embodiments, the therapeutic compound administered according to step b) is selected from pregnanolone, ganaxolone, alphadalone, alphaxalone, and allopregnanolone. In some embodiments, the neuroactive steroid is allopregnanolone. In some embodiments, the neuroactive steroid is deuterated allopregnanolone. In some embodiments, the neuroactive steroid is an estrol. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 and 8,759,330.

In some embodiments, the information related to therapeutic effect of a neuroactive steroid (e.g., allopregnanolone) is measured by reduction in HAM-D, EPDS, CGI, or GAD-7.

In an aspect, provided herein is a method of evaluating (e.g., diagnosing, prognosing, and determining a course of treatment in) a subject suffering from depression or an anxiety disorder, comprising the steps of; a) receiving information related to the therapeutic effect of a neuroactive steroid (e.g., allopregnanolone) in reducing depression or anxiety disorder (e.g., symptoms of the depression or anxiety disorder) in a subject treated with the neuroactive steroid (e.g., allopregnanolone); and b) determining if the depression or anxiety disorder (e.g., symptoms of the depression or anxiety disorder) is reduced in the subject as compared to the subject before receiving the neuroactive steroid (e.g., allopregnanolone), thereby evaluating the subject. In some embodiments, the information is received, e.g., about 1, 2, 3, 4, 5, or 6 days; about 1, 2, or 3 weeks; about 1, 2, or 3 months after administration of the neuroactive steroid (e.g., allopregnanolone).

In some embodiments, the subject is suffering from an anxiety disorder. In some embodiments, the subject is suffering from depression. In some embodiments, the subject is suffering from postpartum depression.

In some embodiments, the subject has been administered the neuroactive steroid less than about 3 months (e.g., less than about 2 or 1 month: 3, 2, or 1 weeks: 6, 5, 4, 3, 2, or 1 days) prior to receiving the information. In some embodiments, the subject has been administered the neuroactive steroid (e.g., allopregnanolone) by intravenous infusion.

In some embodiments, the therapeutic compound is administered by oral administration. In some embodiments, the therapeutic compound is administered as a solid composition (e.g., a solid dosage form).

In some embodiments, the information related to therapeutic effect of a neuroactive steroid (e.g., allopregnanolone) is measured by reduction in HAM-D, EPDS, CGI, or GAD-7.

In an embodiment, where the evaluation shows that the treatment was effective (e.g., using a method described above), the method comprises administering to the subject a second neuoractive steroid (e.g., wherein the second neuroactive steroid is different than the first neuroactive steroid). In an embodiment, the first neuroactive steroid is allopregnanolone. In an embodiment, the first neuroactive steroid is administered parenterally. In some embodiments, the second neuroactive steroid a different neuroactive steroid than the first neuroactive steroid (e.g., is a neuroactive steroid other than allopregnanolone). In some embodiments, the second neuroactive steroid is administered as an oral administration. In some embodiments, the second neuroactive steroid is a compound disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 or 8,759,330.

In an aspect, provided herein is a method of evaluating (e.g., diagnosing, prognosing, or determining a course of treatment in) a subject suffering from depression or an anxiety disorder, comprising the steps of; a) administering to the subject a therapeutic compound (e.g., neuroactive steroid); and b) receiving information related to the therapeutic effect of a neuroactive steroid (e.g., allopregnanolone) in reducing the depression or anxiety disorder (e.g., symptoms of the depression or anxiety disorder) in a subject treated with the neuroactive steroid (e.g., allopregnanolone), thereby evaluating the subject.

In some embodiments, the subject is suffering from an anxiety disorder. In some embodiments, the subject is suffering from depression. In some embodiments, the subject is suffering from postpartum depression.

In some embodiments, the information related to therapeutic effect of a neuroactive steroid (e.g., allopregnanolone) is measured by reduction in HAM-D, EPDS, CGI, or GAD-7.

In some embodiments, the information is acquired by imaging the subject or a sample from the subject. In some embodiments, the information is acquired by fMRI. In some embodiments, the information is acquired by SPECT.

In an embodiment, where the evaluation shows that the treatment was effective (e.g., using a method described above), the method comprises administering to the subject a second neuoractive steroid (e.g., wherein the second neuroactive steroid is different than the first neuroactive steroid). In an embodiment, the first neuroactive steroid is allopregnanolone. In an embodiment, the first neuroactive steroid is administered parenterally. In some embodiments, the second neuroactive steroid a different neuroactive steroid than the first neuroactive steroid (e.g., is a neuroactive steroid other than allopregnanolone). In some embodiments, the second neuroactive steroid is administered as an oral administration. In some embodiments, the second neuroactive steroid is a compound disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 or 8,759,330.

In an aspect, provided herein is a method of treating a subject suffering from a neuroendocrine disease (or neuroendocrine dysfunction), comprising: intravenously administering to the subject a therapeutically effective amount of a neuroactive steroid (e.g., allopregnanolone), wherein administering occurs by continuous intravenous infusion. In some embodiments, the concentrations of allopregnanolone in plasma is greater than that in a normal subject (e.g., a subject not suffering from a neuroendocrine disease (or neuroendocrine dysfunction). In some embodiments, the concentrations of allopregnanolone in plasma is 10 nM in plasma or less.

In some embodiments, the neuroactive steroid is selected from pregnanolone, ganaxolone, alphadalone, alphaxalone, and allopregnanolone. In some embodiments, the neuroactive steroid is allopregnanolone. In some embodiments, the neuroactive steroid is deuterated allopregnanolone. In some embodiments, the neuroactive steroid is an estrol. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 and 8,759,330.

In an aspect, provided herein is a method of treating a symptom of a neuroendocrine diseases (or neuroendocrine dysfunction), comprising: intravenously administering to the subject a therapeutically effective amount of a neuroactive steroid (e.g., allopregnanolone), wherein administering occurs by continuous intravenous infusion. In some embodiments, the symptom is reduced at a magnitude or rate different from that observed in a subject without having received treatment.

In an aspect, provided herein is a method of increasing allopregnanolone levels in a subject (e.g., a subject with low levels of allopregnanolone as compared with a subject with normal levels of allopregnanolone), comprising: intravenously administering to the subject a therapeutically effective amount of a neuroactive steroid (e.g., allopregnanolone), wherein administering occurs by continuous intravenous infusion.

In an aspect, provided herein is a method of prophylactically treating a disease or disorder described herein (e.g., depression (e.g., postpartum depression) or an anxiety disorder) in a human subject (e.g., as described herein, e.g., a subject identified as a subject at risk of suffering from a disease or disorder as described herein), the method comprising administering a therapeutically effective amount of a neuroactive steroid.

In some embodiments, the subject is suffering from an anxiety disorder. In some embodiments, the subject is suffering from depression. In some embodiments, the subject is suffering from postpartum depression.

In some embodiments, the neuroactive steroid is pregnanolone, allopregnanolone, alphadalone, ganaxolone, or alphaxolone. In some embodiments, the neuroactive steroid is selected from pregnanolone, ganaxolone, alphadalone, alphaxalone, and allopregnanolone. In some embodiments, the neuroactive steroid is allopregnanolone. In some embodiments, the neuroactive steroid is deuterated allopregnanolone. In some embodiments, the neuroactive steroid is an estrol. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 and 8,759,330. In some embodiments, the subject is identified as being at risk of suffering from a disease or disorder as described herein In some embodiments, the subject has been identified as being at risk of depression (e.g., postpartum depression) or an anxiety disorder, for example by a method of evaluation as described herein. In some embodiments, the subject is identified based upon information related to therapeutic effect of a neuroactive steroid (e.g., allopregnanolone). In some embodiments, the information is measured by reduction in HAM-D, EPDS, CGI, or GAD-7. In some embodiments, the subject is in her third trimester of pregnancy. In some embodiments, the subject is suffering from perinatal depression. In some embodiments, the subject has reducded levels of allopregnanolone relative to a reference standard (e.g., relative to the level of allopregnanolone in a subject does not later suffer from depression (e.g., postpartum depression, perinatal depression).

In an aspect, the neuroactive steroid is provided in a composition comprising a cyclodextrin, e.g., β-cyclodextrin, e.g., sulfo butyl ether β-cyclodextrin, e.g., CAPTISOL. In some embodiments, the neuroactive steroid is provided at a concentration of 0.1 to 10 mg/mL neuroactive steroid. In some embodiments, the neuroactive steroid is provided at a concentration of 0.1, 0.5, 1, 1.25, 2.5, 3.75, 5, 6.25, 7.5, 8, 9, or 10 mg/mL neuroactive steroid. In some embodiments, the neuroactive steroid is provided at a concentration of 1.25 mg/mL neuroactive steroid. In some embodiments, the neuroactive steroid is provided at a concentration of 2.5 mg/mL neuroactive steroid. In some embodiments, the neuroactive steroid is provided at a concentration of 3.75 mg/mL neuroactive steroid. In some embodiments, the neuroactive steroid is provided at a concentration of 5 mg/mL neuroactive steroid. In some embodiments, the cyclodextrin is present in the composition at 1-30%, 2-18%, 10-15% by weight of cyclodextrin per volume of composition. In some embodiments, the cyclodextrin is present in the composition at 1, 2.5, 5, 10, 12, 13, 15, 30% by weight of cyclodextrin per volume of composition. In some embodiments, the cyclodextrin is present in the composition at 12% by weight of cyclodextrin per volume of composition. In some embodiments, the cyclodextrin is present in the composition at 1-30%, 2-18%, 10-15% by weight of cyclodextrin per volume of composition and the neuroactive steroid is provided at a concentration of 0.1, 0.5, 1, 1.25, 2.5, 3.75, 5, 6.25, 7.5, 8, 9, or 10 mg/mL neuroactive steroid. In some embodiments, the cyclodextrin is present in the composition at 1, 2.5, 5, 10, 12, 13, 15, 30% by weight of cyclodextrin per volume of composition and the neuroactive steroid is provided at a concentration of 0.1, 0.5, 1, 1.25, 2.5, 3.75, 5, 6.25, 7.5, 8, 9, or 10 mg/mL neuroactive steroid. In some embodiments, the cyclodextrin is present in the composition at 12% by weight of cyclodextrin per volume of composition and the neuroactive steroid is provided at a concentration of 5 mg/mL neuroactive steroid. In some embodiments, the cyclodextrin is present in the composition at 12% by weight of cyclodextrin per volume of composition and the neuroactive steroid is provided at a concentration of 3.75 mg/mL neuroactive steroid. In some embodiments, the cyclodextrin is present in the composition at 12% by weight of cyclodextrin per volume of composition and the neuroactive steroid is provided at a concentration of 2.5 mg/mL neuroactive steroid. In some embodiments, the cyclodextrin is present in the composition at 12% by weight of cyclodextrin per volume of composition and the neuroactive steroid is provided at a concentration of 1.25 mg/mL neuroactive steroid.

In another aspect, the disclosure features a composition, the composition comprising a neuroactive steroid, e.g., pregnanolone, allopregnanolone, alphadalone, ganaxolone, or alphaxolone; and cyclodextrin, e.g., a neuroactive steroid, e.g., pregnanolone, allopregnanolone, alphadalone, ganaxolone, or alphaxolone; and optionally a cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, complex. a β-cyclodextrin, e.g., a sulfo butyl ether β-cyclodextrin, e.g., a β-cyclodextrin, e.g., a sulfo butyl ether β-cyclodextrin, e.g., CAPTISOL®, complex.

In some embodiments, the neuroactive steroid is a progestin derivative, e.g., pregnanolone, allopregnanolone, alphadalone, ganaxolone, or alphaxolone. In an embodiment, the neuroactive steroid is allopregnanolone. In an embodiment, the neuroactive steroid is ganaxolone. In an embodiment, the neuroactive steroid is alphaxolone. In some embodiments, the neuroactive steroid is selected from neuroactive steroids that are disclosed in WIPO Publication Nos. WO2013/188792, WO 2013/056181. WO2015/010054, WO2014/169832, WO2014/169836, WO2014/169833, WO2014/169831, WO2015/027227, WO 2014/100228, U.S. Pat. Nos. 5,232,917, 8,575,375 and 8,759,330.

In some embodiments, the cyclodextrin is a β-cyclodextrin. In an embodiment, the cyclodextrin is a sulfo butyl ether β-cyclodextrin, e.g., CAPTISOL®. In some embodiments, the cyclodextrin is a β-cyclodextrin disclosed in U.S. Pat. Nos. 5,874,418: 6,046,177; or 7,635,733, which are herein incorporated by reference.

In some embodiments, the neuroactive steroid is a progestin derivative, e.g., allopregnanolone, and the cyclodextrin is a β-cyclodextrin. In an embodiment, the neuroactive steroid is allopregnanolone and the cyclodextrin is sulfo butyl ether β-cyclodextrin, e.g., CAPTISOL®.

In some embodiments, the neuroactive steroid is ganaxolone, and the cyclodextrin is a β-cyclodextrin. In an embodiment, the neuroactive steroid is ganaxolone and the cyclodextrin is sulfo butyl ether β-cyclodextrin, e.g., CAPTISOL®.

In some embodiments, the neuroactive steroid is alphaxolone, and the cyclodextrin is a β-cyclodextrin. In an embodiment, the neuroactive steroid is alphaxolone and the cyclodextrin is sulfo butyl ether β-cyclodextrin, e.g., CAPTISOL®.

In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated for parenteral administration. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition. In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL. In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 1.5 mg/mL.

In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 5 mg/mL. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid at a concentration of 15 mg/mL.

In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the cyclodextrin, e.g., a β-cyclodextrin, e.g., a sulfo butyl ether β-cyclodextrin, e.g., CAPTISOL®, at a concentration of 60 mg/ml. In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising 6% of the cyclodextrin. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising 15% of the cyclodextrin. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising 30% of the cyclodextrin.

In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and the cyclodextrin, e.g., a β-cyclodextrin, e.g., a sulfo butyl ether β-cyclodextrin, e.g., CAPTISOL®, at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and the cyclodextrin, e.g., a β-cyclodextrin, e.g., a sulfo butyl ether β-cyclodextrin, e.g., CAPTISOL®, at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL.

In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration between 0.25-30 mg/mL, 0.5-30 mg/mL; 1-30 mg/mL; 5-30 mg/mL, 10-30 mg/mL; 15-30 mg/mL, 0.25-20 mg/mL; 0.5-20 mg/mL; 1-20 mg/mL, 0.5-20 mg/mL; 1-20 mg/mL, 5-20 mg/mL, 10-20 mg/mL, 0.25-15 mg/mL, 0.5-15 mg/mL; 0.5-10 mg/mL; 1-15 mg/mL, 1-10 mg/mL; 1-5 mg/mL; 5-15 mg/mL; 5-10 mg/mL; 10-15 mg/mL; 1-10 mg/mL; 2-8 mg/mL; 2-7 mg/mL; 3-5 mg/mL; 5-15 mg/mL; 7-12 mg/mL; 7-10 mg/mL; 8-9 mg/mL; 3-5 mg/mL; or 3-4 mg/mL; and 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®.

In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and the cyclodextrin, e.g., a β-cyclodextrin, e.g., a sulfo butyl ether β-cyclodextrin, e.g., CAPTISOL®; at a concentration between 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 30-100 mg/mL; 45-75 mg/mL; 50-70 mg/mL; 55-65 mg/mL; or 50-60 mg/mL. In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 0.25 mg/mL; 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and the cyclodextrin, e.g., CAPTISOL® at a concentration of 25 mg/mL; 30 mg/mL; 35 mg/mL; 40 mg/mL; 45 mg/mL; 50 mg/mL; 55 mg/mL; 60 mg/mL; 65 mg/mL; 70 mg/mL; 75 mg/mL; 80 mg/mL; 85 mg/mL; 90 mg/mL, 95 mg/mL; 100 mg/mL; 150 mg/mL; 200 mg/mL; 250 mg/mL; 300 mg/mL; 350 mg/mL; or 400 mg/mL.

In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and between 2.5-40%, 2.5-30%, 2.5-20%, 2.5-10%, 5-40%, 5-30%, 5-20%, 5-10%, 6-40%, 6-30%, 6-20%, 6-10%, 10-40%, 10-30%, 10-20%, 20-40%, 20-30%, 25-40%, 25-30%, 3-10%, 4.5-7.5%, 5-7%, 5.5-6.5% of the cyclodextrin, e.g., CAPTISOL®. In some embodiments, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 0.25 mg/mL, 0.5 mg/mL; 1.0 mg/mL; 1.5 mg/mL; 2.0 mg/mL; 2.5 mg/mL; 3.0 mg/mL; 3.5 mg/mL; 4.0 mg/mL; 4.5 mg/mL; 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, 20 mg/mL, 25 mg·mL, or 30 mg/mL; and 2.5%, 3%, 4%, 4.5%, 5%, 5.5%, 6%, 6.5%, 7%, 7.5%, 8%, 8.5%, 9%, 9.5%, 10%, 15%, 20%, 25%, 30%, 35% or 40% of the cyclodextrin, e.g., CAPTISOL®.

In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 1.5 mg/mL, and the cyclodextrin, e.g., a β-cyclodextrin, e.g., a sulfo butyl ether β-cyclodextrin, e.g., CAPTISOL®, at a concentration of 6%. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 10 mg/mL, and the cyclodextrin, e.g., a β-cyclodextrin, e.g., a sulfo butyl ether β-cyclodextrin, e.g., CAPTISOL®, at a concentration of 6%. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 15 mg/mL, and the cyclodextrin, e.g., a β-cyclodextrin, e.g., a sulfo butyl ether β-cyclodextrin, e.g., CAPTISOL®, at a concentration of 6%.

In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 1.5 mg/mL, and the cyclodextrin, e.g., a β-cyclodextrin, e.g., a sulfo butyl ether β-cyclodextrin, e.g., CAPTISOL®, at a concentration of 15%. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 10 mg/mL, and the cyclodextrin, e.g., a β-cyclodextrin, e.g., a sulfo butyl ether β-cyclodextrin, e.g., CAPTISOL®, at a concentration of 15%. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 15 mg/mL, and the cyclodextrin, e.g., a β-cyclodextrin, e.g., a sulfo butyl ether β-cyclodextrin, e.g., CAPTISOL®, at a concentration of 15%.

In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 1.5 mg/mL, and the cyclodextrin, e.g., a β-cyclodextrin, e.g., a sulfo butyl ether β-cyclodextrin, e.g., CAPTISOL®, at a concentration of 30%. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 10 mg/mL, and the cyclodextrin, e.g., a β-cyclodextrin, e.g., a sulfo butyl ether β-cyclodextrin, e.g., CAPTISOL®, at a concentration of 30%. In an embodiment, the neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., CAPTISOL®, complex is formulated as an aqueous composition comprising the neuroactive steroid, e.g., pregnanolone, allopregnanolone, alphadalone, ganaxolone, alphaxolone; at a concentration of 15 mg/mL, and the cyclodextrin, e.g., a β-cyclodextrin, e.g., a sulfo butyl ether β-cyclodextrin, e.g., CAPTISOL®, at a concentration of 30%.

In some embodiments, the pregnanolone, allopregnanolone, alphadalone, ganaxolone, alphaxolone; and CAPTISOL® complex is formulated as an aqueous composition with a pH between 3-10, 4-9, 4-8, 4-7, 4-6, 4-5, 5-9, 5-8, 5-7, 5-6, 4.5-7.5, or 5.5-7.5. In some embodiments, the pregnanolone, allopregnanolone, alphadalone, ganaxolone, alphaxolone; and CAPTISOL® complex is formulated as an aqueous composition with a pH about 3, 3.5, 4, 4.5, 5, 5.5, 6, 6.5, 7, 7.5, 8, 8.5, or 9. In an embodiment, the pregnanolone, allopregnanolone, alphadalone, ganaxolone, alphaxolone; and CAPTISOL® complex is formulated as an aqueous composition with a pH about 6.

In one aspect, the disclosure features a composition, the composition comprising a neuroactive steroid, e.g., pregnanolone, allopregnanolone, alphadalone, ganaxolone, alphaxolone; and cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, complex, wherein the composition comprises less than 100 ppm of a phosphate, and the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a drug-degrading agent, as determined by UV/vis spectrophotometry at a wavelength of 245 nm to 270 nm for an aqueous solution comprising 300 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a color forming agent, as determined by UV/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 20 ppm of a sulfoalkylating agent: less than 0.5% wt. of an underivatized cyclodextrin: less than 1% wt. of an alkali metal halide salt; and less than 0.25% wt. of a hydrolyzed sulfoalkylating agent.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to a drug-degrading agent, as determined by UV/vis spectrophotometry at a wavelength of 245 nm to 270 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises less than 50 ppm of a phosphate: less than 10 ppm of a sulfoalkylating agent: less than 0.2% wt. of an underivatized cyclodextrin: less than 0.5% wt. of an alkali metal halide salt; and less than 0.1% wt. of a hydrolyzed sulfoalkylating agent; and wherein the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.2 A.U. due to the color-forming agent, as determined by U/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 10 ppm of a phosphate: less than 2 ppm of a sulfoalkylating agent: less than 0.1% wt. of an underivatized cyclodextrin: less than 0.2% wt. of an alkali metal halide salt; and less than 0.08% wt. of a hydrolyzed sulfoalkylating agent; and wherein the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, has an absorption of less than 0.1 A.U. due to the color-forming agent, as determined by UV/vis spectrophotometry at a wavelength of 320 nm to 350 nm for an aqueous solution comprising 500 mg of the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, per mL of solution in a cell having a 1 cm path length.

In some embodiments, the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, further comprises: less than 5 ppm of a phosphate: less than 0.1% wt. of an alkali metal halide salt; and less than 0.05% wt. of a hydrolyzed sulfoalkylating agent.

In some embodiments, the pregnanolone, allopregnanolone, alphadalone, ganaxolone, alphaxolone; and the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, is formulated as an aqueous composition with a pH between 3-10, 4-9, 4-8, 4-7, 4-6, 4-5, 5-9, 5-8, 5-7, 5-6, 4.5-7.5, or 5.5-7.5. In some embodiments, the pregnanolone, allopregnanolone, alphadalone, ganaxolone, alphaxolone; and the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, is formulated as an aqueous composition with a pH about 3, 3.5, 4, 4.5, 5, 5.5, 6, 6.5, 7, 7.5, 8, 8.5, or 9. In an embodiment, the pregnanolone, allopregnanolone, alphadalone, ganaxolone, alphaxolone; and the cyclodextrin, e.g., a β-cyclodextrin, e.g., a sulfo butyl ether β-cyclodextrin, e.g., a β-cyclodextrin, e.g., a sulfo butyl ether β-cyclodextrin, e.g., CAPTISOL®, is formulated as an aqueous composition with a pH about 6.

In an aspect, the disclosure features a kit comprising one or more of; a preparation of neuroactive steroid, e.g., a plurality of preparations of neuroactive steroid at concentrations suitable for use at the first, second, and third dosages; and instructions for use for treating a subject suffering from tremor (e.g., essential tremor).

In an aspect, the disclosure features a kit comprising one or more of; a preparation of neuroactive steroid, e.g., a plurality of preparations of neuroactive steroid at concentrations suitable for use at the first, second, and third infusions; and instructions for use for treating a subject suffering from depression (e.g., postpartum depression) or an anxiety disorder.

In some embodiments, the subject is suffering from an anxiety disorder. In some embodiments, the subject is suffering from depression. In some embodiments, the subject is suffering from postpartum depression.

In an aspect, the disclosure features a method of adjusting the amount of diluents and or neuroactive steroid flowing into or out of a delivery device, e.g., a catheter, reservoir, the method comprising altering, e.g., decreasing, the flow rate of neuroactive steroid flowing into the delivery device, so as to release in succession, two or more of a first dose, a second dose and one or more step doses of the third dose.

In some embodiments, the subject is suffering from an anxiety disorder. In some embodiments, the subject is suffering from depression. In some embodiments, the subject is suffering from postpartum depression.

Definitions

Chemical Definitions

Definitions of specific functional groups and chemical terms are described in more detail below. The chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; *Smith and March, March's Advanced Organic Chemistry,* $5^{th}$ Edition, John Wiley & Sons, Inc., New York, 2001: Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts: or preferred isomers can be prepared by asymmetric syntheses. See, for example, Jacques et al., *Enantiomers. Racemates and Resolutions* (Wiley Interscience, New York, 1981): Wilen et al., *Tetrahedron* 33:2725 (1977): Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, I N 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^1$H, $^2$H (D or deuterium), and $^3$H (T or tritium): C may be in any isotopic form, including $^{12}$C, $^{13}$C, and $^{14}$C: O may be in any isotopic form, including $^{16}$O and $^{18}$O; and the like.

The articles "a" and "an" may be used herein to refer to one or to more than one (i.e. at least one) of the grammatical objects of the article. By way of example "an analogue" means one analogue or more than one analogue.

As used herein, the term "modulation" refers to the inhibition or potentiation of GABA receptor function. A "modulator" (e.g., a modulator compound) may be, for example, an agonist, partial agonist, antagonist, or partial antagonist of the GABA receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like: or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, et al., *J. Pharm. Sci.* (1977) 66(1): 1-79.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of x electrons and an atom (usually H). For example, enols and ketones are tautomers because they are rapidly interconverted by treatment with either acid or base. Another example of tautomerism is the aci- and nitro- forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g. infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment")

As used herein, and unless otherwise specified, a "cycle of treatment" comprises administering a first dose of a neuroactive steroid, administering a second dose of the neuroactive steroid, and administering a third dose of the neuroactive steroid, said neuroactive steroid doses being sufficient to treat said subject.

In general, the "effective amount" of a compound refers to an amount sufficient to elicit the desired biological response, e.g., to treat a CNS-related disorder, e.g., a disorder as described herein (e.g., tremor (e.g., essential tremor); depression (e.g., postpartum depression); or an anxiety disorder). As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

BRIEF DESCRIPTION OF THE FIGURES

FIG. 4 depicts the dosing regimen for the clinical trial for the study of the use of allopregnanolone in postpartum depression.

DETAILED DESCRIPTION OF CERTAIN EMBODIMENTS OF THE INVENTION

Methods of Use and Treatment

Figure 1:
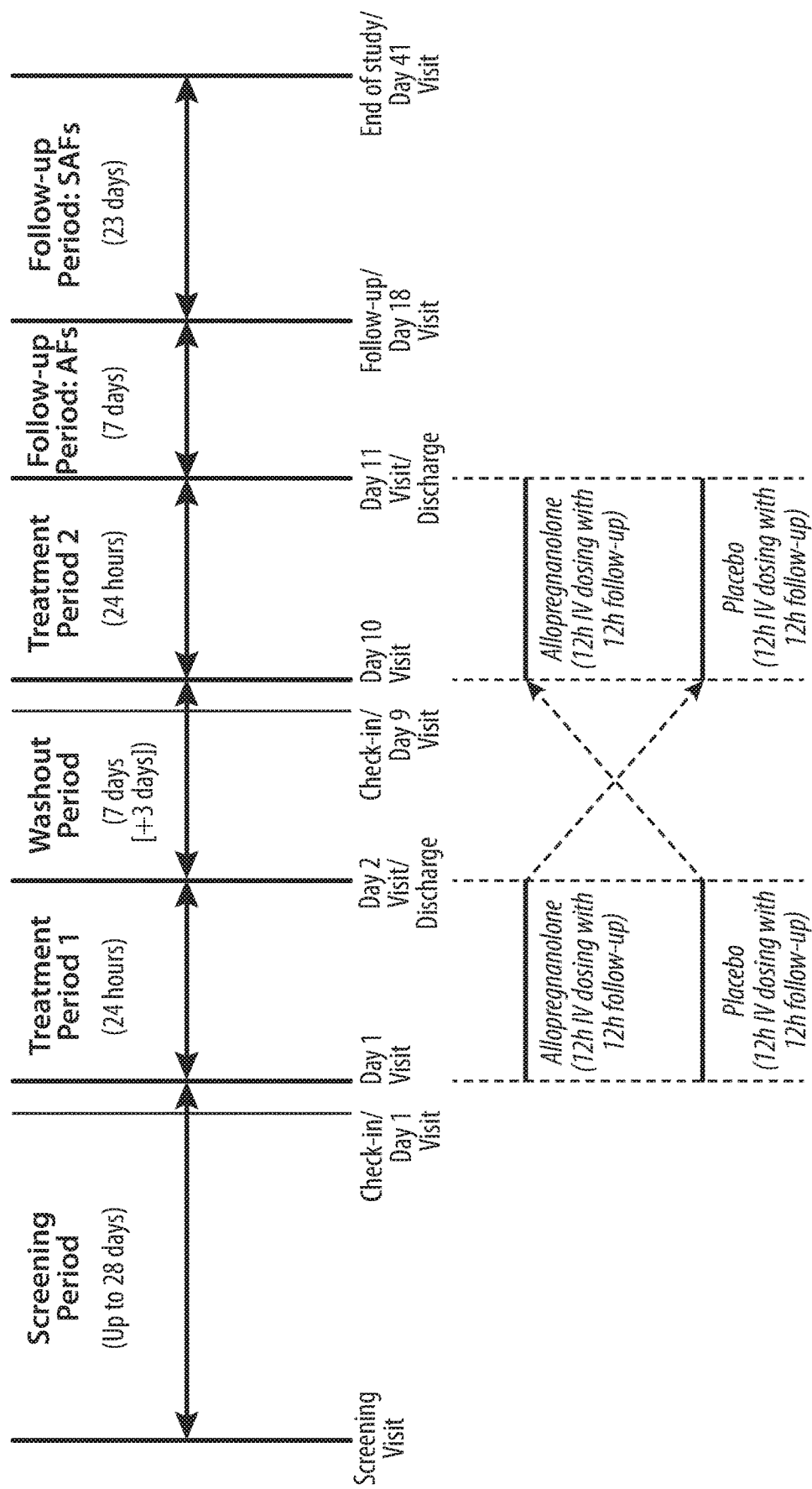
FIG. 1 depicts the clinical trial design for the study of the use of allopregnanolone for treatment of essential tremor.
Figure 2:
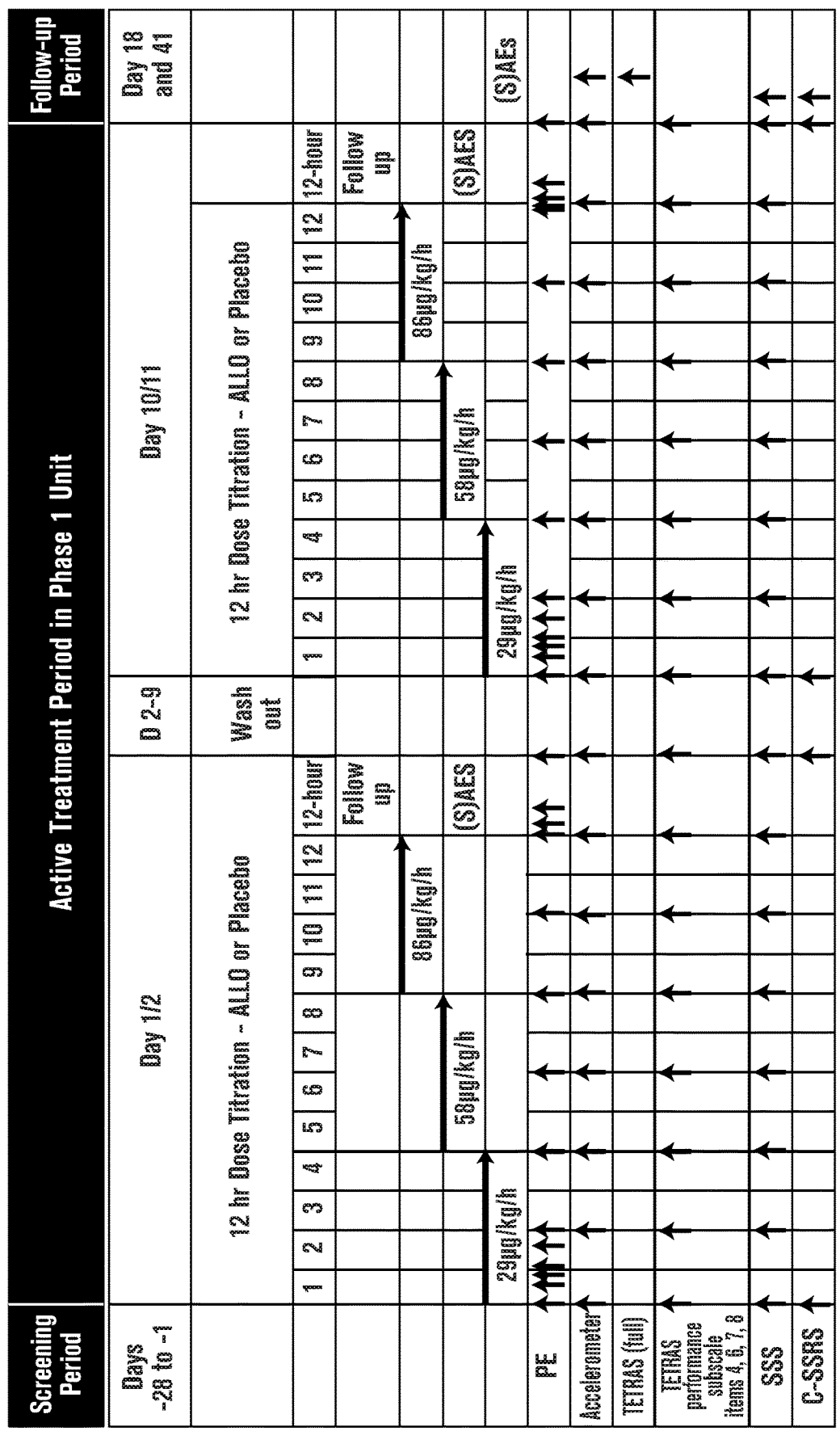
FIG. 2 depicts the dosing regimen for the clinical trial for the study of the use of allopregnanolone in essential tremor.
Figure 3:
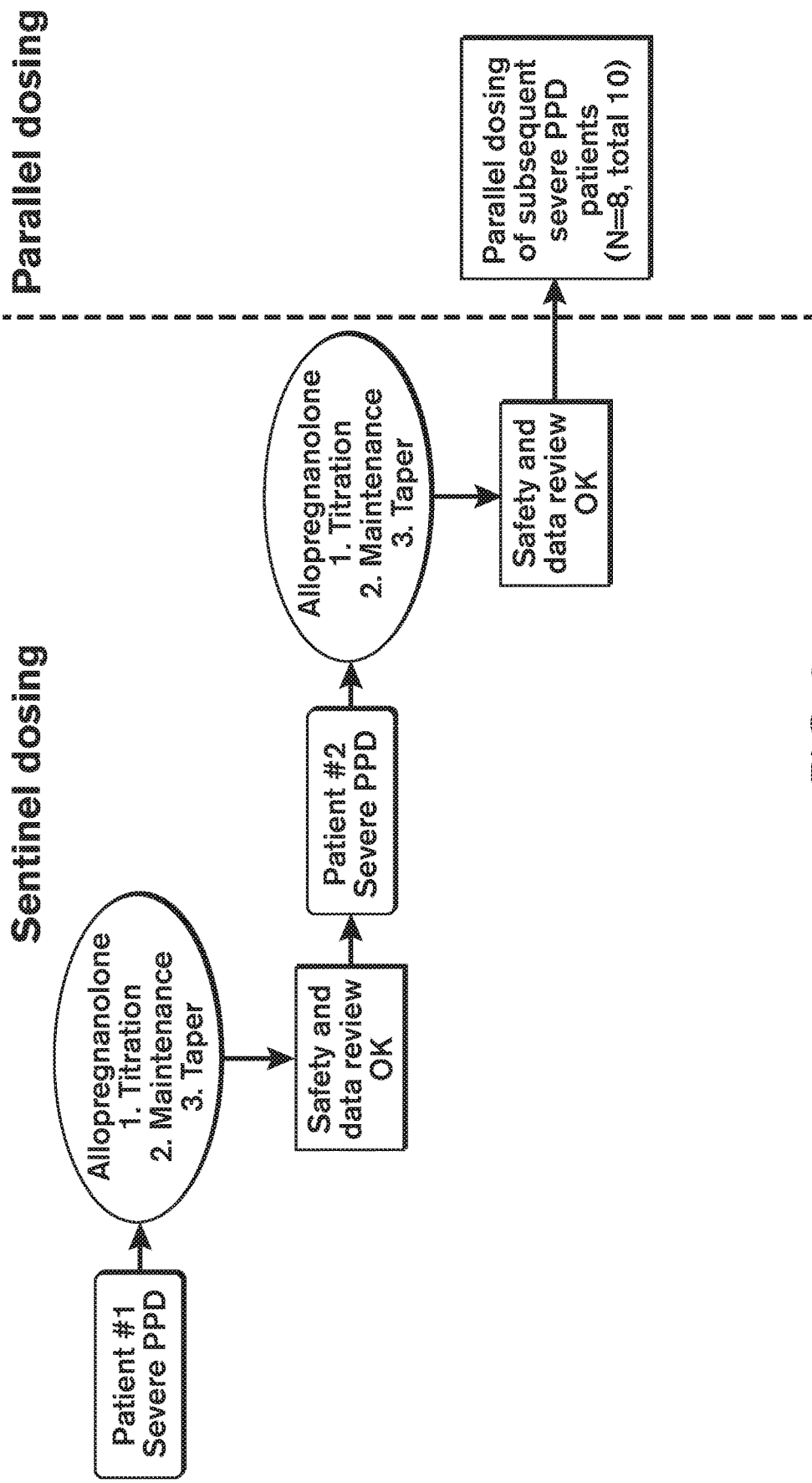
FIG. 3 depicts the study design for the study of the use of allopregnanolone in postpartum depression.

As generally described herein, the present invention is directed to neuroactive steroids that may act, for example, as GABA modulators. In certain embodiments, such compounds are envisioned to be useful as therapeutic agents for treating a disorder described herein, e.g., tremor (e.g., essential tremor): depression (e.g., postpartum depression); an anxiety disorder, comprising administering to the subject an effective amount of a compound of the present invention or a composition thereof. In certain embodiments, the compound is administered by intravenous administration.

Earlier studies (sec, e.g., Gee et al., *European Journal of Pharmacology*, 136:419-423 (1987)) demonstrated that certain 3α-hydroxylated steroids are orders of magnitude more potent as modulators of the GABA receptor complex (GRC) than others had reported (see, e.g., Majewska et al., *Science* 232: 1004-1007 (1986): Harrison et al., *J Pharmacol. Exp. Ther.* 241:346-353 (1987)). Majewska et al, and Harrison et al, taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (sec, e.g., Gee et al., *European Journal of Pharmacology*, 136:419-423 (1987); Wieland et al., *Psychopharmacology* 118(1):65-71 (1995)).

In some embodiments, a compound disclosed herein, for example, a neuroactive steroid described herein such as allopregnanolone, can be administered as a hormone or steroid replacement therapy in a subject. In an embodiment, a subject described herein has experienced a decrease in a steroid or hormone level prior to treatment with a compound described herein. For example, a subject generally experiences a decrease in allopregnanolone subsequent to delivery of an infant. In an embodiment, a subject can be administered a compound described herein (e.g., allopregnanolone) after experiencing a decrease in steroid or hormone level. In an embodiment, the decrease in hormone or steroid level is at least by a factor of 2 (e.g., at least a factor of 3, 4, 5, 10 or 100).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (sec, e.g., Gee, K. W. and Yamamura, H. I., "Benzodiazepines and Barbiturates: Drugs for the Treatment of Anxiety, Insomnia and Seizure Disorders," in *Central Nervous System Disorders*, Horvell, ed., Marcel-Dekker, New York (1985), pp. 123-147: Lloyd, K. G, and Morselli, P. L., "Psychopharmacology of GABAergic Drugs," in *Psychopharmacology: The Third Generation of Progress*, H. Y. Meltzer, ed., Raven Press, N.Y. (1987), pp. 183-195; and Gee et al., *European Journal of Pharmacology*, 136:419-423 (1987). These compounds are desirable for their duration, potency, and oral activity (along with other forms of administration).

Compounds of the present invention, as described herein, can modulate GABA function, and therefore can act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

Exemplary CNS conditions related to GABA-modulation include, but are not limited to, sleep disorders [e.g., insomnia], mood disorders [e.g., depression such as PND or perinatal depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing tremor in a subject, comprising administering to the subject in need of such treatment an effective amount of a compound of the present invention. In certain embodiments the tremor is essential tremor.

In yet another aspect, provided is a method of treating or preventing mood disorders in a subject, comprising administering to the subject in need of such treatment an effective amount of a compound of the present invention. In certain embodiments the mood disorder is depression. In some embodiments, the mood disorder is postpartum depression.

In yet another aspect, provided is a method of alleviating or preventing PMS, PND or perinatal depression in a subject, comprising administering to the subject in need of such treatment an effective amount of a compound of the present invention.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In an embodiment, the method includes acute treatment of a disorder described herein. For example, in an embodiment, a method described herein provides relief from a symptom described herein in less than 1 week (e.g., within 6 days, 5 days, 4 days, 3 days, 2 days, 1 day, or 12 hours). In an embodiment, the subject experiences, upon administration of a compound described herein (e.g., allopregnanolone) rapid onset of efficacy of the compound. For example, in an embodiment, a subject experiences relief from a symptom of a disorder described herein within 1 week (e.g., within 6 days, 5 days, 4 days, 3 days, 2 days, 1 day, or 12 hours).

In an embodiment, a method described herein provides for sustained efficacy upon treatment with a compound described herein. For example, in an embodiment, a subject is treated with a compound described herein, wherein the treatment effectively treats a symptom of a disorder described herein and the efficacy is maintained for at least 1 day (e.g., at least 2 days, 3 days, 4 days, 5 days, 6 days, 1 week, 2 weeks, 3 weeks, 1 month, 2 months, 3 months, 4 months, 5 months, or 6 months). In an embodiment, the efficacy is maintained after a single course of treatment of a compound described herein (e.g., allopregnanolone). Course of treatment, as described herein is a treatment regimen administered to a subject so as to provide efficacy of a symptom of a disorder to the subject. In an embodiment, a course of treatment is a single dose. In another embodiment, a course of treatment includes multiple doses of a compound described herein. In another embodiment, a course of treatment includes a cycle of treatment of a compound described herein.

In an embodiment, a method described herein can include a course of treatment with multiple dosages or cycles of treatment, for example, where a first dose or cycle of treatment is a parenteral dose such as an i.v. dose, and a second dose or cycle of treatment is an oral dose. In an embodiment, the first and second dose or cycle of treatment include the same compound described herein. In another embodiment, the first dose or cycle of treatment includes a first compound (e.g., a first compound described herein such as allopregnanolone) and the second dose or cycle of treatment includes a second compound that is different from the first compound.

In an embodiment, a method described herein provides effective treatment without causing a severe adverse event. In an embodiment, a method described herein provides effective treatment without causing a moderate or severe adverse event. In an embodiment, a method described herein provides effective treatment without causing an adverse event.

In certain embodiments, the compound is administered to the subject chronically. In certain embodiments, the compound is administered to the subject orally, subcutaneously, intramuscularly, or intravenously.

Neuroendocrine Disorders and Dysfunction

Provided herein are methods that can be used for treating neuroendocrine disorders and dysfunction. As used herein, "neuroendocrine disorder" or "neuroendocrine dysfunction" refers to a variety of conditions caused by imbalances in the body's hormone production directly related to the brain. Neuroendocrine disorders involve interactions between the nervous system and the endocrine system. Because the hypothalamus and the pituitary gland are two areas of the brain that regulate the production of hormones, damage to the hypothalamus or pituitary gland, e.g., by traumatic brain injury, may impact the production of hormones and other neuroendocrine functions of the brain.

Symptoms of neuroendocrine disorder include, but are not limited to, behavioral, emotional, and sleep-related symptoms, symptoms related to reproductive function, and somatic symptoms: including but not limited to fatigue, poor memory, anxiety, depression, weight gain or loss, emotional lability, lack of concentration, attention difficulties, loss of lipido, infertility, amenorrhea, loss of muscle mass, increased belly body fat, low blood pressure, reduced heart rate, hair loss, anemia, constipation, cold intolerance, and dry skin.

Neurodegenerative Diseases and Disorders

The methods described herein can be used for treating neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye: neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease: seizure: status epilecticus: stroke: tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

Tremor

The methods described herein can be used to treat tremor, for example cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively: metabolic diseases (e.g., thyoid-parathyroid-, liver disease and hypoglycemia): peripheral neuropathies (associated with Charcot-Marie-Tooth, Roussy-Levy, diabetes mellitus, complex regional pain syndrome): toxins (nicotine, mercury, lead, CO, Manganese, arsenic, toluene): drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawl, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myloclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part. Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormalitiy in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Mood Disorders

Also provided herein are methods for treating a mood disorder, for example clinical depression, postnatal depression or postpartum depression, perinatal depression, atypical depression, melancholic depression, psychotic major depression, cataonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior.

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during preganancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequnces. The need for sleep is usually reduced. During periods of depression there may be crying, poor eye contact with others, and a negative outlook on life. The risk of suicide among those with the disorder is high at greater than 6% over 20 years, while self harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or physchological counseling (psychotherapy) do not case depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants. MAOIs. SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

Anxiety Disorders

Provided herein are methods for treating anxiety disorders. Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical: for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Neuroactive Steroids

Neuroactive steroids (or neurosteroids) are natural, synthetic, or semi-synthetic steroids that rapidly alter neuronal excitability through interaction with neurotransmitter-gated ion channels. Neuroactive steroids effect binding to membrane-bound receptors such as those for inhibitory and (or) excitatory neurotransmitters including $GABA_A$, NMDA, and sigma receptors.

The steroids that may be classified into functional groups according to chemical structure and physiological activity and include estrogenic hormones, progestational hormones, and androgenic hormones. Of particular interest are progestational hormones, referred to herein as "progestins" or "progestogens", and their derivatives and bioactive metabolites. Members of this broad family include steroid hormones disclosed in Remington's Pharmaceutical Sciences, Gennaro et al., Mack Publishing Co. (18th ed. 1990), 990-993. As with all other classes of steroids, stereoisomerism is of fundamental importance with the sex hormones. As used herein, a variety of progestins (e.g., progesterone) and their derivatives, including both synthetic and natural products, can be used, as well as progestin metabolites such as progesterone.

The term "progesterone" as used herein refers to a member of the progestin family and includes a 21 carbon steroid hormone. Progesterone is also known as D4-pregnene-3,20-dione: 44-pregnene-3,20-dione: or pregn-4-ene-3,20-dione. As used herein a "synthetic progestin" is a molecule whose structure is related to that of progesterone, is synthetically derived, and retains the biological activity of progesterone.

Representative synthetic progestins include, but are not limited to, substitutions at the 17-position of the progesterone ring to introduce a hydroxyl, acetyl, hydroxyl acetyl, aliphatic, nitro, or heterocyclic group, modifications to produce 17α-OH esters (e.g., 17 α-hydroxyprogesterone caproate), as well as modifications that introduce 6-methyl, 6-ene, and 6-chloro substituents onto progesterone (e.g., medroxyprogesterone acetate, megestrol acetate, and chlomadinone acetate), and which retains the biological activity of progesterone. Such progestin derivatives include 5-dehydroprogesterone, 6-dehydro-retroprogesterone (dydrogesterone), allopregnanolone (allopregnan-3α, or 3β-ol-20-one), ethynodiol diacetate, hydroxyprogesterone caproate (pregn-4-ene-3,20-dione, 17-(1-oxohexy)oxy): levonorgestrel, norethindrone, norethindrone acetate (19-norpregn-4-en-20-yn-3-one. 17-(acetyloxy)-, (17a)-); norethynodrel, norgestrel, pregnenolone, ganaxolone (also referred to as CCD-1042 or INN), and megestrol acetate. In some embodiments, the neuroactive steroid is ganaxolone.

Useful progestins also can include allopregnone-3α or 3β, 20α or 20β-diol (see Merck Index 258-261); allopregnane-3β,21-diol-11,20-dione; allopregnane-3β,17α-diol-20-one: 3,20-allopregnanedione, allopregnane, 3β, 11β, 17α, 20β, 21-pentol; allopregnane-3β, 17α, 20β, 21-tetrol; allopregnane-3α or 3β, 11β, 17α, 21-tetrol-20-one, allopregnane-3β, 17α or 20β-triol; allopregnane-3β, 17α, 21-triol-11, 20-dione; allopregnane-3β, 11β, 21-triol-20-one; allopregnane-3β, 17α, 21-triol-20-one; allopregnane-3α or 3β-ol-20-one; pregnanediol; 3,20-pregnanedione: pregnan-3α-ol-20-one; 4-pregnene-20,21-diol-3,11-dione; 4-pregnene-11β, 17α, 20β, 21-tetrol-3-one; 4-pregnene-17α, 20β, 21-triol-3,11-dione; 4-pregnene-17α, 20β, 21-triol-3-one, and pregnenolone methyl ether. Further progestin derivatives include esters with non-toxic organic acids such as acetic acid, benzoic acid, maleic acid, malic acid, caproic acid, and citric acid and inorganic salts such as hydrochloride, sulfate, nitrate, bicarbonate and carbonate salts. Other suitable progestins include alphaxalone (also referred to as INN, alfaxolone, and alphaxolone), alphadolone (also referred to as alfadolone), hydroxydione, and minaxolone. In some embodiments, the neuroactive steroid is alphaxolone.

Additional suitable neuroactive steroids are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575, 375 and 8,759,330, which are incorporated herein by reference for the neuroactive steroids described therein.

In particular embodiments, the steroids are one or more of a series of sedative-hypnotic 3 alpha-hydroxy ring A-reduced pregnane steroids that include the major metabolites of progesterone and deoxycorticosterone, 3 alpha-hydroxy-5 alpha-pregnan-20-one (allopregnanolone) and 3 alpha, 21-dihydroxy-5 alpha-pregnan-20-one (allotetrahydroDOC), respectively. These 3 alpha-hydroxysteroids do not interact with classical intracellular steroid receptors but bind stereoselectively and with high affinity to receptors for the major inhibitory neurotransmitter in the brain, gamma-amino-butyric acid (GABA).

In certain embodiments, the neuroactive steroids are progesterone, pregnanolone, allopregnanolone, alphadalone, ganaxolone, or alphaxolone or other progesterone analogs. In a particular embodiment, the neuroactive steroid is allopregnanolone or a derivative thereof. In some embodiments, the neuroactive steroid is allopregnanolone. Exemplary derivatives include, but are not limited to, (20R)-17beta-(1-hydroxy-2,3-butadienyl)-5alpha-androstane-3alpha-ol (HBAO). Additional derivatives are described in WO 2012/127176.

In some embodiments, the neuroactive steroid is allopregnanolone. In some embodiments, the neuroactive steroid is ganaxolone. In some embodiments, the neuroactive steroid is alphaxolone.

As used herein, the neuroactive steroids described herein, e.g., "allopregnanolone," "ganaxolone," and "alphaxolone," also encompasses pharmaceutically acceptable, pharmacologically active derivatives including individual enantiomers (dextrogyral and levrogyral enantiomers) and their pharmaceutically acceptable salts, mixtures of enantiomers and their pharmaceutically acceptable salts, and active metabolites and their pharmaceutically acceptable salts, unless otherwise noted. It is understood that in some cases dosages of enantiomers, derivatives, and metabolites may need to be adjusted based on relative activity of the racemic mixture of the neuroactive steroid, e.g., pregnanolone, allopregnanolone, alphadalone, ganaxolone, or alphaxolone.

The lipophilic nature of the neuroactive steroid (e.g., pregnanolone, allopregnanolone, alphadalone, ganaxolone, or alphaxolone), can make it different to formulate for in vivo administration. As discussed above, the neuroactive steroid (e.g., pregnanolone, allopregnanolone, alphadalone, ganaxolone, or alphaxolone), can be formulated with a host, such as a cyclodextrin to improve the solubility. Alternatively, or additionally, the neuroactive steroid (e.g., pregnanolone, allopregnanolone, alphadalone, ganaxolone, or alphaxolone), can be modified in an attempt to improve the solubility. For example, polar groups can be introduced onto position 16α with the goal of increasing water solubility, brain accessibility, and potency of neuroactive steroids as described in Kasal et al., *J. Med. Chem.*, 52(7), 2119-215 (2009).

Solubilization of Neuroactive Steroids

Some neuroactive steroids possess limited aqueous solubility. In order to provide formulations capable of delivering therapeutically effective dosages, a variety of methods can be employed to enhance the solubility and bioavailability of neuroactive steroids. See, for example, "Water-Insoluble Drug Formulation", 2nd Edition, edited by Rong Liu (CRC Press, Boca Raton, F L, 2008). Using the techniques described below, a solubilized formulation of one or more neuroactive steroids can be prepared.

Inclusion Complexes

The solubility of neuroactive steroids can be improved by inclusion complexation (e.g., host-guest formulations). Inclusion complexes are formed when a nonpolar molecule (i.e., the guest, such as a drug with poor aqueous stability) or portion of a molecule inserts into a nonpolar cavity of another molecule or group of molecules (i.e., the host). If the host molecule or molecules exhibit water good solubility, the solubility of the host-guest complex will be greater than the solubility of the guest alone.

Inclusion complexes containing or comprising one or more neuroactive steroids can be formed using any suitable host molecule or molecules. For example, the water solubility of neuroactive steroids can be increased by inclusion complexation with cyclodextrins. Steroid-cyclodextrin complexes are known in the art. See, for example, U.S. Pat. No. 7,569,557 to Backensfeld, et al., and U.S. Patent Application Publication No. US 2006/0058262 to Zoppetti, et al.

Dextrans are soluble polysaccharides produced by bacteria and yeasts. They are characterized by a predominance (>95%) of a (1-6) backbone linkages and varying proportions of $\alpha$(1-2), $\alpha$(1-3) and $\alpha$(1-4) linkages typically at branch points 1, 2. Dextrins are partially hydrolyzed glucose homopolymers composed exclusively of $\alpha$(1-4) backbone linkages.

Cyclodextrins are cyclic oligosaccharides containing or comprising six ($\alpha$-cyclodextrin), seven ($\beta$-cyclodextrin), eight ($\gamma$-cyclodextrin), or more $\alpha$-(1,4)- linked glucose residues. The hydroxyl groups of the cyclodextrins are oriented to the outside of the ring while the glucosidic oxygen and two rings of the non-exchangeable hydrogen atoms are directed towards the interior of the cavity. As a result, cyclodextrins possess a hydrophobic inner cavity combined with a hydrophilic exterior which conveys water solubility. Upon combination with a hydrophobic drug, such as a neuroactive steroid, the neuroactive steroid (i.e., the guest) inserts into the hydrophobic interior of the cyclodextrin (i.e., the host). The host-guest complex retains water solubility as a consequence of the hydrophobic exterior of the cyclodextrin ring.

Neuroactive steroid-cyclodextrin complexes can, as solubility permits, be incorporated into any of the parenteral and non-parenteral formulations described below. If desired, the aqueous solubility of solid neuroactive steroid-cyclodextrin complexes can be further enhanced by isolating the neuoractive steroid-cyclodextrin complex as a solid via lyophilization and/or via micronizing the solid neuoractive steroid-cyclodextrin complex.

This cyclic orientation provides a truncated cone structure that is hydrophilic on the exterior and lipophilic on the interior. Cyclodextrin complexes are formed when a guest molecule is partially or fully contained in the interior of the cavity. The parent $\alpha$-, $\beta$-, and $\gamma$-cyclodextrins (particularly $\beta$) have limited aqueous solubility and show toxicity when given parenterally. Therefore, the parent cyclodextrin structure can be chemically modified to generate a parenterally safe CD-derivative. The modifications are typically made at one or more of the 2, 3, or 6 position hydroxyls.

Neuroactive steroid-cyclodextrin complexes are preferably formed from a cyclodextrin selected from the group consisting of $\alpha$-cyclodextrin, $\beta$-cyclodextrin, $\gamma$-cyclodextrin, and derivatives thereof. The cyclodextrin may be chemically modified such that some or all of the primary or secondary hydroxyl groups of the macrocycle, or both, are functionalized with a pendant group. Suitable pendant groups include, but are not limited to, sulfinyl, sulfonyl, phosphate, acyl, and $C_1$-$C_{12}$ alkyl groups optionally substituted with one or more (e.g., 1, 2, 3, or 4) hydroxy, carboxy, carbonyl, acyl, oxy, oxo: or a combination thereof. Methods of modifying these alcohol residues are known in the art, and many cyclodextrin derivatives are commercially available, including sulfo butyl ether $\beta$-cyclodextrins available under the trade name CAPTISOL®: from Ligand Pharmaceuticals (La Jolla, CA).

Examples of suitable cyclodextrins for use in neuroactive steroid, e.g., pregnanolone, allopregnanolone, alphadalone, ganaxolone, or alphaxolone formulations, can include cyclodextrins disclosed in U.S. Pat. Nos. 5,874,418; 6,046,177; and 7,635,733, which are herein incorporated by reference. Other examples of suitable cyclodextrins for use in neuroactive steroid formulations non-exclusively include $\alpha$-cyclodextrin; $\beta$-cyclodextrin; $\gamma$-cyclodextrin; methyl $\alpha$-cyclodextrin; methyl $\beta$-cyclodextrin; methyl $\gamma$-cyclodextrin; ethyl $\beta$-cyclodextrin; butyl $\alpha$-cyclodextrin; butyl $\beta$-cyclodextrin; butyl $\gamma$-cyclodextrin; pentyl $\gamma$-cyclodextrin; hydroxyethyl $\beta$-cyclodextrin; hydroxyethyl $\gamma$-cyclodextrin; 2-hydroxypropyl $\alpha$-cyclodextrin; 2-hydroxypropyl $\beta$-cyclodextrin; 2-hydroxypropyl $\gamma$-cyclodextrin; 2-hydroxy butyl $\beta$-cyclodextrin; acetyl $\alpha$-cyclodextrin; acetyl $\beta$-cyclodextrin; acetyl $\gamma$-cyclodextrin; propionyl $\beta$-cyclodextrin; butyryl $\beta$-cyclodextrin; succinyl $\alpha$-cyclodextrin; succinyl $\beta$-cyclodextrin; succinyl $\gamma$-cyclodextrin; benzoyl $\beta$-cyclodextrin; palmityl $\beta$-cyclodextrin; toluenesulfonyl $\beta$-cyclodextrin; acetyl methyl $\beta$-cyclodextrin; acetyl butyl $\beta$-cyclodextrin; glucosyl $\alpha$-cyclodextrin; glucosyl $\beta$-cyclodextrin; glucosyl $\gamma$-cyclodextrin; maltosyl $\alpha$-cyclodextrin; maltosyl $\beta$-cyclodextrin; maltosyl $\gamma$-cyclodextrin; $\alpha$-cyclodextrin carboxymethylether; $\beta$-cyclodextrin carboxymethylether; $\gamma$-cyclodextrin carboxymethylether; carboxymethylethyl $\beta$-cyclodextrin; phosphate ester $\alpha$-cyclodextrin; phosphate ester $\beta$-cyclodextrin; phosphate ester $\gamma$-cyclodextrin; 3-trimethylammonium-2-hydroxypropyl $\beta$-cyclodextrin; sulfobutyl ether $\beta$-cyclodextrin; carboxymethyl $\alpha$-cyclodextrin; carboxymethyl $\beta$-cyclodextrin; carboxymethyl $\gamma$-cyclodextrin, and combinations thereof.

Preferred cyclodextrins include, but are not limited to, alkyl cyclodextrins, hydroxy alkyl cyclodextrins, such as hydroxy propyl $\beta$-cyclodextrin, carboxy alkyl cyclodextrins and sulfoalkyl ether cyclodextrins, such as sulfo butyl ether $\beta$-cyclodextrin.

In particular embodiments, the cyclodextrin is a alpha, beta, or gamma cyclodextrin having a plurality of charges (e.g., negative or positive) on the surface. In more particular embodiments, the cyclodextrin is a $\beta$-cyclodextrin containing or comprising a plurality of functional groups that are negatively charged at physiological pH. Examples of such functional groups include, but are not limited to, carboxylic acid (carboxylate) groups, sulfonate ($RSO_3^-$), phosphonate groups, phosphinate groups, and amino acids that are negatively charged at physiological pH. The charged functional groups can be bound directly to the cyclodextrins or can be linked by a spacer, such as an alkylene chain. The number of carbon atoms in the alkylene chain can be varied, but is generally between about 1 and 10 carbons, preferably 1-6 carbons, more preferably 1-4 carbons. Highly sulfated cyclodextrins are described in U.S. Pat. No. 6,316,613.

In one embodiment, the cyclodextrins is a β-cyclodextrin functionalized with a plurality of sulfobutyl ether groups. Such a cyclodextrins is sold under the trade name CAPTISOL®.

CAPTISOL® is a polyanionic beta-cyclodextrin derivative with a sodium sulfonate salt separated from the lipophilic cavity by a butyl ether spacer group, or sulfobutylether (SBE). CAPTISOL® is not a single chemical species, but comprised of a multitude of polymeric structures of varying degrees of substitution and positional/regional isomers dictated and controlled to a uniform pattern by a patented manufacturing process consistently practiced and improved to control impurities.

CAPTISOL® contains six to seven sulfobutyl ether groups per cyclodextrin molecule. Because of the very low pKa of the sulfonic acid groups. CAPTISOL® carries multiple negative charges at physiologically compatible pH values. The four-carbon butyl chain coupled with repulsion of the end group negative charges allows for an "extension" of the cyclodextrin cavity. This often results in stronger binding to drug candidates than can be achieved using other modified cyclodextrins. It also provides a potential for ionic charge interactions between the cyclodextrin and a positively charged drug molecule. In addition, these derivatives impart exceptional solubility and parenteral safety to the molecule. Relative to beta-cyclodextrin, CAPTISOL® provides higher interaction characteristics and superior water solubility in excess of 100 grams/100 ml, a 50-fold improvement.

In other embodiments, the cyclodextrins has plurality of functional groups that are negatively charged at physiological pH. Suitable positively charged groups include, but are not limited to, quaternary ammonium groups. Exemplary cyclodextrins include, but are not limited to, mono-6(A)-butylammonium-6(A)-deoxy-beta-cyclodextrin tosylate (BuAM-beta-CD) and Amine- and guanidine-derivatised β-cyclodextrin (BCD).

Preferably, the cyclodextrin is present in an amount of from about 0.1% to about 40% w/w of the overall formulation, preferably from about 5% to about 40% w/w, more preferably about 10% to about 40% w/w, most preferably about 10% to about 35% w/w. In certain embodiments, the concentration of the cyclodextrins is from about 15% to about 35% w/w, preferably from about 20% to about 35% w/w, more preferably about 30% to about 35% w/w. In one embodiment, the formulation contains about 1 to about 2, preferably about 1.5 mg neuroactive steroid (e.g., pregnanolone, allopregnanolone, alphadalone, ganaxolone, alphaxolone) per ml of cyclodextrin, e.g., CAPTISOL®.

Pharmaceutical Compositions

In one aspect, the invention provides a pharmaceutical composition comprising a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions.

In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin: or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of the present invention can also be administered in sustained release forms or from sustained release drug delivery systems. A description of representative sustained release materials can be found in *Remington's Pharmaceutical Sciences.*

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* $21^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the composition comprises hexapropyl-β-cyclodextrin. In a more particular embodiment, the composition comprises hexapropyl-β-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ ed., Lippincott Williams & Wilkins, 2005.

Formulations for Administration, e.g., parenteral administration

The compounds (e.g., pregnanolone, allopregnanolone, alphadalone, ganaxolone, alphaxolone) described herein can be formulated for parenteral administration. Preferred doses, dosage forms, or modes of administration are parenteral, e.g., intranasally, buccally, intravenous, intramuscular, subcutaneous, intraparenteral, bucosal, sublingual, intraocular, and topical (e.g., intravenous or intramuscular). In another embodiment, the informational material can include instructions to administer the compound described herein to a suitable subject, e.g., a human, e.g., a human having or at risk for a disorder described herein. In some preferred embodiments, the neuroactive steroid is formulated for parenteral administration.

Parenteral formulations can be prepared as aqueous compositions using techniques known in the art. Typically, such compositions can be prepared as injectable formulations, for example, solutions or suspensions: solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

In some embodiments, the parenteral formulations are prepared as an injectable formulation, e.g., for intravenous administration. In some embodiments, the parenteral formulation comprises a compound (e.g., a neuroactive steroid as described herein, e.g., pregnanolone, allopregnanolone, alphadalone, ganaxolone, alphaxolone), and a cyclodextrin, e.g., a β-cyclodextrin, e.g., a sulfo butyl ether β-cyclodextrin, e.g., CAPTISOL®). In some embodiments, the parenteral formulation comprises pregnanolone, allopregnanolone, alphadalone, ganaxolone, or alphaxolone and a sulfo butyl ether β-cyclodextrin, e.g., CAPTISOL®.

The carrier can be a solvent or dispersion medium containing or comprising, for example, water (e.g., Water for Injection, USP), ethanol, one or more polyols (e.g., glycerol, propylene glycol, and liquid polyethylene glycol), oils, such as vegetable oils (e.g., peanut oil, corn oil, sesame oil, etc.), and combinations thereof.

The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing or comprising carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

The parenteral formulations described herein can be formulated for controlled release including immediate release, delayed release, extended release, pulsatile release, and combinations thereof.

Dosage and Pharmacokinetics

The compositions described herein include a therapeutically effective amount of a neuroactive steroid, such as pregnanolone, allopregnanolone, alphadalone, ganaxolone, or alphaxolone; and a cyclodextrin, e.g., a β-cyclodextrin, e.g., a sulfo butyl ether β-cyclodextrin, e.g., CAPTISOL®) provided in a dosage form suitable for parenteral administration. The compositions described herein include a therapeutically effective amount of a neuroactive steroid, such as pregnanolone, allopregnanolone, alphadalone, ganaxolone, or alphaxolone; and a cyclodextrin, e.g., a β-cyclodextrin, e.g., a sulfo butyl ether β-cyclodextrin, e.g., CAPTISOL®) provided in a dosage form suitable for oral administration. In some embodiments, the neuroactive steroid is allopregnanolone. In some embodiments, the neuroactive steroid is deuterated allopregnanolone. In some embodiments, the neuroactive steroid is an estrol. In some embodiments, the neuroactive steroid is selected from neuroactive steroids that are disclosed in WIPO Publication Nos. WO2013/188792, WO 2013/056181, WO2015/010054, WO2014/169832, WO2014/169836, WO2014/169833, WO2014/169831, WO2015/027227, WO 2014/100228, U.S. Pat. Nos. 5,232,917, 8,575,375 and 8,759,330.

Area under the curve (AUC) refers to the area under the curve that tracks the serum concentration (nmol/L) of neuroactive steroid over a given time following the IV administration of the reference neuroactive steroid standard. By "reference neuroactive steroid" is intended the formulation of neuroactive steroid that serves as the basis for determination of the total hourly neuroactive steroid dose to be administered to a human subject with tremor (e.g., essential tremor), depression (e.g., postpartum depression), or an anxiety disorder to achieve the desired positive effect, i.e., a positive therapeutic response that is improved with respect to that observed without administration of neuroactive steroid. In an embodiment, the dose of neuroactive steroid to be administered provides a final serum level of neuroactive steroid of about 100 ng/mL to about 1000 ng/ml, about 1100 ng/ml to about 1450 ng/ml, 100 ng/ml to about 250 ng/mL, about 200 ng/ml to about 350 ng/ml, about 300 ng/ml to about 450 ng/ml, about 350 ng/ml to about 450 ng/ml, about 400 ng/ml to about 550 ng/ml, about 500 ng/ml to about 650 ng/ml, about 600 ng/ml to about 750 ng/mL, about 700 ng/ml to about 850 ng/ml, about 800 ng/ml to about 950 ng/mL, about 900 ng/ml to about 1050 ng/mL, about 1000 ng/ml to about 1150 ng/mL, about 100 ng/mL to about 1250 ng/mL, about 1200 ng/ml to about 1350 ng/mL, about 1300 ng/ml to about 1500 ng/m. In specific embodiments, the serum level of neuroactive steroid is about 100 ng/ml, 250 ng/ml, 300 ng/ml, 350 ng/ml, 360 ng/ml, 370 ng/ml, 380 ng/ml, 390 ng/ml, 400 ng/ml, 410 ng/mL, 420 ng/mL, 430 ng/mL, 440 ng/mL, 450 ng/mL, 500 ng/ml, 750 ng/ml, 900 ng/ml, 1200 ng/ml, 1400 ng/ml, or 1600 ng/mL.

In an embodiment, the dose of neuroactive steroid to be administered provides a final serum level of neuroactive steroid of about 100 nmoles/L to about 5000 nmoles/L, about 100 nmoles/L to about 2500 nmoles/L, about 100 nmoles/L to about 1000 nmoles/L, 100 nmoles/L to about 500 nmoles/L, about 100 nmoles/L to about 250 nmoles/L, about 100 nmoles/L to about 200 nmoles/L, about 125 nmoles/L to about 175 nmoles/L. or about 140 nmoles/L to about 160 nmoles/L. In specific embodiments, the serum level of neuroactive steroid is about 100 nmoles/L, 125 nmoles/L, 150 nmoles/L, 175 nmoles/L, 200 nmoles/L, 250 nmoles/L, 300 nmoles/L, 350 nmoles/L, 500 nmoles/L, 750 nmoles/L, 1000 nmoles/L, 1500 nmoles/L, 2000 nmoles/L, 2500 nmoles/L, or 5000 nmoles/L.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

EXAMPLES

Materials and Methods

Allopregnanolone is provided to the clinical site as 2 types of kits: shelf packs containing multiple vials of allopregnanolone injection and ancillary supply kits containing IV administration bags, solution sets, and IV bag labels.

Allopregnanolone is provided as a preservative-free, sterile, clear, colorless 5 mg/mL solution of allopregnanolone and 250 mg/mL of beta sulfobutyl-ether sodium, NF (CAPTISOL) for IV injection. All inactive excipients used in the formulation are compendial grade and conform to current USP standards. The product is aseptically processed, sterile filtered, and filled into 20 mL Type 1 parenteral glass vials with coated stopper container closure systems. The product is intended to be used as single use vial and stored under refrigerated conditions (2 to 8° C.)before use. Each single use vial requires dilution with an appropriate volume of sterile water for injection to render it isotonic. The prepared admixture is delivered to the patient area and administered at room temperature. The prepared admixture will be assigned a room temperature (20 to 25° C.)storage shelf life of 24 hours from the time of compounding.

The placebo control, sterile normal saline (0.9% NaCl solution), is supplied in the manufacturer's original 150 mL pre-filled bags.

Example 1. Human Phase 1 Study of Allopregnanolone: A Double-Blind, Placebo-Controlled, Two-Period Crossover, Proof-of-Concept Study Evaluating the Safety, Tolerability, Pharmacokinetics, Efficacy of Allopregnanolone Injection in the Treatment of Patients with Essential Tremor Study Design A double-blind, proof-of-concept study designed to evaluate the safety, tolerability, PK, and efficacy of allopregnanolone injection in male or female patients with essential tremor in the upper limb. Each patient's involvement is up to 72 days, including up to a 28-day Screening Period, 12-hour Treatment Period 1 with 12-hour follow-up, 7-day (+/−3 days) Washout Period, 12-hour Treatment Period 2 with 12-hour follow-up, a 7-day Follow-up Visit (Day 18+/−1 day) plus an additional 23 days of SAE follow-up (with an End-of-Study visit via call on day 41). A representation of the Trial Design and activities is shown on FIG. 1.

Screening Period: As depicted in FIG. 1, the Screening Period begins begins on any one calendar day during the screening period window from Day −28 to Day −1. Patients undergo preliminary screening to determine eligibility, including completion of the full TETRAS questionnaire to establish severity of disease and upper limb tremor. The end of the Screening Period coincides with the beginning of the Treatment Period 1 in the Inpatient Unit.

Treatment Period 1 with 12-hour follow-up: Treatment Period I begins on Day 1 and ends on Day 2. Patients can be admitted the afternoon/evening before (check-in/Day −1 Visit) or on the morning of Day 1 (with enough time prior to initiation of dosing to complete all study procedures). Beginning on the morning of dosing (Day 1), patients will be randomized to receive either a 12-hour intravenous (IV) infusion of allopregnanolone (dose titrated up every 4 hours: 0-4 hrs 29 mg/kg/hr: 5-8 hrs 58 mg/kg/hr: 9-12 hrs 86 mg/kg/hr) or a 12-hour IV infusion of placebo. Patients will be admitted and confined to the Inpatient Unit from check-in/Day −1 or Day I through the end of the 12-hour follow-up period on Day 2.

During the 24-hour period, safety assessments, questionnaires and laboratory assessments will be performed, PK and blood samples will be collected, and outcome measures will be obtained at pre-specified times.

Washout Period: Patients will be discharged home for 7 full calendar days (+3 days) (Days 2 to 9 [+3 days]) to complete the Washout Period before returning to the clinic for the check-in/Day 9 Visit or Day 10 Visit.

Treatment Period 2 with 12-hour follow-up: Treatment Period 2 begins on Day 10 and ends on Day 11. Patients can be admitted the afternoon/evening before (check-in/Day 9 Visit) or on the morning of Day 10 (with enough time prior to initiation of dosing to complete all study procedures). Beginning on the morning of dosing (Day 10), patients will be randomized to receive either a 12-hour intravenous (IV) infusion of allopregnanolone (dose titrated up every 4 hours: 0-4 hrs 29 mg/kg/hr; 5-8 hrs 58 mg/kg/hr; 9-12 hrs 86 mg/kg/hr) or a 12-hour IV infusion of placebo. Patients will be admitted and confined to the Inpatient Unit from check-in through the end of the 12-hour follow-up period on Day 11.

During the 24-hour period, safety assessments, questionnaires and laboratory assessments will be performed, PK and blood samples will be collected, and outcome measures will be obtained at pre-specified times.

7-day Follow-up Visit: 7 days (+/−1 day) following completion of Treatment Period 2 (Day 18+/−1 day), or in the event a patient prematurely withdraws from the study, patients will return to the clinic for a follow-up visit for safety assessments and outcome measures.

End-of-study Visit: 30 days (+/−1 day) following completion of Treatment Period 2 (Day 41+/−1 day), or 30 days following premature withdrawal from the study, patients will be contact by phone for a safety follow-up assessment.

Administration

Investigational product will be provided as a preservative-free, sterile, clear, colorless 5 mg/mL solution of allopregnanolone and 250 mg/mL betadex sulfobutyl-ether sodium (e.g., CAPTISOL) intended for injection.

TABLE 1

Amount and Duration of Infusions

| Study Day | Duration of Infusion | Description |
| --- | --- | --- |
| Day 1 or 10 | 12-hour total infusion | |
| | 4 Hours | 29 µg/kg/hr |
| | 4 Hours | 58 µg/kg/hr |
| | 4 Hours | 86 µg/kg/hr |

Placebo will be provided at a rate equivalent to that of active (to maintain the blind).

Patients can be admitted to the inpatient unit on the afternoon/evening before the day of dosing and are confined during the two 24-hour Treatment and follow-up Periods 1 and 2. Allopregnanolone or placebo dosing will occur on Day 1 and Day 10 beginning at 8 am (+/−2 hours). Each infusion will be 12 hours in duration. The amount and duration of the doses administered is tabulated on Table 1.

Each patient's involvement is up to 72 days, including up to a 28-day Screening Period (the Screening Visit is one day of this 28-day window), 12-hours Treatment Period 1 with 12-hour follow-up, 7-day (+3 days) Washout Period, 12-hour Treatment Period 2 with 12-hour follow-up, a 7-day follow-up visit (Day 18+/−1 day) and an End-of Study visit consisting of safety follow-up via call (Day 41+/−1 day). Patients will be randomized to receive either allopregnanolone or placebo in Treatment Period 1. Those patients who receive allopregnanolone in Treatment Period I will cross over to receive placebo in Treatment Period 2. Those patients who receive placebo in Treatment Period I will cross over to receive allopregnanolone in Treatment Period 2.

Diagnosis and Main Criteria for Inclusion

Adult male or female patients between 35 and 75 years of age (inclusive) at the Screening Visit who have a diagnosis of essential tremor, with symptoms clearly present in at least 1 upper limb, who have signed an ICF and meet the follow main inlusion criteria are eligible for enrollment; a TETRAS Performance Subscale score of ≥2 for at least one maneuver (forward horizontal reach posture, lateral "wing beating" posture, or finger-nose-finger testing) in the 'upper limb tremor' test: tremor present for at least 2 years prior to the Screening Visit: is off medication, or on a stable dose of medication for their tremor for at least 28 days prior to the Screening Visit (with the exception of prohibited medications per protocol): is willing to consent to both IV placebo and allopregnanolone for 2 periods of 12 hours each, and is willing to washout of or delay of start of prohibited medications and any new pharmacotherapy regimens until after completing the 7-day follow-up visit.

24 patients will be enrolled at one center to achieve 16 evaluable patients. Patients evaluable for safety are defined as patients who have initiated the IV infusion during Treatment Period 1. Patients evaluable for efficacy are defined as patients who have completed the IV infusion during Treatment Period 1.

Exclusion Criteria

Patients will be excluded if they meet any of the following exclusion criteria prior to enrollment:

1) Patient has recent history or active clinically significant manifestations of metabolic; hepatic; renal; hematoglogical; pulmonary; cardiovascular; gastrointestinal; musculoskeletal; dermatological; urogenital; eyes, ears, nose, or throat; psychiatric; or neurological (other than essential tremor) disorders.
2) Patient has an acute or chronic condition that would limit the patient's ability to complete or participate in the clinical study.
3) Patient has a known allergy to progesterone, allopregnanolone, or sulfobutyl ether cyclodextrin.
4) Patient has a medical history of seizures.
5) Patient has a current history of active alcoholism or drug addiction (including benzodiazepines) at the time of the Screening Visit or during the year before the Screening Visit.
6) Patient has been exposed to another investigational medication or device within 30 days.

Concomitant Medications and Restrictions

Patients will receive the Inpatient Unit standard of care for patients diagnosed with essential tremor. Any concomitant medication determined necessary for the welfare of the patient may be given at the discretion of the Investigator at any time during the study under the guidance outlined. All concomitant medications should be documented throughout the study from Screening through the end of study visit (Day 41 (+/−1 day)) and recorded on the eCRF. Prior medications, i.e., those taken prior to signing of informed consent (including those that required wash out for study entry and those that are continuing during the study) will also be documented.

Restrictions on specific classes of medications include the following:

Benzodiazepines are to be avoided as much as possible. Eligible patients taking a benzodiazepine at the time of study entry will be permitted to continue to take their current dose of the benzodiazepine (to prevent acute withdrawal), but no new benzodiazepine use or increase of benzodiazepine dose will be permitted during the course of the study. Patients will be allowed to take psychotropics that have been initiated at least 14 days prior to admission to the Inpatient Unit at a stable dose.

The use of gabapentin and pregabalin is to be avoided.

The use of hypnotics for sleepin/insomnia such as Ambien and trazodone is to be avoided and should follow the same guidelines as outlined above for benzodiazepines.

Allopregnanolone has demonstrated inhibitory effects on cytochrome P-450 (CYP) 2C9 (CYP2C9). The following medications are primarily metabolized by CYP2C9 and therefore are prohibited during allopregnanolone administration; fluconazole and miconazole (antifungal), amentoflavone (constituent of Ginkgo biloba and St. John's Wort), sulfaphenazole (antibacterial), valproic acid (anticonvulsant, mood-stabilizing), and apigenin.

Patients who violate the prohibited medication restrictions will be considered for exclusion for the efficacy analysis.

Criteria for Evaluation and Assessments

The safety and tolerability of allopregnanolone injection will be assessed by AEs, clinical laboratory measures, physical examinations, vital signs, electrocardiograms (ECGs), use of concomitant medication, and the Columbia Suicide Severity Rating Scale (C-SSRS) and the Stanford Sleepiness Scale (SSS) as scheduled starting with the Screening Visit, throughout Treatment Periods 1 and 2, and at the 7-day follow-up visit and the end-of-visit (30-day safety follow-up).

Secondary efficacy assessments, including accelerometer (transducer measurement of tremor amplitude), full TETRAS and TETRAS Performance Subscale will be completed as scheduled during Treatment Periods 1 and 2.

Plasma will be collected to assay for allopregnanolone levels prior to dosing through the treatment period and up to 24-hours post infusion.

Safety Assessments

Safety and tolerability will be assessed by AEs, clinical laboratory measures, physical examinations, brief neurological examinations, vital signs, ECGs, and use of concomitant medication. Suicidality will be monitored using the C-SSRS. Sedation will be monitored using the SSS. All safety assessments should be performed per the Inpatient Unit standard of care and will be collected periodically throughout the study according to the Schedule of Events (Table 2). All safety assessments are to be completed within +30 minutes of the scheduled time point.

In addition to the schedule outlined in the scheduled outlined on Table 2, completion of safety assessments including physical examination, vital signs, and clinical laboratory tests (with the exception of the pregnancy test) should occur in the event of an emergency or SAE, if possible.

Adverse Events

Adverse events will be collected after the ICF has been signed. Medical conditions that occur after the ICF has been signed will be captured on the AE eCRF.

Adverse events will be coded using the Medical Dictionary for Regulatory Activities (MedDRA) coding system (version 17.0 or higher).

Clinical Laboratory Tests

Blood samples will be collected for hematology, serum chemistry, and pregnancy tests (females only). Urine samples for urinalysis and pregnancy tests (females only) (after Screening) will also be collected. These assessments should be performed in accordance with the Schedule of Events (Table 2) and as outlined individually below.

Urine assessment for selected drugs of abuse (including amphetamines, barbiturates, benzodiazepines, cocaine, cannabinoid, methadone, and opiates) and a serum alcohol screen will also be collected at the Screening Visit. Patients will also be screened for hepatitis (HBsAg and anti-HCV) and HIV prior to being enrolled in the trial. Patients who have positive tests for drugs of abuse, hepatitis, or HIV will be withdrawn from the study.

All clinical laboratory test results outside the reference range will be interpreted by the Investigator as abnormal, not clinically significant (NCS); or abnormal, clinically significant (CS). Screening results considered abnormal, CS recorded at the Screening Visit may make the patient ineligible for the study pending review by the medical monitor. Clinical laboratory results that are abnormal, CS during the study but within normal range at baseline and/or indicate a worsening from baseline will be considered AEs, and recorded in the eCRF.

Hematology and Serum Chemistry

Blood samples for routine hematology and serum chemistry will be collected at Screening Visit, at Check-in or Day 1, at Check-in or Day 10, and at the 7-day follow-up visit. Blood tests will include hematology and clinical chemistry parameters as follows:

- Hematology: complete blood count (CBC) including white blood cell (WBC) count with differential, platelet count and red blood cell (RBC) count, hemoglobin (Hgb) and hematocrit (Hct), mean corpuscular volume (MCV), and mean corpuscular hemoglobin (MCH).
- Serum chemistry: albumin, alanine aminotransferase (ALT), aspartate aminotransferase (AST), bicarbonate, bilirubin (total), blood urea nitrogen (BUN), calcium, chloride, carbon dioxide, creatinine, gamma glutamyl transferase (GGT), potassium, sodium, total protein, and glucose.

Pregnancy Test

Females of child-bearing potential will be tested for pregnancy by serum pregnancy test at the Screening visit and by urine pregnancy test prior to administration of study drug at Check-in or Day 1, at Check-in or Day 10, and at the 7-day follow-up visit. Female patients with a positive pregnancy test prior to administration of study drug in either Treatment Period 1 or 2 will be withdrawn from study participation.

Urinalysis

Urinalysis will include assessment of protein, blood, glucose, ketones, bile, urobilinogen, Hgb, leukocyte esterase, nitrates, color, turbidity, pH, and specific gravity. Urine will be collected for urinalysis at the Screening Visit, at Check-in or Day 1, at Check-in or Day 10, and at the 7-day follow-up visit.

Physical Examination

Physical examinations will be performed at the Screening Visit, at Check-in or Day 1, Check-in or Day 10, and at the 7-day follow-up visit. Body weight and height will be measured at Screening. Body mass index (BMI) will be programmatically calculated in the eCRF at Screening. Additionally, weight will be measured at Check-in or Day 1 and Check-in or Day 10 to determine dosing for allopregnanolone.

Any condition present at the post treatment physical examination that was not present at or worsened since the baseline examination is to be documented as an AE. Whenever possible, the same individual is to perform all physical examinations. Physical examinations will include assessment of body systems (e.g., eyes, ears, nose, and throat; heart; lungs; abdomen; and extremities) as well as mental health examinations.

Brief Neurological Examination

A brief neurological examination will be performed at the Screening Visit, at Check-in or Day 1, Check-in or Day 10, and at the 7-day follow-up visit.

Any condition present at the post treatment neurological examination result that was not present at or worsened since the baseline examination is to be documented as an AE (with the exception of upper limb ET). Whenever possible, the same individual is to perform all neurological examinations. Neurological examinations will consist of reviews of mental status, cranial nerves, sensation, strength, deep tendon reflexes, and coordination.

Vital Signs

Vital signs include oral temperature (° C.), respiratory rate, heart rate, and blood pressure (supine and standing). A full set of vital signs will be obtained at the Screening Visit, on Days 1 and 10 just prior to beginning the infusion, at the end of each 12-hour infusion, at the end of each 12-hour follow-up, and at the 7-day follow-up visit.

Electrocardiogram

A baseline 12-lead ECG will be performed at the Screening Visit to assess the presence of any current or historical cardiovascular conditions, and will also be conducted at the 7-day follow-up visit. The following ECG parameters will be recorded: heart rate: PR, QRS, and QT intervals; and the corrected QT interval (QTc). Patients with clinically significant abnormalities at the Screening Visit should not be entered into the study.

Columbia Suicide Severity Rating Scale (C-SSRS)

Suicidality will be monitored during the study using the C-SSRS (Posner 2011). This scale consists of a baseline evaluation that assesses the lifetime experience of the patient with suicidal ideation and behavior, and a post-baseline evaluation that focuses on suicidality since the last study visit. The C-SSRS includes 'yes' or 'no' responses for assessment of suicidal ideation and behavior as well as numeric ratings for severity of ideation, if present (from 1 to 5, with 5 being the most severe). The "Baseline" C-SSRS form will be completed on the mornings of Day 1 and Day 10 prior to dosing. The "Since Last Visit" C-SSRS form will be completed on Day 2 and Day 11 (12-hours post infusion). If the Investigator thinks the patient is showing any suicidal tendency, no further study medication will be administered and the patient will be referred to a psychologist or psychiatrist for further evaluation.

Stanford Sleepiness Scale

The SSS is patient-rated scale designed to quickly assess how alert a patient is feeling. Degrees of sleepiness and alertness are rated on a scale of 1 to 7, where the lowest score of '1' indicates the patient is 'feeling active, vital, alert, or wide awake' and the highest score of '7' indicates the patient is 'no longer fighting sleep, sleep onset soon; having dream-like thoughts'. The SSS will be administered at the following time points during Treatment Periods 1 and 2 just prior to the Accelerometer/TETRAS evaluation; pre-dosing, 2 hr, 4 hr, 6 hr, 8 hr, 10 hr and 12 hr (end of infusion), and 24 hr (end of 12 hr follow-up period).

Efficacy Assessments

Secondary Efficacy Outcome Measures

Secondary efficacy assessments include evaluation of patient symptom response by a measurement of tremor amplitude, full TETRAS and TETRAS Performance Subscale (items 4, 6, 7, and 8). All secondary efficacy assessments are to be completed within +30 minutes of the scheduled time point.

Measurements of Tremor Amplitude

In order to measure essential tremor amplitude, patients will wear a wireless ring motion sensor. The motion sensor measures linear acceleration and angular velocity (the kinesia score). Data are transmitted from the sensor to a computer using Bluetooth technology. Information from the motion sensor data correlates to symptoms of tremor. The kinesia score ranges from 0 to 4 in 0.5 step increments. Higher scores indicate more tremor. The accelerometer assessment is completed in conjunction with the TETRAS Performance Subscale Item 4.

The Essential Tremor Rating Scale (TETRAS) Performance Scale

The full TETRAS questionnaire will be administered at Screening and at Day 18, the 7-day follow-up visit. The TETRAS Performance Subscale (items 4, 6, 7, and 8) will be administered at the following time points during Treatment Periods 1 and 2: pre-dosing, 2 hr, 4 hr, 6 hr, 8 hr, 10 hr and 12 hr (end of infusion), and at 24 hr (end of the 12 hr follow up). Item #4 (upper limb tremor) of the TETRAS Performance Subscale will be completed using both the accelerometer and clinician assessment. Testing should be completed within +10 minutes of the planned questionnaire time points. All 3 tests in the upper limb tremor series of assessments (Item 4) will be completed for both arms, first for the RIGHT arm and then for the LEFT. Pre-dose assessments can be done any time within 2 hours prior to the start of infusion. The 7-day follow up visit assessments can be done at any time during the visit.

Patients will complete the TETRAS Performance Subscale, Item #4 (upper limb tremor) while wearing the accelerometer. Simultaneous clinician assessment of item #4 will occur. The accelerometer assessment is completed in conjunction with the TETRAS Performance Subscale at the same time points during Treatment Periods 1 and 2: pre-dosing, 2 hr, 4 hr, 6 hr, 8 hr, 10 hr, 12 hr (end of infusion), and 24 hr (end of 12 hr follow-up), and at the 7-day follow-up visit.

Pharmacokinetics

Plasma will be collected to assay for allopregnanolone levels at pre-infusion (prior to dose level 1); after the start of the infusion at 30 and 45 minutes, and at hours 1, 1.5, 2, 4, 6, 8, 10, 12, 12.5, 12.75, 13, 13.5, 14, 16 and 24 hours. Plasma collection times for PK should be adhered to as strictly as possible. The 30 and 45-minute time point should be collected within a +2 minute window of the scheduled time point. The hourly time points should be collected within +10 minutes of the scheduled time point. The 24-hour post infusion time points should be collected within +30 minutes of the scheduled time point. Additionally, PK samples may be obtained outside the planned collection times if issues administering study drug are encountered, such as incorrect infusion rate, interrupted infusion, or other administration deviations where timing of the blood draw for PK assessment may be important in understanding patient state.

Plasma concentrations of allopregnanolone will be determined using high performance liquid chromatography with tandem mass spectrometry (HPLC MS/MS). The following PK parameters will be calculated where evaluable; area under the concentration-time curve (AUC) from time zero to 12 hours ($AUC_{0-12}$), AUC from time zero to infinity ($AUC_{inf}$), maximum (peak) plasma concentration ($C_{max}$), time at maximum (peak) plasma concentration ($T_{max}$), steady-state drug concentration in the plasma during constant-rate infusion ($C_{ss}$), and average drug concentration in the plasma at steady-state during a dosing interval ($C_{avg}$).

The plasma samples will be drawn from the arm opposite to that used for drug administration. Patient-specific PK kits for sampling, including instructions for collection, processing methods, as well as storage and shipping conditions, will be provided.

TABLE 2

Schedule of assessments

| | Visit Days | | | |
|---|---|---|---|---|
| | Screening Period (Day −28 to Day −1) | | | |
| | Screening Visit | Check-in/ Visit[b] (Day −1) | Treatment Period 1[a] (Day 1 to Day 2) | Check-in/ Visit[b] (Day 9) |
| | | | Day 1    Day 2 | |
| Study Procedure | | | | |
| Informed Consent | X | | | |
| Inclusion/Exclusion Criteria | X | | | |
| Demographics | X | | | |

TABLE 2-continued

Schedule of assessments

| | | | | | |
|---|---|---|---|---|---|
| Medical History | X | | | | |
| Physical Examination (height measured at Screening only) | X | X | (X) | | X |
| Brief Neurological Examination[c] | X | X | (X) | | X |
| Body Weight | X | X | (X) | | X |
| Vital Signs[d] | X | | X | X | |
| Clinical Laboratory Tests[e] | X | X | (X) | | X |
| Drug and Alcohol Screen[f] | X | X | (X) | | X |
| Pregnancy Test[g] | X | X | (X) | | X |
| Hepatitis & HIV Screen | X | | | | |
| 12-Lead ECG[h] | X | | | | |
| Randomization | | X | (X) | | |
| Confined to Inpatient Unit | | X | X | | X |
| Discharge from Inpatient Unit | | | | X | |
| TETRAS[i] | X | | | | |
| TETRAS Performance Subscale (items 4, 6, 7, 8)[j] | X | | X | X | |
| Accelerometer[j] | X | | X | X | |
| C-SSRS | | X | (X) | X | X |
| SSS | | X | (X) | X | X |
| Adverse Event Collection[k] | | X | X | X | X |
| Concomitant Medications | X | X | X | X | X |
| Study Drug Administration[l] | | | X | | |
| Plasma for PK analysis[m] | | | X | X | |
| Study Completion | | | | | |

Visit Days

| | Treatment Period 2[a] (Day 10 to Day 11) | | Follow-up Period | |
|---|---|---|---|---|
| | | | 7-day f/u Visit | 30-day[n] f/u Visit |
| | Day 10 | Day 11 | (Day 18 ± 1) | (Day 41 ± 1) |

Study Procedure

| | | | | |
|---|---|---|---|---|
| Informed Consent | | | | |
| Inclusion/Exclusion Criteria | | | | |
| Demographics | | | | |
| Medical History | | | | |
| Physical Examination (height measured at Screening only) | (X) | | X | |
| Brief Neurological Examination[c] | (X) | | X | |
| Body Weight | (X) | | | |
| Vital Signs[d] | X | X | X | |
| Clinical Laboratory Tests[e] | (X) | | X | |
| Drug and Alcohol Screen[f] | (X) | | | |
| Pregnancy Test[g] | (X) | | X | |
| Hepatitis & HIV Screen | | | | |
| 12-Lead ECG[h] | | | X | |
| Randomization | | | | |
| Confined to Inpatient Unit | X | | | |
| Discharge from Inpatient Unit | | X | | |
| TETRAS[i] | | | X | |
| TETRAS Performance Subscale (items 4, 6, 7, 8)[j] | X | X | X | |

TABLE 2-continued

Schedule of assessments

| | | | | |
|---|---|---|---|---|
| Accelerometer[j] | X | X | X | |
| C-SSRS | (X) | X | X | |
| SSS | (X) | X | | |
| Adverse Event Collection[k] | X | X | X | SAE Only |
| Concomitant Medications | X | X | X | |
| Study Drug Administration[l] | X | | | |
| Plasma for PK analysis[m] | X | X | | |
| Study Completion | | | | X |

CGI-I = Clinical Global Impression of Improvement; C-SSRS = Columbia - Suicide Severity Rating Scale; ECG = electrocardiogram; HIV = human immunodeficiency virus; LFTs = liver function tests; PK = pharmacokinetic; SSS = Stanford Sleepiness Scale; TETRAS = The Essential Tremor Rating Scale.
Note:
(X) indicates that the assessment must be done at this time if it has not been done at the Check-in Visit.

CGI-I=Clinical Global Impression of Improvement; C-SSRS=Columbia–Suicide Severity Rating Scale; ECG=electrocardiogram; HIV=human immunodeficiency virus; LFTs=liver function tests; PK=pharmacokinetic; SSS=Stanford Sleepiness Scale; TETRAS=The Essential Tremor Rating Scale.

Note: (X) indicates that the assessment must be done at this time if it has not been done at the Check-in Visit.

Example 2. Human Phase 1 Study of Allopregnanolone: An Open-Label Proof-of-Concept Study Evaluating the Safety, Tolerability, Pharmacokinetics, and Efficacy of Allopregnanolone Injection in the Treatment of Adult Female Patients with Postpartum Depression Study Design A double-blind, placebo-controlled study designed to evaluate the safety, tolerability, PK, and efficacy of allopregnanolone injection in adult female patients diagnosed (by Structured Clinical Interview for DSM-V Axis I Disorders [SCID-I]) with severe PPD. Each patient's involvement is up to 37 days, including up to a 3-day screening period, 4-day (84-hour) active treatment period, and a 7-day AE follow-up period plus an additional 23 days of SAE follow-up (with a telephone call at day 11 and day 34).

Screening Period: The Screening Period begins with the signature of the informed consent form (ICF) in the Perinatal Psychiatry Inpatient Unit (PPIU) at the Screening Visit, which can occur on any one calendar day of the 3-day window (from Day −3 through Day −1). Potential patients who may be eligible to participate in the study include adult female patients who have been admitted to the PPIU. Patients will undergo preliminary screening procedures at the Screening Visit to determine eligibility, including completion of the HAM-D-17. The end of the Screening Period coincides with the beginning of the Active Treatment Period in the PPIU.

Active Treatment Period: The Active Treatment Period is the period of Day 1 of allopregnanolone intravenous (IV) infusion through completion of the infusion and taper on Day 3 and a 24 hour follow-up on day 4. Patients will be confined to the PPIU from the Screening Visit until after the 84-hour assessments have been conducted on Day 4. On the morning of dosing (Day 1), patients will begin the 12-hour dose titration phase. Upon completion of titration, patients will begin a maintenance infusion that will continue for 36 hours, targeting a plasma concentration of 150 nM. After constant dose therapy with allopregnanolone, the dose will be tapered and discontinued over the course of 12 hours. Total allopregnanolone dosing will occur over 60 hours (12-hour dose titration followed by a 36-hour maintenance infusion followed by a 12-hour taper).

Safety assessments will be performed, blood samples will be collected, and outcome measures will be obtained at pre-specified times over an 84-hour period during the Active Treatment Period.

The Active Treatment Period will end on Day 4, after completion of the 84-hour assessments per the Schedule of Events. The end of the Active Treatment Period coincides with the beginning of the Follow-up Period. Per Investigator discretion and routine clinical care, patients may remain admitted to the PPIU until their clinical condition warrants discharge from the hospital.

As clinical experience with administration of allopregnanolone Injection is limited, sentinel dosing will be applied to the first two patients enrolled in the trial: relevant safety data collected from Day 1 to Day 4 (adverse events [AEs], clinical laboratory evaluations, vital signs, and electrocardiograms [ECGs]) for the first (and subsequently the second) patient will be reviewed by the Medical Monitor, the Sponsor's Chief Medical Officer, and the Principal Investigator prior to concurrent dosing in subsequent patients.

Follow-up Period: Seven days following completion of the Active Treatment Period (Day 11±1 day), patients will be contacted via telephone for a safety follow-up assessment. Patients who have been discharged from the PPIU will be called at home. Patients who remain in the PPIU will have a subsequent evaluation on the day of discharge per standard clinical assessment procedures, not for protocol purposes. This assessment will be recorded in the case report forms.

Thirty days following completion of the Active Treatment Period (Day 34±1 day), patients will again be contacted via telephone for a safety follow-up assessment.

TABLE 3

Amount and Duration of Infusions

| Study Day (D) | Hour (h) | Type and Duration of allopregnanolone Infusion | Description |
|---|---|---|---|
| D 1 | h 1-h 12 | Titration Infusion | |
| | | 4 hours | 21.5 µg/kg/hr (25% of the maintenance rate) |
| | | 4 hours | 43 µg/kg/hr (50% of the maintenance rate) |

TABLE 3-continued

Amount and Duration of Infusions

| Study Day (D) | Hour (h) | Type and Duration of allopregnanolone Infusion | Description | |
|---|---|---|---|---|
| | | 4 hours | 64.5 μg/kg/hr (75% of the maintenance rate) | |
| D 1-D 3 | h 13-h 48 | Maintenance Infusion 36 hours[a] | 86 μg/kg/hr | |
| D 3 | | Taper Infusions | | |
| | h 49-h 52 | 4 hours | 64.5 μg/kg/hr (75% of the maintenance rate) | |
| | h 53-h 56 | 4 hours | 43 μg/kg/hr (50% of the maintenance rate) | |
| | h 57-h 60 | 4 hours | 21.5 μg/kg/hr (25% of the maintenance rate) | |

[a]The 36-hour maintenance infusion will begin immediately following the titration phase and continue through to the morning of Day 3.

Administration

All study-related procedures will occur after written informed consent is obtained at the Screening Visit, which will occur on any one calendar day during the Screening Period window (Day −3 through Day −1). Potential adult female patients admitted to the PPIU will undergo preliminary screening procedures at the Screening Visit to determine eligibility to participate in the trial, including completion of the HAM-D-17. PPIU standard of care data collected prior to obtaining informed consent may also be included as screening data, if appropriate, such as laboratory tests, ECG, physical examination, and vital signs conducted within the preceding 48 hours, as long as the requirement for the screening assessment to be collected retrospectively is met in full. To ensure protocol compliance, any PPIU standard of care data eligible for inclusion as screening data must include the precise nature and timing of data collection.

The end of the Screening Period coincides with the beginning of the Active Treatment Period in the PPIU. The Active Treatment Period is the period of Day 1 of allopregnanolone IV infusion through completion of the infusion and taper on Day 4. Patients will be confined to the PPIU from the Screening Visit until after the 84-hour assessments have been conducted on Day 4. On the morning of dosing (Day 1), patients will begin a 12-hour dose titration period during which doses will be increased (25%, 50%, 75% of target maintenance dose) every 4 hours. Following titration, a maintenance infusion will be administered that will continue for 36 hours, targeting a steady-state plasma concentration of 150 nM. After constant-dose therapy with allopregnanolone, the dose will be tapered and discontinued over the course of 12 hours. Total allopregnanolone dosing will occur over 60 hours (12-hour dose titration, 36-hour maintenance infusion followed by a 12-hour taper). If at any time during the study the Investigator and/or patient conclude that allopregnanolone treatment should be terminated, ideally the 12-hour taper should be initiated. The duration of the taper may however be adjusted based on the individual needs of the patient: the decision to initiate as well as the length of the taper will be determined on a case-by-case basis by the Investigator.

Trial-specific assessments for safety, PK, efficacy, and exploratory outcome measures will be completed at pre-specified times over an 84-hour period during the Active Treatment Period:

The safety and tolerability of allopregnanolone Injection will be assessed by AEs, clinical laboratory measures, physical examinations (including cognitive and mental health examinations), vital signs, ECG, use of concomitant medication, and the Columbia-Suicide Severity Rating Scale (C-SSRS) during the Screening, Active Treatment, and Follow-up Periods (through Study Day 34±1 day).

Plasma will be collected to formally assay for allopregnanolone and metabolite levels prior to dosing through the treatment period and up to 12 hours post infusion on Day 3.

Secondary efficacy assessments, including the HAM-D-17 and CGI-I, will be completed as scheduled during the Screening and Active Treatment Period (through Study Day 4).

Exploratory outcome assessments (EPDS, RMD VAS, GAD-7, PHQ-9, and SSS) will be completed as scheduled during the Screening and Active Treatment Period (through Study Day 4). The individual HAM-D-17 subcategories will be completed as a component of the overall HAM-D-17 (secondary efficacy assessment).

The end of the Active Treatment Period coincides with the beginning of the Follow-up Period. Per Investigator discretion and routine clinical care, patients may remain admitted to the PPIU beyond the protocol-specified Follow-up Period until their clinical condition warrants discharge from the hospital.

Seven days following completion of the Active Treatment Period (Day 11±1 day), patients will be contacted via telephone for a safety follow-up assessment. Patients who have been discharged from the PPIU will be called at home. For patients that remain in the PPIU, patients will have a subsequent evaluation on the day of discharge per standard clinical assessment procedures, not for protocol purposes.

Thirty days following completion of the Active Treatment Period (Day 34±1 day), patients will again be contacted via telephone for a safety follow-up assessment.

Scheduled assessments for all safety, PK, efficacy, and exploratory outcome measures planned for the trial are summarized in Table 4 (Schedule of Events). All patients that receive treatment with allopregnanolone are to complete all study assessments through Study Day 34 (±1 day).

As clinical experience with administration of exogenous allopregnanolone (including allopregnanolone Injection) is limited, sentinel dosing will be applied to the first two patients enrolled in the trial. Relevant safety data collected from Day 1 to Day 4 (AEs, clinical laboratory evaluations, vital signs, and ECGs) will be carefully reviewed by the Medical Monitor, the Sponsor's Chief Medical Officer (CMO), and the Principal Investigator for each of the first two patients prior to continuing with dosing in subsequent patients.

The Medical Monitor will review AEs on an ongoing basis.

Diagnosis and Main Criteria for Inclusion

Adult female patients (between 18 and 45 years of age, inclusive) diagnosed with severe PPD (as diagnosed by SCID-I) who have signed an ICF and meet the following main inclusion criteria are eligible for enrollment: Patient is in good physical health and has no clinically significant findings on a physical examination, 12-lead ECG, and clinical laboratory tests (clinical chemistry, liver function tests [LFTs], thyroid stimulating hormone [TSH], coagulation, hematology, urine drug screen, and urinalysis) before receiving allopregnanolone. Patient must have experienced a Major Depressive Episode in the postpartum period that began within the first 4 weeks following delivery as diagnosed by Structured Clinical Interview for DSM-IV Axis I Disorders (SCID-I), been admitted to the PPIU between 14 days and 6 months postpartum and with history of onset of perinatal Major Depressive Disorder no earlier than the third trimester and no later than 2 months postpartum, and had a baseline HAM-D-17 score of ≥20 at the Screening Visit. Patient agrees to adhere to the study requirements. Patient must have a negative serum pregnancy test at the Screening Visit in the PPIU. Patient has a negative hepatitis panel (including hepatitis B surface antigen [HBsAg] and anti-hepatitis C virus [HCV]) and human immunodeficiency virus [HIV] antibody at the Screening Visit. In addition, patients must be willing to consent to allopregnanolone infusion for 60 hours (inclusive of the 12-hour dose-titration and 12-hour taper) and to delay start of other antidepressant or anxiety medications and any new pharmacotherapy regimens until the 60-hour infusion and post-infusion assessments have been completed. If the patient is breastfeeding, the patient must agree to avoid giving breast milk to the infant during the Active Treatment Period and for 48 hours after the taper has been completed.

Exclusion Criteria

Patients will be excluded if they meet any of the following exclusion criteria prior to enrollment:
1) Recent history or active clinically significant manifestations of metabolic, hepatic, renal, hematological, pulmonary, cardiovascular, gastrointestinal, musculoskeletal, dermatological, urogenital, or eyes, ears, or nose and throat (EENT) disorders.
2) An acute or chronic condition that, in the Investigator's opinion, would limit the patient's ability to complete or participate in this clinical study.
3) Known allergy to progesterone or allopregnanolone.
4) Active psychosis per Investigator assessment.
5) Medical history of seizures.
6) Current history of active alcoholism or drug addiction (including benzodiazepines) at the time of the Screening Visit or during the year before the Screening Visit.
7) Exposure to another investigational medication or device within 30 days.
8) Initiation of benzodiazepines, narcotics, antibiotics, neuroleptics, and other anti-anxiety medications will not be allowed during the Active Treatment Period. Patients will however be allowed to take psychotropics that have been initiated at least 14 days prior to admission to the PPIU and are being taken at a stable dose.

Criteria for Evaluation and Assessments

The safety and tolerability of allopregnanolone injection will be assessed by AEs, clinical laboratory measures, physical examinations, vital signs, electrocardiograms (ECGs), use of concomitant medication. Suicidality will be monitored using the C-SSRS. All safety assessments should be period per the PPIU standard of care and will be collected periodically throughout the study. All safety assessments are to be completed within +/−30 minutes of the scheduled time point.

In additional to the schedule outlined, completion of safety assessments including physical examination, vital signs, and clinical laboratory tests (with the exception of the pregnancy test) should occur in the event of an emergency of SAE, if possible.

Safety Assessments

The Safety Population (SAF) is defined as all patients who begin infusion with allopregnanolone Injection. AEs will be classified by type, incidence, severity, and causality. The analysis of AEs will be based on the concept of treatment-emergent AEs (TEAEs). A TEAE is defined as an AE with onset after the start of allopregnanolone infusion. TEAEs will be recorded until the end of the 7-day follow-up period (day 11) and SAEs will be recorded until 30 days after the last administration of study drug (day 34). The overall incidence of TEAEs will be summarized using the Medical Dictionary for Regulatory Activities (MedDRA™) coding system and classified by System Organ Class (SOC), and preferred term. Data from vital signs, clinical laboratory measures, ECG, and concomitant medication usage will also be summarized. Data from the Columbia-Suicide Severity Rating Scale (C-SSRS) will be listed by patient.

Safety data will be summarized and examined for possible relationships between patient characteristics and plasma allopregnanolone concentrations, as appropriate. Safety assessments will be performed as described in the Safety Assessments section of Example 1.

Efficacy Assessments

The efficacy population will include all SAF patients who complete at least 12 hours of infusion and have efficacy evaluations through the 12 hour time point on Day 1. Change from baseline in overall HAM-D-17 score (range 0-52) at the end of the Active Treatment Period (84 hours, 24 hours post-infusion) will be used as the primary assessment of efficacy. In addition, the CGI-I score (range 1-7) at 84 hours (24 hours post-infusion) will be used to determine physician's assessment of improvement in symptoms. A 50% decrease from baseline in HAM-D-17 score and a CGI-I score≤2 will be considered a relevant clinical signal of efficacy.

Hamilton Rating Scale for Depression-17 (HAM-D-17)

Patient symptom response, defined by the HAM-D-17, will be administered at Screening, Day 1 (prior to dosing and at 12 hours), Day 2 (24 hours and 36 hours), Day 3 (48 hours and 60 hours), and on Day 4 (at 84 hours, 24 hours after the end of the infusion taper, hereafter referred to as '24 hours post-infusion') prior to study completion. The efficacy outcome will be evaluated as a change from baseline in overall HAM-D-17 score at the end of Active Treatment Period (at 84 hours).

Clinical Global Impression-Improvement Scale (CGI-I)

The Clinical Global Impression scales are validated measures often utilized in clinical trials to allow clinicians to integrate several sources of information into a single rating of the patient's condition. The CGI-Improvement (CGI-I) employs a 7-point Likert scale measuring improvement in the patient. The investigator will rate the patient's total improvement whether or not it is due entirely to drug treatment. Response choices include: 0=not assessed, 1=very much improved, 2=much improved, 3=minimally improved, 4=no change, 5=minimally worse, 6=much worse, and 7=very much worse. The CGI-I will be evaluated during infusion with allopregnanolone Injection, as administered by the clinician on Day 1 (at 12 hours), Day 2 (24 hours and 36 hours), Day 3 (48 hours and 60 hours), and on Day 4 (84 hours, 24 hours post-infusion) prior to study completion. By definition, all CGI-I assessments are evaluated against baseline conditions. The efficacy outcome will be evaluated using the CGI-I score at the end of Active Treatment Period (at 84 hours).

Secondary Efficacy Outcome Measures

Secondary efficacy assessments include evaluation of patient symptom response defined by the HAM-D-17 and evaluation of patient treatment response by the CGI-I. All secondary efficacy assessments are to be completed within +30 minutes of the scheduled time point.

Exploratory Efficacy Outcome Measures

Exploratory efficacy outcome measures include a patient-rated depressive symptom severity scale specific to the perinatal period (EPDS), a reproductive mood disorders VAS (RMD VAS), two separate patient-rated depressive symptom severity scales (GAD-7 and PHQ-9), and individual HAM-D-17 subcategories. All exploratory outcome assessments are to be completed within +30 minutes of the scheduled time point.

Edinburgh Postnatal Depression Scale (EPDS)

The EPDS is a patient-rated depressive symptom severity scale specific to the perinatal period (Cox 1987). The EPDS will be administered at Screening, Day 1 (prior to dosing), Day 2 (24 hours and 36 hours), Day 3 (48 hours and 60 hours), and on Day 4 (84 hours, 24 hours post-infusion) prior to study completion.

Reproductive Mood Disorders Visual Analogue Scale (RMD VAS)

The RMD VAS was developed and tested at the National Institute of Mental Health (NIMH) 20 years ago and has been widely used. The VAS provides a measurement instrument for subjective characteristics or attitudes that cannot be directly measured. When responding to a VAS item, respondents specify their level of agreement to a statement by indicating a position along a continuous line between two end-points. The RMD VAS contains 14 items that assess a range of symptoms specific to reproductive mood disorders (i.e., anxiety, insomnia, mood).

Patients rate the way they feel right at the time of assessment by drawing a vertical line through the continuous 100 mm horizontal scale line at the point that best describes how they are feeling on that item. The far left of the line indicates most severe and the far right indicates the least severe, e.g., "most anxious ever versus most calm ever". The subject's placement of the vertical line through the standardized 100 mm horizontal line allows for a precise assessment of a data point corresponding on a scale of 1-100 mm.

The RMD VAS will be administered at Screening, Day 1 (prior to dosing), Day 2 (24 hours and 36 hours), Day 3 (48 hours and 60 hours), and on Day 4 (84 hours, 24 hours post-infusion) prior to study completion.

Generalized Anxiety Disorder 7-Item Scale (GAD-7)

The GAD-7 is a patient-rated depressive symptom severity scale (Spitzer 2006). Scoring for GAD-7 generalized anxiety is calculated by assigning scores of 0, 1, 2, and 3 to the response categories, respectively, of "not at all," "several days," "over half the days," and "nearly every day." GAD-7 total score for the seven items ranges from 0 to 21, where a score of 0 to 4=minimal anxiety, 5 to 9=mild anxiety, 10 to 14=moderate anxiety, and 15 to 21=severe anxiety. In this study, the GAD-7 will be administered at Screening, Day 1 (prior to dosing), Day 2 (24 hours and 36 hours), Day 3 (48 hours and 60 hours), and on Day 4 (84 hours, 24 hours post-infusion) prior to study completion.

Patient Health Questionnaire (PHQ-9)

The PHQ-9 is a patient-rated depressive symptom severity scale. To monitor severity over time for newly diagnosed patients or patients in current treatment for depression, patients may complete questionnaires at baseline and at regular intervals thereafter. Scoring is total based on responses to specific questions, as follows "not at all"=0: "several days"=1: "more than half the days"=2; and "nearly every day=3". Depression severity is based on interpretation of the patient's total score as follows: 1 to 4=minimal depression, 5 to 9=mild depression, 10 to 14=moderate depression, 15 to 19=moderately severe depression; and 20 to 27=severe depression. In this trial, the PHQ-9 will be administered at Screening, Day 1 (prior to dosing), Day 2 (24 hours and 36 hours), Day 3 (48 hours and 60 hours), and on Day 4 (84 hours, 24 hours post-infusion) prior to study completion.

Stanford Sleepiness Scale (SSS)

The Stanford Sleepiness Scale is patient-rated scale designed to quickly assess how alert a patient is feeling. Degrees of sleepiness and alertness are rated on a scale of 1 to 7, where the lowest score of '1' indicates the patient is 'feeling active, vital, alert, or wide awake' and the highest score of '7' indicates the patient is 'no longer fighting sleep, sleep onset soon; having dream-like thoughts'. A score above 7 indicates the patient is asleep. The SSS will be administered on Day 1 (prior to dosing and at 6 hours and 12 hours), Day 2 (at 24 hours and 36 hours), and Day 3 (at 48 hours and 60 hours).

Individual HAM-D-17 Subcategories

Individual HAM-D-17 subcategories related to depression, guilt, suicidal ideation, insomnia, social interactions, anxiety, somatic symptoms, and insight comprise the overall HAM-D-17 and therefore follow the same assessment schedule outlined for the secondary efficacy endpoint HAM-D-17.

Pharmacokinetics

Plasma will be collected to assay for allopregnanolone and metabolite levels at pre-infusion; after the start of the infusion at 30 minutes, and at hours 1, 2, 3, 4, 6, 12, 24, 36, 40, 44, 48 (end of constant infusion); at hour 60 (end of infusion taper); and at hour 72 (12 hours after the end of the infusion taper), or when a patient experiences an SAE considered related to study drug. PK collection times should be adhered to as strictly as possible. Scheduled time points for PK blood draws after the start of infusion will have a window of ±2 minutes for samples collected during the first hour (30 minutes, 1 hour) and ±10 minutes for samples collected after the first hour (beginning with hour 2) and continuing with hours 2, 3, 4, 6, 12, 24, 36, 40, 44, 48, 60 and 72. Additionally, PK samples may be obtained outside the planned collection times if issues administering study drug are encountered, such as incorrect infusion rate, interrupted infusion, or other administration deviations where PK level assessment may be important in understanding patient state.

Plasma concentrations of allopregnanolone and metabolites will be determined using high performance liquid chromatography tandem mass spectrometry (HPLC MS/MS). The following PK parameters will be calculated where evaluable; area under the concentration-time curve (AUC) from time zero to 72 hours ($AUC_{0-72}$), AUC from time zero to infinity ($AUC_{inf}$), maximum (peak) plasma concentration ($C_{max}$), time at maximum (peak) plasma concentration ($T_{max}$), steady-state drug concentration in the plasma during constant-rate infusion ($C_{SS}$), and average drug concentration in the plasma at steady state during a dosing interval ($C_{avg}$).

The plasma samples will be drawn from the arm contralateral to that used for drug administration.

Patient-specific PK kits for sampling including instructions on collection and processing methods, and storage and shipping conditions, will be provided in the study PK manual.

Plasma will also be collected acutely to determine levels of allopregnanolone if a serious adverse event (SAE) occurs.

Exploratory Endpoints

Scores from other depression, mood disorder, and sleepiness rating scales will be summarized by descriptive statistics, including n, mean, SD, median, minimum and maximum values, as change from baseline. These rating scales include: EPDS, RMD VAS, GAD-7, PHQ-9, SSS, and individual HAM-D-17 subcategories related to depression, guilt, suicidal ideation, insomnia, social interactions, anxiety, somatic symptoms, and insight.

The Following Additional Efficacy Outcome Measures Will be Evaluated:

EPDS: Patient-rated depressive symptom severity scale specific to the perinatal period.

RMD VAS: 14-item patient-rated scale to assess a range of symptoms specific to reproductive mood disorders (i.e., anxiety, insomnia, mood).

GAD-7: Patient-rated depressive symptom severity scale.

PHQ-9: Patient-rated depressive symptom severity scale.

SSS: Patient-rated measure of sleepiness (alertness)

Individual HAM-D-17 subcategories related to depression, guilt, suicidal ideation, insomnia, social interactions, anxiety, somatic symptoms, and insight.

The EPDS, RMD VAS, GAD-7, and PHQ-9 will be administered at Screening, Day 1 (prior to dosing), Day 2 (at 24 hours and 36 hours), Day 3 (at 48 hours and 60 hours), and on Day 4 (at 84 hours, 24 hours post-infusion) prior to study completion. The SSS will be administered on Day 1 (prior to dosing and at 6 hours and 12 hours), Day 2 (at 24 hours and 36 hours), and Day 3 (at 48 hours and 60 hours). Individual HAM-D-17 subcategories comprise the overall HAM-D-17 and therefore follow the same assessment schedule outlined for the secondary efficacy endpoint HAM-D-17 described above.

Other Assessments

As an optional assessment per patient consent, breast milk will be collected pre-infusion (defined as the last breast milk sample collected prior to dosing) and after the start of the allopregnanolone infusion throughout the 60-hour infusion and infusion taper for biobanking and PK analysis purposes. Breast milk will be collected and pooled over a period of interest during the Active Treatment Period (e.g., over 0-12, 12-24, and 24-48 hours) including the taper periods (this may also include periods of 48-52, 52-56, 56-60, 60-72, and 72-84 hours). The times of the first and last pumping of each collection period will be recorded. Breast milk will be pooled within each collection period and the total volume will be measured. Two aliquots of 0.5 mL will be taken from each pooled collection and analyzed for PK. Full detailed instructions for breast milk PK sampling, processing and shipping are provided in the study PK manual.

To be eligible for enrollment in this trial, if the patient is breastfeeding, the patient must agree to avoid giving breast milk to the infant during the Active Treatment Period and for 48 hours after the taper has been completed. The conservative restriction of limiting patients to safely resume breast feeding until 48 hours after the taper is based on PK modeling of drug transfer into milk using intravenous medications commonly used for anesthesia or conscious sedation as evaluated in a small group of lactating patients (Nitsun 2006). In this study, the amount of midazolam, propofol, and fentanyl detected in breast milk over a 24-hour period following a single dose (administered as part of a general anesthetic) in lactating women was shown to be very small (exposure of breast-feeding infant estimated to be less than 0.1% of the maternal dose of each of the three medications). Hence for the purposes of the current trial, the 48-hour restriction applied to the study design exceeds the 24-hour time period evaluated in the previous published study.

The Breast Milk Population is defined as all patients who begin receiving allopregnanolone injection and have at least one breast milk sample taken. The PK parameters will be summarized by descriptive statistics including n, mean, SD, median, minimum and maximum values, and will be listed by patient.

Statistical Methods

For the purpose of all safety, efficacy, and exploratory analyses where applicable, baseline is defined as the last pre-dose measurement closest to the start of infusion with allopregnanolone Injection.

The sample size (n=10) for this exploratory study uses a pragmatic design to have a reasonable chance of detecting a clinically meaningful safety or efficacy signal.

TABLE 4

Schedule of Events

| | Screening Period Screening Visit | Active Treatment Period Clinic Period in PPIU (Day 1 to Day 4)[a] | | | | Follow-up Period (via phone) | |
|---|---|---|---|---|---|---|---|
| | | | | | | Follow-up Visit D 11 | Follow-up Visit D 34 |
| | Day −3 to −1 | D 1 | D 2 | D 3 | D 4 | (±1 day) | (±1 day) |
| Study Procedure | | | | | | | |
| Informed Consent | X | | | | | | |
| Inclusion/Exclusion Criteria | X | | | | | | |
| Demographics | X | | | | | | |
| Medical History | X | | | | | | |
| Physical Examination | X | | | | X | | |
| Body Weight and Height for BMI calculation[b] | X | | | | | | |
| Vital Signs[c] | X | X | X | X | X | | |
| CBC and Serum Chemistry[d] | X | | X | X | X | | |
| Drug and Alcohol Screen[e] | X | | | | | | |
| Urinalysis | X | | X | X | X | | |
| Serum Pregnancy Test | X | | | | X | | |

TABLE 4-continued

Schedule of Events

| | Screening Period Screening Visit | Active Treatment Period Clinic Period in PPIU (Day 1 to Day 4)[a] | | | | Follow-up Period (via phone) | |
|---|---|---|---|---|---|---|---|
| | | | | | | Follow-up Visit D 11 | Follow-up Visit D 34 |
| | Day −3 to −1 | D 1 | D 2 | D 3 | D 4 | (±1 day) | (±1 day) |
| Hepatitis & HIV Screen | X | | | | | | |
| 12-Lead ECG[f] | X | | | | X | | |
| C-SSRS[g] | | X | X | X | X | | |
| Confined to PPIU | X | X | X | X | X | | |
| HAM-D-17[h] | X | X | X | X | X | | |
| CGI-I[h,i] | | X | X | X | X | | |
| EPDS[h] | X | X | X | X | X | | |
| RMD VAS[h] | X | X | X | X | X | | |
| GAD-7[h] | X | X | X | X | X | | |
| PHQ-9[h] | X | X | X | X | X | | |
| SSS[h] | | X | X | X | | | |
| Adverse Event Collection[j] | | X | X | X | X | X | SAE only |
| Concomitant Medications | X | X | X | X | X | X | |
| Study Drug Administration[k] | | X | X | X | | | |
| Plasma and breast milk samples for PK Analysis[l,m] | | X | X | X | X | | |
| Study completion | | | | | | | X |

BMI = body mass index; CGI-I = Clinical Global Impression of Improvement; C-SSRS = Columbia - Suicide Severity Rating Scale; ECG = electrocardiogram; EPDS = Edinburgh Postnatal Depression Scale; GAD-7 = Generalized Anxiety Disorder 7-Item Scale; HAM-D-17 = Hamilton Rating Scale for Depression (17-items); PHQ-9 = Patient Health Questionnaire; PK = pharmacokinetic; RMD-VAS = Reproductive Mood Disorders Visual Analogue Scale; PPIU = Perinatal Psychiatry Inpatient Unit; SSS = Stanford Sleepiness Scale.

BMI=body mass index; CGI-I=Clinical Global Impression of Improvement; C-SSRS=Columbia–Suicide Severity Rating Scale; ECG=electrocardiogram; EPDS=Edinburgh Postnatal Depression Scale; GAD-7=Generalized Anxiety Disorder 7-Item Scale; HAM-D-17=Hamilton Rating Scale for Depression (17-items); PHQ-9=Patient Health Questionnaire; PK=pharmacokinetic; RMD-VAS=Reproductive Mood Disorders Visual Analogue Scale; PPIU=Perinatal Psychiatry Inpatient Unit; SSS=Stanford Sleepiness Scale.

Example 3. A Double-Blind, Placebo-Controlled Study Evaluating the Efficacy, Safety, and Pharmacokinetics of Allopregnanolone Injection in the Treatment of Depression
Primary Objective:
  To compare the effects of Allopregnanolone Injection and placebo infused intravenously for 48 hours on subject symptom response as measured by the Hamilton Rating Scale for Depression, 17-item (HAM-D-17)
Secondary Objectives:
  To compare the effects of Allopregnanolone Injection and placebo on:
    Clinician evaluation as measured by the Clinical Global Impression-Improvement Scale (CGI-I)
    Sedation using the Stanford Sleepiness Scale (SSS)
    Safety and tolerability, assessed using adverse event reporting, vital sign measurement, laboratory data, ECG parameters, and suicidal ideation using the Columbia-Suicide Severity Rating Scale (C-SSRS)
    Depressive symptom severity, reproductive mood disorders, and sleepiness as measured by the following clinician- and subject-rated outcome measures: Edinburgh Postnatal Depression Scale (EPDS), Reproductive Mood Disorders Visual Analogue Scale (RMD VAS), Generalized Anxiety Disorder 7-Item Scale (GAD-7), Patient Health Questionnaire (PHQ-9), and evaluation of individual subcategories of the HAM-D-17
Pharmacokinetic Objectives:
  To assess the pharmacokinetic (PK) profile of Allopregnanolone, metabolites of Allopregnanolone, and Captisol and, when possible, the concentration of Allopregnanolone in breast milk.
Study Design and Methodology:
  This is a double-blind, placebo-controlled study of the efficacy, safety, and pharmacokinetics of Allopregnanolone Injection in adult female subjects diagnosed with severe post-partum depression (PPD). Subjects must remain as in-patientpatients during the study Treatment Period, which is of 60 hours' or 2.5 days' duration. The Screening Period assessments may be conducted on an in-patient or an out-patient basis. The Follow Up Period assessments are conducted on an out-patient basis.
  Screening Period: The Screening Period begins with the signature of the informed consent form (ICF). Eligibility is determined by applying the inclusion/exclusion criteria. The diagnosis of PPD must be by Structured Clinical Interview for DSM-V Axis I Disorders (SCID-I).
  Treatment Period: Once subjects are confirmed as qualifying for the study, they will be randomized to one of two treatment groups on a 1: 1 basis: one group will receive Allopregnanolone and one group will receive placebo. The infusions will be continuous intravenous infusions of blinded study drug, with a new bag and line hung every 24 hours during the 48-hour infusion. Infusion rates will increase with subjects receiving 25 mcg/kg/hour (0-2 hours), then 45 mcg/kg/hour (2-4 hours), then 90 mcg/kg/hour (4-48 hours). Subjects may go home after the +60 hour assessments have been completed (12 hours after completion of the study drug infusion). If their clinical condition does not allow discharge, normal standard of care will be employed in their ongoing management.

Initiation of benzodiazepines, narcotics, antibiotics, neuroleptics, and other anti-anxiety medications will not be allowed between screening and completion of the +60 hour assessments. Doses of psychotropics, which must have been initiated at least 14 days prior to screening, must remain at a stable dose until completion of the +60 hour assessments. If at the +60 hour assessment, there has been no treatment response (HAM-D 17 score remains above ten), treatment with anti-depressant medication may be optimized prior to discharge, and the subject may remain in the unit or be followed at an out-patient clinic, as clinically indicated.

Efficacy and safety assessments will be performed periodically during the study, and blood samples will be collected for analysis of Allopregnanolone, metabolite, and Captisol concentrations, as outlined in the Schedule of Events. Blood samples will be collected, and outcome measures will be obtained at pre-specified times over a 60-hour period during the Treatment Period.

Follow-Up Period: Follow up visits will be conducted one week and one and two months (+7d±1 day, 30d±3 days, and 60d±3 days) after the initiation of the study drug infusion.

Number of Subjects:

Recruitment will continue until 22 subjects have been randomized or 20 evaluable subjects have completed the study, whichever occurs first.

Inclusion Criteria:

The following inclusion criteria must be met for individuals to be eligible for the trial:
1. Subject has signed an ICF before any study-specific procedures are performed
2. Subject is an ambulatory, community-dwelling, English-speaking female aged between 18 and 45 years
3. Subject is in good physical health and has no clinically significant findings on physical examination, 12-lead ECG, or clinical laboratory tests
4. Subject agrees to adhere to the study requirements
5. Subject must either have ceased lactating at screening: or if still lactating at screening, patient must have already fully and permanently weaned their infant(s) from breastmilk: or if still actively breastfeeding at screening, patient must agree to cease giving breast milk to their infant(s) prior to receiving study drug. For the avoidance of doubt, subjects who are breastfeeding and do not agree to permanently wean their infant(s) from breastmilk at screening are not eligible for the study.
6. Subject must have a negative serum pregnancy test
7. Subject has had a Major Depressive Episode that began no earlier than the third trimester and no later than the first 4 weeks following delivery, as diagnosed by Structured Clinical Interview for DSM-IV Axis I Disorders (SCID-I)
8. Subject has a baseline HAM-D-17 score of ≥ 26 at screening
9. Subject is ≤ six months postpartum
10. Subject is willing to delay start of other antidepressant or anxiety medications and any new pharmacotherapy regimens until the study drug infusion and +84 hour assessments have been completed Subject has no detectable hepatitis B surface antigen [HBsAg], anti-hepatitis C virus [HCV] and human immunodeficiency virus [HIV] antibody at screening Exclusion Criteria:

Subjects will be excluded if they meet any of the following exclusion criteria:
1. Recent history or active clinically significant manifestations of metabolic, hepatic, renal, hematological, pulmonary, cardiovascular, gastrointestinal, musculoskeletal, dermatological, urogenital, or eyes, ears, or nose and throat disorders, or any other acute or chronic condition that, in the Investigator's opinion, would limit the subject's ability to complete or participate in this clinical study
2. Known allergy to progesterone or allopregnanolone
3. Active psychosis per Investigator assessment
4. Medical history of seizures
5. History of active alcoholism or drug addiction (including benzodiazepines) in the 12 months prior to screening
6. Exposure to another investigational medication or device within 30 days Administration of psychotropics that have been initiated within 14 days prior to screening and are not being taken at a stable dose.

Investigational Product, Dosage, and Mode of Administration;

Allopregnanolone Injection, IV administration; Allopregnanolone Injection is a sterile clear colorless 5 mg/mL solution of Allopregnanolone (allopregnanolone) and 250 mg/mL betadex sulfobutyl-ether sodium, National Formulary (NF) (Captisol®) supplied in single use 20 mL vials for IV administration. As supplied, Allopregnanolone Injection, which is hypertonic, requires further dilution with Sterile Water for Injection (SWFI) to render it isotonic for IV infusion. The specific infusion dose of Allopregnanolone Injection will be calculated based on weight for each subject and administered according to the randomization schedule. Infusion bags will be changed every 12 hours. Details about the preparation of the study drug infusions by an unblinded pharmacist will be included in the Pharmacy Manual.

Reference Therapy, Dosage, and Mode of Administration;

An identical placebo intravenous infusion will be prepared for intravenous administration according to the randomization schedule.

Randomization and Stopping Rules:

Subjects will be randomized into Group A or B (as shown below on Table 5); subjects and unit staff and clinicians will be blinded as to treatment allocation. Only the pharmacist who will prepare the infusion bags, according to the randomization schedule, will be unblinded. The infusion rates are the same for all subjects within a particular dosing period (0-12 hours, 12-24 hours, etc).

If any subject has an SSS score of seven for two or more consecutive assessments during normal waking hours, the infusion rate will be decreased to the next lowest infusion dose (or turned off if this occurs on the 25 mcg/kg/hour dose level) for the remainder of the study.

TABLE 5

Treatment Groups

| | Day 1<br>25 mcg/kg/hour | Day 1<br>45 mcg/kg/hour | Day ½<br>90 mcg/kg/hour |
|---|---|---|---|
| Randomization Group | 0-2 hours | 2-4 hours | 4-48 hours |

TABLE 5-continued

| | Treatment Groups | | |
|---|---|---|---|
| | Day 1<br>25 mcg/kg/hour | Day 1<br>45 mcg/kg/hour | Day ½<br>90 mcg/kg/hour |
| A | Allopregnanolone | Allopregnanolone | Allopregnanolone |
| B | Placebo | Placebo | Placebo |

Criteria for Evaluation;
Primary Endpoint

The primary endpoint will be the Hamilton Rating Scale for Depression-17 (HAM-D-17). Subject symptom response, defined by the HAM-D-17, will be administered before, during, and after the infusion of blinded study drug. The efficacy outcome will be evaluated as a change from baseline in overall HAM-D-17 score at the end of the treatment period (at +482 hours), comparing the two treatment groups to evaluate the difference between Allopregnanolone and placebo.

Secondary Endpoints

A key secondary endpoint will be the Clinical Global Impression-Improvement Scale (CGI-I): clinical evaluation of subject treatment response, defined by the CGI-I, will be administered by the clinician before, during, and after the infusions of blinded study drug. The change in CGI-I will be evaluated as comparing the two treatment groups to evaluate the difference between Allopregnanolone and placebo.

A key safety endpoint will be the assessment of sedation using the Stanford Sleepiness Scale. This will be assessed periodically before, during, and after the infusion of blinded study drug. Changes in score over time will be represented graphically, and change from baseline will be measured.

Safety and tolerability of Allopregnanolone Injection will be evaluated by summarization of AEs by frequency, severity and seriousness; mean changes from baseline in clinical laboratory measures, vital signs, and ECGs; and concomitant medication usage. Suicidality will be monitored using the Columbia-Suicide Severity Rating Scale (C-SSRS).

The following outcome measures will be collected and analyzed during the study: EPDS, a subject-rated depressive symptom severity scale specific to the perinatal period; RMD VAS, a 14-item subject-rated scale to assess a range of symptoms specific to reproductive mood disorders (i.e., anxiety, insomnia, mood); GAD-7, a subject-rated depressive symptom severity scale; PHQ-9, a subject-rated depressive symptom severity scale: individual HAM-D-17 subcategories related to depression, guilt, suicidal ideation, insomnia, social interactions, anxiety, somatic symptoms, and insight.

Plasma will be collected to assay for concentrations of Allopregnanolone, Allopregnanolone metabolites, and Captisol. The following PK parameters will be derived from the plasma concentrations (where evaluable); area under the concentration-time curve (AUC) from time zero to 48 hours ($AUC_{0-48}$), AUC from time zero to infinity ($AUC_{inf}$), maximum (peak) plasma concentration ($C_{max}$), time at maximum (peak) plasma concentration ($T_{max}$), steady-state drug concentration in the plasma during constant-rate infusion ($C_{SS}$), and average drug concentration in the plasma at steady state during a dosing interval ($C_{avg}$).

Breast milk may be collected as an optional assessment if consent is received from the subject. Samples will be analyzed for Allopregnanolone concentrations.

Statistical Methods:

For the purpose of all safety, efficacy, and exploratory analyses where applicable, baseline is defined as the last pre-dose measurement closest to the start of blinded study drug infusion.

Sample Size Calculation

Assuming a two-sided test at an alpha level of 0.1, a sample size of 10 evaluable patients per group would provide 80% power to detect an effect size of 1.2 between the Allopregnanolone and placebo groups with regard to the primary outcome variable of change from baseline in HAM-D total score. An effect size of 1.2 corresponds to a placebo adjusted difference of 12 points in the change from baseline in HAM-D total score at 48 hours with an assumed standard deviation of 10 points. By including two treatment groups and using a 1:1 randomization ratio, a total of 20 evaluable patients are required. Assuming a non-evaluability rate of 10%, approximately 223 patients will be randomized.

Efficacy Analysis

The efficacy population will include all subjects who complete at least 12 hours of infusion and have efficacy evaluations through the 12 hour time point on Day 1. All analyses will be conducted Group A versus Group B. Change from baseline in overall HAM-D-17 score (range 0-52) at +48 hours will be the primary assessment of efficacy. Additional analyses of the HAM-D-17 score will be undertaken comparing across the groups change from baseline to +12 h, +24 h, +36 h, +60 h, +84 h, +7 d, +30 d, and +60 d.

The CGI-I score will be used to determine physician's assessment of improvement in symptoms, and will be analysed as a secondary endpoint in the same way as the primary endpoint.

Scores from other depression and mood disorder rating scales will be summarized by descriptive statistics, including n, mean, SD, median, minimum and maximum values, as change from baseline. These rating scales include: EPDS, RMD VAS, GAD-7, PHQ-9, and individual HAM-D-17 subcategories related to depression, guilt, suicidal ideation, insomnia, social interactions, anxiety, somatic symptoms, and insight.

Safety Analysis

The Safety Population (SAF) is defined as all subjects who begin a study drug infusion. Safety will be assessed using SSS, adverse events, vital signs, ECG, clinical laboratory tests, C-SSRS, and concomitant medication data. Safety data will be listed by individual and summarized by treatment group. In addition, an analysis of SSS data will be performed comparing the treatment groups in the same way as for the primary endpoint.

Safety data will be examined for possible relationships between subject characteristics and plasma allopregnanolone concentrations, as appropriate.

TABLE 6

| Schedule of Events | | | | | | | | |
|---|---|---|---|---|---|---|---|---|
| Screen<br>D −5-<br>D −1 | D 1<br>H 0 | D 1<br>H 2 +<br>2 h | D 1<br>H 4 +<br>4 h | D 1<br>H 8 +<br>8 h | D 1<br>H 12 +<br>12 h | D 1<br>H 38 +<br>18 h | D 1<br>H 24 +<br>14 h | D 2<br>H 6 +<br>30 h |

TABLE 6-continued

Schedule of Events

| | | | | | | | | | |
|---|---|---|---|---|---|---|---|---|---|
| Informed Consent | X | | | | | | | | |
| Inclusion/Exclusion | X | | | | | | | | |
| Demographics | X | | | | | | | | |
| Medical/Family History | X | | | | | | | | |
| Physical Examination | X | | | | | | | | |
| Body Weight/Height | X | | | | | | | | |
| CBC/Serum Chemistry[a] | X | | | | | | | | |
| Urinalysis | X | | | | | | | | |
| Drug/Alcohol Screen[b] | X | | | | | | | | |
| Serum Pregnancy Test | X | | | | | | | | |
| Hepatitis & HIV Screen | X | | | | | | | | |
| Genetic Sample[c] | X | | | | | | | | |
| Vital Signs[d] | X | X | X | X | X | X | X | X | X |
| 12-Lead ECG[e] | X | | | | | | | | |
| C-SSRS[f] | | X | | | | | | X | |
| Confined to unit | | X | X | X | X | X | X | X | X |
| HAM-D-17[g] | X | X | X | X | X | X | | X | |
| CGI-I[h] | | X | X | X | | X | | X | |
| SSS[i] | | X | X | X | X | X | X | X | X |
| EPDS[j] | | X | | | | | | | |
| RMD VAS[j] | | X | | | | | | | |
| GAD-7[j] | | X | | | | | | | |
| PHQ-9[j] | | X | | | | | | | |
| Plasma PK Samples[k] | | X | X | X | X | X | X | X | X |
| Adverse Events | | X | X | X | X | X | X | X | X |
| Concomitant Meds | X | X | X | X | X | X | X | X | X |
| Study Drug infusion | | X | X | X | X | X | X | X | X |
| Breast milk for PK[l] | | X | X | X | X | X | X | X | X |
| Study completion | | | | | | | | | |

| | D 2 H 12 + 36 h | D 2 H 18 + 42 h | D 2 H 24 + 48 h | D 3 H 6 + 54 h | D 3 H 12 + 60 h | D 7 (+7 D ± 1 d) | D 7 (+ 30 D ± 3 d) | D 7 (+60 D ± 3 d) |
|---|---|---|---|---|---|---|---|---|
| Informed Consent | | | | | | | | |
| Inclusion/Exclusion | | | | | | | | |
| Demographics | | | | | | | | |
| Medical/Family History | | | | | | | | |
| Physical Examination | | | | | | X | | |
| Body Weight/Height | | | | | | | | |
| CBC/Serum Chemistry[a] | | | | | | X | | |
| Urinalysis | | | | | | X | | |
| Drug/Alcohol Screen[b] | | | | | | | | |
| Serum Pregnancy Test | | | | | | | | |
| Hepatitis & HIV Screen | | | | | | | | |
| Genetic Sample[c] | | | | | | | | |
| Vital Signs[d] | X | X | X | X | X | X | | |
| 12-Lead ECG[e] | | | X | | X | X | | |
| C-SSRS[f] | | | X | | X | X | | |
| Confined to unit | X | X | X | X | X | | | |
| HAM-D-17[g] | X | | X | | X | X | X | X |
| CGI-I[h] | X | | X | | X | X | X | X |
| SSS[i] | X | X | X | X | X | | | |
| EPDS[j] | | | X | | | X | X | X |

TABLE 6-continued

Schedule of Events

| | | | | | | | | |
|---|---|---|---|---|---|---|---|---|
| RMD VAS[j] | | | X | | | X | X | X |
| GAD-7[j] | | | X | | | X | X | X |
| PHQ-9[j] | | | X | | | X | X | X |
| Plasma PK Samples[k] | X | X | X | X | X | | | |
| Adverse Events | X | | X | X | X | X | X | X |
| Concomitant Meds | X | X | X | X | X | X | X | X |
| Study Drug infusion | X | X | X | | | | | |
| Breast milk for PK[l] | X | X | X | X | X | | | |
| Study completion | | | | | | | | |

BMI = body mass index; CGI-I = Clinical Global Impression of Improvement; C-SSRS = Columbia - Suicide Severity Rating Scale; ECG = electrocardiogram; EPDS = Edinburgh Postnatal Depression Scale; GAD-7 = Generalized Anxiety Disorder 7-Item Scale; HAM-D-17 = Hamilton Rating Scale for Depression (17-items); PHQ-9 = Subject Health Questionnaire; PK = pharmacokinetic; RMD-VAS = Reproductive Mood Disorders Visual Analogue Scale; PPIU = Perinatal Psychiatry Insubject Unit; SSS = Stanford Sleepiness Scale.

[a]Safety laboratory tests will include complete blood count, renal function tests, liver function tests, and thyroid-stimulating hormone. Other laboratory data collected will include progesterone, estrogen, and oxytocin. The urine test will be a urinalysis. All clinical laboratory assessments are to be completed within ±30 minutes of the scheduled time point.
[b]Urine assessment for selected drugs of abuse and a serum alcohol screen will be assessed at screening.
[c]A cheek swab/blood sample will be taken for genetic analysis.
[d]Vital signs include oral temperature (° C.), respiratory rate, heart rate and blood pressure (supine and standing). A full set of vital signs will be obtained at all specified timepoints (±30 minutes), unless the subject is asleep between the hours of 23.00 h and 06.00 h each day.
[e]A 12-lead ECG will be performed at the specified times (within ±30 minutes of the scheduled time point on Day 4) and the standard intervals recorded, as well as any abnormalities.
[f]The "Baseline" C-SSRS form will be completed on the morning of Day 1 prior to dosing. The "Since Last Visit" C-SSRS form will be completed at all subsequent scheduled timepoints.
[g]The HAM-D-17 will be administered per the time points in the Schedule of Events. The HAM-D 17 assessments are to be completed within ±30 minutes of the scheduled time point, but prior to starting dosing on D 1 H 0.
[h]The CGI-I will be administered per the time points in the Schedule of Events. The CGI-I assessments are to be completed within ±30 minutes of the scheduled time point.
[i]The SSS will be administered every two hours from D 1 H 0 to D 3 H 12 unless the subject is asleep between the hours of 23.00 h and 06.00 h each day. All these SSS assessments are to be completed within ±15 minutes of the scheduled time point.
[j]The questionnaires (EPDS, RMD VAS, GAD-7, PHQ-9) will be administered per the time points in the Schedule of Events. All assessments are to be completed within ±30 minutes of the scheduled time point.
[k]Blood samples for PK analysis will be collected at pre-infusion; and at +0.5, 1, 2, 2.5, 3, 4, 4.5, 5, 6, 8, 12, 18, 24, 30, 36, 42, 48, 50, 52, 54, 56, 58, and 60 hours after the start of the infusion. Scheduled time points for PK blood draws after the start of infusion will have a window of ±2 minutes for samples collected during the first six hours (to D 1 H 6), and ±10 minutes for samples collected after that. Samples will be processed according to the PK Manual, and analyzed for concentrations of Allopregnanolone, metabolites of Allopregnanolone, and Captisol.
[l]As an optional assessment per subject consent, breast milk will be collected pre-infusion and collected and pooled over the following time periods of interest: 0-12, 12-24, 24-36, 36-48, and 48-60 hours after the start of the infusion. The times of the first and last pumping of each collection period will be recorded. Breast milk will be pooled within each collection period and the total volume will be measured. Two aliquots of 0.5 mL will be taken from each pooled collection and analyzed for PK. Full detailed instructions for breast milk PK sampling, processing and shipping will be provided in the study PK Manual.

BMI=body mass index; CGI-I=Clinical Global Impression of Improvement; C-SSRS=Columbia–Suicide Severity Rating Scale; ECG=electrocardiogram; EPDS=Edinburgh Postnatal Depression Scale; GAD-7=Generalized Anxiety Disorder 7-Item Scale; HAM-D-17=Hamilton Rating Scale for Depression (17-items); PHQ-9=Subject Health Questionnaire; PK=pharmacokinetic; RMD-VAS=Reproductive Mood Disorders Visual Analogue Scale; PPIU=Perinatal Psychiatry Insubject Unit; SSS=Stanford Sleepiness Scale.

[a] Safety laboratory tests will include complete blood count, renal function tests, liver function tests, and thyroid-stimulating hormone. Other laboratory data collected will include progesterone, estrogen, and oxytocin. The urine test will be a urinalysis. All clinical laboratory assessments are to be completed within ±30 minutes of the scheduled time point.

[b] Urine assessment for selected drugs of abuse and a serum alcohol screen will be assessed at screening.

[c] A cheek swab/blood sample will be taken for genetic analysis.

[d] Vital signs include oral temperature (° C.), respiratory rate, heart rate and blood pressure (supine and standing). A full set of vital signs will be obtained at all specified timepoints (+30 minutes), unless the subject is asleep between the hours of 23.00 h and 06.00 h each day.

[e] A 12-lead ECG will be performed at the specified times (within +30 minutes of the scheduled time point on Day 4) and the standard intervals recorded, as well as any abnormalities.

[f] The "Baseline" C-SSRS form will be completed on the morning of Day I prior to dosing. The "Since Last Visit" C-SSRS form will be completed at all subsequent scheduled timepoints.

[g] The HAM-D-17 will be administered per the time points in the Schedule of Events. The HAM-D 17 assessments are to be completed within ±30 minutes of the scheduled time point, but prior to starting dosing on DI HO.

[h] The CGI-I will be administered per the time points in the Schedule of Events. The CGI-I assessments are to be completed within ±30 minutes of the scheduled time point.

[i] The SSS will be administered every two hours from DIHO to D3H12 unless the subject is asleep between the hours of 23.00 h and 06.00 h each day. All these SSS assessments are to be completed within ±15 minutes of the scheduled time point.

[j] The questionnaires (EPDS, RMD VAS, GAD-7, PHQ-9) will be administered per the time points in the Schedule of Events. All assessments are to be completed within ±30 minutes of the scheduled time point.

[k] Blood samples for PK analysis will be collected at pre-infusion; and at +0.5, 1, 2, 2.5, 3, 4, 4.5, 5, 6, 8, 12, 18, 24, 30, 36, 42, 48, 50, 52, 54, 56, 58, and 60 hours after the start of the infusion. Scheduled time points for PK blood draws after the start of infusion will have a window of +2 minutes for samples collected during the first six hours (to DIH6), and +10 minutes for samples collected after that. Samples will be processed according to the PK Manual, and analyzed for concentrations of Allopregnanolone, metabolites of Allopregnanolone, and Captisol.

[1] As an optional assessment per subject consent, breast milk will be collected pre-infusion and collected and pooled over the following time periods of interest: 0-12, 12-24, 24-36, 36-48, and 48-60 hours after the start of the infusion. The times of the first and last pumping of each collection period will be recorded. Breast milk will be pooled within each collection period and the total volume will be measured. Two aliquots of 0.5 mL will be taken from each pooled collection and analyzed for PK. Full detailed instructions for breast milk PK sampling, processing and shipping will be provided in the study PK Manual.

Results

Two subjects enrolled and agreed to enter the study, meeting all inclusion and exclusion criteria. Enrollment is constrained by lactation exclusion, co-morbidity, use of other psychotropics.

Figure 5:
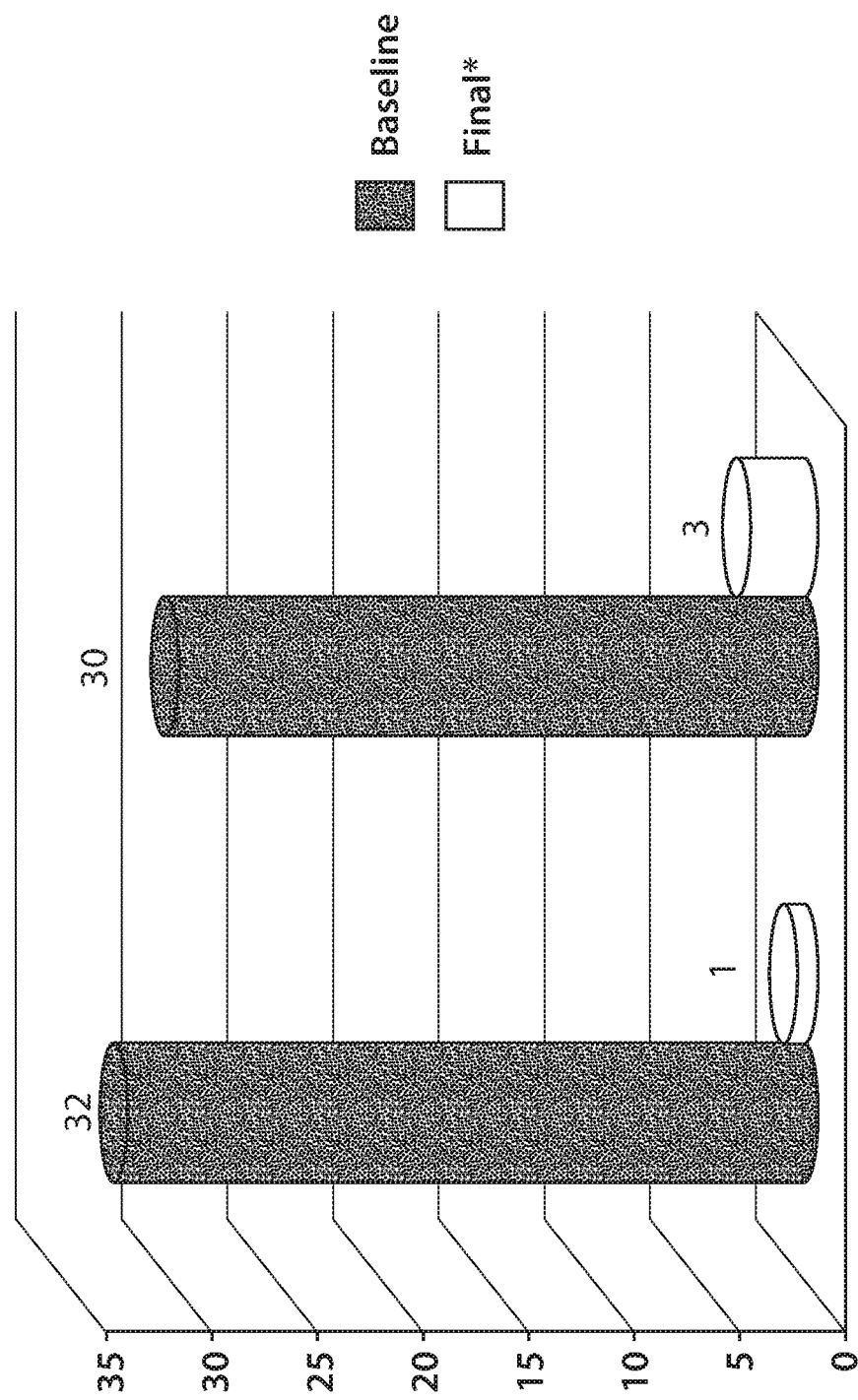
FIG. 5 depicts the baseline and final Hamilton Rating Scale for two subjects undergoing the clinical study
Figure 6:
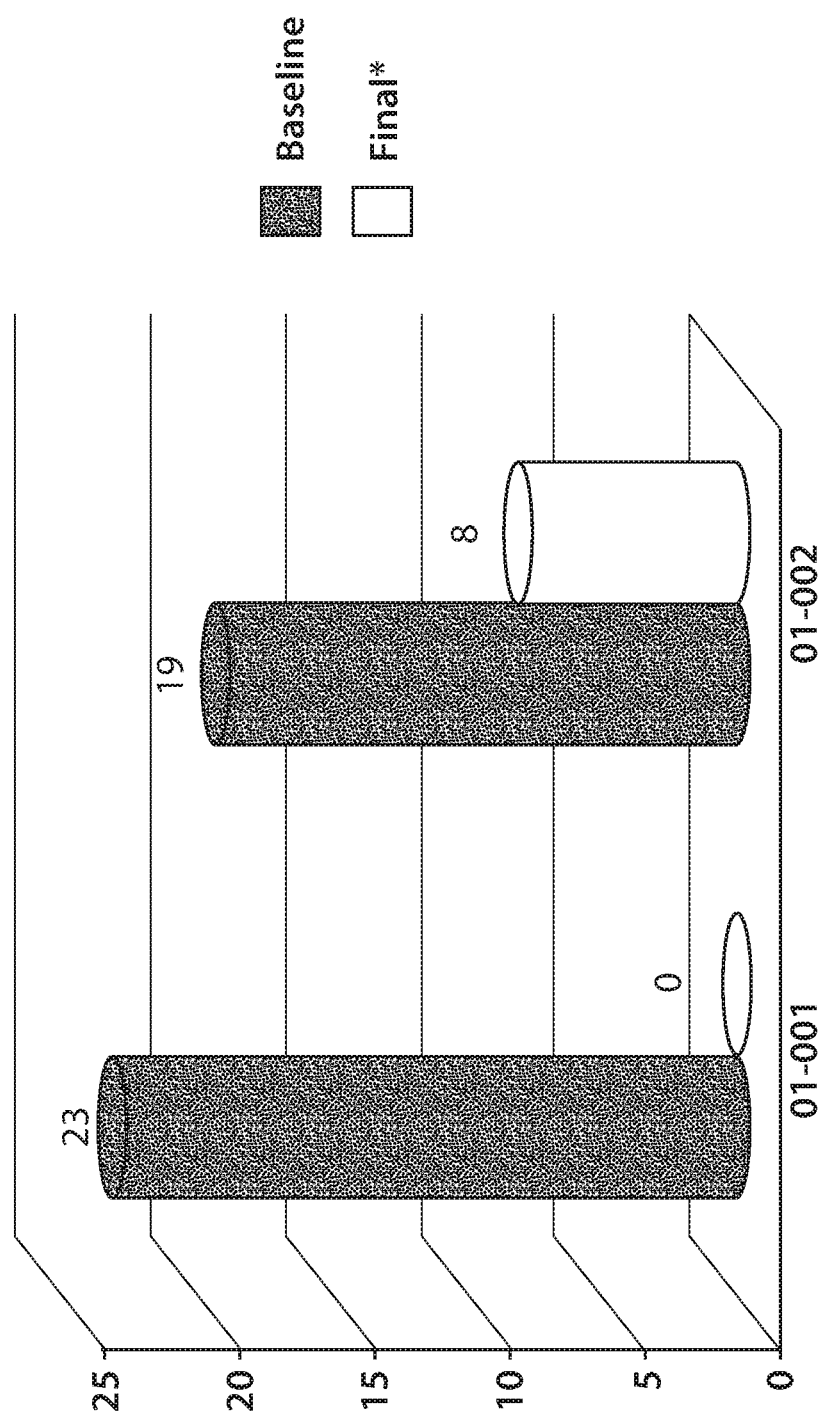
FIG. 6 depicts the baseline and final Clinical Impression-Improvement for two subjects undergoing the clinical study
Figure 7:
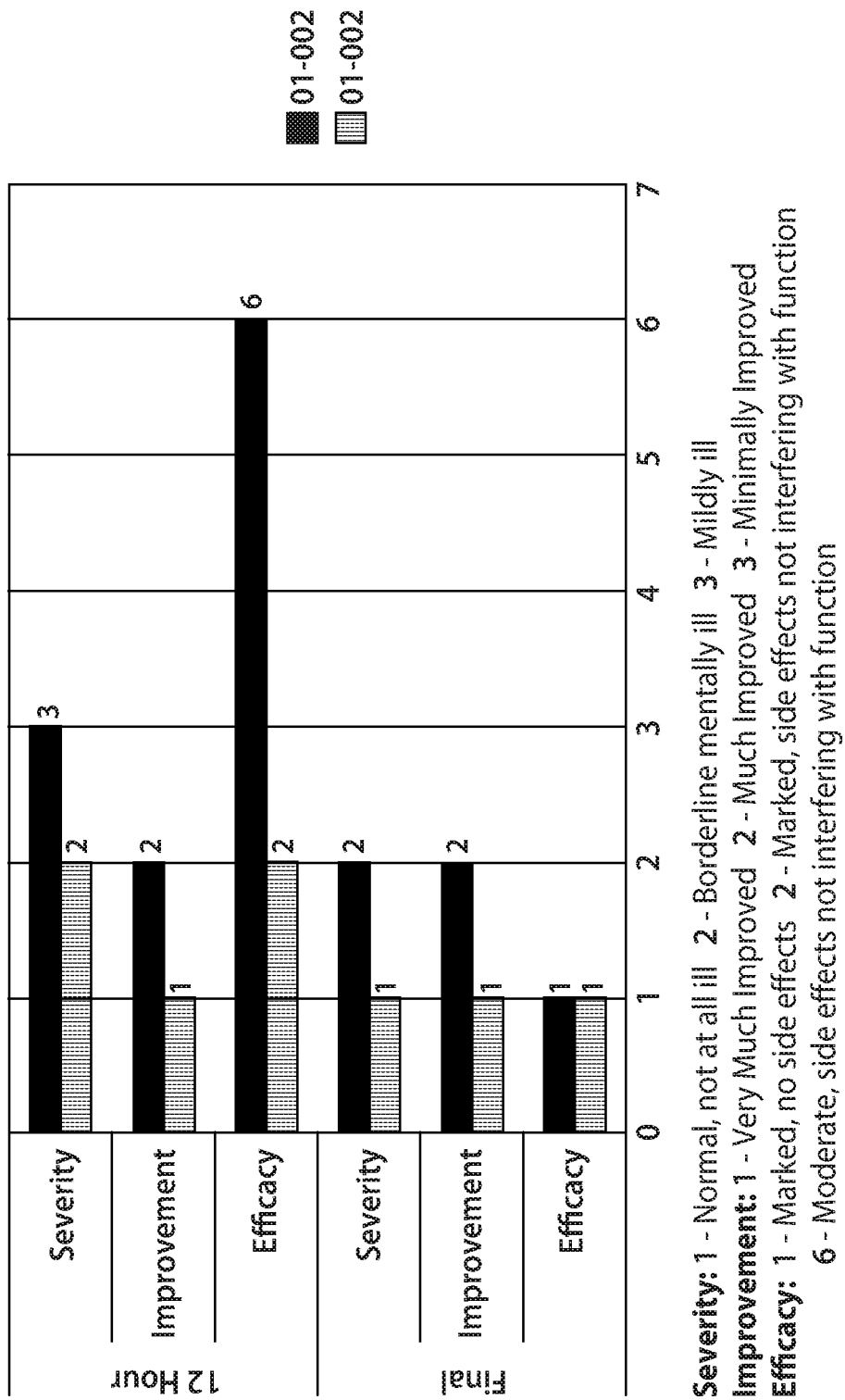
FIG. 7 depicts the severity, improvement, and efficacy for two subjects undergoing the clinical study after 12 hours and at the completion of the study.
Figure 8:
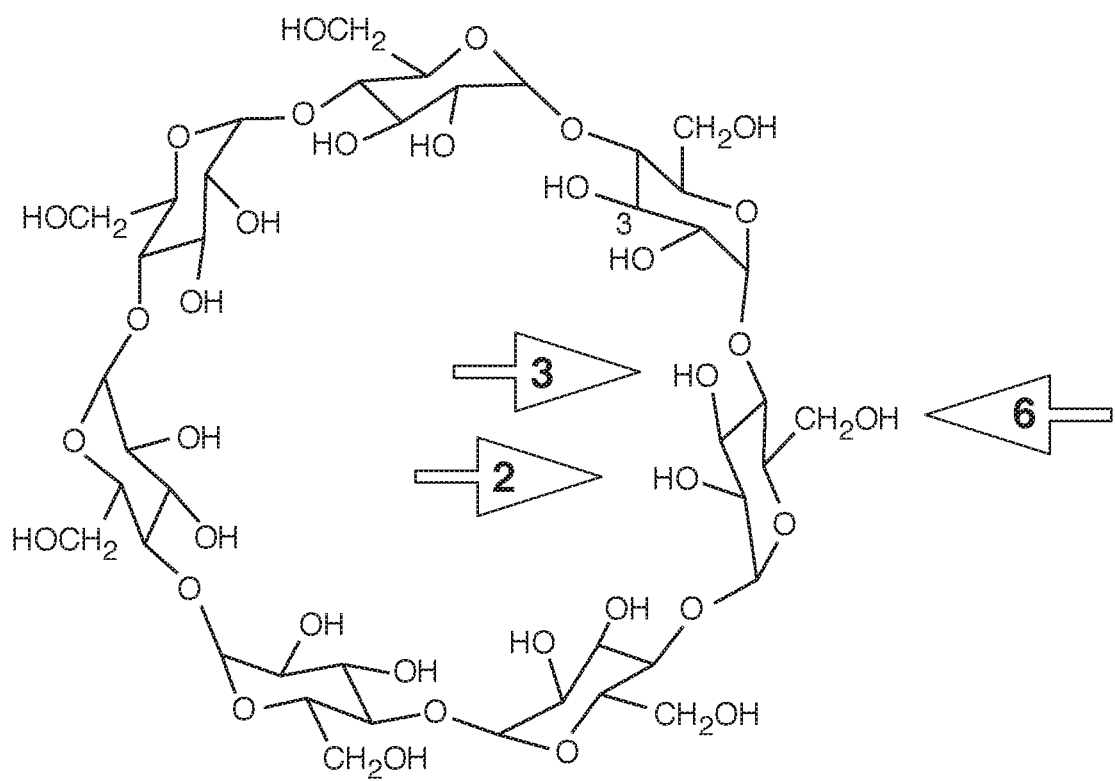
FIG. 8 depicts an exemplary structure of cyclodextrins with arrows pointing at 2, 3, and 6 position hydroxyls.

Treatment response was observed with the two subjects. Changes were observed on HAM-D, EPDS, CGI (defined above). FIG. 5 shows the HAM-D-17 for two subjects, Patient 01-001 and Patient 01-002. FIG. 6 shows the EPDS for Patient 01-001 and Patient 01-002. FIG. 7 shows the CGI-I for Patient 01-001 and Patient 01-002.

The first subject did not report worsening of symptoms during the taper phase. The second subject did report subjective return of mild anxiety during the taper phase (finishing final day).

Results

Improvement in depression in four of four women with severe postpartum depression (PPD) within 24 hours after administration of intravenous allopregnanlone. During the allopregnanlone treatment period, all four patients rapidly achieved remission, as measured by the Hamilton Rating Scale for Depression (HAM-D). The patients had a mean HAM-D score of 26.5 at baseline and improved to a mean HAM-D score of 1.8 by the end of the treatment period. A HAM-D rating of greater than 24.0 is considered severe and a score below 7.0 is considered symptom-free. All four patients demonstrated consistent improvement as measured by the Clinical Global Impression-Improvement (CGI-I) scale. Allopregnanlone was well-tolerated in all patients treated on therapy or during the 30-day follow-up period.

Surprisingly, unlike certain treatments for depression, e.g., antidepressant medicines such as Selective Serotonin Reuptake Inhibitors (SSRIs), that typically are not effective for weeks (e.g., at least 1 to 3 weeks after taking antidepressant medicines, and as many as 6 to 8 weeks to effect improvement in depression symptoms), allopregnanolone improved four patients' symptoms within one day of treatment (e.g., within 24 hours after treatment, within 12 hours after treatment, about 12 hours after treatment).

Further, the response (e.g., relief from symptoms) was sustained after treatment with allopregnanolone.

All of the patients enrolled had severe depression as measured on the HAM-D at baseline and were treated as inpatients. All four patients had an inadequate response to prior antidepressant therapy.

Example 4. A Double-Blind, Placebo-Controlled, Two-Period Crossover, Proof-of-Concept Study Evaluating the Safety, Tolerability, Pharmacokinetics, and Efficacy of Allopregnanolone Injection in the Treatment of Subjects with Essential Tremor Primary Objective:
To evaluate the safety and tolerability of Allopregnanolone Injection when administered to subjects with essential tremor Secondary Objectives:
To assess the effect of Allopregnanolone Injection on subject response as measured by accelerometer (transducer measurement of tremor amplitude)

To assess the effect of Allopregnanolone Injection on subject response as measured globally by The Essential Tremor Rating Scale (TETRAS) and more frequently by the Performance Subscale (Items 4, 6, 7 and 8) as assessed by a clinician To assess the effects of Allopregnanolone Injection on sleepiness as measured by the Stanford Sleepiness Scale (SSS)

To assess the pharmacokinetic (PK) profile of allopregnanolone in subjects receiving Allopregnanolone Injection Overview of Study Design Stage One of this trial is a double-blind, placebo-controlled, proof-of-concept study designed to evaluate the safety, tolerability, PK, and efficacy of Allopregnanolone Injection in male or female subjects with essential tremor in the upper limb. Each subject's involvement is up to 72 days, including up to a 28-day Screening Period (the Screening Visit is I day of this 28-day window), 12-hour Treatment Period 1 with 12-hour follow-up, 7-day (+3 days) Washout Period, 12-hour Treatment Period 2 with 12-hour follow-up, and a 7-day Follow-up/End of Study Visit (Day 18, ±1 day).

Screening Period: The Screening Period begins on any I calendar day during the screening period window from Day −28 through Day −1 and begins with the signing of the ICF at the Screening Visit. Subjects will undergo preliminary screening procedures at the Screening Visit to determine eligibility, including completion of the TETRAS Performance Subscale to establish severity of upper limb tremor. Subjects must score >2 for at least one maneuver in the upper limb tremor assessment of the Performance Subscale (forward horizontal reach posture, lateral "wing beating" posture, or finger-nose-finger testing).

The end of the Screening Period coincides with the beginning of Treatment Period 1 in the Insubject Unit.

Treatment Period 1 with 12-hour follow-up: Treatment Period I begins on Day 1 and ends on Day 2. Subjects can be admitted to the Insubject Unit the afternoon/evening before (Check-in/Day −1 Visit) or on the morning of Day 1 (with enough time prior to initiation of dosing to complete all pre-dose study procedures). Beginning on the morning of dosing (Day 1), subjects will be randomized to receive either a 12-hour IV infusion of allopregnanolone (dose titrated up in 3 dose levels to about 90 µg/kg/hr (e.g., dose titrated up every 4 hours: 0-4 hours 29 µg/kg/hr; 5-8 hours 58 µg/kg/hr; 9-12 hours 86 µg/kg/hr) or a 12-hour IV infusion of placebo. Subjects will be admitted and confined to the Insubject Unit from Check-in/Day −1 or Day 1 through the end of the 12-hour follow-up period on Day 2.

During this 24-hour period, safety assessments and laboratory assessments will be performed, PK and blood samples will be collected, and outcome measures will be obtained at pre-specified times (Table 1).

Washout Period: Subjects will be discharged home for 7 full calendar days (+3 days: Days 2 to 9 [+3 days]) to complete the Washout Period before returning to the clinic for the Check-in/Day 9 Visit or Day 10 Visit.

Treatment Period 2 with 12-hour follow-up: Treatment Period 2 begins on Day 10 and ends on Day 11. Subjects can be admitted to the Insubject Unit the afternoon/evening before the day of dosing (Check-in/Day 9 Visit) or on the morning of Day 10 (with enough time prior to initiation of dosing to complete all pre-dose study procedures). Beginning on the morning of dosing (Day 10), subjects will receive either a 12-hour IV infusion of allopregnanolone (dose titrated up in 3 dose levels to about 90 µg/kg/hr (e.g., dose titrated up every 4 hours: 0-4 hours 29 µg/kg/hr; 5-8 hours 58 µg/kg/hr; 9-12 hours 86 µg/kg/hr) or a 12-hour IV infusion of placebo. Subjects will receive whichever study drug (allopregnanolone or placebo) they did not receive during Treatment Period 1. Subjects will be admitted and confined to the Insubject Unit from check-in through the end of the 12-hour follow-up period on Day 11.

During this 24-hour period, safety assessments and laboratory assessments will be performed, PK and blood samples will be collected, and outcome measures will be obtained at pre-specified times (Table 7).

7-day Follow-up/End of Stage One Study Visit: 7 days (±1 day) following completion of Treatment Period 2 (Day 18±1 day), or in the event a subject prematurely withdraws from the study, subjects will return to the clinic for the 7-day follow-up visit for final safety assessments (Table 6).

Stage Two: This is an open-label study designed to evaluate the safety, tolerability, PK, and effectiveness of Allopregnanolone Injection at a higher dose than in Stage One in male and female subjects with essential tremor in the upper limb. Subjects recruited for Stage One will be invited to participate in Stage Two. Each subject's involvement in Stage Two will be approximately nine days.

Stage Two Treatment Period: Subjects will have their eligibility confirmed during the screening process for Stage Two. They will check-in to the unit the evening prior or on the morning of Day 1 (with enough time prior to initiation of dosing to complete all study procedures) prior to initiating the 10-hour intravenous (IV) infusion of allopregnanolone will begin [dose titrated up after one (90 mcg/kg/hour) and two (120 mcg/kg/hour) hours to reach a maintenance infusion rate of 150 mcg/kg/hour]. Subjects will be admitted and confined to the Insubject Unit from Check-in on Day 1 through completion of the 24-hour assessments.

During the 24-hour treatment period, safety and activity assessments will be performed and blood and urine samples will be collected for analysis of allopregnanolone, Captisol®, and metabolites of allopregnanolone.

Day 7 Follow-up/End of Stage Two Study Visit: Six days (Day 7±1 day) following completion of the Stage Two treatment period, or in the event a subject prematurely withdraws from the study, subjects will return to the clinic for a follow-up visit for safety assessments and outcome measures (see Schedule of Assessments).

Subjects 24 subjects will be enrolled at 2 study centers to achieve at least 16 evaluable subjects for Stage One. Subjects evaluable for safety are defined as subjects who have initiated the IV infusion during Treatment Period 1. Subjects evaluable for efficacy are defined as subjects who have completed the IV infusion during Treatment Period 1. Subjects who completed Stage One will be invited to return for Stage Two, with no pre-specified minimum or maximum number of subjects.

Inclusion Criteria

Adult male or female English-speaking subjects between 35 and 75 years of age (inclusive) at the Screening Visit who have a diagnosis of essential tremor, with symptoms clearly present in at least 1 upper limb, who have signed an ICF and meet the following main inclusion criteria are eligible for enrollment; a TETRAS Performance Subscale score of ≥ 2 for at least one maneuver (forward horizontal reach posture, lateral "wing beating" posture, or finger-nose-finger testing) in the 'upper limb tremor' test (item 4): tremor present for at least 2 years prior to the Screening Visit: is off medication, or on a stable dose of medication for their tremor for at least 28 days prior to the Screening Visit (with the exception of prohibited medications per protocol): is willing to consent to both IV placebo and allopregnanolone for 2 periods of 12 hours each, and is willing to washout of or delay of start of prohibited medications and any new pharmacotherapy regimens until after completing the 7-day follow-up visit.

Subjects willing to return for Stage Two will be asked to stop prohibited medications 28 days prior to dosing and to be on a stable dose of permitted medications for their tremor for at least 28 days prior to dosing. They must agree to delay the start of any prohibited medications and not to change their pharmacotherapy regimens for tremor until after the final study visit. Specfically, subject has signed an ICF before any study-specific procedures are performed. Subject is off medication, or on a stable dose of medication for their tremor for at least 28 days prior to the start of the allopregnanolone infusion in Stage Two or must have been off prohibited medication for at least 28 days prior to the start of the allopregnanolone infusion. Subject is willing to abstain from alcohol and caffeine for at least 48 hours prior to check-in to the Insubject Unit and throughout the stay. Subject is in good health and has no clinically significant findings on physical examination, 12-lead ECG, and clinical laboratory tests (clinical chemistry, liver function tests [LFTs], hematology, urine drug screen, and urinalysis) after signing the ICF but before receiving the IV infusion in Stage Two. Subject agrees to adhere to the study requirements. All non-menopausal female subjects must have a negative serum pregnancy test prior to receiving allopregnanolone in Stage Two and agree to use of an effective form of contraception during the study and for 30-days after the last infusion. Subject is willing to washout of or delay of start of prohibited medications and any new pharmacotherapy regimens until after completing the Stage Two End-of study Visit. Subjects may not have developed an active clinically significant (in the Investigator's opinion) manifestation of metabolic; hepatic; renal; hematological; pulmonary; cardiovascular; gastrointestinal; musculoskeletal; dermatological; urogenital; eyes, cars, nose, or throat; psychiatric; or neurological (including seizures but except essential tremor) disorders since completion of Stage One. Subject has a current history of active alcoholism or drug addiction (including benzodiazepines) since completion of Stage One. Subject has been exposed to another investigational medication or device within 30 days.

Exclusion Criteria

Subjects will be excluded if they meet any of the following exclusion criteria prior to enrollment: Subject has a recent history or active clinically significant (in the Investigator's opinion) manifestations of metabolic; hepatic; renal; hematological; pulmonary; cardiovascular; gastrointestinal; musculoskeletal; dermatological; urogenital; eyes, cars, nose, or throat; psychiatric; or neurological (other than essential tremor) disorders. Subject has an acute or chronic condition that, in the Investigator's opinion, would limit the subject's ability to complete or participate in this clinical study. Subject has a known allergy to progesterone, allopregnanolone, or Captisol®. Subject has a medical history of seizures. Subject has a current history of active alcoholism or drug addiction (including benzodiazepines) at the time of the Screening Visit or during the year before the Screening Visit. Subject has been exposed to another investigational medication or device within 30 days.

TABLE 8

Schedule of Assessments (Stage One)

| | Visit Days | | | | | | |
|---|---|---|---|---|---|---|---|
| | Screening Period (Day −28 to Day −1) | | | | | | Follow-up Period |
| | Screening Visit | Check-in/ Visit[b] | Treatment Period 1[a] (Day 1 to Day 2) | | Check-in/ Visit[b] | Treatment Period 2[a] (Day 10 to Day 11) | | 7-day f/u Visit (Day |
| | Visit | (Day −1) | Day 1 | Day 2 | (Day 9) | Day 10 | Day 11 | 18 ± 1)[n] |
| Informed Consent | X | | | | | | | |
| Inclusion/ Exclusion Criteria | X | | | | | | | |
| Demographics | X | | | | | | | |
| Medical History | X | | | | | | | |
| Physical Examination (height measured at Screening only) | X | X | (X) | | X | (X) | | X |
| Brief Neurological Examination[c] | X | X | (X) | | X | (X) | | X |
| Body Weight | X | X | (X) | | X | (X) | | |
| Vital Signs[d] | X | | X | X | | X | X | X |
| Clinical Laboratory Tests[e] | X | X | (X) | X | X | (X) | X | X |
| Drug and Alcohol Screen[f] | X | X | (X) | | X | (X) | | |
| Pregnancy Test[g] | X | X | (X) | | X | (X) | | X |
| Hepatitis & HIV Screen | X | | | | | | | |
| 12-Lead ECG[h] | X | | X | | | X | | X |
| Randomization | | X | (X) | | | | | |
| Confined to Inpatient Unit | | X | X | | X | X | | |
| Discharge from Inpatient Unit | | | | X | | | X | |
| TETRAS[i] | X | | | | | | | X |
| TETRAS Performance Subscale (items 4, 6, 7, 8)[j] | X | | X | X | | X | X | X |
| Accelerometer[j] | X | | X | X | | X | X | X |
| C-SSRS | | X | (X) | X | X | (X) | X | X |
| SSS | | X | (X) | X | X | (X) | X | |
| Adverse Event Collection[k] | | X | X | X | X | X | X | X |
| Concomitant Medications | X | X | X | X | X | X | X | X |
| Study Drug Administration[l] | | | X | | | X | | |

TABLE 8-continued

Schedule of Assessments (Stage One)

| | Visit Days | | | | | | |
|---|---|---|---|---|---|---|---|
| | Screening Period (Day −28 to Day −1) | | | | | | Follow-up Period |
| | Screening Visit | Check-in/ Visit[b] (Day −1) | Treatment Period 1[a] (Day 1 to Day 2) | | Check-in/ Visit[b] (Day 9) | Treatment Period 2[a] (Day 10 to Day 11) | | 7-day f/u Visit (Day 18 ± 1)[n] |
| | | | Day 1 | Day 2 | | Day 10 | Day 11 | |
| Plasma for PK analysis[m] | | | X | X | | X | X | |
| Study Completion | | | | | | | | X |

[a]Subjects will be confined to the Insubject Unit during the two 24-hour Treatment Periods 1 and 2. Subjects receiving allopregnanolone for Treatment Period 1 will receive placebo for Treatment Period 2, and subjects receiving placebo for Treatment Period 1 will receive allopregnanolone for Treatment Period 2.
[b]To assist with scheduling, subjects can be admitted to the Insubject Unit the day prior to each Treatment Period at the Check-in/Day −1 and Check-in/Day 9 Visits or on Day 1 and Day 10 in advance of initiating the infusion. If subjects are admitted to the Insubject Unit on Day 1 or Day 10, they must be admitted with sufficient time to complete all Check-in Visit procedures.
[c]The brief neurological examination consists of review of the following: mental status, cranial nerves, sensation, strength, deep tendon reflexes, and coordination.
[d]Vital signs include oral temperature (° C.), respiratory rate, heart rate (supine and standing), and blood pressure (supine and standing). Heart rate and blood pressure measurements should be taken after the subject has been supine for at least 5 minutes and standing for 2 minutes. A full set of vital signs will be obtained at the Screening Visit, on Days 1 and 10 just prior to beginning the infusion, at 4 hours and 8 hours after initiating the infusion, at the end of each 12-hour infusion, at the end of each 12-hour follow-up, and at the 7-day follow-up visit.
[e]Clinical laboratory samples (blood and urinalysis) will be collected at the Screening Visit, at Check-in or Day 1 and Check-in or Day 10, at the end of each 12-hour follow-up, and at the 7-day follow-up visit. Blood tests include clinical chemistry, LFTs, and hematology.
[f]Subjects will complete a urine drug screen for selected drugs of abuse and an alcohol screen at the Screening Visit, Check-in or Day 1, and at Check-in or Day 10. Subjects should abstain from using alcohol for at least 48 hours prior to check-in. The alcohol screen will be a serum alcohol test at the Screening Visit and a breath test at subsequent visits.
[g]A serum pregnancy test will be done at the Screening Visit and urine pregnancy tests will be done at Check-in or Day 1 at Check-in or Day 10 in advance of initiating the infusion. An additional urine pregnancy test will be done at the 7-day follow-up visit.
[h]A baseline 12-lead ECG will be performed during the Screening Visit to assess the presence of any current or historical cardiovascular conditions, on Days 1 and 10 just prior to beginning the infusion, at 4 hours and 8 hours after initiating the infusion, at the end of each 12-hour infusion, and will also be conducted at the 7-day follow-up visit.
[i]The full TETRAS questionnaire will be administered at Screening and at day-18 (7-day follow-up visit). The TETRAS Performance Subscale (items 4, 6, 7, and 8) will be administered at the following time points during Treatment Periods 1 and 2: pre-dosing, 2 hr, 4 hr, 6 hr, 8 hr, 10 hr and 12 hr (end of infusion), and at 24-hours of each treatment period. Item #4 (upper limb tremor) of the TETRAS Performance Subscale will be completed using both the accelerometer and clinician assessment. Testing should be completed after the SSS and within ±30 minutes of the planned questionnaire time points. All 3 tests in the upper limb tremor series of assessments (item 4) will be completed for both arms, first for the RIGHT arm and then for the LEFT. Pre-dose assessments can be done any time within 2 hours prior to the start of infusion. Day-18 assessments can be done at any time during the visit.
[j]Subjects will complete the TETRAS Performance Subscale, Item #4 (upper limb tremor) while wearing the accelerometer. Simultaneous clinician assessment of item #4 will occur. The accelerometer assessment is completed in conjunction with the TETRAS Performance Subscale at Screening and at the same time points during Treatment Periods 1 and 2: pre-dosing, 2 hr, 4 hr, 6 hr, 8 hr, 10 hr, 12 hr (end of infusion), and 24 hr (end of 12 hr follow-up), and at the 7-day follow-up visit.
[k]Serious AEs will be reported through 30 days after the last infusion.
[l]Study drug dosing will occur over 12 hours (3 × 4 hr dose levels) on Day 1 and Day 10, beginning at 8 AM (±2 hours).
[m]Blood samples for PK analysis for all subjects will be collected at the following time points during each dose level: pre-infusion, after the start of the infusion at 30 and 45 minutes, and at hours 1, 1.5, 2, 4, 6, 8, 10, 12, 12.5, 12.75, 13, 13.5, 14, 16 and 24 hours. The 30 and 45-minute time points should be collected within a ±2 minute window of the scheduled time point. The hourly time points should be collected within ±10 minutes of the schedule time point. The 24-hour post-follow-up time point should be collected within ±30 minutes of the scheduled time point.
[n]Subjects will report any SAEs occurring since the 7-day follow-up visit through 30 days after the last infusion.

Materials and Methods

Allopregnanolone Injection

The pharmacy will be responsible for preparing allopregnanolone Injection for subject dosing. allopregnanolone Injection is not intended to be administered to subjects undiluted. Each single use vial of Allopregnanolone Injection, which is hypertonic, will require dilution with an appropriate volume of Sterile Water for Injection to render it isotonic. The prepared admixture will be delivered to the subject area and administered at room temperature. The prepared admixture will be assigned a room temperature (20 to 25° C.)storage shelf life of 24 hours from time of compounding.

Placebo

The pharmacy will be responsible for preparing placebo for subject dosing. Commercially available sterile normal saline (0.9% NaCl Solution) will be used as the reference product in this study.

Route of Administration, Dosage, Dosage Regimen, and Treatment Period

In Stage One, Allopregnanolone Injection or matching placebo will be administered by an IV infusion according to the dose regimen shown in Table 7. Total dosing with allopregnanolone will occur in 1 Treatment Period for 12 hours. Total dosing with placebo will occur in 1 Treatment Period for 12 hours.

In Stage Two, there will be one treatment period comprising a 10-hour infusion of allopregnanolone (90 mcg/kg/hour for one hour, 120 mcg/kg/hour for one hour, and 150 mcg/kg/hour for eight hours).

Dose Rationale

The infusion rate of allopregnanolone to be studied in Stage One of this trial was chosen to achieve a maximum mean exposure of 150 nM. Since pregnant women tolerate this level without apparent AEs (Luisi 2000), 150 nM was selected as the target exposure for this study and 50 nM as the starting dose. This level of exposure has already been achieved in the clinic in the 6 subjects treated with continuous infusion allopregnanolone under emergency-use INDs for SRSE, with no drug-related SAEs reported. A similar $C_{max}$ was also achieved in several other studies conducted with intravenous allopregnanolone (Timby 2011b), with excellent tolerability.

An intra-subject dose escalation design was chosen to permit titration of treatment effect vs adverse events, specifically sedation, since this will be important as development proceeds. The selection of exposure in the current trial is based on a cautious approach adapted to the anticipated benefit-risk in the ET subject population. The starting dose in this trial (29 μg/kg/hr) is approximately 7 to 16-fold lower than the NOAEL observed in rats and dogs, although this is not the first in human study. Three dose levels (increased every four hours) will be utilized in this trial (29 μg/kg/hr, 58 μg/kg/hr and 86 μg/kg/hr) to achieve a 150 nM target plasma level. Overall the exposure to allopregnanolone in this trial will be substantially less than that of subjects treated under emergency-use INDs and included in the SRSE trial.

Subjects will be hospitalized and continually monitored for safety; and if any severe tolerability issues arise, the infusion will be terminated. The Stanford Sleepiness Scale will be regularly administered to monitor sedation and allow dose adjustment based on tolerability, with a formal dose interruption and reduction scheme implemented for this and other adverse events.

The starting dose in this study has already been used to treat 11 subjects with TBI with no SAEs reported. The maximum level of exposure has already been achieved in the clinic in the subjects treated with continuous infusion allopregnanolone under emergency-use INDs for SRSE, with no drug-related SAEs reported. A similar $C_{max}$ was also achieved in several other studies conducted with intravenous allopregnanolone, with good tolerability (Timby 2011b).

At the conclusion of Stage One of the trial, there was no clear difference between the allopregnanolone and placebo groups for the measures of activity in essential tremor (accelerometer and TETRAS scores) and for the sedation scores. There were 10 adverse events reported, as follows: one case each of phlebitis, somnolence, abnormal dreams, back pain, nasal congestion, headache, fatigue, and nausea, and two cases of dizziness. A maintenance dose of 150 mcg/kg/hour has been administered to six subjects with SRSE without any drug-related serious adverse events. Given the good tolerability of the maintenance dose of 86 mcg/kg/hour in Stage One of this study, the plan is to increase the maintenance dose to 150 mcg/kg/hour in Stage Two to seek a higher tolerated dose and determine if there is an effect on measurements of activity in essential tremor. To de-risk the administration of this higher maintenance dose, a short step up through 90 mcg/kg/hour and 120 mcg/kg/hour will be undertaken, and the same subjects that participated in Stage One will be invited to participate in Stage Two, as they have all tolerated the 86 mcg/kg/hour dose in Stage One.

The doses have been rounded to comply with updated dosing regimens in other studies with allopregnanolone, so 86 mcg/kg/hour becomes 90 mcg/kg/hour. The purpose of the rounding is to make calculation of the dose by weight easier. Pharmacokinetic modelling predicts that this will result in a less than 5% increase in average plasma concentrations of allopregnanolone.

Allopregnanolone Injection clinical supplies will be provided to the site as 2 types of kits: shelf packs containing multiple vials of allopregnanolone Injection and ancillary supply kits containing IV administration bags, solution sets, and IV bag labels.

Allopregnanolone Injection is a preservative-free, sterile, clear, colorless 5 mg/mL solution of allopregnanolone (allopregnanolone) and 250 mg/mL betadex sulfobutyl-ether sodium, NF (Captisol®) intended for IV injection. All inactive excipients used in the formulation are compendial grade and conform to current USP standards. The product is aseptically processed, sterile filtered, and filled into 20 mL Type 1 parenteral glass vials with West FluroTec® coated stopper container closure systems, under current Good Manufacturing Practice conditions. Allopregnanolone Injection is intended to be used as a single use vial. An appropriate number of single use vials to support the dosing duration of the study are packaged into vial kits and delivered to the site. Allopregnanolone Injection vial kits should be stored under refrigerated conditions (2 to 8° C.).

The placebo control, sterile normal saline (0.9% NaCl Solution), will be supplied in the manufacturer's original 150 mL pre-filled bags.

Intravenous administration bags (150 mL volume), solution sets, and IV bag labels are packaged and provided to the site as ancillary supply kits. Ancillary supply kits should be stored at controlled room temperature (20 to 25° C.).

All study drug labels will contain information to meet the applicable regulatory requirements and to ensure that subjects and study staff (excluding the unblinded pharmacist) remain blinded to treatment during Stage One.

Criteria for Evaluation
Safety Assessments (Stages One and Two)
    Adverse events (AEs), vital signs, clinical laboratory measures, physical examination, electrocardiograms (ECGs), and use of concomitant medications
    Columbia Suicidality Severity Rating Scale (C-SSRS)
    Stanford Sleepiness Scale (SSS)
Efficacy Assessments (Stages One and Two)
    Transducer measurement of tremor amplitude using an accelerometer
    TETRAS Performance Subscale
Exploratory Assessments (Stage Two)
    EEG
Pharmacokinetic (PK) Assessments Plasma will be collected to assay for allopregnanolone levels during both Treatment Period 1 and Treatment Period 2 in Stage One at the following time points during each dose level: pre-infusion at the first dose level (any time within 2 hours of beginning the infusion); after the start of the infusion at 30 and 45 minutes (±2 minutes), and at hours 1, 1.5, 2, 4 (±10 minutes: just prior to infusion rate change), 6 (2 h into dose level 2), 8 (just prior to infusion rate change), 10 (2 h into dose level 3), 12 (end of infusion), 12.5 (30 min after end of infusion), 12.75 (45 min after end of infusion), 13 (1 h after end of infusion), 13.5 (90 min after end of infusion), 14 (2 h after end of infusion), 16 (4 h after end of infusion) and 24 hours (end of 12 hr follow-up). In addition, samples may be analyzed for allopregnanolone metabolites and Captisol® concentrations.

In Stage Two, plasma will be collected to assay for allopregnanolone levels at the following time points: pre-infusion (any time within 2 hours of beginning the infusion); after the start of the infusion at 30, 60 (just before the infusion rate change), 90 and 120 (just before the infusion rate change) minutes (±2 minutes), and at hours 2.5, 3, 4, 5, 6, 7, 8, 9 and 10 (just before turning off the infusion) and at 10.5 (30 minutes after end of infusion), 10.75 (45 minutes after end of infusion), 11 (60 minutes after end of infusion), 11.5 (90 minutes after end of infusion), 12 (120 minutes after end of infusion), 14 (4 hours after end of infusion), 16 (6 hours after end of infusion) and 24 hours (22 hours after the end of the infusion). In addition, samples may be analyzed for allopregnanolone metabolites and Captisol® concentrations.

In Stage Two, all urine voided during the following time periods will be collected, pooled over the collections period, the volume measured, and a 20 ml sample taken before the urine is discarded. All subjects should void to empty their bladders within 30 minutes of the start of the infusion; this urine may be discarded. The collection periods are: 0-2 hours: 2-6 hours: 6-10 hours: 10-24 hours.

Primary Endpoints

Safety

Safety and tolerability of allopregnanolone will be evaluated by summarization of AEs, vital signs, clinical laboratory measures, physical examinations, ECGs, and concomitant medication usage. Safety will also be assessed by C-SSRS (treatment emergence of suicidal ideation and/or suicidal behavior).

Safety Analysis

The Safety Population (SAF) is defined as all subjects admitted into the Inpatient Unit for Stage One who meet all eligibility criteria, sign an informed consent, and who begin infusion with allopregnanolone or placebo in Treatment Period 1. Adverse Events will be classified by type, incidence, severity, and causality. The overall incidence of AEs will be summarized using the Medical Dictionary for Regulatory Activities (MedDRA) coding system and classified by System Organ Class (SOC), and preferred term. Data for vital signs, clinical laboratory measurements, ECG, physical examinations, brief neurological examinations, and concomitant medication usage will also be summarized.

Suicidality data collected from the C-SSRS at baseline and by visit during the active treatment periods will be listed for all subjects. The C-SSRS listings will include behavior type and/or category for suicidal ideation and suicidal behavior of the C-SSRS.

Safety data will be summarized and examined for possible relationships between subject characteristics and plasma allopregnanolone concentrations, as appropriate.

Secondary Endpoints

Safety

The Stanford Sleepiness Scale will be utilized to evaluate sedation. The Bond-Lader Mood Rating Scale and a Drug Effects Questionnaire will be used to assess mood and perception of drug effects.

Safety Analysis

Stanford Sleepiness Scale (SSS): Scores from the SSS (actual values and change from baseline) will be summarized by descriptive statistics and quantitated versus the treatment effect documented through the secondary efficacy assessments.

Efficacy

Maximum change from baseline (pre-dose) tremor, as measured by accelerometer

Change from baseline in upper limb tremor measured by items 4, 6, 7 and 8 of the TETRAS Performance Subscale Efficacy Analysis (Stage One)

The Efficacy Population (EFF) is defined as all SAF subjects who complete at least 12 hours of infusion in Treatment Period 1 and 2 and have efficacy evaluations through the 12-hour visits. Efficacy will be evaluated by maximum reduction from baseline (pre-dose) tremor, as measured by accelerometer and by maximum change from baseline in TETRAS Performance Subscale. Endpoints will be analyzed using a mixed effects analysis of variance model for crossover design where the fixed effects are sequence, period and treatment while the random effect includes subject within sequence. Due to possible carryover, baseline measures (baseline to the start of each period) will be included as covariates.

Accelerometer measurements and TETRAS data will be assessed and analyzed by treatment at each evaluation time point.

Efficacy Analysis (Stage Two)

The Stage Two Efficacy Population (EFF2) is defined as all subjects who complete the open-label 10-hour infusion of allopregnanolone and have efficacy evaluations through the 24-hour visit. Efficacy will be evaluated by maximum reduction from baseline (pre-dose) tremor, as measured by accelerometer and by maximum change from baseline in TETRAS Performance Subscale. Accelerometer measurements and TETRAS data will be assessed and summarized at each evaluation time point.

Pharmacokinetics

Plasma and urine (in Stage Two) concentrations of allopregnanolone at each assessed time point Pharmacokinetic Analysis The Stage One PK population will consist of all SAF subjects who complete at least 12 hours of allopregnanolone IV infusion in Treatment Period 1 or Treatment Period 2 with sufficient plasma concentrations for PK evaluations. The Stage Two PK population will consist of all subjects who complete the 10-hour allopregnanolone IV infusion with sufficient plasma concentrations for PK evaluations. The PK parameters, which include area under the concentration-time curve (AUC) from time zero to 12 hours ($AUC_{0-12}$), AUC from time zero to infinity ($AUC_{inf}$), maximum (peak) plasma concentration of the drug ($C_{max}$), time to maximum (peak) plasma concentration of the drug ($T_{max}$), steady-state drug concentration in the plasma during constant-rate infusion ($C_{ss}$), and average drug concentration in the plasma at steady-state during a dosing interval ($C_{avg}$), will be summarized (where evaluable) with descriptive statistics and listed by subject.

Table 8: Schedule of Assessments (Stage One)

TABLE 8

| | Schedule of Assessments (Stage One) | | | | | | |
|---|---|---|---|---|---|---|---|
| | | Screening Period (Day −28 to Day − 1) | Treatment Period 1[a] (Day 1 to Day 2) | | Check-in/ | Treatment Period 2[a] (Day 10 to Day 11) | | Follow-up Period 7-day |
| Visit Days | Screening Visit | Check-in/Visit[b] (Day − 1) | Day 1 | Day 2 | Visit[b] (Day 9) | Day 10 | Day 11 | f/u Visit (Day 18 ± 1)[n] |
| Informed Consent | X | | | | | | | |
| Inclusion/Exclusion Criteria | X | | | | | | | |
| Demographics | X | | | | | | | |
| Medical History | X | | | | | | | |

TABLE 8-continued

Schedule of Assessments (Stage One)

| Visit Days | Screening Period (Day −28 to Day − 1) Screening Visit | Check-in/Visit[b] (Day − 1) | Treatment Period 1[a] (Day 1 to Day 2) Day 1 | Treatment Period 1[a] (Day 1 to Day 2) Day 2 | Check-in/ Visit[b] (Day 9) | Treatment Period 2[a] (Day 10 to Day 11) Day 10 | Treatment Period 2[a] (Day 10 to Day 11) Day 11 | Follow-up Period 7-day f/u Visit (Day 18 ± 1)[n] |
|---|---|---|---|---|---|---|---|---|
| Physical Examination (height measured at Screening only) | X | X | (X) | | X | (X) | | X |
| Brief Neurological Examination[c] | X | X | (X) | | X | (X) | | X |
| Body Weight | X | X | (X) | | X | (X) | | |
| Vital Signs[d] | X | | X | X | | X | X | X |
| Clinical Laboratory Tests[e] | X | X | (X) | X | X | (X) | X | X |
| Drug and Alcohol Screen[f] | X | X | (X) | | X | (X) | | |
| Pregnancy Test[g] | X | X | (X) | | X | (X) | | X |
| Hepatitis & HIV Screen | X | | | | | | | |
| 12-Lead ECG[h] | X | | X | | | X | | X |
| Randomization | | X | (X) | | | | | |
| Confined to Inpatient Unit | | X | X | | X | X | | |
| Discharge from Inpatient Unit | | | | X | | | X | |
| TETRAS[i] | X | | | | | | | X |
| TETRAS Performance Subscale (items 4, 6, 7, 8)[i] | X | | X | X | | X | X | X |
| Accelerometer[j] | X | | X | X | | X | X | X |
| C-SSRS | | X | (X) | X | X | (X) | X | X |
| SSS | | X | (X) | X | X | (X) | X | |
| Adverse Event Collection[k] | | X | X | X | X | X | X | X |
| Concomitant Medications | X | X | X | X | X | X | X | X |
| Study Drug Administration[l] | | | X | | | X | | |
| Plasma for PK analysis[m] | | | X | X | | X | X | |
| Study Completion | | | | | | | | X | a. Subjects will be confined to the Insubject Unit during the two 24-hour Treatment Periods 1 and 2. Subjects receiving allopregnanolone for Treatment Period I will receive placebo for Treatment Period 2, and subjects receiving placebo for Treatment Period I will receive allopregnanolone for Treatment Period 2.
b. To assist with scheduling, subjects can be admitted to the Insubject Unit the day prior to each Treatment Period at the Check-in/Day −1 and Check-in/Day 9 Visits or on Day 1 and Day 10 in advance of initiating the infusion. If subjects are admitted to the Insubject Unit on Day 1 or Day 10, they must be admitted with sufficient time to complete all Check-in Visit procedures.
c. The brief neurological examination consists of review of the following: mental status, cranial nerves, sensation, strength, deep tendon reflexes, and coordination.
d. Vital signs include oral temperature (° C.), respiratory rate, heart rate (supine and standing), and blood pressure (supine and standing). Heart rate and blood pressure measurements should be taken after the subject has been supine for at least 5 minutes and standing for 2 minutes. A full set of vital signs will be obtained at the Screening Visit, on Days 1 and 10 just prior to beginning the infusion, at 4 hours and 8 hours after initiating the infusion, at the end of each 12-hour infusion, at the end of each 12-hour follow-up, and at the 7-day follow-up visit.
e. Clinical laboratory samples (blood and urinalysis) will be collected at the Screening Visit, at Check-in or Day 1 and Check-in or Day 10, at the end of each 12-hour follow-up, and at the 7-day follow-up visit. Blood tests include clinical chemistry, LFTs, and hematology.
f. Subjects will complete a urine drug screen for selected drugs of abuse and an alcohol screen at the Screening Visit, Check-in or Day 1, and at Check-in or Day 10. Subjects should abstain from using alcohol for at least 48 hours prior to check-in. The alcohol screen will be a serum alcohol test at the Screening Visit and a breath test at subsequent visits.
g. A serum pregnancy test will be done at the Screening Visit and urine pregnancy tests will be done at Check-in or Day 1 at Check-in or Day 10 in advance of initiating the infusion. An additional urine pregnancy test will be done at the 7-day follow-up visit.
h. A baseline 12-lead ECG will be performed during the Screening Visit to assess the presence of any current or historical cardiovascular conditions, on Days 1 and 10 just prior to beginning the infusion, at 4 hours and 8 hours after initiating the infusion, at the end of each 12-hour infusion, and will also be conducted at the 7-day follow-up visit.
i. The full TETRAS questionnaire will be administered at Screening and at day-18 (7-day follow-up visit). The TETRAS Performance Subscale (items 4, 6, 7, and 8) will be administered at the following time points during Treatment Periods 1 and 2: pre-dosing, 2 hr, 4 hr, 6 hr, 8 hr, 10 hr and 12 hr (end of infusion), and at 24-hours of each treatment period. Item #4 (upper limb tremor)

of the TETRAS Performance Subscale will be completed using both the accelerometer and clinician assessment. Testing should be completed after the SSS and within +30 minutes of the planned questionnaire time points. All 3 tests in the upper limb tremor series of assessments (item 4) will be completed for both arms, first for the RIGHT arm and then for the LEFT. Pre-dose assessments can be done any time within 2 hours prior to the start of infusion. Day-18 assessments can be done at any time during the visit.

j. Subjects will complete the TETRAS Performance Subscale, Item #4 (upper limb tremor) while wearing the accelerometer. Simultaneous clinician assessment of item #4 will occur. The accelerometer assessment is completed in conjunction with the TETRAS Performance Subscale at Screening and at the same time points during Treatment Periods 1 and 2: pre-dosing, 2 hr, 4 hr, 6 hr, 8 hr, 10 hr, 12 hr (end of infusion), and 24 hr (end of 12 hr follow-up), and at the 7-day follow-up visit.

k. Serious AEs will be reported through 30 days after the last infusion.

l. Study drug dosing will occur over 12 hours (3×4 hr dose levels) on Day 1 and Day 10, beginning at 8 AM (+2 hours).

m. Blood samples for PK analysis for all subjects will be collected at the following time points during each dose level: pre-infusion, after the start of the infusion at 30 and 45 minutes, and at hours 1, 1.5, 2, 4, 6, 8, 10, 12, 12.5, 12.75, 13, 13.5, 14, 16 and 24 hours. The 30 and 45-minute time points should be collected within a ±2 minute window of the scheduled time point. The hourly time points should be collected within ±10 minutes of the schedule time point. The 24-hour post-follow-up time point should be collected within ±30 minutes of the scheduled time point.

n. Subjects will report any SAEs occurring since the 7-day follow-up visit through 30 days after the last infusion.

TABLE 9

Schedule of Assessments (Stage Two)

| Procedures | Stage Two Screening Visit (Day −1- Day −7) | Day 1 Treatment Visit (0-24 h)[a] | Day 2 (>24 h) | Day 7 Follow Up Visit (±1)[n] |
|---|---|---|---|---|
| Informed Consent | X | | | |
| Inclusion/Exclusion Criteria | X | | | |
| Physical Examination | X | | | X |
| Brief Neurological Examination[b] | X | | | X |
| Body Weight | X | | | |
| Vital Signs[c] | X | X | | X |
| Clinical Laboratory Tests[d] | X | | | X |
| Drug and Alcohol Screen[e] | X | X | | |
| Pregnancy Test[f] | X | | | X |
| 12-Lead ECG[g] | | X | | X |
| Confined to Insubject Unit | | X | | |
| Discharge from Insubject Unit | | | X | |
| TETRAS[h] | X | | | X |
| TETRAS Performance Subscale (Items 4, 6, 7, 8)[i] | | X | | |
| Accelerometer | | X | X | |
| C-SSRS | X | X | | X |
| SSS[j] | | X | | |
| Bond-Lader VAS Mood Scale | | X | | X |
| Drug Effects Questionnaire | | X | | |
| Continuous EEG | | X | | |
| Adverse Event Collection[n] | X | X | X | X |
| Concomitant Medications | X | X | X | X |
| Study Drug Administration[k] | | X | | |
| Plasma for PK Analysis[l] | | X | | |
| Urine for PK Analysis[m] | | X | | |
| Study Completion | | | | X |

[a]To assist with scheduling, subjects can be admitted to the Insubject Unit the day prior or on Day 1 in advance of initiating the infusion. If subjects are admitted to the Insubject Unit on Day 1, they must be admitted with sufficient time to complete all pre-infusion procedures.
[b]The brief neurological examination consists of review of the following: mental status, cranial nerves, sensation, strength, deep tendon reflexes, and coordination.
[c]Vital signs include oral temperature (° C.), respiratory rate, heart rate (supine and standing), and blood pressure (supine and standing). Heart rate and blood pressure measurements should be taken after the subject has been supine for at least 5 minutes and standing for 2 minutes. A full set of vital signs will be obtained at the Screening Visit, on Days 1 just prior to beginning the infusion, at 2, 4, 6, 8, 10, 12, 14 and 24 hours after initiating the infusion and at the 7-day follow-up visit.
[d]Clinical laboratory samples (blood and urinalysis) will be collected at the Screening Visit and at the 7-day follow-up visit. Blood tests include clinical chemistry, LFTs, and hematology.
[e]Subjects will complete a urine drug screen for selected drugs of abuse and an alcohol screen at the Screening Visit and or Day 1. Subjects should abstain from using alcohol for at least 48 hours prior to check-in. The alcohol screen will be a serum alcohol test at the Screening Visit and a breath test at subsequent visits.
[f]A serum pregnancy test will be done at the Screening Visit and urine pregnancy tests will be done at Day 1. An additional urine pregnancy test will be done at the 7-day follow-up visit.
[g]A baseline 12-lead ECG will be performed during the Screening Visit to assess the presence of any current or historical cardiovascular conditions, on Days just prior to beginning the infusion, the end of the 10-hour infusion, and will also be conducted at the 7-day follow-up visit.
[h]The full TETRAS questionnaire will be administered at Screening and at Day 7. The TETRAS Performance Subscale (items 4, 6, 7, and 8) will be administered at the following time points during: pre-dose, 2 hr, 3 hr, 4 hr, 6 hr, 8 hr, 10 hr (end of infusion), 12 hr, 14 hr and at 24-hours. Item #4 (upper limb tremor) of the TETRAS Performance Subscale will be completed using both the accelerometer and clinician assessment. Testing should be completed after the SSS and within ±30 minutes of the planned questionnaire time points. All 3 tests in the upper limb tremor series of assessments (item 4) will be completed for both arms, first for the RIGHT arm and then for the LEFT. Pre-dose assessments can be done any time within 2 hours prior to the start of infusion. Day 7 assessments can be done at any time during the visit.
[i]Subjects will complete the TETRAS Performance Subscale, Item #4 (upper limb tremor) while wearing the accelerometer. Simultaneous clinician assessment of item #4 will occur. The accelerometer assessment is completed in conjunction with the TETRAS Performance Subscale at Screening and at: pre-dosing, pre-dose, 2 hr, 3 hr, 4 hr, 6 hr, 8 hr, 10 hr (end of infusion), 12 hr, 14 hr and at 24-hours and at the 7-day follow-up visit.
[j]Administered at the following time points (just prior to the Accelerometer/TETRAS evaluation): pre-dose and at 1, 2, 3, 4, 5, 6, 7, 8, 9, 10, 11, 12, 14, and 24 hours after starting the infusion.
[k]Study drug dosing will occur over 10 hours, beginning at 8 AM (±2 hours).
[l]Blood samples for PK analysis for all subjects will be collected at the following time points: pre-infusion (any time within 2 hours of beginning the infusion); after the start of the infusion at 30, 60 (just before the infusion rate change), 90 and 120 (just before the infusion rate change) minutes (±2 minutes), and at hours 2.5, 3, 4, 5, 6, 7, 8, 9 and 10 (just before turning off the infusion) and at 10.5 (30 minutes after end of infusion), 10.75 (45 minutes after end of infusion), 11 (60 minutes after end of infusion), 11.5 (90 minutes after end of infusion), 12 (120 minutes after end of infusion), 14 (4 hours after end of infusion), 16 (6 hours after end of infusion) and 24 hours (22 hours after the end of the infusion). The 30 and 45 minute time points should be collected within a ±2 minute window of the scheduled time point. The hourly time points should be collected within ±10 minutes of the schedule time point. The 24 hour post-follow-up time point should be collected within ±30 minutes of the scheduled time point.
[m]All urine voided during the following time periods will be collected, pooled over the collections period, the volume measured, and a 20 ml sample taken before the urine is discarded. All subjects should void to empty their bladders within 30 minutes of the start of the infusion; this urine may be discarded. The collection periods are: 0-2 hours; 2-6 hours; 6-10 hours; 10-24 hours.
[n]Subjects will report any SAEs occurring since the 7-day follow-up visit through 30 days after the last infusion.
C-SSRS = Columbia-Suicide Severity Rating Scale; ECG = electrocardiogram; HIV = human immunodeficiency virus; LFTs = liver function tests; PK = pharmacokinetic; SSS = Stanford Sleepiness Scale; TETRAS = The Essential Tremor Rating Scale.

a. To assist with scheduling, subjects can be admitted to the Insubject Unit the day prior or on Day 1 in advance of initiating the infusion. If subjects are admitted to the Insubject Unit on Day 1, they must be admitted with sufficient time to complete all pre-infusion procedures.

b. The brief neurological examination consists of review of the following: mental status, cranial nerves, sensation, strength, deep tendon reflexes, and coordination.

c. Vital signs include oral temperature (° C.), respiratory rate, heart rate (supine and standing), and blood pressure (supine and standing). Heart rate and blood pressure measurements should be taken after the subject has been supine for at least 5 minutes and standing for 2 minutes. A full set of vital signs will be obtained at the Screening Visit, on Days 1 just prior to beginning the infusion, at 2, 4, 6, 8, 10, 12, 14 and 24 hours after initiating the infusion and at the 7-day follow-up visit.

d. Clinical laboratory samples (blood and urinalysis) will be collected at the Screening Visit and at the 7-day follow-up visit. Blood tests include clinical chemistry, LFTs, and hematology.

c. Subjects will complete a urine drug screen for selected drugs of abuse and an alcohol screen at the Screening Visit and or Day 1. Subjects should abstain from using alcohol for at least 48 hours prior to check-in. The alcohol screen will be a serum alcohol test at the Screening Visit and a breath test at subsequent visits.

f. A serum pregnancy test will be done at the Screening Visit and urine pregnancy tests will be done at Day 1. An additional urine pregnancy test will be done at the 7-day follow-up visit.

g. A baseline 12-lead ECG will be performed during the Screening Visit to assess the presence of any current or historical cardiovascular conditions, on Days just prior to beginning the infusion, the end of the 10-hour infusion, and will also be conducted at the 7-day follow-up visit.

h. The full TETRAS questionnaire will be administered at Screening and at Day 7. The TETRAS Performance Subscale (items 4, 6, 7, and 8) will be administered at the following time points during: pre-dose, 2 hr, 3 hr, 4 hr, 6 hr, 8 hr, 10 hr (end of infusion), 12 hr, 14 hr and at 24-hours. Item #4 (upper limb tremor) of the TETRAS Performance Subscale will be completed using both the accelerometer and clinician assessment. Testing should be completed after the SSS and within +30 minutes of the planned questionnaire time points. All 3 tests in the upper limb tremor series of assessments (item 4) will be completed for both arms, first for the RIGHT arm and then for the LEFT. Pre-dose assessments can be done any time within 2 hours prior to the start of infusion. Day 7 assessments can be done at any time during the visit.

i. Subjects will complete the TETRAS Performance Subscale, Item #4 (upper limb tremor) while wearing the accelerometer. Simultaneous clinician assessment of item #4 will occur. The accelerometer assessment is completed in conjunction with the TETRAS Performance Subscale at Screening and at: pre-dosing, pre-dose, 2 hr, 3 hr, 4 hr, 6 hr, 8 hr, 10 hr (end of infusion), 12 hr, 14 hr and at 24-hours and at the 7-day follow-up visit.

j. Administered at the following time points (just prior to the Accelerometer/TETRAS evaluation): pre-dose and at 1, 2, 3, 4, 5, 6, 7, 8, 9, 10, 11, 12, 14, and 24 hours after starting the infusion.

k. Study drug dosing will occur over 10 hours, beginning at 8 AM (+2 hours).

l. Blood samples for PK analysis for all subjects will be collected at the following time points: pre-infusion (any time within 2 hours of beginning the infusion); after the start of the infusion at 30, 60 (just before the infusion rate change), 90 and 120 (just before the infusion rate change) minutes (±2 minutes), and at hours 2.5, 3, 4, 5, 6, 7, 8, 9 and 10 (just before turning off the infusion) and at 10.5 (30 minutes after end of infusion), 10.75 (45 minutes after end of infusion), 11 (60 minutes after end of infusion), 11.5 (90 minutes after end of infusion), 12 (120 minutes after end of infusion), 14 (4 hours after end of infusion), 16 (6 hours after end of infusion) and 24 hours (22 hours after the end of the infusion). The 30 and 45 minute time points should be collected within a ±2 minute window of the scheduled time point. The hourly time points should be collected within ±10 minutes of the schedule time point. The 24 hour post-follow-up time point should be collected within ±30 minutes of the scheduled time point.

m. All urine voided during the following time periods will be collected, pooled over the collections period, the volume measured, and a 20 ml sample taken before the urine is discarded. All subjects should void to empty their bladders within 30 minutes of the start of the infusion; this urine may be discarded. The collection periods are: 0-2 hours: 2-6 hours: 6-10 hours: 10-24 hours.

n. Subjects will report any SAEs occurring since the 7-day follow-up visit through 30 days after the last infusion.

C-SSRS=Columbia–Suicide Severity Rating Scale; ECG=electrocardiogram; HIV=human immunodeficiency virus; LFTs=liver function tests; PK=pharmacokinetic; SSS=Stanford Sleepiness Scale; TETRAS=The Essential Tremor Rating Scale.

Assessments

The safety and tolerability of Allopregnanolone Injection will be assessed by AEs, clinical laboratory measures, physical examinations, vital signs, electrocardiograms (ECGs), use of concomitant medication, and the Columbia Suicide Severity Rating Scale (C-SSRS) and the Stanford Sleepiness Scale (SSS) as scheduled starting with the Screening Visit (if appropriate), throughout Treatment Periods 1 and 2, and at the 7-day Follow-up/End of Study visit in Stage One, and periodically during Stage Two.

Secondary efficacy assessments, including accelerometer (transducer measurement of tremor amplitude), full TETRAS and TETRAS Performance Subscale will be completed as scheduled during Treatment Periods 1 and 2 of Stage One, and during Stage Two.

Plasma will be collected to assay for allopregnanolone levels prior to dosing through the treatment period and up to 24-hours post infusion. In addition, samples may be analyzed for allopregnanolone metabolites and Captisol® concentrations.

Dosing of intravenous allopregnanolone in the case of AEs

In Stage One, since allopregnanolone levels in the proposed clinical trial are similar to physiological levels seen in the third trimester of pregnancy, and all the AEs reported with allopregnanolone or allopregnanolone to date were mild and non-serious, it is anticipated that the AEs associated with allopregnanolone will be mild and manageable without dose interruption or reduction. However, in the case of severe or life-threatening toxicity occurring, the investigator is advised to interrupt infusion until regression of the AE to mild or resolution, and only resume infusion if it is deemed in the best interest of the subject (see Table). In Stage One at the 58 and 86 μg dose levels, resumption of infusion at the next lowest dose level for one hour, followed by re-escalation to the current rate may be considered to address potential recurrence of the AE. If the AE recurs at severe or life-threatening levels, infusion should be definitively discontinued.

In Stage Two, the same general guidance outlined in Table 10 will be applied to dose escalation/interruption. If there is a persistent SSS score of 7, the investigator may maintain the current dose or reduce the dose to the one lower than the current one.

TABLE 10

Allopregnanolone dose modifications in the case of AEs

| AE | Action on first occurrence | Action on recurrence |
|---|---|---|
| Mild-moderate | None | None, unless subject request |
| Severe [1] | Interruption until resolution to mild or resolution. Resume infusion at next lowest dose rate for 1 hour then if no recurrence of severe or life-threatening AE, re-escalate to maintenance rate For the lowest dose level, discontinue allopregnanolone. | Discontinue allopregnanolone |
| Life-threatening [1] | Discontinue allopregnanolone | Discontinue allopregnanolone |

[1] If possible at time of observation of severe or life-threatening toxicity take blood for PK Concomitant Medications and Restrictions
Concomitant Medications Subjects will receive the Insubject Unit standard of care for subjects diagnosed with essential tremor. Any concomitant medication determined necessary for the welfare of the subject may be given at the discretion of the Investigator at any time during the study. All concomitant medications should be documented throughout the study from Screening through the last visit of the study and recorded on the eCRF. Prior medications, i.e., those taken prior to signing of informed consent (including those that required wash out for study entry and those that are continuing during the study) will also be documented.

Prohibited Medications
Restrictions on specific classes of medications include the following:
Benzodiazepines are to be avoided as much as possible. Eligible subjects taking a benzodiazepine at the time of study entry will be permitted to continue to take their current dose of the benzodiazepine (to prevent acute withdrawal), but no new benzodiazepine use or increase of benzodiazepine dose will be permitted during the course of the study. Subjects will be allowed to take psychotropics that have been initiated at least 14 days prior to admission to the Insubject Unit at a stable dose.
The use of gabapentin and pregabalin is to be avoided. The use of hypnotics for sleep/insomnia such as Ambien® and trazodone is to be avoided and should follow the same guidelines as outlined above for benzodiazepines.
Allopregnanolone has demonstrated inhibitory effects on cytochrome P-450 (CYP) 2C9 (CYP2C9). The following medications are primarily metabolized by CYP2C9 and therefore are prohibited during allopregnanolone administration; fluconazole and miconazole (antifungal), amentoflavone (constituent of Ginkgo biloba and St. John's Wort), sulfaphenazole (antibacterial), valproic acid (anticonvulsant, mood-stabilizing), and apigenin.

Subjects who violate the prohibited medication restrictions will be considered for exclusion from the efficacy analysis.
Safety Assessments Safety and tolerability will be assessed by AEs, clinical laboratory measures, physical examinations, brief neurological examinations, vital signs, ECGs, and use of concomitant medication. Suicidality will be monitored using the C-SSRS. Sedation will be monitored using the SSS. All safety assessments should be performed per the Insubject Unit standard of care and will be collected periodically throughout the study according to the Schedule of Events. All safety assessments are to be completed within ±30 minutes of the scheduled time point.

Adverse Events

Adverse events will be collected after the ICF has been signed. Medical conditions that occur after the ICF has been signed will be captured on the AE eCRF.

Adverse events will be coded using the Medical Dictionary for Regulatory Activities (MedDRA) coding system (version 17.0 or higher).

Clinical Laboratory Tests

Blood samples will be collected for hematology, serum chemistry, and pregnancy tests (females only). Urine samples for urinalysis and pregnancy tests (females only) will also be collected. These assessments should be performed in accordance with the Schedule of Events and as outlined individually below.

Urine assessment for selected drugs of abuse (including amphetamines, barbiturates, benzodiazepines, cocaine, cannabinoid, methadone, and opiates) and a serum alcohol screen will also be collected at the screening visits. Subjects will also be screened for hepatitis (HBsAg and anti-HCV) and HIV prior to being enrolled in the trial. Subjects who have positive tests for drugs of abuse, hepatitis, or HIV will be withdrawn from the study.

All clinical laboratory test results outside the reference range will be interpreted by the Investigator as abnormal, not clinically significant (NCS): or abnormal, clinically significant (CS). Screening results considered abnormal, CS recorded at the screening visits may make the subject ineligible for the study pending review by the medical monitor. Clinical laboratory results that are abnormal, CS during the study but within normal range at baseline and/or indicate a worsening from baseline will be considered AEs, and recorded in the eCRF.

Hematology and Serum Chemistry

Blood samples for routine hematology and serum chemistry will be collected in Stage One at Screening Visit, at Check-in or Day 1, at Check-in or Day 10, at the end of each 12-hour follow-up, and at the 7-day follow-up visit; and in Stage Two at the Screening Visit and Day 7 visit. Blood tests will include hematology and clinical chemistry parameters as follows:
Hematology: complete blood count (CBC) including white blood cell (WBC) count with differential, platelet count and red blood cell (RBC) count, hemoglobin (Hgb) and hematocrit (Hct), mean corpuscular volume (MCV), and mean corpuscular hemoglobin (MCH).
Serum chemistry; albumin, alanine aminotransferase (ALT), alkaline phosphatase, aspartate aminotransferase (AST), bicarbonate, bilirubin (total), blood urea nitrogen (BUN), calcium, chloride, cholesterol, creatine phosphokinase, creatinine, gamma glutamyl transferase (GGT), lactate dehydrogenase, potassium, phosphorus, sodium, total protein, triglycerides, uric acid, and glucose.

Pregnancy Test

Females of child-bearing potential will be tested for pregnancy by serum pregnancy test at the Screening visit and by urine pregnancy test prior to administration of study drug at Check-in or Day 1, at Check-in or Day 10, and at the 7-day follow-up visit in Stage One and at the Screening Visit and Day 7 visit in Stage Two. Female subjects with a positive pregnancy test prior to administration of study drug in either Treatment Period 1 or 2 will be withdrawn from study participation.

Urinalysis

Urinalysis will include assessment of protein, blood, glucose, ketones, bile, urobilinogen, Hgb, leukocyte esterase, nitrites, color, turbidity, pH, and specific gravity. Urine will be collected for urinalysis at the Screening Visit, at Check-in or Day 1, at Check-in or Day 10, at the end of each 12-hour follow-up, and at the 7-day follow-up visit in Stage One and at the Screening Visit and Day 7 visit in Stage Two.

Physical Examination

Physical examinations will be performed at the Screening Visit, at Check-in or Day 1, Check-in or Day 10, and at the 7-day follow-up visit in Stage One and at the Screening Visit and Day 7 visit in Stage Two. Body weight and height will be measured at Screening. Body mass index (BMI) will be programmatically calculated in the eCRF at Screening. Additionally, weight will be measured at Check-in or Day 1 and Check-in or Day 10 in Stage One and at the Screening Visit in Stage Two to determine dosing for allopregnanolone.

Any condition present at the post treatment physical examination that was not present at or worsened since the baseline examination is to be documented as an AE. Whenever possible, the same individual is to perform all physical examinations. Physical examinations will include assessment of body systems (e.g., eyes, ears, nose, and throat: heart: lungs; abdomen; and extremities) as well as mental health examinations.

Brief Neurological Examination

A brief neurological examination will be performed at the Screening Visit, at Check-in or Day 1, Check-in or Day 10, and at the 7-day follow-up visit in Stage one and at the Screening Visit and Day 7 visit in Stage Two.

Any condition present at the post treatment neurological examination result that was not present at or worsened since the baseline examination is to be documented as an AE (with the exception of upper limb ET). Whenever possible, the same individual is to perform all neurological examinations. Neurological examinations will consist of reviews of mental status, cranial nerves, sensation, strength, deep tendon reflexes, and coordination.

Vital Signs

Vital signs include oral temperature (° C.), respiratory rate, heart rate (supine and standing), and blood pressure (supine and standing). Heart rate and blood pressure measurements should be taken after the subject has been supine for at least 5 minutes and standing for 2 minutes. A full set of vital signs will be obtained at the Screening Visit, on Days 1 and 10 just prior to beginning the infusion, at 4 hours and 8 hours after initiating the infusion, at the end of each 12-hour infusion, at the end of each 12-hour follow-up, and at the 7-day follow-up visit in Stage One. In Stage Two, a full set of vital signs will be obtained just prior to beginning the infusion, and at 2, 4, 6, 8, 10, 12, 14, and 24 hours after initiating the infusion, and at the Day 7 visit.

Electrocardiogram

In Stage One, a baseline 12-lead ECG will be performed at the Screening Visit to assess the presence of any current or historical cardiovascular conditions, on Days 1 and 10 just prior to beginning the infusion, at 4 hours and 8 hours after initiating the infusion, at the end of each 12-hour infusion, and will also be conducted at the 7-day follow-up visit. In Stage Two, a 12-lead ECG will be performed prior the beginning of the infusion, at the end of the 10-hour infusion, and at the Day 7 visit. The following ECG parameters will be recorded: heart rate: PR, QRS, and QT intervals; and the corrected QT interval (QTc). Subjects with clinically significant abnormalities at the Screening Visit should not be entered into the study.

Columbia Suicide Severity Rating Scale (C-SSRS)

Suicidality will be monitored during the study using the C-SSRS (Posner 2011). This scale consists of a baseline evaluation that assesses the lifetime experience of the subject with suicidal ideation and behavior, and a post-baseline evaluation that focuses on suicidality since the last study visit. The C-SSRS includes 'yes' or 'no' responses for assessment of suicidal ideation and behavior as well as numeric ratings for severity of ideation, if present (from 1 to 5, with 5 being the most severe). In Stage One, the "Baseline" C-SSRS form will be completed on the mornings of Day I and Day 10 prior to dosing. The "Since Last Visit" C-SSRS form will be completed on Day 2 and Day 11 (12-hours post infusion). In Stage Two, the "Baseline" C-SSRS will be completed at the Screening Visit. The "Since Last Visit" C-SSRS form will be completed at the end of the 10-hours infusion of allopregnanolone, and again at Day 7. If the Investigator thinks the subject is showing any suicidal tendency, no further study medication will be administered and the subject will be referred to a psychologist or psychiatrist for further evaluation. Copies of both versions of the C-SSRS are provided in Appendix 2.

Stanford Sleepiness Scale

The SSS is subject-rated scale designed to quickly assess how alert a subject is feeling. Degrees of sleepiness and alertness are rated on a scale of 1 to 7, where the lowest score of '1' indicates the subject is 'feeling active, vital, alert, or wide awake' and the highest score of '7' indicates the subject is 'no longer fighting sleep, sleep onset soon; having dream-like thoughts'. In Stage One, the SSS will be administered at the following time points during Treatment Periods 1 and 2 just prior to the Accelerometer/TETRAS evaluation; pre-dosing, 2 hr, 4 hr, 6 hr, 8 hr, 10 hr and 12 hr (end of infusion), and 24 hr (end of 12 hr follow-up period). In Stage Two, the SSS will be administered at the following time points (just prior to the Accelerometer/TETRAS evaluation): pre-dose and at 1, 2, 3, 4, 5, 6, 7, 8, 9, 10, 11, 12, 14, and 24 hours after starting the infusion.

A copy of the SSS is provided in Appendix 4.

Concomitant Medication

Concomitant medications will be recorded at each study visit for concomitant and restricted medications). Contraceptives will be recorded as concomitant medications.

Bond-Lader Mood Rating Scale

The Bond-Lader Mood Rating Scale is designed to assess subjective mood. It is a self-administered visual analogue score that will be administered in Stage Two of the study at the following timepoints: prior to the start of the infusion, at 10 hours after that start of the infusion, and at the Day 7 visit.

Drug Effects Questionnaire

A Drug Effects Questionnaire will be administered in Stage Two of the study at the following timepoints: prior to the start of the infusion, and at 6 and 9 hours after the start of the infusion. The questions are as follows:

a. Do you feel a drug effect right now?
b. Are you high right now?
c. Do you like any of the drug effects that you are feeling right now?
d. Do you dislike any of the drug effects that you are feeling right now?
e. Would you like more of the drug you are being administered right now?

The answers are recorded on a 100 mm visual analogue scale with the answer for each being "Not at all" and "Very much" at the extremes. There will be options to record "Not applicable" for c and d if no drug effects are felt and for e prior to administration of the allopregnanolone infusion.

Efficacy Assessments
Secondary Efficacy Outcome Measures

Secondary efficacy assessments include evaluation of subject symptom response by a measurement of tremor amplitude, full TETRAS and TETRAS Performance Subscale. All secondary efficacy assessments are to be completed within ±30 minutes of the scheduled time point.

Measurements of Tremor Amplitude

In order to measure essential tremor amplitude, subjects will wear a wireless ring motion sensor. The motion sensor measures linear acceleration and angular velocity (the kinesia score). Data are transmitted from the sensor to a computer using Bluetooth technology. Information from the motion sensor data correlates to symptoms of tremor. The kinesia score ranges from 0 to 4 in 0.5 step increments. Higher scores indicate more tremor. The accelerometer assessment is completed in conjunction with the TETRAS Performance Subscale Item 4.

The Essential Tremor Rating Scale (TETRAS) Performance Scale

The full TETRAS questionnaire will be administered at Screening and at Day 18, the 7-day follow-up visit in Stage One and at the Screening Visit and Day 7 visit in Stage Two.

The TETRAS Performance Subscale (Items 4, 6, 7, and 8) will be administered at the following time points during Treatment Periods 1 and 2 in Stage One: pre-dosing, 2 hr, 4 hr, 6 hr, 8 hr, 10 hr and 12 hr (end of infusion), and at 24 hr (end of the 12 hr follow up).

The TETRAS Performance Subscale (Items 4, 6, 7, and 8) will be administered at the following time points during Stage Two: pre-dose (twice, 30 minutes apart), and at 2 (before the dose change), 3, 4, 6, 8, 10, 12, 14, and 24 hours after starting the infusion.

Item #4 (upper limb tremor) of the TETRAS Performance Subscale will be completed using both the accelerometer and clinician assessment. Testing should be completed within +10 minutes of the planned questionnaire time points. All 3 tests in the upper limb tremor series of assessments (Item 4) will be completed for both arms, first for the RIGHT arm and then for the LEFT. Pre-dose assessments can be done any time within 2 hours prior to the start of infusion. The Day 7 follow up visit assessments can be done at any time during the visit.

Subjects will complete the TETRAS Performance Subscale, Item #4 (upper limb tremor) while wearing the accelerometer. Simultaneous clinician assessment of item #4 will occur. The accelerometer assessment is completed in conjunction with the TETRAS Performance Subscale at the same time points during the study.

Pharmacokinetics

In Stage One plasma will be collected to assay for allopregnanolone levels at pre-infusion (prior to dose level 1); after the start of the infusion at 30 and 45 minutes, and at hours 1, 1.5, 2, 4, 6, 8, 10, 12, 12.5, 12.75, 13, 13.5, 14, 16 and 24 hours. Plasma collection times for PK should be adhered to as strictly as possible. The 30 and 45-minute time point should be collected within a ±2 minute window of the scheduled time point. The hourly time points should be collected within ±10 minutes of the scheduled time point. The 24-hour post infusion time points should be collected within ±30 minutes of the scheduled time point. Additionally, PK samples may be obtained outside the planned collection times if issues administering study drug are encountered, such as incorrect infusion rate, interrupted infusion, or other administration deviations where timing of the blood draw for PK assessment may be important in understanding subject state.

In Stage Two, plasma will be collected to assay for allopregnanolone levels at the following time points: pre-infusion (any time within 2 hours of beginning the infusion); after the start of the infusion at 30, 60 (just before the infusion rate change), 90 and 120 (just before the infusion rate change) minutes (±2 minutes), and at hours 2.5, 3, 4, 5, 6, 7, 8, 9 and 10 (just before turning off the infusion) and at 10.5 (30 minutes after end of infusion), 10.75 (45 minutes after end of infusion), 11 (60 minutes after end of infusion), 11.5 (90 minutes after end of infusion), 12 (120 minutes after end of infusion), 14 (4 hours after end of infusion), 16 (6 hours after end of infusion) and 24 hours (22 hours after the end of the infusion). In addition, samples may be analyzed for allopregnanolone metabolites and Captisol R concentrations. In Stage Two, all urine voided during the following time periods, pooled over the collections period, the volume measured and recorded, and a 20 ml sample taken before the urine is discarded. All subjects should void to empty their bladders within 30 minutes of the start of the infusion; this urine may be discarded. The collection periods are: 0-2 hours: 2-6 hours: 6-10 hours: 10-24 hours.

Plasma concentrations of allopregnanolone will be determined using high performance liquid chromatography with tandem mass spectrometry (HPLC MS/MS). The following PK parameters will be calculated where evaluable; area under the concentration-time curve (AUC) from time zero to 12 hours ($AUC_{0-12}$), AUC from time zero to infinity ($AUC_{inf}$), maximum (peak) plasma concentration ($C_{max}$), time at maximum (peak) plasma concentration ($T_{max}$), steady-state drug concentration in the plasma during constant-rate infusion ($C_{SS}$), and average drug concentration in the plasma at steady-state during a dosing interval ($C_{avg}$). In addition, samples may be analyzed for allopregnanolone metabolites and Captisol R concentrations.

The plasma samples will be drawn from the arm opposite to that used for drug administration. Subject-specific PK kits for sampling, including instructions for collection, processing methods, as well as storage and shipping conditions, will be provided.

Exploratory Endpoints: EEG

Continuous EEG will be recorded in Stage Two from one hour prior to starting the infusion to two hours after the end of the infusion (13 hours of recording in total). The data will be subjected to quantitative EEG analysis in order to correlate the degree of sleepiness on the SSS and the depth of sedation on the EEG.

Statistical Methods and Considerations

In general, summary statistics for all study endpoints will be presented as mean, standard deviation (SD), median, ranges (minimum, maximum) for continuous endpoints, and as counts and percentages for categorical endpoints. For the purpose of all safety, efficacy, and exploratory analyses where applicable, baseline is defined as the last pre-dose measurement closest to the start of infusion. Separate baseline values will be calculated for each Stage of the study (where applicable). All statistical analyses will be conducted using SAS (version 9.1.3, or higher), unless otherwise specified.

Data Analysis Sets

Stage One

Safety Population (SAF): All subjects admitted into the Insubject Unit who meet all eligibility criteria, sign an informed consent, and begin receiving allopregnanolone Injection or placebo on Treatment Period 1 will be included in the safety population and will be considered evaluable for safety.

Efficacy Population (EFF): All SAF subjects who complete at least 12 hours of infusion and have efficacy evaluations through the 12-hour visit for treatment periods 1 and 2 will be considered evaluable for efficacy. Subjects with data available for one infusion may be included in some of the analyses but will not be considered fully evaluable for efficacy. Subjects that are evaluable for efficacy and who complete the D18 visit will be considered to be study completers.

PK Population; All SAF subjects who complete at least 12 hours of allopregnanolone IV infusion in Treatment Period 1 or Treatment Period 2 with sufficient plasma concentrations for PK evaluations.

Stage Two

Safety Population (SAF): All subjects admitted into the Insubject Unit who meet all eligibility criteria, sign an informed consent, and begin receiving allopregnanolone Injection will be included in the safety population and will be considered evaluable for safety.

Efficacy Population (EFF): All SAF subjects who complete at least 10 hours of infusion and have efficacy evaluations through the 10-hour visit will be considered evaluable for efficacy. Subjects that are evaluable for efficacy and who complete the D7 visit will be considered to be study completers.

PK Population; All SAF subjects who complete at least 10 hours of allopregnanolone IV infusion in with sufficient plasma concentrations for PK evaluations.

Primary Endpoints

Safety and tolerability are the primary objectives of this protocol. Tolerability will be evaluated by AEs and concomitant medications, while safety will be evaluated by changes from baseline in physical examination, vital signs, hematology, serum chemistry, urinalysis, and 12-lead ECG. Suicidality will be monitored by the C-SSRS. All safety and tolerability summaries will be performed on the SAF population for each Stage. Results will be summarized separately for each Stage: Stage One displays will be summarized by treatment group.

Adverse events: The analysis of AEs will be based on the concept of treatment-emergent AEs (TEAEs). A TEAE is defined as an AE with onset after the start of the initial infusion in each Stage. All TEAEs will be summarized and grouped by MedDRA System Organ Class (SOC) and specific AE preferred term (PT). Results will be displayed in order of decreasing frequency by SOC and PT: Stage One results will also be displayed by treatment group. For presentation, AE verbatim text will be coded into a MedDRA term, and classified by SOC and PT using MedDRA version 17.0 or higher. In addition, summaries will be provided by severity (mild, moderate, severe), and by causality (related, not related) to study drug: for Stage One, summaries will be presented by treatment group.

Treatment-emergent SAEs and TEAEs leading to discontinuation will be summarized and listed by Stage. Adverse events with onset after the completion of screening but prior to the start of the initial infusion in either Stage (considered non-treatment emergent) will be listed by subject.

Clinical laboratory tests: Clinical chemistry, hematology, and urinalysis samples will be collected at scheduled time points unless an unscheduled visit warrants an additional laboratory test. Results will be listed by subject ID and timing of collection. The listings will be annotated with out of range results noted to be clinically significant or non-clinically significant.

Physical examinations: Physical examinations will be evaluated at the at scheduled time points. Any clinically significant change in physical examination compared to those observed at Screening should be noted as an AE.

Brief neurological examinations: Brief neurological examinations will be evaluated at the scheduled time points. Any clinically significant change in neurological examination compared to those observed at Screening should be noted as an AE.

Vital signs: Vital signs, including oral temperature (° C.), respiratory rate, heart rate (supine and standing), and blood pressure (supine and standing), will be obtained at the scheduled time points described. Actual vital signs and change from pre-infusion will be summarized separately for each Stage and listed for each subject at each evaluation period.

12-Lead ECG: ECGs will be collected at the scheduled time points described. The following ECG parameters will be listed for each subject: heart rate, PR, QRS, QT, and QTc. Any clinically significant abnormalities or changes in ECGs should be listed as an AE. Electrocardiogram findings will be listed by subject and visit.

Concomitant medications: Concomitant medications will be collected at the scheduled time points described. A summary of all concomitant medications taken during the course of the study will be presented in tabular form by therapeutic drug class and generic drug name using the World Health Organization (WHO) Collaborating Centre for Drug Statistics Methodology Norwegian Institute of Public Health (http://www.whocc.no).

C-SSRS: The C-SSRS will be completed at the scheduled time points described. Suicidality data collected on the C-SSRS at baseline and by visit during the active treatment period will be listed and tabulated for all subjects by Stage: Stage One tabulations will also be presented by treatment group. Listings will include behavior type and/or category for Suicidal Ideation and Suicidal Behavior of the C-SSRS.

Secondary Endpoints

Safety Analysis

The Stanford Sleepiness Scale (SSS) will assess the effect on sedation and will be summarized by Stage; Stage One summaries will be displayed by treatment group.

Efficacy Analysis

Efficacy will be evaluated by maximum reduction from baseline (pre-dose) tremor, as measured by accelerometer and by maximum change from baseline in TETRAS Performance Subscale Items 4, 6, 7, and 8.

Stage One: Endpoints will be analyzed using a mixed effects analysis of variance model for crossover design where the fixed effects are sequence, period, and treatment while the random effect includes subject within sequence. Due to possible carryover, baseline measures (baseline to the start of each period) will be included as covariates.

Symptom responses, accelerometer measurements, and TETRAS will be analyzed and tabulated by treatment group at each evaluation time point and will be listed by subject.

Stage Two: Symptom responses, accelerometer measurements, and TETRAS will be summaried and tabulated at each evaluation time point and will be listed by subject.

Pharmacokinetic Analysis

Plasma samples for concentrations of allopregnanolone will be collected as described. The PK parameters of $AUC_{0-12}$, $AUC_{inf}$, $C_{max}$, $T_{max}$, $C_{SS}$, and $C_{avg}$ will be calculated (where evaluable) for all subjects in the PK population for each Stage. These PK parameters will be summarized by Stage using descriptive statistics and listed by subject.

Plasma concentrations will be listed by subject and summarized by collection period. Pharmacokinetic parameters will be summarized for each subject and overall by Stage. Correlations between concentrations and AEs or tolerability measures will be performed as deemed necessary.

Determination of Sample Size

Described is a proof-of-concept study to determine if Allopregnanolone Injection is safe and tolerable and whether treatment with allopregnanolone Injection exhibits a clinical signal in improvement in essential tremor. The kinesia score ranges from 0 to 4 in 0.5 step increments. Higher scores indicate more tremor. A minimum sample size of 16 subjects (8 per sequence group) is sufficient to detect a 2 point change in kinesia scores at alpha=0.05 with at least 80% power if the estimated mean square error from the crossover model is 0.93 or smaller. Therefore, up to 24 subjects (12 per sequence group) will be enrolled to ensure at least 16 are evaluable in Stage One. As Stage Two is exploratory in nature, only those subjects who completed Stage One will be invited to return for Stage Two, with no pre-specified minimum or maximum number of subjects.

Results

An exploratory clinical trial evaluating the $GABA_A$ mechanism of action as a treatment for essential tremor, using allopregnanolone injection. In the randomized, double-blind, placebo-controlled, crossover trial of 25 patients affected by essential tremor, where patients were exposed to the target steady state dose for two hours, low-dose allopregnanolone injection demonstrated a clinically meaningful reduction of tremor amplitude (>30% reduction from baseline) in 35% of patients, compared with 12.5% of patients in the placebo arm. The patients also received high-dose of allopregnanolone injection and demonstrated a similar reduction of tremor amplitude (in 17 of the same patients). Allopregnanolone injection was safe and well-tolerated with no serious adverse events observed on therapy or during the 30-day follow-up period. In addition, little sedation was observed in patients on allopregnanolone injection in the placebo-controlled, low-dose portion of the trial.

The randomized, double-blind, placebo-controlled crossover trial was designed to evaluate the safety, tolerability, pharmacokinetics and efficacy of the $GABA_A$ mechanism in patients with essential tremor.

The exploratory trial consisted of randomized, double-blind, placebo-controlled crossover treatment of 25 patients receiving either allopregnanolone injection or placebo in two crossover treatment periods. An open-label, dose-escalation extension of patients returning from the crossover stage was used to explore high-dose administration of allopregnanolone injection to study the range of pharmacodynamics and dose-limiting effect of the $GABA_A$ modulator mechanism in conscious patients. Patients were monitored for up to 30 days following treatment. The trial was designed as a dose escalation, proof-of-mechanism and methodology trial designed to enroll patients aged 35 to 75 years old, with moderate to severe essential tremor as assessed by a clinician rating scale, TETRAS. Tremor was measured during the trial by physical measures of tremor amplitude and frequency using accelerometry. Patients enrolled in the trial were required to have had diagnosed essential tremor for at least two years and to be off medication, or on a stable dose of medication for their tremor, for at least 28 days prior to screening.

A clear reduction in tremor amplitude, as measured by accelerometer, was observed when comparing administration of low-dose allopregnanolone injection to placebo. Anti-tremor activity of allopregnanolone injection without sedative effect was observed at low-dose levels of allopregnanolone injection, suggesting that the clinical activity could be achieved without sedation and peak anti-tremor activity correlated with steady state allopregnanolone injection levels. At open-label, high-dose administration of allopregnanolone injection, a dose-related anti-tremor benefit was observed with some sedative effect, but even during drug administration patients began to tolerate to sedation, becoming less sedated in the hours they were administered drug. The data suggests that the anti-tremor effect may be uncoupled from sedation and that tolerance to sedation may occur quickly. The findings are consistent with the extrasynaptic activity of allopregnanolone injection.

Allopregnanolone injection was safe and well-tolerated with no serious adverse events reported during the treatment and follow-up periods. Of the 25 patients enrolled, three patients reported at least one adverse event on low-dose allopregnanolone injection, compared to five patients reporting at least one adverse event while on placebo. In the open-label, high-dose allopregnanolone injection portion of the study, eight patients reported at least one adverse event. The only adverse events reported more than once across all allopregnanolone injection treatment priors were five reports each of fatigue and dizziness, one in the low-dose portion and 4 in the higher dose portion of the study. There was one discontinuation in the high-dose allopregnanolone injection extension due to sedation and hypotension, with rapid recovery on drug discontinuation.

APPENDIX 1. THE ESSENTIAL TREMOR RATING ASSESSMENT SCALE (TETRAS)

TRG ESSENTIAL TREMOR RATING ASSESSMENT SCALE (TETRAS©) V 3.1

Activities of Daily Living Subscale

Rate tremor's impact on activities of daily living (0 - 4 scoring).

1. Speaking
0 = Normal.
1 = Slight voice tremulousness, only when "nervous".
2 = Mild voice tremor. All words easily understood.
3 = Moderate voice tremor. Some words difficult to understand.
4 = Severe voice tremor. Most words difficult to understand.

2. Feeding with a spoon
0 = Normal
1 = Slightly abnormal. Tremor is present but does not interfere with feeding with a spoon.
2 = Mildly abnormal. Spills a little.
3 = Moderately abnormal. Spills a lot or changes strategy to complete task such as using two hands or leaning over.
4 = Severely abnormal. Cannot feed with a spoon.

3. Drinking from a glass
0 = Normal.
1 = Slightly abnormal. Tremor is present but does not interfere with drinking from a glass.
2 = Mildly abnormal. Spills a little.
3 = Moderately abnormal. Spills a lot or changes strategy to complete task such as using two hands or leaning over.
4 = Severely abnormal. Cannot drink from a glass or uses straw or sippy cup.

4. Hygiene
0 = Normal.
1 = Slightly abnormal. Tremor is present but does not interfere with hygiene.
2 = Mildly abnormal. Some difficulty but can complete task.
3 = Moderately abnormal. Unable to do most fine tasks such as putting on lipstick or shaving unless changes strategy such as using two hands or using the less affected hand.
4 = Severely abnormal. Cannot complete hygiene activities independently.

5. Dressing
0 = Normal.
1 = Slightly abnormal. Tremor is present but does not interfere with dressing.
2 = Mildly abnormal. Able to do everything but has difficulty due to tremor.
3 = Moderately abnormal. Unable to do most dressing unless uses strategy such as using Velcro, buttoning shirt before putting it on or avoiding shoes with laces.
4 = Severely abnormal. Cannot dress independently.

6. Pouring
0 = Normal.
1 = Slightly abnormal. Tremor is present but does not interfere with pouring.
2 = Mildly abnormal. Must be very careful to avoid spilling but may spill occasionally.
3 = Moderately abnormal. Must use two hands or uses other strategies to avoid spilling.
4 = Severely abnormal. Cannot pour.

7. Carrying food trays, plates or similar items
0 = Normal
1 = Slightly abnormal. Tremor is present but does not interfere with carrying food trays, plates or similar items.
2 = Mildly abnormal. Must be very careful to avoid spilling items on food tray.
3 = Moderately abnormal. Uses strategies such as holding tightly against body to carry.
4 = Severely abnormal. Cannot carry food trays or similar items.

8. Using Keys
0 = Normal
1 = Slightly abnormal. Tremor is present but can insert key with one hand without difficulty.
2 = Mildly abnormal. Commonly misses target but still routinely puts key in lock with one hand.
3 = Moderately abnormal. Needs to use two hands or other strategies to put key in lock.
4 = Severely abnormal. Cannot put key in lock.

9. Writing
0 = Normal
1 = Slightly abnormal. Tremor present but does not interfere with writing.
2 = Mildly abnormal. Difficulty writing due to the tremor
3 = Moderately abnormal. Cannot write without using strategies such as holding the writing hand with the other hand, holding pen differently or using large pen.
4 = Severely abnormal. Cannot write.

10. Working. If patient is retired, ask as if they were still working. If the patient is a housewife, ask the question as it relates to housework:
0 = Normal .
1 = Slightly abnormal. Tremor is present but does not affect performance at work or at home.
2 = Mildly abnormal. Tremor interferes with work; able to do everything, but with errors. .
3 = Moderately abnormal. Unable to continue working without using strategies such as changing jobs or using special equipment.
4 = Severely abnormal. Cannot perform any job or household work.

11. Overall disability with the most affected task (Name task, e.g. using computer mouse, writing, etc)
        Task _____
0 = Normal.
1 = Slightly abnormal. Tremor present but does not affect task.
2 = Mildly abnormal. Tremor interferes with task but is still able to perform task.
3 = Moderately abnormal. Can do task but must use strategies.
4 = Severely abnormal. Cannot do the task.

12. Social Impact
0 = None
1 = Aware of tremor, but it does not affect lifestyle or professional life.
2 = Feels embarrassed by tremor in some social situations or professional meetings.
3 = Avoids participating in some social situations or professional meetings because of tremor.
4 = Avoids participating in most social situations or professional meetings because of tremor.

Performance Subscale

Instructions

Scoring is 0 – 4. For most items, the scores are defined only by whole numbers, but 0.5 increments may be used if you believe the rating is between two whole number ratings and cannot be reconciled to a whole number. Each 0.5 increment in rating is specifically defined for the assessment of upper limb postural and kinetic tremor and the dot approximation task (items 4 and 8). All items of the examination, except standing tremor, are performed with the patient seated comfortably. For each item, score the highest amplitude seen at any point during the exam. Instruct patients not to attempt to suppress the tremor, but to let it come out.

1. Head tremor: The head is rotated fully left and right and then observed for 10s in mid position. Patient then is instructed to gaze fully to the left and then to the right with the head in mid position. The nose should be used as the landmark to assess and rate the largest amplitude excursions during the examination.

0 = no tremor
    1 = slight tremor (< 0.5 cm)
    2 = mild tremor (0.5- < 2.5 cm)
    3 = moderate tremor (2.5-5 cm)
    4 = severe or disfiguring tremor (> 5 cm)

2. Face (including jaw) tremor: Smile, close eyes, open mouth, purse lips. The highest amplitude of the most involved facial anatomy is scored, regardless of whether it occurs during rest or activation. Repetitive blinking or eye fluttering should not be considered as part of facial tremor.

0 = no tremor
    1 = slight; barely perceptible tremor
    2 = mild: noticeable tremor
    3 = moderate: obvious tremor, present in most voluntary facial contractions
    4 = severe: gross disfiguring tremor 3. Voice tremor: First ask subject to produce an extended "aaah" sound and eee" sound for 5 seconds each. Then assess speech during normal conversation by asking patients "How do you spend your average day?".

0 = no tremor
    1 = slight: tremor during aaah, and eee and no tremor during speech
    2 = mild: tremor in "aaah" and "eee" and minimal tremor in speech
    3 = moderate: obvious tremor in speech that is fully intelligible
    4 = severe: some words difficult to understand 4. Upper limb tremor: Tremor is assessed during three maneuvers: forward horizontal reach posture, lateral "wing beating" posture and finger-nose-finger testing. Each upper limb is assessed and scored individually. The forward horizontal reach posture is held for 5 seconds.

The lateral wing beating posture is held for 20 seconds. The finger-nose-finger movement is executed three times. Amplitude assessment should be estimated using the maximally displaced point of the hand at the point of greatest displacement along any single plane. For example, the amplitude of a pure supination-pronation tremor, pivoting around the wrist would be assessed at either the thumb or fifth digit.

a. Forward outstretched postural tremor: Subjects should bring their arms forward, slightly lateral to midline and parallel to the ground. The wrist should also be straight and the fingers abducted so that they do not touch each other.

b. Lateral "wing beating" postural tremor: Subjects will abduct their arms parallel to the ground and flex the elbows so that the two hands do not quite touch each other and are at the level of the nose. The fingers are abducted so that they do not touch each other. The posture should be held for 20 seconds.

c. Kinetic tremor: Subjects extend only their index finger. They then touch a set object or the examiners finger located to the full extent of their reach, which is located at the same height (parallel to the ground) and slightly lateral to the midline. Subjects then touch their own nose (or chin if the tremor is severe) and repeat this back and forth three times. Only the position along the trajectory of greatest tremor amplitude is assessed. This will typically be either at the nose or at the point of full limb extension.

For all three hand tremor ratings
- 0 = no tremor
- 1 = tremor is barely visible
- 1.5 = tremor is visible, but less than 1 cm
- 2 = tremor is 1- < 3 cm amplitude
- 2.5 = tremor is 3- < 5 cm amplitude
- 3 = tremor is 5- < 10 cm amplitude
- 3.5 = tremor is 10- < 20 cm amplitude
- 4 = tremor is ≥ 20 cm amplitude 5. Lower limb tremor: Raise each lower limb horizontally parallel to the ground for 5 seconds each. Then perform a standard heel to shin maneuver with each leg, three times. The maximum tremor in either maneuver is scored, and only the limb with the largest tremor is scored. Tremor may exist in any part of the limb, including foot.
    - 0 = no tremor
    - 1 = slight: barely perceptible
    - 2 = mild, less than 1 cm at any point
    - 3 = moderate tremor, less than 5 cm at any point
    - 4 = severe tremor, greater than 5 cm 6. Archimedes spirals: Demonstrate how to draw Archimedes spiral that approximately fills ¼ of an unlined page of standard (letter) paper. The lines of the spiral should be approximately 1.3 cm (0.5 inch) apart. Then ask the subject to copy the spiral. Test and score each hand separately. Use a ballpoint pen. The pen should be held such that no part of the limb touches the table. Secure the paper on the table in a location that is suitable for the patient's style of drawing. Score the tremor in the spiral, not the movement of the limb.

0 = normal
   1 = slight: tremor barely visible.
   2 = mild: obvious tremor
   3 = moderate: portions of figure not recognizable.
   4 = severe: figure not recognizable 7. Handwriting: Have patient write the standard sentence "This is a sample of my best handwriting" using the dominant hand only. Patients must write cursively (i.e., no printing). They cannot hold or stabilize their hand with the other hand.. Use a ballpoint pen. Secure the paper on the table in a location that is suitable for the patient's style of writing. Score the tremor in the writing, not the movement of the limb.

0 = normal
   1 = slight: untidy due to tremor that is barely visible.
   2 = mild: legible, but with considerable tremor.
   3 = moderate: some words illegible.
   4 = severe: completely illegible 8. Dot approximation task: The examiner makes a dot or X and instructs the subject to hold the tip of the pen "as close as possible to the dot (or center of an X) without touching it, (ideally approximately 1 mm) for 10 seconds ". Each hand is score separately.

0 = no tremor
   1 = tremor is barely visible
   1.5 = tremor is visible, but less than 1 cm
   2 = tremor is 1- < 3 cm amplitude
   2.5 = tremor is 3- < 5 cm amplitude
   3 = tremor is 5- < 10 cm amplitude
   3.5 = tremor is 10- < 20 cm amplitude
   4 = tremor is $\geq$ 20 cm amplitude 9. Standing tremor: Subjects are standing, unaided if possible. The knees are 10-20 cm apart and are flexed 10-20°. The arms are down at the subject's side. Tremor is assessed at any point on the legs or trunk
   0 = no tremor
   1 = barely perceptible tremor
   2 = obvious but mild tremor, does not cause instability
   3 = moderate tremor, impairs stability of stance
   4 = severe tremor, unable to stand without assistance

APPENDIX 2. COLUMBIA - SUICIDE SEVERITY RATING SCALE (C-SSRS)

COLUMBIA-SUICIDE SEVERITY RATING SCALE (C-SSRS)

Baseline/Screening Version

Phase 1 study

Version 1/14/09

*Posner, K.; Brent, D.; Lucas, C.; Gould, M.; Stanley, B.; Brown, G.; Fisher, P.; Zelazny, J.; Burke, A.; Oquendo, M.; Mann, J.*

*Disclaimer:*

*This scale is intended to be used by individuals who have received training in its administration. The questions contained in the Columbia-Suicide Severity Rating Scale are suggested probes. Ultimately, the determination of the presence of suicidal ideation or behavior depends on the judgment of the individual administering the scale.*

Definitions of behavioral suicidal events in this scale are based on those used in The Columbia Suicide History Form, developed by John Mann, MD and Maria Oquendo, MD, Conte Center for the Neuroscience of Mental Disorders (CCNMD), New York State Psychiatric Institute, 1051 Riverside Drive, New York, NY, 10032. (Oquendo M. A., Halberstam B. & Mann J. J., Risk factors for suicidal behavior: utility and limitations of research instruments. In M.B. First [Ed.] Standardized Evaluation in Clinical Practice, pp. 103 -130, 2003.)

For reprints of the C-SSRS contact Kelly Posner, Ph.D., New York State Psychiatric Institute, 1051 Riverside Drive, New York, New York, 10032; inquiries and training requirements contact posnerk@childpsych.columbia.edu © 2008 The Research Foundation for Mental Hygiene, Inc.

| SUICIDAL IDEATION | Lifetime: Time He/She Felt Most Suicidal | Past 6 Months |
|---|---|---|
| *Ask questions 1 and 2. If both are negative, proceed to "Suicidal Behavior" section. If the answer to question 2 is "yes", ask questions 3, 4 and 5. If the answer to question 1 and/or 2 is "yes", complete "Intensity of Ideation" section below.* | | |
| 1. Wish to be Dead<br>Subject endorses thoughts about a wish to be dead or not alive anymore, or wish to fall asleep and not wake up.<br>*Have you wished you were dead or wished you could go to sleep and not wake up?*<br><br>If yes, describe: | Yes ☐  No ☐ | Yes ☐  No ☐ |
| 2. Non-Specific Active Suicidal Thoughts<br>General non-specific thoughts of wanting to end one's life/commit suicide (e.g., *"I've thought about killing myself"*) without thoughts of ways to kill oneself/associated methods, intent, or plan during the assessment period.<br>*Have you actually had any thoughts of killing yourself?*<br><br>If yes, describe: | Yes ☐  No ☐ | Yes ☐  No ☐ |
| 3. Active Suicidal Ideation with Any Methods (Not Plan) without Intent to Act<br>Subject endorses thoughts of suicide and has thought of at least one method during the assessment period. This is different than a specific plan with time, place or method details worked out (e.g., thought of method to kill self but not a specific plan). Includes person who would say, *"I thought about taking an overdose but I never made a specific plan as to when, where or how I would actually do it...and I would never go through with it."*<br>*Have you been thinking about how you might do this?*<br><br>If yes, describe: | Yes ☐  No ☐ | Yes ☐  No ☐ |
| 4. Active Suicidal Ideation with Some Intent to Act, without Specific Plan<br>Active suicidal thoughts of killing oneself and subject reports having some intent to act on such thoughts, as opposed to *"I have the thoughts but I definitely will not do anything about them."*<br>*Have you had these thoughts and had some intention of acting on them?*<br><br>If yes, describe: | Yes ☐  No ☐ | Yes ☐  No ☐ |
| 5. Active Suicidal Ideation with Specific Plan and Intent<br>Thoughts of killing oneself with details of plan fully or partially worked out and subject has some intent to carry it out.<br>*Have you started to work out or worked out the details of how to kill yourself? Do you intend to carry out this plan?*<br><br>If yes, describe: | Yes ☐  No ☐ | Yes ☐  No ☐ |
| INTENSITY OF IDEATION | | |
| *The following features should be rated with respect to the most severe type of ideation (i.e., 1-5 from above, with 1 being the least severe and 5 being the most severe). Ask about time he/she was feeling the most suicidal.*<br><br>Lifetime - *Most Severe Ideation:* _____  _____<br>                         *Type # (1-5)*   *Description of Ideation*<br><br>Past 6 Months - *Most Severe Ideation:* _____  _____<br>                         *Type # (1-5)*   *Description of Ideation* | Most Severe | Most Severe |
| Frequency<br>*How many times have you had these thoughts?*<br>(1) Less than once a week  (2) Once a week  (3) 2-5 times in week  (4) Daily or almost daily  (5) Many times each day | _____ | _____ |
| Duration<br>*When you have the thoughts how long do they last?*<br>(1) Fleeting - few seconds or minutes    (4) 4-8 hours/most of day<br>(2) Less than 1 hour/some of the time    (5) More than 8 hours/persistent or continuous<br>(3) 1-4 hours/a lot of time | _____ | _____ |
| Controllability<br>*Could/can you stop thinking about killing yourself or wanting to die if you want to?*<br>(1) Easily able to control thoughts    (4) Can control thoughts with a lot of difficulty<br>(2) Can control thoughts with little difficulty    (5) Unable to control thoughts<br>(3) Can control thoughts with some difficulty    (0) Does not attempt to control thoughts | _____ | _____ |
| Deterrents<br>*Are there things - anyone or anything (e.g., family, religion, pain of death) - that stopped you from wanting to die or acting on thoughts of committing suicide?*<br>(1) Deterrents definitely stopped you from attempting suicide    (4) Deterrents most likely did not stop you<br>(2) Deterrents probably stopped you    (5) Deterrents definitely did not stop you<br>(3) Uncertain that deterrents stopped you    (0) Does not apply | _____ | _____ |
| Reasons for Ideation<br>*What sort of reasons did you have for thinking about wanting to die or killing yourself? Was it to end the pain or stop the way you were feeling (in other words you couldn't go on living with this pain or how you were feeling) or was it to get attention, revenge or a reaction from others? Or both?*<br>(1) Completely to get attention, revenge or a reaction from others    (4) Mostly to end or stop the pain (you couldn't go on<br>(2) Mostly to get attention, revenge or a reaction from others        living with the pain or how you were feeling)<br>(3) Equally to get attention, revenge or a reaction from others    (5) Completely to end or stop the pain (you couldn't go on<br>    and to end/stop the pain                                        living with the pain or how you were feeling)<br>                                                                               (0) Does not apply | _____ | _____ |

Version 1/14/09

| SUICIDAL BEHAVIOR<br>(Check all that apply, so long as these are separate events; must ask about all types.) | Lifetime |
|---|---|
| Actual Attempt:<br>A potentially self-injurious act committed with at least some wish to die, *as a result of act.* Behavior was in part thought of as method to kill oneself. Intent does not have to be 100%. If there is *any* intent/desire to die associated with the act, then it can be considered an actual suicide attempt. *There does not have to be any injury or harm*, just the potential for injury or harm. If person pulls trigger while gun is in mouth but gun is broken so no injury results, this is considered an attempt.<br>Inferring Intent: Even if an individual denies intent/wish to die, it may be inferred clinically from the behavior or circumstances. For example, a highly lethal act that is clearly not an accident so no other intent but suicide can be inferred (e.g., gunshot to head, jumping from window of a high floor/story). Also, if someone denies intent to die, but they thought that what they did could be lethal, intent may be inferred.<br>*Have you made a suicide attempt?*<br>*Have you done anything to harm yourself?*<br>*Have you done anything dangerous where you could have died?*<br>    *What did you do?*<br>    *Did you_____ as a way to end your life?*<br>    *Did you want to die (even a little) when you_____?*<br>    *Were you trying to end your life when you_____?*<br>    *Or Did you think it was possible you could have died from_____?*<br>*Or did you do it purely for other reasons / without ANY intention of killing yourself (like to relieve stress, feel better, get sympathy, or get something else to happen)?* (Self-Injurious Behavior without suicidal intent)<br>If yes, describe:<br><br>Has subject engaged in Non-Suicidal Self-Injurious Behavior? | Yes  No<br>☐    ☐<br><br><br><br><br><br>Total # of Attempts<br>_____<br><br><br><br><br><br>Yes  No<br>☐    ☐ |
| Interrupted Attempt:<br>When the person is interrupted (by an outside circumstance) from starting the potentially self-injurious act *(if not for that, actual attempt would have occurred).*<br>Overdose: Person has pills in hand but is stopped from ingesting. Once they ingest any pills, this becomes an attempt rather than an interrupted attempt. Shooting: Person has gun pointed toward self, gun is taken away by someone else, or is somehow prevented from pulling trigger. Once they pull the trigger, even if the gun fails to fire, it is an attempt. Jumping: Person is poised to jump, is grabbed and taken down from ledge. Hanging: Person has noose around neck but has not yet started to hang - is stopped from doing so.<br>*Has there been a time when you started to do something to end your life but someone or something stopped you before you actually did anything?*<br>If yes, describe: | Yes  No<br>☐    ☐<br><br><br><br><br>Total # of interrupted<br>_____ |
| Aborted Attempt:<br>When person begins to take steps toward making a suicide attempt, but stops themselves before they actually have engaged in any self-destructive behavior. Examples are similar to interrupted attempts, except that the individual stops him/herself, instead of being stopped by something else.<br>*Has there been a time when you started to do something to try to end your life but you stopped yourself before you actually did anything?*<br>If yes, describe: | Yes  No<br>☐    ☐<br><br><br>Total # of aborted<br>_____ |
| Preparatory Acts or Behavior:<br>Acts or preparation towards imminently making a suicide attempt. This can include anything beyond a verbalization or thought, such as assembling a specific method (e.g., buying pills, purchasing a gun) or preparing for one's death by suicide (e.g., giving things away, writing a suicide note).<br>*Have you taken any steps towards making a suicide attempt or preparing to kill yourself (such as collecting pills, getting a gun, giving valuables away or writing a suicide note)?*<br>If yes, describe: | Yes  No<br>☐    ☐ |
| Suicidal Behavior:<br>Suicidal behavior was present during the assessment period? | Yes  No<br>☐    ☐ |

| *Answer for Actual Attempts Only* | Most Recent Attempt Date: | Most Lethal Attempt Date: | Initial/First Attempt Date: |
|---|---|---|---|
| Actual Lethality/Medical Damage:<br>0. No physical damage or very minor physical damage (e.g., surface scratches).<br>1. Minor physical damage (e.g., lethargic speech; first-degree burns; mild bleeding; sprains).<br>2. Moderate physical damage; medical attention needed (e.g., conscious but sleepy, somewhat responsive; second-degree burns; bleeding of major vessel).<br>3. Moderately severe physical damage; *medical* hospitalization and likely intensive care required (e.g., comatose with reflexes intact; third-degree burns less than 20% of body; extensive blood loss but can recover; major fractures).<br>4. Severe physical damage; *medical* hospitalization with intensive care required (e.g., comatose without reflexes; third-degree burns over 20% of body; extensive blood loss with unstable vital signs; major damage to a vital area).<br>5. Death | Enter Code<br><br>_____ | Enter Code<br><br>_____ | Enter Code<br><br>_____ |
| Potential Lethality: Only Answer if Actual Lethality=0<br>Likely lethality of actual attempt if no medical damage (the following examples, while having no actual medical damage, had potential for very serious lethality: put gun in mouth and pulled the trigger but gun fails to fire so no medical damage; laying on train tracks with oncoming train but pulled away before run over).<br><br>0 = Behavior not likely to result in injury<br>1 = Behavior likely to result in injury but not likely to cause death<br>2 = Behavior likely to result in death despite available medical care | Enter Code<br><br><br>_____ | Enter Code<br><br><br>_____ | Enter Code<br><br><br>_____ |

COLUMBIA-SUICIDE SEVERITY RATING SCALE (C-SSRS)

Since Last Visit

Version 1/14/09

*Posner, K.; Brent, D.; Lucas, C.; Gould, M.; Stanley, B.; Brown, G.; Fisher, P.; Zelazny, J.; Burke, A.; Oquendo, M.; Mann, J.*

*Disclaimer:*

*This scale is intended to be used by individuals who have received training in its administration. The questions contained in the Columbia-Suicide Severity Rating Scale are suggested probes. Ultimately, the determination of the presence of suicidal ideation or behavior depends on the judgment of the individual administering the scale.*

*Definitions of behavioral suicidal events in this scale are based on those used in* The Columbia Suicide History Form*, developed by John Mann, MD and Maria Oquendo, MD, Conte Center for the Neuroscience of Mental Disorders (CCNMD), New York State Psychiatric Institute, 1051 Riverside Drive, New York, NY, 10032. (Oquendo M. A., Halberstam B. & Mann J. J., Risk factors for suicidal behavior: utility and limitations of research instruments. In M.B. First [Ed.] Standardized Evaluation in Clinical Practice, pp. 103-130, 2003.)*

*For reprints of the C-SSRS contact Kelly Posner, Ph.D., New York State Psychiatric Institute, 1051 Riverside Drive, New York, New York, 10032; inquiries and training requirements contact posnerk@nyspi.columbia.edu*

© 2008 The Research Foundation for Mental Hygiene, Inc.

| SUICIDAL IDEATION | |
|---|---|
| Ask questions 1 and 2. If both are negative, proceed to "Suicidal Behavior" section. If the answer to question 2 is "yes", ask questions 3, 4 and 5. If the answer to question 1 and/or 2 is "yes", complete "Intensity of Ideation" section below. | Since Last Visit |
| 1. Wish to be Dead<br>Subject endorses thoughts about a wish to be dead or not alive anymore, or wish to fall asleep and not wake up.<br>*Have you wished you were dead or wished you could go to sleep and not wake up?*<br><br>If yes, describe: | Yes ☐ No ☐ |
| 2. Non-Specific Active Suicidal Thoughts<br>General, non-specific thoughts of wanting to end one's life/commit suicide (e.g., *"I've thought about killing myself"*) without thoughts of ways to kill oneself/associated methods, intent, or plan during the assessment period.<br>*Have you actually had any thoughts of killing yourself?*<br><br>If yes, describe: | Yes ☐ No ☐ |
| 3. Active Suicidal Ideation with Any Methods (Not Plan) without Intent to Act<br>Subject endorses thoughts of suicide and has thought of at least one method during the assessment period. This is different than a specific plan with time, place or method details worked out (e.g., thought of method to kill self but not a specific plan). Includes person who would say, *"I thought about taking an overdose but I never made a specific plan as to when, where or how I would actually do it...and I would never go through with it."*<br>*Have you been thinking about how you might do this?*<br><br>If yes, describe: | Yes ☐ No ☐ |
| 4. Active Suicidal Ideation with Some Intent to Act, without Specific Plan<br>Active suicidal thoughts of killing oneself and subject reports having some intent to act on such thoughts, as opposed to *"I have the thoughts but I definitely will not do anything about them."*<br>*Have you had these thoughts and had some intention of acting on them?*<br><br>If yes, describe: | Yes ☐ No ☐ |
| 5. Active Suicidal Ideation with Specific Plan and Intent<br>Thoughts of killing oneself with details of plan fully or partially worked out and subject has some intent to carry it out.<br>*Have you started to work out or worked out the details of how to kill yourself? Do you intend to carry out this plan?*<br><br>If yes, describe: | Yes ☐ No ☐ |
| INTENSITY OF IDEATION | |
| The following features should be rated with respect to the most severe type of ideation (i.e., 1-5 from above, with 1 being the least severe and 5 being the most severe).<br><br>*Most Severe Ideation:* _____  _____<br>  Type # (1-5)        Description of Ideation | Most Severe |
| Frequency<br>*How many times have you had these thoughts?*<br>(1) Less than once a week  (2) Once a week  (3) 2-5 times in week  (4) Daily or almost daily  (5) Many times each day | _____ |
| Duration<br>*When you have the thoughts, how long do they last?*<br>(1) Fleeting - few seconds or minutes  (4) 4-8 hours/most of day<br>(2) Less than 1 hour/some of the time  (5) More than 8 hours/persistent or continuous<br>(3) 1-4 hours/a lot of time | _____ |
| Controllability<br>*Could/can you stop thinking about killing yourself or wanting to die if you want to?*<br>(1) Easily able to control thoughts  (4) Can control thoughts with a lot of difficulty<br>(2) Can control thoughts with little difficulty  (5) Unable to control thoughts<br>(3) Can control thoughts with some difficulty  (0) Does not attempt to control thoughts | _____ |
| Deterrents<br>*Are there things - anyone or anything (e.g., family, religion, pain of death) - that stopped you from wanting to die or acting on thoughts of committing suicide?*<br>(1) Deterrents definitely stopped you from attempting suicide  (4) Deterrents most likely did not stop you<br>(2) Deterrents probably stopped you  (5) Deterrents definitely did not stop you<br>(3) Uncertain that deterrents stopped you  (0) Does not apply | _____ |
| Reasons for Ideation<br>*What sort of reasons did you have for thinking about wanting to die or killing yourself? Was it to end the pain or stop the way you were feeling (in other words you couldn't go on living with this pain or how you were feeling) or was it to get attention, revenge or a reaction from others? Or both?*<br>(1) Completely to get attention, revenge or a reaction from others  (4) Mostly to end or stop the pain (you couldn't go on living with the pain or how you were feeling)<br>(2) Mostly to get attention, revenge or a reaction from others<br>(3) Equally to get attention, revenge or a reaction from others and to end/stop the pain  (5) Completely to end or stop the pain (you couldn't go on living with the pain or how you were feeling)<br>  (0) Does not apply | _____ |

Version 1/14/09

| *SUICIDAL BEHAVIOR* *(Check all that apply, so long as these are separate events, must ask about all types)* | Since Last Visit |
|---|---|
| Actual Attempt:<br>A potentially self-injurious act committed with at least some wish to die, *as a result of act*. Behavior was in part thought of as method to kill oneself. Intent does not have to be 100%. If there is *any* intent/desire to die associated with the act, then it can be considered an actual suicide attempt. *There does not have to be any injury or harm*, just the potential for injury or harm. If person pulls trigger while gun is in mouth but gun is broken so no injury results, this is considered an attempt.<br>Inferring Intent: Even if an individual denies intent/wish to die, it may be inferred clinically from the behavior or circumstances. For example, a highly lethal act that is clearly not an accident so no other intent but suicide can be inferred (e.g., gunshot to head, jumping from window of a high floor/story). Also, if someone denies intent to die, but they thought that what they did could be lethal, intent may be inferred.<br>*Have you made a suicide attempt?*<br>*Have you done anything to harm yourself?*<br>*Have you done anything dangerous where you could have died?*<br>    *What did you do?*<br>    *Did you_____ as a way to end your life?*<br>    *Did you want to die (even a little) when you____?*<br>    *Were you trying to end your life when you____?*<br>    *Or did you think it was possible you could have died from____?*<br>*Or did you do it purely for other reasons / without ANY intention of killing yourself (like to relieve stress, feel better, get sympathy, or get something else to happen)?* (Self-Injurious Behavior without suicidal intent)<br>If yes, describe:<br><br>Has subject engaged in Non-Suicidal Self-Injurious Behavior? | Yes   No<br>☐    ☐<br><br>Total # of Attempts<br>_____<br><br><br><br><br><br><br><br><br><br>Yes   No<br>☐    ☐ |
| Interrupted Attempt:<br>When the person is interrupted (by an outside circumstance) from starting the potentially self-injurious act *(if not for that, actual attempt would have occurred)*.<br>Overdose: Person has pills in hand but is stopped from ingesting. Once they ingest any pills, this becomes an attempt rather than an interrupted attempt. Shooting: Person has gun pointed toward self, gun is taken away by someone else, or is somehow prevented from pulling trigger. Once they pull the trigger, even if the gun fails to fire, it is an attempt. Jumping: Person is poised to jump, is grabbed and taken down from ledge. Hanging: Person has noose around neck but has not yet started to hang - is stopped from doing so.<br>*Has there been a time when you started to do something to end your life but someone or something stopped you before you actually did anything?*<br>If yes, describe: | Yes   No<br>☐    ☐<br><br><br>Total # of interrupted<br>_____ |
| Aborted Attempt:<br>When person begins to take steps toward making a suicide attempt, but stops themselves before they actually have engaged in any self-destructive behavior. Examples are similar to interrupted attempts, except that the individual stops him/herself, instead of being stopped by something else.<br>*Has there been a time when you started to do something to try to end your life but you stopped yourself before you actually did anything?*<br>If yes, describe: | Yes   No<br>☐    ☐<br><br>Total # of aborted<br>_____ |
| Preparatory Acts or Behavior:<br>Acts or preparation towards imminently making a suicide attempt. This can include anything beyond a verbalization or thought, such as assembling a specific method (e.g., buying pills, purchasing a gun) or preparing for one's death by suicide (e.g., giving things away, writing a suicide note).<br>*Have you taken any steps towards making a suicide attempt or preparing to kill yourself (such as collecting pills, getting a gun, giving valuables away or writing a suicide note)?*<br>If yes, describe: | Yes   No<br>☐    ☐ |
| Suicidal Behavior:<br>Suicidal behavior was present during the assessment period? | Yes   No<br>☐    ☐ |
| Suicide: | Yes   No<br>☐    ☐ |
| *Answer for Actual Attempts Only* | Most Lethal Attempt Date: |
| Actual Lethality/Medical Damage:<br>0. No physical damage or very minor physical damage (e.g., surface scratches).<br>1. Minor physical damage (e.g., lethargic speech; first-degree burns; mild bleeding; sprains).<br>2. Moderate physical damage; medical attention needed (e.g., conscious but sleepy, somewhat responsive; second-degree burns; bleeding of major vessel).<br>3. Moderately severe physical damage; *medical* hospitalization and likely intensive care required (e.g., comatose with reflexes intact; third-degree burns less than 20% of body; extensive blood loss but can recover; major fractures).<br>4. Severe physical damage; *medical* hospitalization with intensive care required (e.g., comatose without reflexes; third-degree burns over 20% of body; extensive blood loss with unstable vital signs; major damage to a vital area).<br>5. Death | Enter Code<br><br>_____ |
| Potential Lethality: Only Answer if Actual Lethality=0<br>Likely lethality of actual attempt if no medical damage (the following examples, while having no actual medical damage, had potential for very serious lethality: put gun in mouth and pulled the trigger but gun fails to fire so no medical damage; laying on train tracks with oncoming train but pulled away before run over).<br><br>0 = Behavior not likely to result in injury<br>1 = Behavior likely to result in injury but not likely to cause death<br>2 = Behavior likely to result in death despite available medical care | Enter Code<br><br><br>_____ |

APPENDIX 3. HAMILTON RATING SCALE FOR DEPRESSION (17-ITEMS) (HAM-D-17)

Study ID: _____  Date: _____

Hamilton Rating Scale for Depression (17-items)

Instructions: For each item select the "cue" which best characterizes the patient during the past week.

1. Depressed Mood
   (sadness, hopeless, helpless, worthless)
   - 0 Absent
   - 1 These feeling states indicated only on questioning
   - 2 These feeling states spontaneously reported verbally
   - 3 Communicates feeling states nonverbally, i.e., through facial expression, posture, voice and tendency to weep
   - 4 Patient reports VIRTUALLY ONLY these feeling states in his spontaneous verbal and nonverbal communication 2. Feelings of Guilt
   - 0 Absent
   - 1 Self-reproach, feels he has let people down
   - 2 Ideas of guilt or rumination over past errors or sinful deeds
   - 3 Present illness is a punishment. Delusions of guilt
   - 4 Hears accusatory or denunciatory voices and/or experiences threatening visual hallucinations 3. Suicide
   - 0 Absent
   - 1 Feels life is not worth living
   - 2 Wishes he were dead or any thoughts of possible death to self
   - 3 Suicide ideas or gesture
   - 4 Attempts at suicide (any serious attempt rates 4)

4. Insomnia - Early
   - 0 No difficulty falling asleep
   - 1 Complains of occasional difficulty falling asleep i.e., more than ½ hour
   - 2 Complains of nightly difficulty falling asleep 5. Insomnia - Middle
   - 0 No difficulty
   - 1 Patient complains of being restless and disturbed during the night
   - 2 Waking during the night – any getting out of bed rates 2 (except for purposes of voiding)

6. Insomnia - Late
   - 0 No difficulty
   - 1 Waking in early hours of the morning but goes back to sleep
   - 2 Unable to fall asleep again if gets out of bed 7. Work and Activities
   - 0 No difficulty
   - 1 Thoughts and feelings of incapacity, fatigue or weakness related to activities; work or hobbies
   - 2 Loss of interest in activity; hobbies or work – either directly reported by patient, or indirect in listlessness, indecision and vacillation (feels he has to push self to work or activities)
   - 3 Decrease in actual time spent in activities or decrease in productivity. In hospital, rate 3 if patient does not spend at least three hours a day in activities (hospital job or hobbies) exclusive of ward chores.
   - 4 Stopped working because of present illness. In hospital, rate 4 if patient engages in no activities except ward chores, or if patient fails to perform ward chores unassisted.

8. Retardation
   (slowness of thought and speech, impaired ability to concentrate; decreased motor activity)
   - 0 Normal speech and thought
   - 1 Slight retardation at interview
   - 2 Obvious retardation at interview
   - 3 Interview difficult
   - 4 Complete stupor 9. Agitation
   - 0 None
   - 1 "Playing with" hand, hair, etc.
   - 2 Hand-wringing, nail-biting, biting of lips 10. Anxiety - Psychic
    - 0 No difficulty
    - 1 Subjective tension and irritability
    - 2 Worrying about minor matters
    - 3 Apprehensive attitude apparent in face or speech
    - 4 Fears expressed without questioning 11. Anxiety - Somatic
    - 0 Absent — Physiological concomitants of anxiety such as:
    - 1 Mild — Gastrointestinal - dry mouth, wind, indigestion.
    - 2 Moderate — diarrhea, cramps, belching
    - 3 Severe — Cardiovascular – palpitations, headaches
    - 4 Incapacitating — Respiratory - hyperventilation, sighing
       Urinary frequency
       Sweating 12. Somatic Symptoms - Gastrointestinal
    - 0 None
    - 1 Loss of appetite but eating without staff encouragement. Heavy feelings in abdomen.
    - 2 Difficulty eating without staff urging. Requests or requires laxatives or medications for bowels or medication for G.I. symptoms.

13. Somatic Symptoms - General
    - 0 None
    - 1 Heaviness in limbs, back or head, backaches, headache, muscle aches, loss of energy and fatigability
    - 2 Any clear-cut symptom rates 2

14. Genital Symptoms
    - 0 Absent    0 Not ascertained
    - 1 Mild      Symptoms such as: loss of libido,
    - 2 Severe    menstrual disturbances 15. Hypochondriasis
    - 0 Not present
    - 1 Self-absorption (bodily)
    - 2 Preoccupation with health
    - 3 Frequent complaints, requests for help, etc
    - 4 Hypochondriacal delusions 16. Loss of Weight
    A. When Rating by History:
    - 0 No weight loss
    - 1 Probable weight loss associated with present illness
    - 2 Definite (according to patient) weight loss B. On Weekly Ratings by Ward Psychiatrist, When Actual Changes are Measured:
    - 0 Less than 1 lb. weight loss in week
    - 1 Greater than 1 lb. weight loss in week
    - 2 Greater than 2 lb. weight loss in week 17. Insight
    - 0 Acknowledges being depressed and ill
    - 1 Acknowledges illness but attributes cause to bad food, climate, overwork, virus, need for rest, etc.
    - 2 Denies being ill at all Total Score: _____

APPENDIX 4. STANFORD SLEEPINESS SCALE (SSS)

Stanford Sleepiness Scale

This is a quick way to assess how alert you are feeling. If it is during the day when you go about your business, ideally you would want a rating of a one. Take into account that most people have two peak times of alertness daily, at about 9 a.m. and 9 p.m. Alertness wanes to its lowest point at around 3 p.m.; after that it begins to build again. Rate your alertness at different times during the day. If you go below a three when you should be feeling alert, this is an indication that you have a serious sleep debt and you need more sleep.

| An Introspective Measure of Sleepiness The Stanford Sleepiness Scale (SSS) | |
|---|---|
| Degree of Sleepiness | Scale Rating |
| Feeling active, vital, alert, or wide awake | 1 |
| Functioning at high levels, but not at peak; able to concentrate | 2 |
| Awake, but relaxed; responsive but not fully alert | 3 |
| Somewhat foggy, let down | 4 |
| Foggy; losing interest in remaining awake; slowed down | 5 |
| Sleepy, woozy, fighting sleep; prefer to lie down | 6 |
| No longer fighting sleep, sleep onset soon; having dream-like thoughts | 7 |
| Asleep | X |

The invention claimed is:

1. A method of treating postpartum depression in a human subject, the method comprising administering a continuous intravenous infusion of allopregnanolone, wherein the infusion comprises administering a first infusion, second infusion, and third infusion to the subject in need thereof, and wherein the first infusion delivers a smaller amount, as measured in μg/kg/hour, of allopregnanolone/unit time than the second infusion, and wherein the third infusion delivers a smaller amount, as measured in μg/kg/hour, of allopregnanolone/unit time than the second infusion, and wherein
said first infusion comprises administering a continuously increasing amount of allopregnanolone at an amount of allopregnanolone/unit time of 5-100 μg/kg/hour, 10-80 μg/kg/hour, or 15-70 μg/kg/hour;
said second infusion comprises administering an amount of allopregnanolone/unit time of 50-100 μg/kg/hour, 70-100 μg/kg/hour, or 86 μg/kg/hour; and
said third infusion comprises administering a continuously decreasing amount of allopregnanolone at an amount of allopregnanolone/unit time of 5-100 μg/kg/hour, 10-80 μg/kg/hour, or 15-70 μg/kg/hour.

2. The method of claim 1, wherein the first infusion comprises administering a plurality of step doses, wherein each subsequent step dose delivers a larger amount of allopregnanolone/unit time than the step dose that precedes it.

3. The method of claim 1, wherein the third infusion comprises administering a plurality of step doses, wherein each subsequent step dose delivers a smaller amount, as measured in μg/kg/hour, of allopregnanolone/unit time than the step dose that precedes it, wherein the plurality of step doses comprises a first, second, and third step dose.

4. The method of claim 1, wherein the allopregnanolone is administered at a dose of 60-100 μg/kg/hour during the second infusion.

5. The method of claim 1, wherein the allopregnanolone is administered at the same amount of allopregnanolone/unit time over the entire second infusion.

6. The method of claim 1, wherein
said first infusion comprises administering a continuously increasing amount of allopregnanolone at an amount allopregnanolone/unit time of 15-70 μg/kg/hour;
said second infusion comprises administering an amount of allopregnanolone/unit time of 50-100 μg/kg/hour; and
said third infusion comprises administering a continuously decreasing amount of allopregnanolone at an amount of allopregnanolone/unit time of 15-70 μg/kg/hour.

7. The method of claim 1, wherein
said first infusion comprises administering a plurality of step doses, wherein each subsequent step dose delivers a larger amount of allopregnanolone/unit time than the step dose that precedes it, and the amount of allopregnanolone/unit time administered is 5-100 μg/kg/hour, 10-80 μg/kg/hour, or 15-70 μg/kg/hour;
said second infusion comprises administering an amount of allopregnanolone/unit time of 50-100 μg/kg/hour, 70-100 μg/kg/hour, or 86 μg/kg/hour; and
said third infusion comprising administering a plurality of step doses, wherein each subsequent step dose delivers a lower amount of allopregnanolone/unit time than the step dose that precedes it and the amount of allopregnanolone/unit time is 5-100 μg/kg/hour, 10-80 μg/kg/hour, or 15-70 μg/kg/hour.

8. The method of claim 1, wherein the allopregnanolone is provided in a composition comprising a cyclodextrin.

9. The method of claim 8, wherein the cyclodextrin is present in the composition at 1-30% by weight of cyclodextrin per volume of composition.

10. The method of claim 9, wherein the cyclodextrin is present in the composition at 2-18% by weight of cyclodextrin per volume of composition.

11. The method of claim 1, wherein the allopregnanolone is provided at a concentration of 0.1 to 10 mg/mL.

12. The method of claim 11, wherein the allopregnanolone is provided at a concentration of 1 to 5 mg/mL.

13. The method of claim 8, wherein the cyclodextrin is present in the composition at 2-18% by weight of cyclodextrin per volume of composition, and the allopregnanolone is provided at a concentration of 1 to 5 mg/mL.

14. The method of claim 8, wherein the cyclodextrin is present in the composition at 1-30% by weight of cyclodextrin per volume of composition, and the allopregnanolone is provided at a concentration of 1 to 5 mg/mL.

15. The method of claim 8, wherein the cyclodextrin is present in the composition at 25% by weight of cyclodextrin per volume of composition, and the allopregnanolone is provided at a concentration of 5 mg/mL.

16. The method of claim 1, wherein the infusion is carried out over 60 hours.

* * * * *